(12) United States Patent
Chen et al.

(10) Patent No.: US 11,525,123 B2
(45) Date of Patent: Dec. 13, 2022

(54) DIVERSE CARBENE TRANSFERASE ENZYME CATALYSTS DERIVED FROM A P450 ENZYME

(71) Applicant: California Institute of Technology, Pasadena, CA (US)

(72) Inventors: Kai Chen, Pasadena, CA (US); Noah P. Dunham, Pasadena, CA (US); Daniel J. Wackelin, Pasadena, CA (US); Andrew Z. Zhou, Pasadena, CA (US); Zhen Liu, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 17/200,394

(22) Filed: Mar. 12, 2021

(65) Prior Publication Data
US 2021/0292718 A1    Sep. 23, 2021

Related U.S. Application Data

(60) Provisional application No. 62/988,589, filed on Mar. 12, 2020.

(51) Int. Cl.
| | | |
|---|---|---|
| *C12N 9/02* | (2006.01) | |
| *C12P 17/04* | (2006.01) | |
| *C12P 7/62* | (2022.01) | |
| *C12P 17/16* | (2006.01) | |

(52) U.S. Cl.
CPC .............. *C12N 9/0042* (2013.01); *C12P 7/62* (2013.01); *C12P 17/04* (2013.01); *C12P 17/16* (2013.01); *C12Y 106/02004* (2013.01)

(58) Field of Classification Search
None
See application file for complete search history.

(56) References Cited

U.S. PATENT DOCUMENTS

| | | | |
|---|---|---|---|
| 8,993,262 B2 | 3/2015 | Coelho et al. | |
| 9,493,799 B2 | 11/2016 | Coelho et al. | |
| 10,208,322 B2 | 2/2019 | Coelho et al. | |
| 10,829,792 B2 | 11/2020 | Chen et al. | |
| 10,934,531 B2 | 3/2021 | Zhang et al. | |
| 11,008,596 B2 | 5/2021 | Coelho et al. | |
| 2016/0010065 A1* | 1/2016 | Osborne .............. | C12N 9/0042 435/189 |
| 2018/0148745 A1 | 5/2018 | Arnold et al. | |
| 2018/0305721 A1 | 10/2018 | Chen et al. | |
| 2019/0276805 A1 | 9/2019 | Zhang et al. | |

FOREIGN PATENT DOCUMENTS

| | | |
|---|---|---|
| WO | 2014/058729 A1 | 4/2014 |

OTHER PUBLICATIONS

Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Accession P14779. Apr. 1, 1990 (Year: 1990).*
Chica et al. CurrOpin Biotechnol. Aug. 2005;16(4):378-84. (Year: 2005).*
Singh et al. Curr Protein Pept Sci. 2017, 18, 1-11 (Year: 2017).*
Chen, et al. "Alternate Heme Ligation Steers Activity and Selectivity in Engineered Cytochrome P450-Catalyzed Carbene-Transfer Reactions." *Journal of the American Chemical Society*, 2018, 140: 16402-16407.
Chen, et al. "Engineering Cytochrome P450s for Enantioselective Cyclopropenation of Internal Alkynes." *Journal of the American Chemical Society*, 2020, 142: 6891-6895.
Coelho, et al. "A serine-substituted P450 catalyzes highly efficient carbene transfer to olefins in vivo." *Nature Chemical Biology*, 2013, 9: 485-487.
Coelho, et al. "Olefin Cyclopropanation via Carbene Transfer Catalyzed by Engineered Cytochrome P450 Enzymes." *Science*, 2013, 339: 307-310.
Renata, et al. "Expanding the Enzyme Universe: Accessing Non-Natural Reactions by Mechanism-Guided Directed Evolution." *Angewandte Chemie International Edition*, 2015, 54:3351-3367.
Renata, et al. "Identification of Mechanism-Based Inactivation in P450-Catalyzed Cyclopropanation Facilitates Engineering of Improved Enzymes." *Journal of the American Chemical Society*, 2016, 138:12527-12533.
Zhang, et al. "Enzymatic assembly of carbon-carbon bonds via iron-catalysed sp3 C—H functionalization." *Nature*, 2019, 565(7737): 97-72.
Zhang, et al. "Selective C—H bond functionalization with engineered heme proteins: New tools to generate complexity." *Current Opinion in Chemical Biology*, 2019, 49: 67-75.
Zhou, et al. "Enzymatic Lactone-Carbene C—H Insertion to Build Contiguous Chiral Centers." *ACS Catalysis*, 2020, 10: 5393-5398.

* cited by examiner

*Primary Examiner* — Christian L Fronda
(74) *Attorney, Agent, or Firm* — Kilpatrick Townsend & Stockton LLP

(57) ABSTRACT

The present disclosure provides cytochrome P450 variants useful for carrying out in vivo and in vitro carbene insertion reactions. Methods for preparing carbene insertion products including cyclopropenes, cyclopropanes, bicyclobutanes, substituted lactones, cyclized compounds, and substituted amines are also described.

20 Claims, 14 Drawing Sheets
Specification includes a Sequence Listing.

other substrates and corresponding products:

2h
L6: 600 TTN, 78:22 d.r., 41% ee/-30% ee
L9: 850 TTN, 94:6 d.r., 81% ee/-15% ee
L10: 740 TTN, 99:1 d.r., -94.5% ee/-19% ee

2i
L6: 2550 TTN, 52:48 d.r., 94.5% ee/-24% ee
L9: 1430 TTN, 88:12 d.r., 86.5% ee/-72.5% ee
L10: 1490 TTN, 96:4 d.r., -72% ee/-30% ee

2j
L6: 960 TTN, 34:66 d.r., 95% ee/-27% ee
L8: 860 TTN, 41:59 d.r., 96% ee/7% ee
L9: 1460 TTN, 88:12 d.r., 91% ee/14% ee

2k
L7: 2400 TTN, 22:78 d.r., 96.5% ee/86% ee
L8: 2730 TTN, 18:82 d.r., 96.5% ee/91% ee
L9: 4000 TTN, 38:62 d.r., 89% ee/85% ee

2l
L6: 960 TTN, 52:48 d.r., 93% ee/-26% ee
L7: 1260 TTN, 58:42 d.r., 98% ee/-52% ee
L9: 310 TTN, 80:20 d.r., 88% ee/78.5% ee

2m
L10: 140 TTN, >98:5 d.r., 13% ee

Carbene formation in enzyme's active site

Carbene transfer to amines promoted by enzyme scaffold

Stereoselective proton shift controlled by enzyme scaffold

C2: P411-C4    C7: P411-WIRF    C9: P411-L5

C10: P411-L7    D7: Rma cyt c-WT    D10: Cyt c-BOR$^{Lac}$

SEQUENCE LISTING

<160> NUMBER OF SEQ ID NOS: 27

<210> SEQ ID NO 1
<211> LENGTH: 664
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Thr Ile Lys Glu Met Pro Gln Pro Lys Thr Phe Gly Glu Leu Lys Asn
1               5                   10                  15
Leu Pro Leu Leu Asn Thr Asp Lys Pro Val Gln Ala Leu Met Lys Ile
            20                  25                  30
Ala Asp Glu Leu Gly Glu Ile Phe Lys Phe Glu Ala Pro Gly Arg Val
                35                  40                  45
Thr Arg Tyr Leu Ser Ser Gln Arg Leu Ile Lys Glu Ala Cys Asp Glu
    50                  55                  60
Ser Arg Phe Asp Lys Glu Leu Ser Gln Gly Leu Lys Phe Leu Arg Asp
65                  70                  75                  80
Phe Leu Gly Asp Gly Leu Ala Thr Ser Trp Thr His Glu Lys Asn Trp
                85                  90                  95
Lys Lys Ala His Asn Ile Leu Leu Pro Ser Phe Ser Gln Gln Ala Met
                100                 105                 110
Lys Gly Tyr His Ala Ser Met Val Asp Ile Ala Val Gln Leu Val Gln
            115                 120                 125
Lys Trp Glu Arg Leu Asn Ala Asp Glu His Ile Glu Val Ser Glu Asp
130                 135                 140
Met Thr Arg Leu Thr Leu Asp Thr Ile Gly Leu Cys Gly Phe Asn Tyr
145                 150                 155                 160
Arg Leu Asn Ser Phe Tyr Arg Asp Gln Pro His Pro Phe Ile Ile Ser
                165                 170                 175
Leu Val Arg Ala Leu Asp Glu Val Met Asn Lys Leu Gln Arg Ala Asn
            180                 185                 190
Pro Asp Asp Pro Ala Tyr Asp Glu Asn Lys Arg Gln Phe Gln Glu Asp
            195                 200                 205
Ile Lys Val Met Asn Asp Leu Val Asp Lys Ile Ile Ala Asp Arg Lys
    210                 215                 220
Ala Arg Gly Glu Gln Ser Asp Asp Leu Leu Thr Gln Met Leu Asn Gly
225                 230                 235                 240
Lys Asp Pro Glu Thr Gly Glu Pro Leu Asp Asp Gly Asn Ile Arg Tyr
                245                 250                 255
Gln Ile Ile Thr Phe Leu Tyr Ala Gly Val Glu Gly Thr Ser Gly Leu
                260                 265                 270
Leu Ser Phe Ala Leu Tyr Phe Leu Val Lys Asn Pro His Val Leu Gln
            275                 280                 285
Lys Val Ala Glu Glu Ala Ala Arg Val Leu Val Asp Pro Val Pro Ser
290                 295                 300
Tyr Lys Gln Val Lys Gln Leu Lys Tyr Val Gly Met Val Leu Asn Glu
305                 310                 315                 320
Ala Leu Arg Leu Trp Pro Thr Val Pro Tyr Phe Ser Leu Tyr Ala Lys
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Val Trp Gly
            355                 360                 365
Asp Asp Val Glu Glu Phe Arg Pro Glu Arg Phe Glu Asn Pro Ser Ala
            370                 375                 380
Ile Pro Gln His Ala Phe Lys Pro Phe Gly Asn Gly Gln Arg Ala Ser
385                 390                 395                 400
Leu Gly Gln Gln Phe Ala Leu His Glu Ala Thr Leu Val Leu Gly Met
```

```
                    405                 410                 415
Met Leu Lys His Phe Asp Phe Glu Asp His Thr Asn Tyr Glu Leu Asp
            420                 425                 430

Ile Lys Glu Leu Gln Thr Leu Lys Pro Lys Gly Phe Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
            660

<210> SEQ ID NO 2
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Glu Leu Ser Gln Gly Leu Lys Phe Leu Arg Asp
65                  70                  75                  80

Phe Leu Gly Asp Gly Leu Ala Thr Ser Trp Thr His Glu Lys Asn Trp
                85                  90                  95
```

```
Lys Lys Ala His Asn Ile Leu Leu Pro Ser Phe Ser Gln Gln Ala Met
                100                 105                 110

Lys Gly Tyr His Ala Ser Met Val Asp Ile Ala Val Gln Leu Val Gln
            115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Trp Ala Gly Val Glu Gly Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Tyr Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Leu Gln Thr Leu Lys Pro Lys Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
```

```
            515                 520                 525
Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
                595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
                660

<210> SEQ ID NO 3
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
                35                  40                  45

Thr Arg Tyr Leu Ser Ser Gln Arg Leu Ile Lys Glu Ala Cys Asp Glu
    50                  55                  60

Ser Arg Phe Asp Lys Glu Leu Ser Gln Gly Leu Lys Phe Leu Arg Asp
65                  70                  75                  80

Phe Leu Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
                100                 105                 110

Lys Gly Tyr His Ala Ser Met Val Asp Ile Ala Val Gln Leu Val Gln
                115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Phe Gln Glu Asp
                195                 200                 205
```

-continued

```
Ile Lys Val Met Asn Asp Leu Val Asp Lys Ile Ile Ala Asp Arg Lys
210                 215                 220
Ala Arg Gly Glu Gln Ser Asp Asp Leu Leu Thr Gln Met Leu Asn Gly
225                 230                 235                 240
Lys Asp Pro Glu Thr Gly Glu Pro Leu Asp Asp Gly Asn Ile Arg Tyr
            245                 250                 255
Gln Ile Ile Thr Phe Leu Trp Ala Gly Val Glu Gly Thr Ser Gly Leu
            260                 265                 270
Leu Ser Phe Ala Leu Tyr Phe Leu Val Lys Asn Pro His Val Leu Gln
        275                 280                 285
Lys Val Ala Glu Glu Ala Ala Arg Val Leu Val Asp Pro Val Pro Ser
290                 295                 300
Tyr Lys Gln Val Lys Gln Leu Lys Tyr Val Gly Met Val Leu Asn Glu
305                 310                 315                 320
Ala Leu Arg Leu Trp Pro Thr Val Pro Tyr Phe Ser Leu Tyr Ala Lys
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Val Trp Gly
        355                 360                 365
Asp Asp Val Glu Glu Phe Arg Pro Glu Arg Phe Glu Asn Pro Ser Ala
370                 375                 380
Ile Pro Gln His Ala Phe Lys Pro Phe Gly Asn Gly Gln Arg Ala Ser
385                 390                 395                 400
Leu Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
            420                 425                 430
Ile Lys Glu Leu Ile Thr Leu Lys Pro Lys Gly Phe Val Val Lys Ala
        435                 440                 445
Lys Ser Lys Lys Ile Pro Leu Gly Gly Ile Pro Ser Pro Ser Thr Glu
450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
        515                 520                 525
Val Leu Ile Val Thr Ala Ser Tyr Asn Gly His Pro Pro Asp Asn Ala
530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
        595                 600                 605
Phe Glu Gly Thr Tyr Glu Glu Trp Arg Glu His Met Trp Ser Asp Val
610                 615                 620
Ala Ala Tyr Phe Asn Leu Asp Ile Glu Asn Ser Glu Asp Asn Lys Ser
```

```
                        625                 630                 635                 640

Thr Leu Ser Leu Gln Phe Val Asp Ser Ala Ala Asp Met Pro Leu Ala
                        645                 650                 655

Lys Met His Gly Ala Phe Ser Thr
                        660

<210> SEQ ID NO 4
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Glu Leu Phe Gln Gly Leu Lys Phe Leu Arg Asp
65                  70                  75                  80

Phe Leu Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Ser Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Trp Ala Gly Val Gly Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Asp Pro Val Pro Ser
    290                 295                 300

Tyr Lys Gln Val Lys Gln Leu Lys Tyr Val Gly Met Val Leu Asn Glu
305                 310                 315                 320
```

Ala Leu Arg Leu Trp Pro Thr Val Pro Tyr Phe Ser Leu Tyr Ala Lys
            325                 330                 335

Glu Asp Thr Val Leu Gly Gly Glu Tyr Pro Leu Glu Lys Gly Asp Glu
        340                 345                 350

Val Met Val Leu Ile Pro Gln Leu His Arg Asp Lys Thr Val Trp Gly
    355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
        420                 425                 430

Ile Lys Glu Leu Ile Thr Leu Lys Pro Lys Gly Phe Val Val Lys Ala
    435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
        500                 505                 510

Val Ala Thr Leu Asp Ser His Ala Gly Asn Leu Pro Arg Glu Gly Ala
    515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
        580                 585                 590

Gly Ala Glu Asn Ile Ala Asp Arg Gly Glu Ala Asp Ala Ser Asp Asp
    595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
            645                 650                 655

Lys Met His Gly Ala Phe Ser Thr
            660

<210> SEQ ID NO 5
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Thr Ile Lys Glu Met Pro Gln Pro Lys Thr Phe Gly Glu Leu Lys Asn
1               5                   10                  15

-continued

Leu Pro Leu Leu Asn Thr Asp Lys Pro Val Gln Ala Leu Met Lys Ile
           20              25              30

Ala Asp Glu Leu Gly Glu Ile Phe Lys Phe Glu Ala Pro Gly Arg Val
       35              40              45

Thr Arg Tyr Leu Ser Ser Gln Arg Leu Ile Lys Glu Ala Cys Asp Glu
   50              55              60

Ser Arg Phe Asp Lys Glu Leu Phe Gln Gly Leu Lys Phe Leu Arg Asp
65              70              75              80

Phe Leu Gly Asp Gly Leu Ala Thr Ser Trp Thr His Glu Lys Asn Trp
               85              90              95

Lys Lys Ala His Asn Ile Leu Leu Pro Ser Phe Ser Gln Gln Ala Met
           100             105             110

Lys Gly Tyr His Ala Ser Met Val Asp Ile Ala Val Gln Leu Val Gln
       115             120             125

Lys Trp Glu Arg Leu Asn Ala Asp Glu His Ile Glu Val Ser Glu Asp
   130             135             140

Met Thr Arg Leu Thr Leu Asp Thr Ile Gly Leu Cys Gly Phe Asn Tyr
145             150             155             160

Arg Leu Asn Ser Phe Tyr Arg Asp Gln Pro His Pro Phe Ile Ile Ser
               165             170             175

Leu Val Arg Ala Leu Asp Glu Val Met Asn Lys Leu Gln Arg Ala Asn
           180             185             190

Pro Asp Asp Pro Ala Tyr Asp Glu Asn Lys Arg Gln Phe Gln Glu Asp
       195             200             205

Ile Lys Val Met Asn Asp Leu Val Asp Lys Ile Ile Ala Asp Arg Lys
   210             215             220

Ala Arg Gly Glu Gln Ser Asp Asp Leu Leu Thr Gln Met Leu Asn Gly
225             230             235             240

Lys Asp Pro Glu Thr Gly Glu Pro Leu Asp Asp Gly Asn Ile Arg Tyr
               245             250             255

Gln Ile Ile Thr Phe Leu Trp Ala Gly Val Glu Gly Thr Ser Gly Leu
           260             265             270

Leu Ser Phe Ala Leu Tyr Phe Leu Val Lys Asn Pro His Val Leu Gln
       275             280             285

Lys Val Ala Glu Glu Ala Ala Arg Val Leu Val Asp Pro Val Pro Ser
   290             295             300

Tyr Lys Gln Val Lys Gln Leu Lys Tyr Val Gly Met Val Leu Asn Glu
305             310             315             320

Ala Leu Arg Leu Trp Pro Thr Val Pro Tyr Phe Ser Leu Tyr Ala Lys
               325             330             335

Glu Asp Thr Val Leu Gly Gly Glu Tyr Pro Leu Glu Lys Gly Asp Glu
           340             345             350

Val Met Val Leu Ile Pro Gln Leu His Arg Asp Lys Thr Val Trp Gly
       355             360             365

Asp Asp Val Glu Glu Phe Arg Pro Glu Arg Phe Glu Asn Pro Ser Ala
   370             375             380

Ile Pro Gln His Ala Phe Lys Pro Phe Gly Asn Gly Gln Arg Ala Ser
385             390             395             400

Leu Gly Gln Gln Phe Ala Leu His Glu Ala Thr Leu Val Leu Gly Met
               405             410             415

Met Leu Lys His Phe Asp Phe Glu Asp His Thr Asn Tyr Glu Leu Asp
           420             425             430

Ile Lys Glu Arg Ile Thr Leu Lys Pro Lys Gly Phe Val Lys Ala
435 440 445

Lys Ser Lys Lys Ile Pro Leu Gly Gly Ile Pro Ser Pro Ser Thr Glu
450 455 460

Gln Ser Ala Lys Lys Val Arg Lys Lys Ala Glu Asn Ala His Asn Thr
465 470 475 480

Pro Leu Leu Val Leu Tyr Gly Ser Asn Met Gly Thr Ala Glu Gly Thr
485 490 495

Ala Arg Asp Leu Ala Asp Ile Ala Met Ser Lys Gly Phe Ala Pro Gln
500 505 510

Val Ala Thr Leu Asp Ser His Ala Gly Asn Leu Pro Arg Glu Gly Ala
515 520 525

Val Leu Ile Val Thr Ala Ser Tyr Asn Gly His Pro Pro Asp Asn Ala
530 535 540

Lys Gln Phe Val Asp Trp Leu Asp Gln Ala Ser Ala Asp Glu Val Lys
545 550 555 560

Gly Val Arg Tyr Ser Val Phe Gly Cys Gly Asp Lys Asn Trp Ala Thr
565 570 575

Thr Tyr Gln Lys Val Pro Ala Phe Ile Asp Glu Thr Leu Ala Ala Lys
580 585 590

Gly Ala Glu Asn Ile Ala Asp Arg Gly Glu Ala Asp Ala Ser Asp Asp
595 600 605

Phe Glu Gly Thr Tyr Glu Glu Trp Arg Glu His Met Trp Ser Asp Val
610 615 620

Ala Ala Tyr Phe Asn Leu Asp Ile Glu Asn Ser Glu Asp Asn Lys Ser
625 630 635 640

Thr Leu Ser Leu Gln Phe Val Asp Ser Ala Ala Asp Met Pro Leu Ala
645 650 655

Lys Met His Gly Ala Phe Ser Thr
660

<210> SEQ ID NO 6
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Glu Leu Phe Gln Gly Leu Lys Phe Leu Arg Asp
65                  70                  75                  80

Phe Leu Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Ser Met Val Asp Ile Ala Val Gln Leu Val Gln
        115                 120                 125

-continued

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Phe Gln Glu Asp
                195                 200                 205

Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Trp Ala Gly Val Glu Gly Thr Ser Gly Leu
                260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Tyr Phe Gly Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Val Trp Gly
                355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Arg Ile Thr Leu Lys Pro Lys Gly Phe Val Val Lys Ala
                435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
530                 535                 540

```
Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
        580                 585                 590

Gly Ala Glu Asn Ile Ala Asp Arg Gly Glu Ala Asp Ala Ser Asp Asp
    595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
            645                 650                 655

Lys Met His Gly Ala Phe Ser Thr
            660

<210> SEQ ID NO 7
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Glu Leu Phe Gln Ala Leu Lys Phe Leu Arg Asp
65                  70                  75                  80

Phe Leu Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Ser Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240
```

```
Lys Asp Pro Glu Thr Gly Glu Pro Leu Asp Asp Gly Asn Ile Arg Tyr
                245                 250                 255

Gln Ile Ile Thr Phe Leu Trp Ala Gly Val Glu Gly Thr Ser Gly Leu
                260                 265                 270

Leu Ser Phe Ala Leu Tyr Phe Leu Val Lys Asn Pro His Val Leu Gln
                275                 280                 285

Lys Val Ala Glu Glu Ala Ala Arg Val Leu Val Asp Pro Val Pro Ser
                290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Tyr Phe Gly Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Val Trp Gly
                355                 360                 365

Asp Asp Val Glu Glu Phe Arg Pro Glu Arg Phe Glu Asn Pro Ser Ala
                370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Arg Ile Thr Leu Lys Pro Lys Gly Phe Val Val Lys Ala
                435                 440                 445

Lys Ser Lys Lys Ile Pro Leu Gly Gly Ile Pro Ser Pro Ser Thr Glu
                450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
                530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
                595                 600                 605

Phe Glu Gly Thr Tyr Glu Glu Trp Arg Glu His Met Trp Ser Asp Val
                610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655
```

```
Lys Met His Gly Ala Phe Ser Thr
            660

<210> SEQ ID NO 8
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Lys Leu Phe Gln Ala Leu Lys Phe Leu Arg Asp
65                  70                  75                  80

Phe Leu Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Ser Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Trp Ala Gly Val Glu Gly Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Tyr Phe Gly Leu Tyr Ala Lys
                325                 330                 335

Glu Asp Thr Val Leu Gly Gly Glu Tyr Pro Leu Glu Lys Gly Asp Glu
            340                 345                 350
```

```
Val Met Val Leu Ile Pro Gln Leu His Arg Asp Lys Thr Val Trp Gly
            355                 360                 365

Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Arg Ile Thr Leu Lys Pro Lys Gly Phe Val Val Lys Ala
            435                 440                 445

Lys Ser Lys Lys Ile Pro Leu Gly Gly Ile Pro Ser Pro Ser Thr Glu
        450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
        610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
            660

<210> SEQ ID NO 9
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
```

```
                35                  40                  45
Thr Arg Tyr Leu Ser Ser Gln Arg Leu Ile Lys Glu Ala Cys Asp Glu
 50                  55                  60

Ser Arg Phe Asp Lys Glu Leu Ser Gln Gly Leu Lys Phe Leu Arg Asp
 65                  70                  75                  80

Phe Leu Gly Asp Gly Leu Ala Thr Ser Trp Thr His Glu Lys Asn Trp
                 85                  90                  95

Lys Lys Ala His Asn Ile Leu Leu Pro Ser Phe Ser Gln Gln Ala Met
                100                 105                 110

Lys Gly Tyr His Ala Ser Met Val Asp Ile Ala Val Gln Leu Val Gln
                115                 120                 125

Lys Trp Glu Arg Leu Asn Ala Asp Glu His Ile Glu Val Ser Glu Asp
                130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Phe Gln Glu Asp
                195                 200                 205

Ile Lys Val Met Asn Asp Leu Val Asp Lys Ile Ile Ala Asp Arg Lys
                210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Tyr Ala Gly Val Glu Gly Thr Ser Gly Leu
                260                 265                 270

Leu Ser Phe Ala Leu Tyr Phe Leu Val Lys Asn Pro His Val Leu Gln
                275                 280                 285

Lys Val Ala Glu Glu Ala Ala Arg Val Leu Val Asp Pro Val Pro Ser
                290                 295                 300

Tyr Lys Gln Val Lys Gln Leu Lys Tyr Val Gly Met Val Leu Asn Glu
305                 310                 315                 320

Ala Leu Arg Leu Trp Pro Val Val Pro Tyr Phe Cys Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Val Trp Gly
                355                 360                 365

Asp Asp Val Glu Glu Phe Arg Pro Glu Arg Phe Glu Asn Pro Ser Ala
                370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Leu Leu Thr Leu Lys Pro Lys Gly Phe Val Val Lys Ala
                435                 440                 445

Lys Ser Lys Lys Ile Pro Leu Gly Gly Ile Pro Ser Pro Ser Thr Glu
                450                 455                 460
```

Gln Ser Ala Lys Lys Val Arg Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
            660

<210> SEQ ID NO 10
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Glu Leu Ser Gln Thr Leu Lys Phe Leu Arg Asp
65                  70                  75                  80

Phe Leu Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr

```
                145                 150                 155                 160
        Arg Phe Asn Ser Phe Tyr Arg Asp Gln Pro His Pro Phe Ile Ile Ser
                        165                 170                 175

Leu Val Arg Ala Leu Asp Glu Val Met Asn Lys Leu Gln Arg Ala Asn
                        180                 185                 190

Pro Asp Pro Ala Tyr Asp Glu Asn Lys Arg Gln Phe Gln Glu Asp
                        195                 200                 205

Ile Lys Val Met Asn Asp Leu Val Asp Lys Ile Ala Asp Arg Lys
            210                 215                 220

Ala Arg Gly Glu Gln Ser Asp Asp Leu Leu Thr Gln Met Leu Asn Gly
        225                 230                 235                 240

Lys Asp Pro Glu Thr Gly Glu Pro Leu Asp Asp Gly Asn Ile Arg Tyr
                        245                 250                 255

Gln Ile Ile Thr Phe Leu Tyr Ala Gly Val Glu Gly Thr Ser Gly Leu
                        260                 265                 270

Leu Ser Phe Ala Leu Tyr Phe Leu Val Lys Asn Pro His Val Leu Gln
                        275                 280                 285

Lys Val Ala Glu Glu Ala Arg Val Leu Val Asp Pro Val Pro Ser
            290                 295                 300

Tyr Lys Gln Val Lys Gln Leu Lys Tyr Val Gly Met Val Leu Asn Glu
        305                 310                 315                 320

Ala Leu Arg Leu Trp Pro Thr Val Pro Tyr Phe Ser Leu Tyr Ala Lys
                        325                 330                 335

Glu Asp Thr Val Leu Gly Gly Glu Tyr Pro Leu Glu Lys Gly Asp Glu
                        340                 345                 350

Val Met Val Leu Ile Pro Gln Leu His Arg Asp Lys Thr Val Trp Gly
                        355                 360                 365

Asp Asp Val Glu Glu Phe Arg Pro Glu Arg Phe Glu Asn Pro Ser Ala
            370                 375                 380

Ile Pro Gln His Ala Phe Lys Pro Phe Gly Asn Gly Gln Arg Ala Ser
        385                 390                 395                 400

Ile Gly Gln Gln Phe Ala Leu His Glu Ala Thr Leu Val Leu Gly Met
                        405                 410                 415

Met Leu Lys His Phe Asp Phe Glu Asp His Thr Asn Tyr Glu Leu Asp
                        420                 425                 430

Ile Lys Glu Leu Leu Thr Leu Lys Pro Lys Gly Phe Val Val Lys Ala
                        435                 440                 445

Lys Ser Lys Lys Ile Pro Leu Gly Gly Ile Pro Ser Pro Ser Thr Glu
            450                 455                 460

Gln Ser Ala Lys Lys Val Arg Lys Lys Ala Glu Asn Ala His Asn Thr
        465                 470                 475                 480

Pro Leu Leu Val Leu Tyr Gly Ser Asn Met Gly Thr Ala Glu Gly Thr
                        485                 490                 495

Ala Arg Asp Leu Ala Asp Ile Ala Met Ser Lys Gly Phe Ala Pro Gln
                        500                 505                 510

Val Ala Thr Leu Asp Ser His Ala Gly Asn Leu Pro Arg Glu Gly Ala
                        515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
        545                 550                 555                 560

Gly Val Arg Tyr Ser Val Phe Gly Cys Gly Asp Lys Asn Trp Ala Thr
                        565                 570                 575
```

```
Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
            660
```

<210> SEQ ID NO 11
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Glu Leu Ser Gln Gly Leu Lys Phe Leu Arg Asp
65                  70                  75                  80

Phe Leu Gly Asp Gly Leu Pro Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Ser Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Tyr Ser Gly Val Asp Gly Thr Ser Gly Leu
```

```
              260                 265                 270
Leu Ser Phe Ala Leu Tyr Phe Leu Val Lys Asn Pro His Val Leu Gln
        275                 280                 285
Lys Val Ala Glu Glu Ala Ala Arg Val Leu Val Asp Pro Val Pro Ser
        290                 295                 300
Tyr Lys Gln Val Lys Gln Leu Lys Tyr Val Gly Met Val Leu Asn Glu
305                 310                 315                 320
Ala Leu Arg Leu Trp Pro Pro Val Pro Tyr Phe Ala Leu Tyr Ala Lys
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Val Trp Gly
            355                 360                 365
Asp Asp Val Glu Glu Phe Arg Pro Glu Arg Phe Glu Asn Pro Ser Ala
        370                 375                 380
Ile Pro Gln His Ala Phe Lys Pro Phe Gly Asn Gly Gln Arg Ala Ser
385                 390                 395                 400
Leu Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
                420                 425                 430
Ile Lys Glu Leu Leu Thr Leu Lys Pro Lys Gly Phe Val Val Lys Ala
                435                 440                 445
Lys Ser Lys Lys Ile Pro Leu Gly Gly Ile Pro Ser Pro Ser Thr Glu
        450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
            515                 520                 525
Val Leu Ile Val Thr Ala Ser Tyr Asn Gly His Pro Pro Asp Asn Ala
        530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
                580                 585                 590
Gly Ala Glu Asn Ile Ala Asp Arg Gly Glu Ala Asp Ala Ser Asp Asp
                595                 600                 605
Phe Glu Gly Thr Tyr Glu Glu Trp Arg Glu His Met Trp Ser Asp Val
            610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr
            660

<210> SEQ ID NO 12
```

<211> LENGTH: 664
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Thr Ile Lys Glu Met Pro Gln Pro Lys Thr Phe Gly Glu Leu Lys Asn
1               5                   10                  15
Leu Pro Leu Leu Asn Thr Asp Lys Pro Val Gln Ala Leu Met Lys Ile
            20                  25                  30
Ala Asp Glu Leu Gly Glu Ile Phe Lys Phe Glu Ala Pro Gly Arg Val
        35                  40                  45
Thr Arg Tyr Leu Ser Ser Gln Arg Leu Ile Lys Glu Ala Cys Asp Glu
    50                  55                  60
Ser Arg Phe Asp Lys Glu Leu Ser Gln Gly Leu Lys Phe Leu Arg Asp
65                  70                  75                  80
Phe Leu Gly Asp Gly Leu Ala Thr Ser Trp Thr His Glu Lys Asn Trp
                85                  90                  95
Lys Lys Ala His Asn Ile Leu Leu Pro Ser Phe Ser Gln Gln Ala Met
            100                 105                 110
Lys Gly Tyr His Ala Ser Met Val Asp Ile Ala Val Gln Leu Val Gln
        115                 120                 125
Lys Trp Glu Arg Leu Asn Ala Asp Glu His Ile Glu Val Ser Glu Asp
    130                 135                 140
Met Thr Arg Leu Thr Leu Asp Thr Ile Gly Leu Cys Gly Phe Asn Tyr
145                 150                 155                 160
Arg Leu Asn Ser Phe Tyr Arg Asp Gln Pro His Pro Phe Ile Ile Ser
                165                 170                 175
Leu Val Arg Ala Leu Asp Glu Val Met Asn Lys Leu Gln Arg Ala Asn
            180                 185                 190
Pro Asp Asp Pro Ala Tyr Asp Glu Asn Lys Arg Gln Phe Gln Glu Asp
        195                 200                 205
Ile Lys Val Met Asn Asp Leu Val Asp Lys Ile Ile Ala Asp Arg Lys
    210                 215                 220
Ala Arg Gly Glu Gln Ser Asp Asp Leu Leu Thr Gln Met Leu Asn Gly
225                 230                 235                 240
Lys Asp Pro Glu Thr Gly Glu Pro Leu Asp Asp Gly Asn Ile Arg Tyr
                245                 250                 255
Gln Ile Ile Thr Phe Leu Tyr Ala Gly Val Glu Gly Thr Ser Gly Leu
            260                 265                 270
Leu Ser Phe Ala Leu Tyr Phe Leu Val Lys Asn Pro His Val Leu Gln
        275                 280                 285
Lys Val Ala Glu Glu Ala Ala Arg Val Leu Val Asp Pro Val Pro Ser
    290                 295                 300
Tyr Lys Gln Val Lys Gln Leu Lys Tyr Val Gly Met Val Leu Asn Glu
305                 310                 315                 320
Ala Leu Arg Leu Trp Pro Pro Val Pro Tyr Phe Ser Leu Tyr Ala Lys
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Val Trp Gly
        355                 360                 365
Asp Asp Val Glu Glu Phe Arg Pro Glu Arg Phe Glu Asn Pro Ser Ala
```

```
            370                 375                 380
Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Leu Gln Thr Leu Lys Pro Lys Gly Phe Val Lys Ala
                435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
                530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
                595                 600                 605

Phe Glu Gly Thr Tyr Glu Glu Trp Arg Glu His Met Trp Ser Asp Val
                610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
                660

<210> SEQ ID NO 13
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
                35                  40                  45

Thr Arg Tyr Leu Ser Ser Gln Arg Leu Ile Lys Glu Ala Cys Asp Glu
                50                  55                  60
```

```
Ser Arg Phe Asp Lys Glu Leu Ser Gln Gly Leu Lys Phe Leu Arg Asp
 65                  70                  75                  80

Phe Leu Gly Asp Gly Leu Ala Thr Ser Trp Thr His Glu Lys Asn Trp
                 85                  90                  95

Lys Lys Ala His Asn Ile Leu Leu Pro Ser Phe Ser Gln Gln Ala Met
                100                 105                 110

Lys Gly Tyr His Ala Ser Met Val Asp Ile Ala Val Gln Leu Val Gln
                115                 120                 125

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Phe Gln Glu Asp
                195                 200                 205

Ile Lys Val Met Asn Asp Leu Val Asp Lys Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Tyr Ala Gly Val Glu Gly Thr Ser Gly Leu
                260                 265                 270

Leu Ser Phe Ala Leu Tyr Phe Leu Val Lys Asn Pro His Val Leu Gln
                275                 280                 285

Lys Val Ala Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Pro Val Pro Tyr Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Val Trp Gly
                355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Leu Tyr Thr Leu Lys Pro Lys Gly Phe Val Val Lys Ala
                435                 440                 445

Lys Ser Lys Lys Ile Pro Leu Gly Gly Ile Pro Ser Pro Ser Thr Glu
                450                 455                 460

Gln Ser Ala Lys Lys Val Arg Lys Lys Thr Glu Asn Ala His Asn Thr
465                 470                 475                 480

Pro Leu Leu Val Leu Tyr Gly Ser Asn Met Gly Thr Ala Glu Gly Thr
```

```
                    485                 490                 495
Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
            660

<210> SEQ ID NO 14
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Glu Leu Asn Gln Gly Leu Lys Phe Leu Arg Asp
65                  70                  75                  80

Phe Leu Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Ser Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175
```

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Tyr Ala Gly Val Glu Gly Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Val Pro Tyr Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Leu Tyr Thr Leu Lys Pro Lys Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Thr Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp

```
                595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Asp Met Pro Leu Ala
                645                 650                 655

Lys Met His Gly Ala Phe Ser Thr
                660

<210> SEQ ID NO 15
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Glu Leu Asn Gln Gly Leu Lys Phe Leu Arg Asp
65                  70                  75                  80

Phe Leu Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
                100                 105                 110

Lys Gly Tyr His Ala Gly Met Val Asp Ile Ala Val Gln Leu Val Gln
            115                 120                 125

Lys Trp Glu Arg Leu Asn Ala Asp Glu His Ile Glu Val Ser Glu Asp
        130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Phe Gln Glu Asp
            195                 200                 205

Ile Lys Val Met Asn Asp Leu Val Asp Lys Ile Ile Ala Asp Arg Lys
        210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Tyr Ser Gly Val Glu Gly Thr Ser Gly Leu
                260                 265                 270

Leu Ser Phe Ala Leu Tyr Phe Leu Val Lys Asn Pro His Val Leu Gln
            275                 280                 285
```

```
Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Val Pro Tyr Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Leu Tyr Thr Leu Lys Pro Lys Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Thr Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
                660
```

<210> SEQ ID NO 16
<211> LENGTH: 664
<212> TYPE: PRT
<213> ORGANISM: Artificial Sequence
<220> FEATURE:
<223> OTHER INFORMATION: Description of Artificial Sequence: Synthetic

```
    polypeptide

<400> SEQUENCE: 16

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Gln Val
        35                  40                  45

Thr Arg Tyr Leu Ser Ser Gln Arg Leu Ile Lys Glu Ala Cys Asp Glu
    50                  55                  60

Ser Arg Phe Asp Lys Glu Leu Asn Gln Gly Leu Lys Phe Leu Arg Asp
65                  70                  75                  80

Phe Leu Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Gly Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Tyr Ser Gly Val Glu Gly Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Pro Val Pro Tyr Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Ser
385                 390                 395                 400
```

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Leu Tyr Thr Leu Lys Pro Lys Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Thr Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
            660

<210> SEQ ID NO 17
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Glu Leu Ser Gln Gly Leu Lys Phe Leu Arg Asp
65                  70                  75                  80

Phe Leu Gly Asp Gly Leu Pro Thr Ser Trp Thr His Glu Lys Asn Trp
                85                  90                  95

```
Lys Lys Ala His Asn Ile Leu Leu Pro Ser Phe Ser Gln Gln Ala Met
                100                 105                 110
Lys Gly Tyr His Ala Ser Met Val Asp Ile Ala Val Gln Leu Val Gln
                115                 120                 125
Lys Trp Glu Arg Leu Asn Ala Asp Glu His Ile Glu Val Ser Glu Asp
    130                 135                 140
Met Thr Arg Leu Thr Leu Asp Thr Ile Gly Leu Cys Gly Phe Asn Tyr
145                 150                 155                 160
Arg Leu Asn Ser Phe Tyr Arg Asp Gln Pro His Pro Phe Ile Ile Ser
                165                 170                 175
Leu Val Arg Ala Leu Asp Glu Val Met Asn Lys Leu Gln Arg Ala Asn
                180                 185                 190
Pro Asp Asp Pro Ala Tyr Asp Glu Asn Lys Arg Gln Phe Gln Glu Asp
                195                 200                 205
Ile Lys Val Met Asn Asp Leu Val Asp Lys Ile Ile Ala Asp Arg Lys
                210                 215                 220
Ala Arg Gly Glu Gln Ser Asp Asp Leu Leu Thr Gln Met Leu Asn Gly
225                 230                 235                 240
Lys Asp Pro Glu Thr Gly Glu Pro Leu Asp Asp Gly Asn Ile Arg Tyr
                245                 250                 255
Gln Ile Ile Thr Phe Leu Tyr Ser Gly Val Glu Gly Thr Ser Gly Leu
                260                 265                 270
Leu Ser Phe Ala Leu Tyr Phe Leu Val Lys Asn Pro His Val Leu Gln
                275                 280                 285
Lys Val Ala Glu Glu Ala Ala Arg Val Leu Val Asp Pro Val Pro Ser
                290                 295                 300
Tyr Lys Gln Val Lys Gln Leu Lys Tyr Val Gly Met Val Leu Asn Glu
305                 310                 315                 320
Ala Leu Arg Leu Trp Pro Val Val Pro Tyr Phe Ala Leu Tyr Ala Lys
                325                 330                 335
Glu Asp Thr Val Leu Gly Gly Glu Tyr Pro Leu Glu Lys Gly Asp Glu
                340                 345                 350
Val Met Val Leu Ile Pro Gln Leu His Arg Asp Lys Thr Val Trp Gly
                355                 360                 365
Asp Asp Val Glu Glu Phe Arg Pro Glu Arg Phe Glu Asn Pro Ser Ala
                370                 375                 380
Ile Pro Gln His Ala Phe Lys Pro Phe Gly Asn Gly Gln Arg Ala Ser
385                 390                 395                 400
Leu Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
                420                 425                 430
Ile Lys Glu Leu Leu Thr Leu Lys Pro Lys Gly Phe Val Val Lys Ala
                435                 440                 445
Lys Ser Lys Lys Ile Pro Leu Gly Gly Ile Pro Ser Pro Ser Thr Glu
                450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
                500                 505                 510
```

```
Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
                660

<210> SEQ ID NO 18
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
    50                  55                  60

Ser Arg Phe Asp Lys Glu Leu Ser Gln Gly Leu Lys Phe Leu Arg Asp
65                  70                  75                  80

Phe Leu Gly Asp Gly Leu Pro Thr Ser Trp Thr His Glu Lys Asn Trp
                85                  90                  95

Lys Lys Ala His Asn Ile Leu Leu Pro Ser Phe Ser Gln Gln Ala Met
                100                 105                 110

Lys Gly Tyr His Ala Ser Met Val Asp Ile Ala Val Gln Leu Val Gln
            115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
    195                 200                 205
```

```
Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Tyr Ser Gly Val Glu Gly Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Pro Val Pro Tyr Phe Ala Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Leu Leu Thr Leu Lys Pro Lys Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
610                 615                 620
```

```
Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
            645                 650                 655

Lys Met His Gly Ala Phe Ser Thr
            660
```

<210> SEQ ID NO 19
<211> LENGTH: 1048
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
50                  55                  60

Ser Arg Phe Asp Lys Glu Leu Ser Gln Gly Leu Lys Phe Leu Arg Asp
65                  70                  75                  80

Phe Leu Gly Asp Gly Leu Pro Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Ser Met Val Asp Ile Ala Val Gln Leu Val Gln
            115                 120                 125

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
            195                 200                 205

Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Tyr Ser Gly Val Glu Gly Thr Ser Gly Leu
            260                 265                 270

Leu Ser Phe Ala Leu Tyr Phe Leu Val Lys Asn Pro His Val Leu Gln
            275                 280                 285

Lys Val Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320
```

```
Ala Leu Arg Leu Trp Pro Val Pro Tyr Phe Ala Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Leu Leu Thr Leu Lys Pro Lys Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735
```

-continued

```
His Leu Pro Leu Ala Lys Thr Val Ser Val Glu Glu Leu Leu Gln Tyr
                740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
        770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045
```

<210> SEQ ID NO 20
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45
```

```
Thr Arg Tyr Leu Ser Ser Gln Arg Leu Ile Lys Glu Ala Cys Asp Glu
    50              55                  60

Ser Arg Phe Asp Lys Glu Leu Ser Gln Gly Leu Lys Phe Leu Arg Asp
65              70                  75                  80

Phe Leu Gly Asp Gly Leu Pro Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Ser Met Val Asp Ile Ala Val Gln Leu Val Gln
            115                 120                 125

Lys Trp Glu Arg Leu Asn Ala Asp Glu His Ile Glu Val Ser Glu Asp
            130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
            195                 200                 205

Ile Lys Val Met Asn Asp Leu Val Asp Lys Ile Ile Ala Asp Arg Lys
            210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Tyr Ser Gly Val Asp Gly Thr Ser Gly Leu
            260                 265                 270

Leu Ser Phe Ala Leu Tyr Phe Leu Val Lys Asn Pro His Val Leu Gln
            275                 280                 285

Lys Val Ala Glu Glu Ala Ala Arg Val Leu Val Asp Pro Val Pro Ser
            290                 295                 300

Tyr Lys Gln Val Lys Gln Leu Lys Tyr Val Gly Met Val Leu Asn Glu
305                 310                 315                 320

Ala Leu Arg Leu Trp Pro Pro Val Pro Tyr Phe Ala Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
            355                 360                 365

Asp Asp Val Glu Glu Phe Arg Pro Glu Arg Phe Glu Asn Pro Ser Ala
            370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Leu Leu Thr Leu Lys Pro Lys Gly Phe Val Val Lys Ala
            435                 440                 445

Lys Ser Lys Lys Ile Pro Leu Gly Gly Ile Pro Ser Pro Ser Thr Glu
            450                 455                 460
```

```
Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
            660

<210> SEQ ID NO 21
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Glu Leu Ser Gln Gly Leu Lys Phe Leu Arg Asp
65                  70                  75                  80

Phe Leu Gly Asp Gly Leu Pro Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Ser Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160
```

```
Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Tyr Ser Gly Val Asp Gly Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Pro Leu Pro Tyr Phe Ala Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Leu Leu Thr Leu Lys Pro Lys Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575
```

```
Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
                660
```

<210> SEQ ID NO 22
<211> LENGTH: 664
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Thr Ile Lys Glu Met Pro Gln Pro Lys Thr Phe Gly Glu Leu Lys Asn
1               5                  10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
50                  55                  60

Ser Arg Phe Asp Lys Glu Leu Ser Gln Gly Leu Lys Phe Leu Arg Asp
65                  70                  75                  80

Phe Leu Gly Asp Gly Leu Pro Thr Ser Trp Thr His Glu Lys Asn Trp
                85                  90                  95

Lys Lys Ala His Asn Ile Leu Leu Pro Ser Phe Ser Gln Gln Ala Met
                100                 105                 110

Lys Gly Tyr His Ala Ser Met Val Asp Ile Ala Val Gln Leu Val Gln
            115                 120                 125

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Leu Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Tyr Ser Gly Val Asp Gly Thr Ser Gly Leu
            260                 265                 270
```

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Pro Arg Pro Tyr Phe Ala Leu Tyr Ala Lys
                    325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
                355                 360                 365

Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
                    405                 410                 415

Met Leu Lys His Phe Asp Phe Glu Asp His Thr Asn Tyr Glu Leu Asp
            420                 425                 430

Ile Lys Glu Leu Leu Thr Leu Lys Pro Lys Gly Phe Val Val Lys Ala
                435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                    485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                    565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
                595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                    645                 650                 655

Lys Met His Gly Ala Phe Ser Thr
            660

<210> SEQ ID NO 23
<211> LENGTH: 664

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Thr Thr Lys Glu Met Pro Gln Pro Lys Thr Phe Gly Glu Leu Lys Asn
1               5                   10                  15
Leu Pro Leu Leu Asn Thr Asp Lys Pro Val Gln Ala Leu Met Lys Ile
            20                  25                  30
Ala Asp Glu Leu Gly Glu Ile Phe Lys Phe Glu Ala Pro Gly Arg Val
        35                  40                  45
Thr Arg Tyr Leu Ser Ser Gln Arg Leu Ile Lys Glu Ala Cys Asp Glu
50                  55                  60
Ser Arg Phe Asp Lys Glu Leu Val Gln Ala Leu Lys Phe Leu Arg Glu
65                  70                  75                  80
Phe Leu Gly Asp Gly Leu Val Thr Ser Trp Thr Phe Glu Lys Asn Trp
                85                  90                  95
Lys Lys Ala His Asn Ile Leu Leu Pro Ser Phe Ser Gln Gln Ala Met
            100                 105                 110
Lys Gly Tyr His Ala Ser Met Val Asp Ile Ala Val Gln Leu Val Gln
        115                 120                 125
Lys Trp Glu Arg Leu Asn Ala Asp Glu His Ile Glu Val Gly Glu Asp
130                 135                 140
Met Thr Arg Leu Thr Leu Asp Thr Ile Gly Leu Cys Gly Phe Asn Tyr
145                 150                 155                 160
Arg Phe Asn Ser Phe Tyr Arg Asp Gln Pro His Pro Phe Ile Ile Ser
                165                 170                 175
Leu Val Arg Ala Leu Asp Glu Val Met Asn Lys Leu Gln Arg Ala Asn
            180                 185                 190
Pro Asp Asp Pro Ala Tyr Asp Glu Asn Lys Arg Gln Phe Gln Glu Asp
        195                 200                 205
Ile Lys Val Met Asn Asp Leu Val Asp Lys Ile Ile Ala Asp Arg Lys
210                 215                 220
Ala Ser Gly Glu Gln Ser Asp Asp Leu Leu Thr Gln Met Leu Asn Arg
225                 230                 235                 240
Lys Asp Pro Glu Thr Gly Glu Pro Leu Asp Asp Arg Asn Ile Arg Tyr
                245                 250                 255
Gln Ile Ile Thr Phe Leu Trp Ala Gly Val Glu Gly Thr Ser Gly Leu
            260                 265                 270
Leu Ser Phe Ala Leu Tyr Leu Leu Val Lys Asn Pro His Val Leu Gln
        275                 280                 285
Lys Val Ala Glu Glu Ala Ala Arg Val Leu Val Asp Pro Val Pro Ser
290                 295                 300
Tyr Lys Gln Val Lys Gln Leu Lys Tyr Val Gly Met Val Leu Asn Glu
305                 310                 315                 320
Ala Leu Arg Leu Trp Pro Pro Ile Pro Tyr Phe Gly Leu Tyr Ala Lys
                325                 330                 335
Glu Asp Thr Val Leu Gly Gly Tyr Pro Leu Glu Lys Gly Asp Glu
            340                 345                 350
Val Met Val Leu Ile Pro Gln Leu His Arg Asp Lys Thr Ile Trp Gly
        355                 360                 365
Asp Asp Val Glu Glu Phe Arg Pro Glu Arg Phe Glu Asn Pro Ser Ala
370                 375                 380
```

Ile Pro Gln His Ala Phe Lys Pro Phe Gly Asn Gly Gln Arg Ala Ser
385                 390                 395                 400

Leu Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
        420                 425                 430

Ile Lys Glu Arg Ile Thr Leu Lys Pro Lys Gly Phe Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
            660

<210> SEQ ID NO 24
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Glu Leu Ser Gln Gly Leu Lys Phe Met Arg Asp

```
                65                  70                  75                  80
            Phe Leu Gly Asp Gly Leu Ala Ser Ser Trp Thr His Glu Lys Asn Trp
                            85                  90                  95
            Lys Lys Ala His Asn Ile Leu Leu Pro Ser Phe Ser Gln Gln Ala Met
                            100                 105                 110
            Lys Gly Tyr His Ala Ser Met Val Asp Ile Ala Val Gln Leu Val Gln
                            115                 120                 125
            Lys Trp Glu Arg Leu Asn Ala Asp Glu His Ile Glu Val Ser Glu Asp
                            130                 135                 140
            Met Thr Arg Leu Thr Leu Asp Thr Ile Gly Leu Cys Gly Phe Asn Tyr
            145                 150                 155                 160
            Arg Leu Asn Ser Phe Tyr Arg Asp Gln Pro His Pro Phe Ile Ile Ser
                            165                 170                 175
            Leu Val Arg Ala Leu Asp Glu Val Met Asn Lys Leu Gln Arg Ala Asn
                            180                 185                 190
            Pro Asp Asp Pro Ala Tyr Asp Glu Asn Lys Arg Gln Phe Gln Glu Asp
                            195                 200                 205
            Ile Lys Val Met Asn Asp Leu Val Asp Lys Ile Ile Ala Asp Arg Lys
                            210                 215                 220
            Ala Arg Gly Glu Gln Ser Asp Asp Leu Leu Thr Gln Met Leu Asn Gly
            225                 230                 235                 240
            Lys Asp Pro Glu Thr Gly Glu Pro Leu Asp Asp Gly Asn Ile Arg Tyr
                            245                 250                 255
            Gln Ile Ile Thr Phe Leu Tyr Ala Gly Val Glu Gly Thr Ser Gly Leu
                            260                 265                 270
            Leu Ser Phe Ala Leu Tyr Phe Leu Val Lys Asn Pro His Val Leu Gln
                            275                 280                 285
            Lys Val Ala Glu Glu Ala Ala Arg Val Leu Val Asp Pro Val Pro Ser
                            290                 295                 300
            Tyr Lys Gln Val Lys Gln Leu Lys Tyr Val Gly Met Val Leu Asn Glu
            305                 310                 315                 320
            Ala Leu Arg Leu Trp Pro Thr Val Pro Tyr Phe Ser Leu Tyr Ala Lys
                            325                 330                 335
            Glu Asp Thr Val Leu Gly Gly Glu Tyr Pro Leu Glu Lys Gly Asp Glu
                            340                 345                 350
            Val Met Val Leu Ile Pro Gln Leu His Arg Asp Lys Thr Val Trp Gly
                            355                 360                 365
            Asp Asp Val Glu Glu Phe Arg Pro Glu Arg Phe Glu Asn Pro Ser Ala
                            370                 375                 380
            Ile Pro Gln His Ala Phe Lys Pro Phe Gly Asn Gly Gln Arg Ala Ser
            385                 390                 395                 400
            Val Gly Gln Gln Phe Ala Leu His Glu Ala Thr Leu Val Leu Gly Met
                            405                 410                 415
            Met Leu Lys His Phe Asp Phe Glu Asp His Thr Asn Tyr Glu Leu Asp
                            420                 425                 430
            Ile Lys Glu Arg Ile Thr Leu Lys Pro Lys Gly Phe Val Val Lys Ala
                            435                 440                 445
            Lys Ser Lys Lys Ile Pro Leu Gly Gly Ile Pro Ser Pro Ser Thr Glu
                            450                 455                 460
            Gln Ser Ala Lys Lys Val Arg Lys Lys Ala Glu Asn Ala His Asn Thr
            465                 470                 475                 480
            Pro Leu Leu Val Leu Tyr Gly Ser Asn Met Gly Thr Ala Glu Gly Thr
                            485                 490                 495
```

```
Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
            660

<210> SEQ ID NO 25
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Ser Leu Ser Gln Gly Leu Lys Phe Met Arg Asp
65                  70                  75                  80

Phe Leu Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Ser Met Val Asp Ile Ala Val Gln Leu Val Gln
            115                 120                 125

Lys Trp Glu Arg Leu Asn Ala Asp Glu His Ile Glu Val Ser Glu Asp
        130                 135                 140

Met Thr Arg Leu Thr Leu Asp Thr Ile Gly Leu Cys Gly Phe Asn Tyr
145                 150                 155                 160

Arg Ile Asn Ser Phe Tyr Arg Asp Gln Pro His Pro Phe Ile Ile Ser
                165                 170                 175

Leu Val Arg Ala Leu Asp Glu Val Met Asn Lys Leu Gln Leu Ala Asn
```

-continued

```
                180                 185                 190
Pro Asp Asp Pro Ala Tyr Asp Glu Asn Lys Arg Gln Phe Gln Glu Asp
                195                 200                 205
Ile Lys Val Met Asn Asp Leu Val Asp Lys Ile Ile Ala Asp Arg Lys
                210                 215                 220
Ala Arg Gly Glu Gln Ser Asp Asp Leu Leu Thr Gln Met Leu Asn Gly
225                 230                 235                 240
Lys Asp Pro Glu Thr Gly Glu Pro Leu Asp Asp Gly Asn Ile Arg Tyr
                245                 250                 255
Gln Ile Ile Thr Phe Leu Tyr Ala Gly Val Glu Gly Thr Ser Gly Leu
                260                 265                 270
Leu Ser Phe Ala Leu Tyr Phe Leu Val Lys Asn Pro His Val Leu Gln
                275                 280                 285
Lys Val Ala Glu Glu Ala Ala Arg Val Leu Val Asp Pro Val Pro Ser
                290                 295                 300
Tyr Lys Gln Val Lys Gln Leu Lys Tyr Val Gly Met Val Leu Asn Glu
305                 310                 315                 320
Ala Leu Arg Leu Trp Pro Thr Ile Pro Tyr Phe Ser Leu Tyr Ala Lys
                325                 330                 335
Glu Asp Thr Val Leu Gly Gly Glu Tyr Pro Leu Glu Lys Gly Asp Glu
                340                 345                 350
Val Met Val Leu Ile Pro Gln Leu His Arg Asp Lys Thr Val Trp Gly
                355                 360                 365
Asp Asp Val Glu Glu Phe Arg Pro Glu Arg Phe Glu Asn Pro Ser Ala
                370                 375                 380
Ile Pro Gln His Ala Phe Lys Pro Phe Gly Asn Gly Gln Arg Ala Ser
385                 390                 395                 400
Val Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
                420                 425                 430
Ile Lys Glu Arg Ile Thr Leu Lys Pro Lys Gly Phe Val Val Lys Ala
                435                 440                 445
Lys Ser Lys Lys Ile Pro Leu Gly Gly Ile Pro Ser Pro Ser Thr Glu
                450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
                500                 505                 510
Val Ala Thr Leu Asp Ser His Ala Gly Asn Leu Pro Arg Glu Gly Ala
                515                 520                 525
Val Leu Ile Val Thr Ala Ser Tyr Asn Gly His Pro Pro Asp Asn Ala
                530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
                580                 585                 590
Gly Ala Glu Asn Ile Ala Asp Arg Gly Glu Ala Asp Ala Ser Asp Asp
                595                 600                 605
```

```
Phe Glu Gly Thr Tyr Glu Glu Trp Arg Glu His Met Trp Ser Asp Val
    610             615                 620

Ala Ala Tyr Phe Asn Leu Asp Ile Glu Asn Ser Glu Asp Asn Lys Ser
625             630                 635                 640

Thr Leu Ser Leu Gln Phe Val Asp Ser Ala Ala Asp Met Pro Leu Ala
                645             650                 655

Lys Met His Gly Ala Phe Ser Thr
            660

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 26

His His His His His His
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Glu His His His His His His
1               5
```

DIVERSE CARBENE TRANSFERASE ENZYME CATALYSTS DERIVED FROM A P450 ENZYME

CROSS-REFERENCES TO RELATED APPLICATIONS

The present application claims priority to U.S. Provisional Pat. Appl. No. 62/988,589, filed on Mar. 12, 2020, which application is incorporated herein by reference in its entirety.

STATEMENT AS TO RIGHTS TO INVENTIONS MADE UNDER FEDERALLY SPONSORED RESEARCH AND DEVELOPMENT

This invention was made with government support under Grant No. MCB1513007 awarded by the National Science Foundation and Grant No(s). W911NF-19-2-0026 & W911NF-19-D0001 awarded by the Army. The government has certain rights in the invention.

REFERENCE TO A "SEQUENCE LISTING," A TABLE, OR A COMPUTER PROGRAM LISTING APPENDIX SUBMITTED ON A COMPACT DISK

The instant application contains a Sequence Listing which has been submitted electronically in ASCII format and is hereby incorporated by reference in its entirety. Said ASCII copy, created on May 17, 2021, is named 086544-1218805-023410US SL.txt and is 149,029 bytes in size.

Background of the Invention

Compared to traditional catalytic methods, which require careful selection of metal catalysts, elaborate design, synthesis and screening of ligand scaffolds, and intensive optimization of reaction conditions, biocatalytic strategies offer immense benefits for constructing diverse molecular scaffolds. Enzymes are typically easy to access in useful quantities and can be readily tuned through simple genetic manipulation, for example using directed evolution.[1] Moreover, enzymes can also function with high efficiency and selectivity (chemo-, regio- and/or stereo-) under mild conditions, offering significant advantages in terms of reduced environmental impact and greater cost-effectiveness.[2]

Responsible for numerous types of oxidative transformations, cytochromes P450 are one of Nature's most versatile enzyme families.[3] They employ an iron-heme complex as their catalytic cofactor and NAD(P)H as a biological reductant to form a highly reactive iron-oxo intermediate by activation of molecular oxygen ($O_2$), which allows for oxidative functions such as C—H oxidation, alkene epoxidation, alkane desaturation, heteroatom oxidation, dealkylation, aromatic dehydrogenative coupling, oxidative decarboxylation, and much more.[3-4] Laboratory engineering through directed evolution has enabled the expansion of this catalytic platform to include the selective oxidation of simple alkanes and alkenes, feedstock substrates that serve as useful building blocks, in addition to the late-stage oxidative modification of more complex organic molecules.[5]

Over the past decade, the Arnold group and other labs have repurposed cytochrome P450s and other hemeproteins for non-biological activities through selective carbene- or nitrene-transfer reactions.[6-7] The putative intermediates in these non-natural transformations, iron-carbene or -nitrene species, are structural and electronic analogs of the native iron-oxo intermediate. Inspired by the expansion of P450s' oxidative functions as a result of natural evolution (vide supra), we reasoned that directed evolution could be used to enhance the reaction diversity of P450-mediated non-natural chemistries. Directed evolution of these novel activities requires identification of a catalytically promiscuous enzyme, capable of catalyzing different classes of reactions, as the starting template for evolution.[8]

BRIEF SUMMARY OF THE INVENTION

Provided herein are cytochrome P450-based enzyme catalysts for use in the preparation of various products. Exemplary embodiments provided in accordance with the presently disclosed subject matter include, but are not limited to, the claims and the following embodiments:

1. A $P450_{BM3}$ carbene insertion catalyst comprising the amino acid sequence set forth in SEQ ID NO:1 and optionally 1-30 mutations at positions 2, 47, 70, 72, 74, 78, 80, 82, 87, 88, 92, 118, 142, 162, 190, 226, 240, 252, 263, 264, 267, 279, 327, 328, 332, 366, 401, 436, 437, and 474.

2. The $P450_{BM3}$ carbene insertion catalyst of embodiment 1, wherein the enzyme catalyst comprises 1-4 mutations at positions 72, 263, 436, and 437, and wherein:
the mutation at position 72 is a mutation to phenylanine,
the mutation at position 263 is a mutation to tryptophan,
the mutation at position 436 is a mutation to arginine, and
the mutation at position 437 is a mutation to isoleucine.

3. The $P450_{BM3}$ carbene insertion catalyst of embodiment 2, wherein the enzyme catalyst further comprises 1-3 mutations at positions 70, 74, and 332.

4. The $P450_{BM3}$ carbene insertion catalyst of embodiment 3, wherein:
the mutation as position 332 is a mutation to glycine,
the mutation at position 74 is a mutation to alanine, and
the mutation at position 70 mutation is a mutation to lysine.

5. The $P450_{BM3}$ carbene insertion catalyst of embodiment 1, wherein the enzyme catalyst comprises 1-6 mutations a positions 87, 264, 267, 327, 332, and 437.

6. The $P450_{BM3}$ carbene insertion catalyst of embodiment 5, wherein:
the mutation at position 87 is a mutation to proline,
the mutation at position 264 is a mutation to serine,
the mutation at position 267 is a mutation to aspartic acid,
the mutation at position 327 is a mutation to proline,
the mutation at position 332 is a mutation to alanine, and
the mutation at position 437 is a mutation to leucine.

7. The $P450_{BM3}$ carbene insertion catalyst of embodiment 1, wherein the enzyme catalyst contains 1-7 mutations at position 47, 72, 118, 264, 327, 437, and 474.

8. The $P450_{BM3}$ carbene insertion catalyst of embodiment 7, wherein:
the mutation at position 47 is a mutation to glutamine,
the mutation at position 72 is a mutation to asparagine,
the mutation at position 118 is a mutation to glycine,
the mutation at position 264 is a mutation to serine,
the mutation at position 327 is a mutation to proline,
the mutation at position 437 is a mutation to tyrosine, and
the mutation at position 474 is a mutation to threonine.

9. The $P450_{BM3}$ carbene insertion catalyst of embodiment 1, wherein the enzyme comprises 1-8 mutations at positions 327, 437, 332, 87, 264, 327, 267, and 328.

10. The P450$_{BM3}$ carbene insertion catalyst of embodiment 9, wherein:
the mutation at position 327 is a mutation to valine,
the mutation at position 437 is a mutation to leucine,
the mutation at position 332 is a mutation to alanine,
the mutation at position 87 is a mutation to proline,
the mutation at position 264 is a mutation to serine,
the mutation at position 327 is a mutation to proline,
the mutation at position 267 is a mutation to aspartic acid, and
the mutation at position 328 is a mutation to leucine or arginine 11. The P450$_{BM3}$ carbene insertion catalyst of embodiment 1, wherein the enzyme catalyst comprises 1-5 mutations at positions 78, 88, 401, 436, and 437.

12. The P450$_{BM3}$ carbene insertion catalyst of embodiment 11, wherein:
the mutation at position 78, is a mutation to methionine,
the mutation at position 88, is a mutation to serine,
the mutation at position 401, is a mutation to valine,
the mutation at position 436, is a mutation to arginine, and
the mutation at position 437, is a mutation to isoleucine.

13. The P450$_{BM3}$ carbene insertion catalyst of embodiment 1, wherein the enzyme catalyst comprises 1-8 mutations at positions 70, 78, 162, 190, 328, 401, 436, and 437.

14. The P450$_{BM3}$ carbene insertion catalyst of embodiment 13, wherein:
the mutation at position 70 is a mutation to serine,
mutation at position 78 is a mutation to methionine,
mutation at position 162 is a mutation to isoleucine,
mutation at position 190 is a mutation to leucine,
mutation at position 328 is a mutation to isoleucine,
mutation at position 401 is a mutation to valine,
mutation at position 436 is a mutation to arginine, and
mutation at position 437 is a mutation to isoleucine.

15. The P450$_{BM3}$ carbene insertion catalyst of embodiment 1, wherein the enzyme catalyst comprises 1-19 mutations at positions 2, 72, 74, 80, 87, 92, 142, 162, 226, 240, 252, 263, 279, 327, 328, 332, 366, 436, and 437.

16. The P450$_{BM3}$ carbene insertion catalyst of embodiment 15, wherein:
the mutation at position 2 is a mutation to threonine,
wherein the mutation at position 72 is a mutation to valine,
wherein the mutation at position 74 is a mutation to alanine,
wherein the mutation at position 80 is a mutation to glutamic acid,
wherein the mutation at position 87 is a mutation to valine,
wherein the mutation at position 92 is a mutation to phenylalanine,
wherein the mutation at position 142 is a mutation to glycine,
wherein the mutation at position 162 is a mutation to phenylalanine,
wherein the mutation at position 226 is a mutation to serine,
wherein the mutation at position 240 is a mutation to arginine,
wherein the mutation at position 252 is a mutation to arginine,
wherein the mutation at position 263 is a mutation to tryptophan,
wherein the mutation at position 279 is a mutation to leucine,
wherein the mutation at position 327 is a mutation to proline,
wherein the mutation at position 328 is a mutation to isoleucine,
wherein the mutation at position 332 is a mutation to glycine,
wherein the mutation at position 366 is a mutation to isoleucine,
wherein the mutation at position 436 is a mutation to arginine, and
wherein the mutation at position 437 is a mutation to isoleucine.

17. The P450$_{BM3}$ carbene insertion catalyst of embodiment 1, wherein the enzyme catalyst comprises 1-6 mutations at positions 327, 437, 332, 87, 264, and 327.

18. The P450$_{BM3}$ carbene insertion catalyst of embodiment 17, wherein:
the mutation at position 327 is a mutation to valine,
the mutation at position 437 is a mutation to leucine,
the mutation at position 332 is a mutation to alanine,
the mutation at position 87 is a mutation to proline,
the mutation at position 264 is a mutation to serine, and
the mutation at position 327 is a mutation to proline.

19. A method for forming a carbene insertion product, the method comprising:
forming a reaction mixture comprising an enzyme catalyst and one or two enzyme substrates, and
incubating the mixture to form the carbene insertion product,
wherein at least one of the substrate comprises a carbene precursor moiety,
wherein the enzyme catalyst comprises the amino acid sequence set forth in SEQ ID NO:1 and optionally 1-30 mutations at positions 2, 47, 70, 72, 74, 78, 80, 82, 87, 88, 92, 118, 142, 162, 190, 226, 240, 252, 263, 264, 267, 279, 327, 328, 332, 366, 401, 436, 437, and 474.

20. The method of embodiment 19, wherein the carbene precursor moiety is a diazo moiety.

21. The method of embodiment 19 or embodiment 20, wherein the carbene insertion product is a cyclopropene, a cyclopropane, a bicyclobutane, a substituted lactone, a cyclized compound, or a substituted amine.

22. The method of embodiment 19, wherein:
the reaction mixture comprises a first enzyme substrate according to Formula I

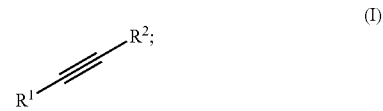

and a second enzyme substrate according to Formula II

the carbene insertion product is a cyclopropene according to Formula III

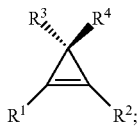

and the enzyme catalyst optionally comprises 1-11 mutations at positions 70, 72, 74, 87, 263, 264, 267, 327, 332, 436, and 437;

and wherein:

$R^1$, $R^2$, $R^3$, $R^4$, $R^5$ and $R^6$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and each $R^7$, $R^8$, and $R^9$ is independently selected from the group consisting of H, $C_{1-6}$ alkyl and optionally substituted $C_{6-10}$ aryl.

23. The method of embodiment 22, wherein $R^1$ and $R^2$ are independently selected from the group consisting of substituted $C_{1-6}$ alkyl, $C_{2-6}$ alkenyl, $C_{2-6}$ alkynyl, substituted $C_{6-10}$ aryl, and substituted 6- to 10-membered heteroaryl;

$R^3$ is selected from the group consisting of $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, cyano, and $P(O)(OR^7)_2$;

$R^4$ is selected from the group consisting of H, substituted $C_{1-6}$ alkyl, $C_{2-6}$ alkenyl, $C_{2-6}$ alkynyl, substituted $C_{6-10}$ aryl, and substituted 6- to 10-membered heteroaryl; and each $R^7$ and $R^8$ is independently selected from the group consisting of H, $C_{1-6}$ alkyl, and substituted $C_{6-10}$ aryl.

24. The method of embodiment 22 or embodiment 23, wherein the enzyme catalyst comprises 1-4 mutations at positions 72, 263, 436, and 437, and wherein:

the mutation at position 72 is a mutation to phenylanine,
the mutation at position 263 is a mutation to tryptophan,
the mutation at position 436 is a mutation to arginine, and
the mutation at position 437 is a mutation to isoleucine.

25. The method of embodiment 24, wherein the enzyme catalyst further comprises 1-3 mutations at positions 70, 74, and 332.

26. The method of embodiment 25, wherein:

the mutation as position 332 is a mutation to glycine,
the mutation at position 74 is a mutation to alanine, and
the mutation at position 70 mutation is a mutation to lysine.

27. The method of embodiment 22, wherein the enzyme catalyst comprises 1-6 mutations a positions 87, 264, 267, 327, 332, and 437.

28. The method of embodiment 27, wherein:

the mutation at position 87 is a mutation to proline,
the mutation at position 264 is a mutation to serine,
the mutation at position 267 is a mutation to aspartic acid,
the mutation at position 327 is a mutation to proline,
the mutation at position 332 is a mutation to alanine, and
the mutation at position 437 is a mutation to leucine.

29. The method of any one of embodiments 22-28, further comprising hydrogenating the cyclopropene to form a cyclopropane.

30. The method of embodiment 19, wherein:

the reaction mixture comprises a first enzyme substrate according to Formula IV

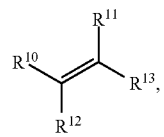

and a second enzyme substrate according to Formula II

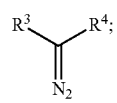

and the carbene insertion product is a cyclopropane according to Formula V

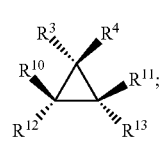

and wherein:

$R^3$, $R^4$, $R^{10}$, $R^{11}$, $R^{12}$, and $R^{13}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and each $R^7$, $R^8$, and $R^9$ is independently selected from the group consisting of H, $C_{1-6}$ alkyl and optionally substituted $C_{6-10}$ aryl.

31. The method of embodiment 30, wherein:

$R^{10}$, $R^{11}$, $R^{12}$ and $R^{13}$ are independently selected from the group consisting of substituted $C_{1-6}$ alkyl, $C_{2-6}$ alkenyl, $C_{2-6}$ alkynyl, substituted $C_{6-10}$ aryl, substituted 6- to 10-membered heteroaryl and $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;

$R^3$ is selected from the group consisting of $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, cyano, and $P(O)(OR^7)_2$;

$R^4$ is selected from the group consisting of H, substituted $C_{1-6}$ alkyl, $C_{2-6}$ alkenyl, $C_{2-6}$ alkynyl, substituted $C_{6-10}$ aryl, and substituted 6- to 10-membered heteroaryl; and each $R^7$ and $R^8$ is independently selected from the group consisting of H, $C_{1-6}$ alkyl and substituted $C_{6-10}$ aryl.

32. The method of embodiment 19, wherein:
the reaction mixture comprises a first enzyme substrate according to Formula VI

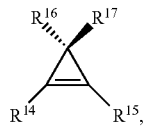

(VI)

and
a second enzyme substrate according to Formula II

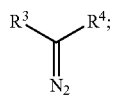

(II)

the carbene insertion product is a bicyclobutane according to Formula V

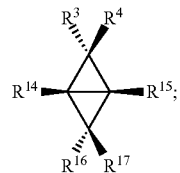

(V)

and
the enzyme catalyst optionally comprises 1-7 mutations at positions 47, 72, 118, 264, 327, 437, 474;
and wherein:
$R^3$, $R^4$, $R^{14}$, $R^{15}$, $R^{16}$ and $R^{17}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and
each $R^7$, $R^8$, and $R^9$ is independently selected from the group consisting of H, $C_{1-6}$ alkyl and optionally substituted $C_{6-10}$ aryl.

33. The method of embodiment 32, wherein:
$R^{14}$ and $R^{15}$ are independently selected from the group consisting of substituted $C_{1-6}$ alkyl, $C_{2-6}$ alkenyl, $C_{2-6}$ alkynyl, substituted $C_{6-10}$ aryl, and substituted 6- to 10-membered heteroaryl;
$R^3$ and $R^{16}$ are independently selected from the group consisting of $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, cyano and $P(O)(OR^7)_2$;
$R^4$ and $R^{17}$ are independently selected from the group consisting of H, substituted $C_{1-6}$ alkyl, $C_{2-6}$ alkenyl, $C_{2-6}$ alkynyl, substituted $C_{6-10}$ aryl, and substituted 6- to 10-membered heteroaryl; and
each $R^7$ and $R^8$ is independently selected from the group consisting of H, $C_{1-6}$ alkyl and substituted $C_{6-10}$ aryl.

34. The method of embodiment 32 or embodiment 33, wherein the enzyme catalyst contains 1-7 mutations at position 47, 72, 118, 264, 327, 437, and 474.

35. The method of any one of embodiments 32-34, wherein:
the mutation at position 47 is a mutation to glutamine,
the mutation at position 72 is a mutation to asparagine,
the mutation at position 118 is a mutation to glycine,
the mutation at position 264 is a mutation to serine,
the mutation at position 327 is a mutation to proline,
the mutation at position 437 is a mutation to tyrosine, and
the mutation at position 474 is a mutation to threonine.

36. The method of embodiment 19, wherein:
the reaction mixture comprises a first enzyme substrate according to Formula VIII

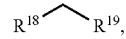

(VIII)

and
a second enzyme substrate according to Formula IX

(IX)

the carbene insertion product is a substituted lactone according to Formula X

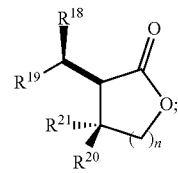

(X)

and
the enzyme catalyst optionally comprises 1-8 mutations at positions 327, 437, 332, 87, 264, 327, 267, 328;
and wherein:
$R^{18}$, $R^{19}$, $R^{20}$, and $R^{21}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$;
each $R^7$, $R^8$, and $R^9$ is independently selected from the group consisting of H, $C_{1-6}$ alkyl, and optionally substituted $C_{6-10}$ aryl; and
subscript n is an integer ranging from 0 to 10.

37. The method of embodiment 36, wherein:
$R^{18}$, $R^{20}$, and $R^{21}$ are independently selected from the group consisting of substituted $C_{1-6}$ alkyl, $C_{2-6}$ alkenyl, substituted $C_{6-10}$ aryl, and substituted 6- to 10-membered heteroaryl;
$R^{19}$ is selected from the group consisting of substituted $C_{1-6}$ alkyl, substituted $C_{6-10}$ aryl, $N(R^7)_2$ and $OR^7$; and each $R^7$ is independently selected from the group consisting of H, $C_{1-6}$ alkyl, and substituted $C_{6-10}$ aryl.

38. The method of embodiment 36 or embodiment 37, wherein the enzyme comprises 1-8 mutations at positions 327, 437, 332, 87, 264, 327, 267, and 328.

39. The method of embodiment 38, wherein:
the mutation at position 327 is a mutation to valine,
the mutation at position 437 is a mutation to leucine,
the mutation at position 332 is a mutation to alanine,
the mutation at position 87 is a mutation to proline,
the mutation at position 264 is a mutation to serine,
the mutation at position 327 is a mutation to proline,
the mutation at position 267 is a mutation to aspartic acid, and
the mutation at position 328 is a mutation to leucine or arginine 40. The method of embodiment 19, wherein:
the reaction mixture comprises an enzyme substrate according to Formula XI

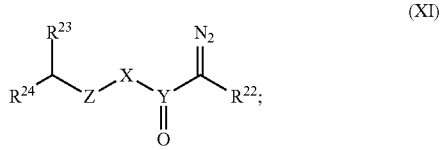

the carbene insertion product is a cyclized compound according to Formula XII

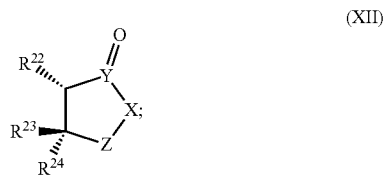

and
the enzyme catalyst optionally comprises 1-25 mutations at positions 2, 70, 72, 78, 74, 80, 82, 87, 88, 92, 142, 162, 190, 226, 240, 252, 263, 279, 327, 328, 332, 366, 401, 436, 437;
and wherein:
$R^{22}$, $R^{23}$, and $R^{24}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$;
Y is selected from the group consisting of C, S(O) and $P(OR^{25})$;
X is selected from the group consisting of O, S, $N(R^{26})$ and $C(R^{27})_2$;
Z is $(C(R^{28})_2)_nX^1(C(R^{28})_2)_m$;
$X^1$ is selected from the group consisting of O, S, $N(R^{26})$ and $C(R^{27})_2$, and can also be linked to other parts in the same molecule including $R^1$, $R^2$, $R^3$, X and Y;
subscripts n and m are independently integers ranging from 0 to 10;
and each $R^7$, $R^8$, $R^9$, $R^{25}$, $R^{26}$, $R^{27}$, and $R^{28}$ is independently selected from the group consisting of H, $C_{1-6}$ alkyl, and optionally substituted $C_{6-10}$ aryl.

41. The method of embodiment 40, wherein:
$R^{22}$, $R^{23}$ and $R^{24}$ are independently selected from the group consisting of substituted $C_{1-6}$ alkyl, $C_{2-6}$ alkenyl, substituted $C_{6-10}$ aryl, and substituted 6- to 10-membered heteroaryl;
X is selected from the group consisting of O, $N(R^{26})$ and $C(R^{27})_2$;
$X^1$ is selected from the group consisting of O and $C(R^{27})_2$
subscripts n and m are independently integers ranging from 0 to 4;
$R^{28}$ is independently selected from the group consisting of H, $C_{1-6}$ alkyl, and substituted $C_{6-10}$ aryl.

42. The method of embodiment 40 or embodiment 41, wherein the enzyme catalyst comprises 1-5 mutations at positions 78, 88, 401, 436, and 437.

43. The method of embodiment 42, wherein:
the mutation at position 78, is a mutation to methionine,
the mutation at position 88, is a mutation to serine,
the mutation at position 401, is a mutation to valine,
the mutation at position 436, is a mutation to arginine, and
the mutation at position 437, is a mutation to isoleucine.

44. The method of embodiment 42 or embodiment 43, wherein the cyclized compound contains a six-membered ring.

45. The method of embodiment 40 or embodiment 41, wherein the enzyme catalyst comprises 1-8 mutations at positions 70, 78, 162, 190, 328, 401, 436, and 437.

46. The method of embodiment 45, wherein:
the mutation at position 70 is a mutation to serine,
mutation at position 78 is a mutation to methionine,
mutation at position 162 is a mutation to isoleucine,
mutation at position 190 is a mutation to leucine,
mutation at position 328 is a mutation to isoleucine,
mutation at position 401 is a mutation to valine,
mutation at position 436 is a mutation to arginine, and
mutation at position 437 is a mutation to isoleucine.

47. The method of embodiment 45 or embodiment 46, wherein the cyclized compound contains is a five membered ring.

48. The method of embodiment 40 or embodiment 41 comprising, wherein the enzyme catalyst comprises 1-19 mutations at positions 2, 72, 74, 80, 87, 92, 142, 162, 226, 240, 252, 263, 279, 327, 328, 332, 366, 436, and 437.

49. The method of embodiment 48, wherein:
the mutation at position 2 is a mutation to threonine,
wherein the mutation at position 72 is a mutation to valine,
wherein the mutation at position 74 is a mutation to alanine,
wherein the mutation at position 80 is a mutation to glutamic acid,
wherein the mutation at position 87 is a mutation to valine,
wherein the mutation at position 92 is a mutation to phenylalanine,
wherein the mutation at position 142 is a mutation to glycine,
wherein the mutation at position 162 is a mutation to phenylalanine,
wherein the mutation at position 226 is a mutation to serine,
wherein the mutation at position 240 is a mutation to arginine,
wherein the mutation at position 252 is a mutation to arginine,
wherein the mutation at position 263 is a mutation to tryptophan, wherein the mutation at position 279 is a mutation to leucine,
wherein the mutation at position 327 is a mutation to proline,
wherein the mutation at position 328 is a mutation to isoleucine,
wherein the mutation at position 332 is a mutation to glycine,
wherein the mutation at position 366 is a mutation to isoleucine,
wherein the mutation at position 436 is a mutation to arginine, and
wherein the mutation at position 437 is a mutation to isoleucine.

50. The method of embodiment 48 or 49, wherein the cyclized compound contains a seven membered ring.

51. The method of embodiment 19, wherein:
the reaction mixture comprises a first enzyme substrate according to Formula XIII

(XIII)

and
a second enzyme substrate according to Formula II

(II)

the insertion product is a substituted amine according to Formula XIV

(XIV)

and
the enzyme catalyst optionally comprises 1-6 mutations at positions 327, 437, 332, 87, 264, 327;
and wherein:
$R^3$, $R^4$, $R^{29}$, and $R^{30}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$; and
each $R^7$, $R^8$, and $R^9$ is independently selected from the group consisting of H, $C_{1-6}$ alkyl, and optionally substituted $C_{6-10}$ aryl.

52. The method of embodiment 51, wherein:
$R^3$, $R^{29}$, and $R^{30}$ are independently selected from the group consisting of substituted $C_{1-6}$ alkyl, $C_{2-6}$ alkenyl, substituted $C_{6-10}$ aryl, and substituted 6- to 10-membered heteroaryl;

$R^4$ is selected from the group consisting of $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, cyano and $P(O)(OR^7)_2$; and
each $R^7$ and $R^8$ is independently selected from the group consisting of H, $C_{1-6}$ alkyl, and substituted $C_{6-10}$ aryl.

53. The method of embodiment 51 or embodiment 52, wherein the enzyme catalyst comprises 1-6 mutations at positions 327, 437, 332, 87, 264, and 327.

54. The method of embodiment 53, wherein:
the mutation at position 327 is a mutation to valine,
the mutation at position 437 is a mutation to leucine,
the mutation at position 332 is a mutation to alanine,
the mutation at position 87 is a mutation to proline,
the mutation at position 264 is a mutation to serine, and
the mutation at position 327 is a mutation to proline.

DETAILED DESCRIPTION OF THE INVENTION

Figure 1:
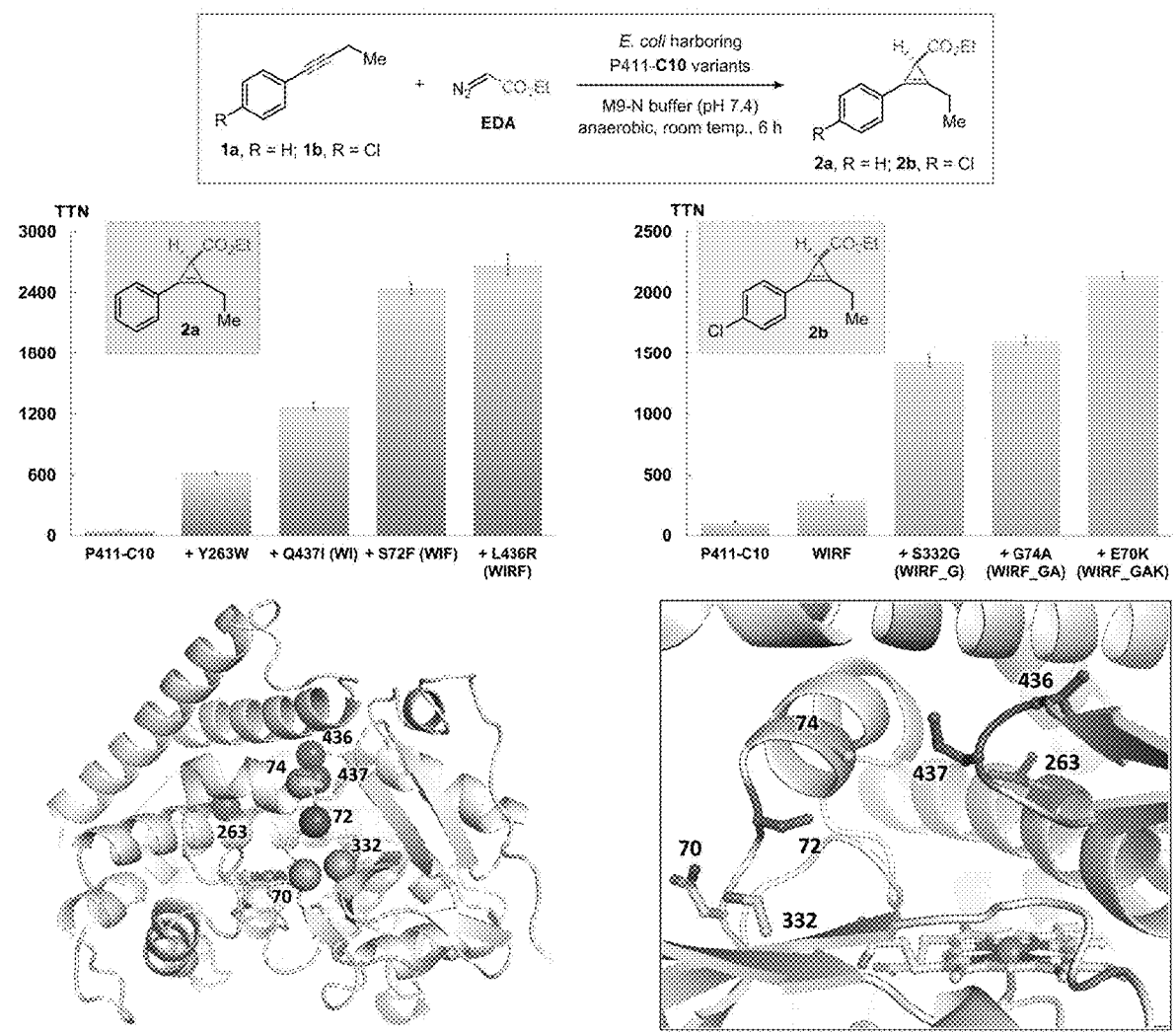
FIG. 1 summarized the directed evolution of P411-C10 for internal cyclopropene synthesis. Reaction conditions: 10 mM alkyne, 10 mM EDA, E. coli harboring P411-C10 variants ($OD_{600}$=15 to 60), D-glucose (25 mM), M9-N buffer/EtOH (19:1), anaerobic, 6 h. Product formation was quantified by gas chromatography (GC) and TTNs were determined based on P411 protein concentration. The heme-domain structure of P411-E10 variant (pdb: 5UCW) was used to guide site-saturation mutagenesis; mutation sites are highlighted.

The present invention is based, in part, on the discovery that a P411 enzyme variant (a P411 is a P450 in which the heme-ligating cysteine residue has been replaced by serine)[6], P411-C10, is capable of catalyzing a diverse array of carbene-transfer reactions for the construction of challenging chemical scaffolds. P411-C10 has shown high promiscuity as a carbene transferase, albeit with low activity towards the desired transformations. This promiscuity is unusually broad and thus provides a starting point for engineering diverse enzyme catalysts by directed evolution. It has now been found that directed evolution of P411-C10, and other enzyme variants in the C10 family, improves the catalytic efficiency of the carbene-transfer reactions.

Using P411-C10 as the parent for further engineering, directed evolution leads to lineages of enzymes that catalyze a broad set of carbene-transfer reactions, including but not limited to: 1) enantioselective carbene transfer to internal alkynes for internal cyclopropene synthesis; 2) stereo-selective carbene transfer to internal alkenes for multi-substituted cyclopropane formation; 3) stereo-selective carbene transfer to cyclopropenes for the construction of structurally diverse bicyclobutanes; 4) enantio-divergent lactone-carbene C—H insertion for chiral β-amino lactone derivative synthesis; 5) enantioselective intramolecular carbene C—H insertion for the rapid synthesis of structurally diverse lactone and lactam derivatives; and 6) enantioselective carbene N—H insertion for the synthesis of α-amino acid derivatives. With these engineered P411 enzymes, stereo-/regio-/chemoselective carbene-transfer reactions can be achieved with total turnover numbers (TTNs) up to 6500 and enantiomeric excesses (ee's) >99.9%.

I. DEFINITIONS

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the reagent" includes reference to one or more reagents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The terms "enzyme catalyst variant" and "heme enzyme variant" include any heme-containing enzyme comprising at least one amino acid mutation with respect to wild-type and also include any chimeric protein comprising recombined sequences or blocks of amino acids from two, three, or more different heme-containing enzymes.

The term "whole cell catalyst" includes cells expressing heme-containing enzymes, wherein the whole cell catalyst displays cyclopropene formation activity or bicyclobutane formation activity.

The term "carbene precursor" includes molecules that can be decomposed in the presence of metal (or enzyme) catalysts to form structures that contain at least one divalent carbon with two unshared valence shell electrons (i.e., carbenes) and that can be transferred to a carbon-hydrogen bond, a carbon-carbon bond, a carbon-sulfur bond, a carbon-nitrogen bond, a carbon-boron bond, or a carbon-phosphorus bond to form various carbon ligated products. Examples of carbene precursors include, but are not limited to, diazo reagents, diazirene reagents, and epoxide reagents.

As used herein, the term "anaerobic", when used in reference to a reaction, culture or growth condition, is intended to mean that the concentration of oxygen is less than about 25 µM, preferably less than about 5 µM, and even more preferably less than 1 µM. The term is also intended to include sealed chambers of liquid or solid medium maintained with an atmosphere of less than about 1% oxygen. Preferably, anaerobic conditions are achieved by sparging a reaction mixture with an inert gas such as nitrogen or argon.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Alkyl groups can be unsubstituted or substituted. For example, "substituted alkyl" groups can be substituted with one or more moieties selected from halo, hydroxy, amino, alkylamino, alkoxy, haloalkyl, carboxy, amido, nitro, oxo, and cyano.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be unsubstituted or substituted. For example, "substituted alkenyl" groups can be substituted with one or more moieties selected from halo, hydroxy, amino, alkylamino, alkoxy, haloalkyl, carboxy, amido, nitro, oxo, and cyano.

As used herein, the term "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be unsubstituted or substituted.

For example, "substituted alkynyl" groups can be substituted with one or more moieties selected from halo, hydroxy, amino, alkylamino, alkoxy, haloalkyl, carboxy, amido, nitro, oxo, and cyano.

As used herein, the term "aryl" refers to an aromatic carbon ring system having any suitable number of ring atoms and any suitable number of rings. Aryl groups can include any suitable number of carbon ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be unsubstituted or substituted. For example, "substituted aryl" groups can be substituted with one or more moieties selected from halo, hydroxy, amino, alkylamino, alkoxy, haloalkyl, carboxy, amido, nitro, oxo, and cyano.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbomane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Cycloalkyl groups can be unsubstituted or substituted. For example, "substituted cycloalkyl" groups can be substituted with one or more moieties selected from halo, hydroxy, amino, alkylamino, alkoxy, haloalkyl, carboxy, amido, nitro, oxo, and cyano.

As used herein, the term "heterocyclyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 4 to 6, or 4 to 7 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. Examples of heterocyclyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocyclyl groups can be unsubstituted or substituted. For example, "substituted heterocyclyl" groups can be substituted with one or more moieties selected from halo, hydroxy, amino, alkylamino, alkoxy, haloalkyl, carboxy, amido, nitro, oxo, and cyano.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms including, but not limited to, B, Al, Si and P can also be present in a heteroaryl group. The heteroatoms can be oxidized to form moieties such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. Examples of heteroaryl groups include, but are not limited to, pyrrole, pyridine, imidazole, pyrazole, triazole, tetrazole, pyrazine, pyrimidine, pyridazine, triazine (1,2,3-, 1,2,4- and 1,3,5- isomers), thiophene, furan, thiazole, isothiazole, oxazole, and isoxazole. Heteroaryl groups can be unsubstituted or substituted. For example, "substituted heteroaryl" groups can be substituted with one or more moieties selected from halo, hydroxy, amino, alkylamino, alkoxy, haloalkyl, carboxy, amido, nitro, oxo, and cyano.

As used herein, the term "alkoxy" refers to an alkyl group having an oxygen atom that connects the alkyl group to the point of attachment: i.e., alkyl-O—. As for alkyl group, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups can be unsubstituted or substituted. For example, "substituted alkoxy" groups can be substituted with one or more moieties selected from halo, hydroxy, amino, alkylamino, alkoxy, haloalkyl, carboxy, amido, nitro, oxo, and cyano.

As used herein, the terms "halo" and "halogen" refer to fluorine, chlorine, bromine and iodine.

As used herein, the term "haloalkyl" refers to an alkyl moiety as defined above substituted with at least one halogen atom.

As used herein, the term "acyl" refers to a moiety —C(O)R, wherein R is an alkyl group.

As used herein, the term "oxo" refers to an oxygen atom that is double-bonded to a compound (i.e., O=).

As used herein, the term "carboxy" refers to a moiety —C(O)OH. The carboxy moiety can be ionized to form the carboxylate anion. "Alkyl carboxylate" refers to a moiety —C(O)OR, wherein R is an alkyl group as defined herein.

As used herein, the term "amino" refers to a moiety —NR$_3$, wherein each R group is H or alkyl.

As used herein, the term "amido" refers to a moiety —NRC(O)R or —C(O)NR$_2$, wherein each R group is H or alkyl.

The terms "protein," "peptide," and "polypeptide" are used interchangeably herein to refer to a polymer of amino acid residues, or an assembly of multiple polymers of amino acid residues. The terms apply to amino acid polymers in which one or more amino acid residues are an artificial chemical mimic of a corresponding naturally occurring amino acid, as well as to naturally occurring amino acid polymers and non-naturally occurring amino acid polymers.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups or modified peptide backbones, e.g, homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g, r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g, G, A, I, L, or V) is substituted with another member of the group. Similarly, an aliphatic polar-uncharged group such as C, S, T, M, N, or Q, may be substituted with another member of the group; and basic residues, e.g, K, R, or H, may be substituted for one another. In some embodiments, an amino acid with an acidic side chain, e.g, E or D, may be substituted with its uncharged counterpart, e.g., Q or N, respectively; or vice versa. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, 1993).

The term "oligonucleotide," "nucleic acid," "nucleotide," or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g, degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991), Ohtsuka et al., *J. Biol. Chem.* 260:2605-2608 (1985), and Rossolini et al., *Mol. Cell. Probes* 8:91-98 (1994)). The term nucleic acid is used interchangeably with gene, cDNA, and mRNA encoded by a gene.

The term "site-directed mutagenesis" refers to various methods in which specific changes are intentionally made introduced into a nucleotide sequence (i.e., specific nucleotide changes are introduced at pre-determined locations). Known methods of performing site-directed mutagenesis include, but are not limited to, PCR site-directed mutagenesis, cassette mutagenesis, whole plasmid mutagenesis, and Kunkel's method.

The term "site-saturation mutagenesis," also known as "saturation mutagenesis," refers to a method of introducing random mutations at predetermined locations with a nucleotide sequence, and is a method commonly used in the context of directed evolution (e.g, the optimization of proteins (e.g, in order to enhance activity, stability, and/or stability), metabolic pathways, and genomes). In site-saturation mutagenesis, artificial gene sequences are synthesized using one or more primers that contain degenerate codons; these degenerate codons introduce variability into the position(s) being optimized. Each of the three positions within a degenerate codon encodes a base such as adenine (A), cytosine (C), thymine (T), or guanine (G), or encodes a degenerate position such as K (which can be G or T), M (which can be A or C), R (which can be A or G), S (which can be C or G), W (which can be A or T), Y (which can be C or T), B (which can be C, G, or T), D (which can be A, G, or T), H (which can be A, C, or T), V (which can be A, C, or G), or N (which can be A, C, G, or T). Thus, as a non-limiting example, the degenerate codon NDT encodes an A, C, G, or T at the first position, an A, G, or T at the second position, and a T at the third position. This particular combination of 12 codons represents 12 amino acids (Phe, Leu, Ile, Val, Tyr, His, Asn, Asp, Cys, Arg, Ser, and Gly). As another non-limiting example, the degenerate codon VHG encodes an A, C, or G at the first position, an A, C, or T at the second position, and G at the third position. This particular combination of 9 codons represents 8 amino acids (Lys, Thr, Met, Glu, Pro, Leu, Ala, and Val). As another non-limiting example, the "fully randomized" degenerate codon NNN includes all 64 codons and represents all 20 naturally-occurring amino acids.

In some instances, a mixture of degenerate primers is used. A mixture of degenerate primers can contain any number of different degenerate primers in any ratio. As a non-limiting example, a mixture of primers containing the NDT, VHG, and TGG primers can be used. Such a mixture can contain, for example, an amount of each primer in a 12:9:1 ratio (e.g., a NDT:VHG:TGG ratio of 12:9:1). Based on various considerations, non-limiting examples being desired redundancy, the desired presence of stop codons, and/or desired amino acid characteristics (e.g., the presence of nonpolar residues, charged residues, or small side chain residues), different combinations of degenerate primers can be used. Considerations and methods for choosing optimal combinations of degenerate primers will be known to one of skill in the art.

The term "nucleotide sequence encoding a peptide" means the segment of DNA involved in producing a peptide chain. The term can include regions preceding and following the coding region (leader and trailer) involved in the transcription/translation of a gene product and the regulation of the transcription/translation, as well as intervening sequences (introns) between individual coding segments (exons).

The term "homolog," as used herein with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In particular embodiments, the homology between two proteins is indicative of its shared ancestry, related by evolution.

II. ENZYMES CATALYSTS FOR DIVERSE CHEMICAL TRANSFORMATIONS

Provided herein is an enzyme family based on a cytochrome P450 variant named P411-C10. The P411-C10 enzyme is derived from cytochrome P450 BM3 (also known as CYP102A1)[9], containing mutations N70E A74G V78L A82L F87A M118S P142S F162L T175I M177L A184V S226R H236Q E252G I263Y H266V T268G A290V A328V A330Y L353V I366V C400S I401L T436L L437Q E442K (mature peptide numbering convention) with truncation of the FAD domain (Δ665-1048). The enzyme variants in the family of P411-C10 can contain further mutations (to any other amino acid residue that is among the naturally occurring twenty amino acids) at any residue throughout the holo-protein.

Cytochrome P450 enzymes constitute a large superfamily of heme-thiolate proteins involved in the metabolism of a wide variety of both exogenous and endogenous compounds. Usually, they act as the terminal oxidase in multicomponent electron transfer chains, such as P450-containing monooxygenase systems. Members of the cytochrome P450 enzyme family catalyze myriad oxidative transformations, including, e.g., hydroxylation, epoxidation, oxidative ring coupling, heteroatom release, and heteroatom oxygenation (E. M. Isin et al., *Biochim. Biophys. Acta* 1770, 314 (2007)). P450s typically contain a single polypeptide, ranging from 40 to 55 kDa in molecular weight, and the same general fold has been observed in all P450s with known structures (T. L. Poulous, *Chem Rev.*, 114, 3919 (2014)). Conserved secondary structures included in the so-called "CYP fold" are commonly referred to as αA-L and β1-5. The active site of these enzymes contains an $Fe^{III}$-protoporphyrin IX cofactor (heme) ligated proximally by a conserved cysteine thiolate (M. T. Green, *Current Opinion in Chemical Biology* 13, 84 (2009)). The remaining axial iron coordination site is occupied by a water molecule in the resting enzyme, but during native catalysis, this site is capable of binding molecular oxygen. P450 structure is also typically characterized by a long "I helix" (typically around 50 angstroms in length) which runs over the surfaces of the heme and interacts with oxygen and the oxidation substrate. In the presence of an electron source, typically provided by NADH or NADPH from an adjacent fused reductase domain or an accessory cytochrome P450 reductase enzyme, the heme center of cytochrome P450 activates molecular oxygen, generating a high valent iron(IV)-oxo porphyrin cation radical species intermediate and a molecule of water. Cytochrome $P450_{BM3}$ (CYP102A1) is found in the soil bacterium *Bacillus megaterium* and catalyzes the NADPH-dependent hydroxylation of long-chain fatty acids at the ω-1 through ω-3 positions. Unlike most other cytochrome P450 proteins, $P450_{BM3}$ is a natural fusion between the cytochrome P450 domain and an electron donating cofactor. Thus, $P450_{BM3}$ and variants thereof are useful in a number of biotechnological applications.

Engineering certain regions of the enzyme as described in more detail below, including amino acids 70-92 in the B' helix of $P450_{BM3}$ and the loop regions nearby, 175-190 in the F helix, 256-272 in the I helix, 324-335 in the K helix and β1 sheet, 395-409 in the L helix and cysteine loop, and 434-442 in β4 sheet (mature peptide numbering convention, as shown in citation 9), can provide improved efficiency and selectivity toward a desired reaction.

Accordingly, the present disclosure provides new enzyme catalysts and methods for employing them in various chemical transformations. In some embodiments, methods for forming carbene insertion products are provided. The methods include:

forming a reaction mixture comprising an enzyme catalyst and one or two enzyme substrates, and incubating the mixture to form the carbene insertion product, wherein at least one of the substrate comprises a carbene precursor moiety, wherein the enzyme catalyst comprises the amino acid sequence set forth in SEQ ID NO:1 and optionally 1-30 mutations at positions 2, 47, 70, 72, 74, 78, 80, 82, 87, 88, 92, 118, 142, 162, 190, 226, 240, 252, 263, 264, 267, 279, 327, 328, 332, 366, 401, 436, 437, and 474.

A number of carbene precursors can be used in the methods and reaction mixtures including, but not limited to, amines, azides, hydrazines, hydrazones, epoxides, diazirines, and diazo reagents. In some embodiments, the carbene precursor is an epoxide (i.e., a compound containing an epoxide moiety). The term "epoxide moiety" refers to a three-membered heterocycle having two carbon atoms and one oxygen atom connected by single bonds. In some embodiments, the carbene precursor is a diazirine (i.e., a compound containing a diazirine moiety). The term "diazirine moiety" refers to a three-membered heterocycle having one carbon atom and two nitrogen atoms, wherein the nitrogen atoms are connected via a double bond. Diazirines are chemically inert, small hydrophobic carbene precursors described, for example, in US 2009/0211893, by Turro (*J. Am. Chem. Soc.* 1987, 109, 2101-2107), and by Brunner (*J. Biol. Chem.* 1980, 255, 3313-3318), which are incorporated herein by reference in their entirety.

In some embodiments, the carbene precursor is a diazo reagent, e.g., an α-diazoester, an α-diazoamide, an α-diazonitrile, an α-diazoketone, an α-diazoaldehyde, or an α-diazosilane. Diazo reagents can be formed from a number of starting materials using procedures that are known to those of skill in the art. Ketones (including 1,3-diketones), esters (including β-ketones), acyl chlorides, and carboxylic acids can be converted to diazo reagents employing diazo transfer conditions with a suitable transfer reagent (e.g., aromatic and aliphatic sulfonyl azides, such as toluenesulfonyl azide, 4-carboxyphenylsulfonyl azide, 2-naphthalenesulfonyl azide, methylsulfonyl azide, and the like) and a suitable base (e.g., triethylamine, triisopropylamine, diazobicyclo[2.2.2]octane, 1,8-diazabicyclo[5.4.0]undec-7-ene, and the like) as described, for example, in U.S. Pat. No. 5,191,069 and by Davies (*J. Am. Chem. Soc.* 1993, 115, 9468-9479), which are incorporated herein by reference in their entirety. The preparation of diazo compounds from azide and hydrazone precursors is described, for example, in U.S. Pat. Nos. 8,350,014 and 8,530,212, which are incorporated herein by reference in their entirety. Alkylnitrite reagents (e.g., (3-methylbutyl)nitrite) can be used to convert α-aminoesters to the corresponding diazo compounds in non-aqueous media as described, for example, by Takamura (*Tetrahedron*, 1975, 31: 227), which is incorporated herein by reference in its entirety. Alternatively, a diazo compound can be formed from an aliphatic amine, an aniline or other arylamine, or a hydrazine using a nitrosating agent (e.g., sodium nitrite) and an acid (e.g., p-toluenesulfonic acid) as described, for example, by Zollinger (*Diazo Chemistry I and II*, VCH Weinheim, 1994) and in US 2005/0266579, which are incorporated herein by reference in their entirety.

In some embodiments, the carbene precursor moiety is a diazo moiety. In some embodiments, the carbene insertion product is a cyclopropene (e.g., a compound according to Formula III as described below), a cyclopropane (e.g., a compound according to Formula V as described below), a bicyclobutane (e.g., a compound according to Formula VII as described below), a substituted lactone (e.g., a compound according to Formula X as described below), a cyclized compound (e.g., a compound according to Formula XII as described below), or a substituted amine (e.g., a compound according to Formula XIV as described below).

A. Catalysts and Reactions for Cyclopropene Formation

P411-C10 can be engineered through single or iterative rounds of site-saturation mutagenesis or random mutagenesis and screening to provide enzyme variants capable of internal cyclopropene synthesis in presence of diazo substrates and internal alkynes as shown, for example, in Scheme 1. In some embodiments, a lineage of enzymes derived from P411-C10, having mutations at positions Y263, Q437, L436, S72, S332, G74, and E70 to other amino acids, is provided for internal cyclopropene synthesis.

Scheme 1

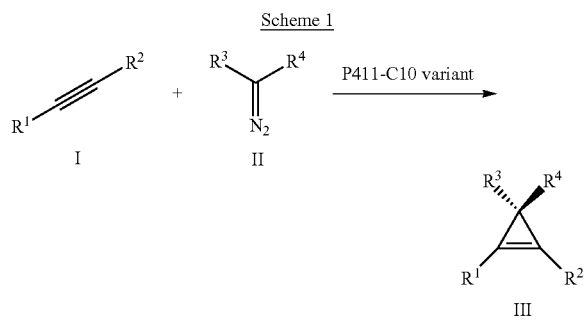

Accordingly, some embodiments of the present disclosure provide methods wherein:

the reaction mixture comprises a first enzyme substrate according to Formula I

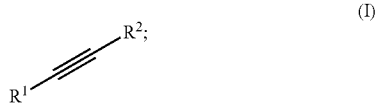

(I)

and a second enzyme substrate according to Formula II

(II)

the carbene insertion product is a cyclopropene according to Formula III

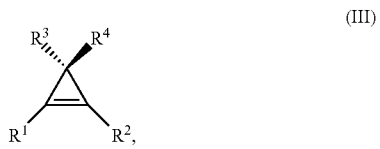

(III)

and
the enzyme catalyst optionally comprises 1-11 mutations at positions 70, 72, 74, 87, 263, 264, 267, 327, 332, 436, and 437;
and wherein:
$R^1$, $R^2$, $R^3$, $R^4$, $R^5$ and $R^6$ are independently selected from the group consisting of H, optionally substituted $C_{1-18}$ alkyl (e.g., $C_{1-18}$ polyfluoroalkyl), $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and
each $R^7$, $R^8$, and $R^9$ is independently selected from the group consisting of H, $C_{1-6}$ alkyl and optionally substituted $C_{6-10}$ aryl.

In some embodiments:
$R^1$ and $R^2$ are independently selected from the group consisting of substituted $C_{1-6}$ alkyl, $C_{2-6}$ alkenyl, $C_{2-6}$ alkynyl, substituted $C_{6-10}$ aryl, and substituted 6- to 10-membered heteroaryl;
$R^3$ is selected from the group consisting of $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, cyano, and $P(O)(OR^7)_2$;
$R^4$ is selected from the group consisting of H, substituted $C_{1-6}$ alkyl, $C_{2-6}$ alkenyl, $C_{2-6}$ alkynyl, substituted $C_{6-10}$ aryl, and substituted 6- to 10-membered heteroaryl; and
each $R^7$ and $R^8$ is independently selected from the group consisting of H, $C_{1-6}$ alkyl, and substituted $C_{6-10}$ aryl.

In some embodiments, the enzyme catalyst for cyclopropene formation includes 1-4 mutations at positions 72, 263, 436, and 437. In some embodiments:
the mutation at position 72 is a mutation to phenylanine or another aromatic amino acid,
the mutation at position 263 is a mutation to tryptophan or another aromatic amino acid,
the mutation at position 436 is a mutation to arginine or another charged amino acid, and
the mutation at position 437 is a mutation to isoleucine or another hydrophobic amino acid.

In some embodiments, the enzyme catalyst for cyclopropene formation further comprises 1-3 mutations at positions 70, 74, and 332. In some embodiments:
the mutation as position 332 is a mutation to glycine or another hydrophobic amino acid,
the mutation at position 74 is a mutation to alanine or another hydrophobic amino acid, and
the mutation at position 70 mutation is a mutation to lysine or another charged amino acid.

In some embodiments, the enzyme catalyst comprises 1-6 mutations a positions 87, 264, 267, 327, 332, and 437. In some embodiments:
the mutation at position 87 is a mutation to proline or another hydrophobic amino acid,
the mutation at position 264 is a mutation to serine or another polar amino acid,
the mutation at position 267 is a mutation to aspartic acid or another charged amino acid,
the mutation at position 327 is a mutation to proline or another hydrophobic amino acid,
the mutation at position 332 is a mutation to alanine or another hydrophobic amino acid, and
the mutation at position 437 is a mutation to leucine or another hydrophobic amino acid.

B. Catalysts and Reactions for Cyclopropane Formation

P411-C10 can also be evolved through single or iterative rounds of site-saturation mutagenesis or random mutagenesis and screening to provide enzyme variants capable of internal cyclopropane synthesis in presence of diazo substrates and internal alkenes as shown, for example, in Scheme 2. In some embodiments, a lineage of enzymes derived from P411-C10, having mutations at the positions S72, G74, L82, T327, Q437, A87, Y263, A264, G268, S332, E267, and V328 to other amino acids, is provided for internal cyclopropane synthesis.

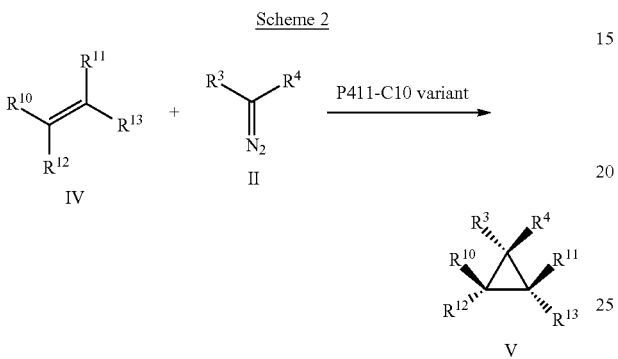

Accordingly, some embodiments provide methods wherein:

the reaction mixture comprises a first enzyme substrate according to Formula IV

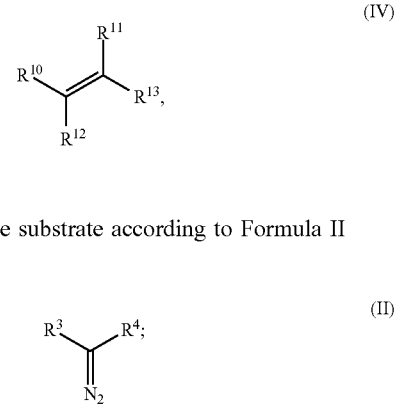

and a second enzyme substrate according to Formula II

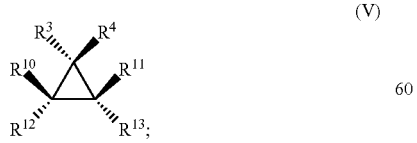

and the carbene insertion product is a cyclopropane according to Formula V (V)

and wherein:

$R^3$, $R^4$, $R^{10}$, R, $R^{12}$, and $R^{13}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R')_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and each $R^7$, $R^8$, and $R^9$ is independently selected from the group consisting of H, $C_{1-6}$ alkyl and optionally substituted $C_{6-10}$ aryl.

In some embodiments:

$R^{10}$, $R^{11}$, $R^{12}$ and $R^{13}$ are independently selected from the group consisting of substituted $C_{1-6}$ alkyl, $C_{2-6}$ alkenyl, $C_{2-6}$ alkynyl, substituted $C_{6-10}$ aryl, substituted 6- to 10-membered heteroaryl and $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$;

$R^3$ is selected from the group consisting of $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, cyano, and $P(O)(OR^7)_2$;

$R^4$ is selected from the group consisting of H, substituted $C_{1-6}$ alkyl, $C_{2-6}$ alkenyl, $C_{2-6}$ alkynyl, substituted $C_{6-10}$ aryl, and substituted 6- to 10-membered heteroaryl; and each $R^7$ and $R^8$ is independently selected from the group consisting of H, $C_{1-6}$ alkyl and substituted $C_{6-10}$ aryl.

C. Catalysts and Reactions for Bicyclobutane Formation

P411-C10 can also evolved through single or iterative rounds of site-saturation mutagenesis or random mutagenesis and screening to provide enzyme variants capable of bicyclobutane synthesis in presence of diazo substrates and cyclopropenes as shown, for example, in Scheme 3. In some embodiments, a lineage of enzymes derived from P411-C10, having mutations at the positions R47, S72, A264, T327, and Q437 to other amino acids, is provided for bicyclobutane synthesis.

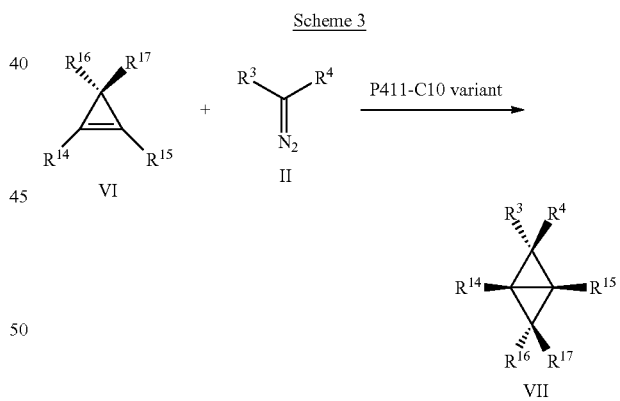

Accordingly, some embodiments of the present disclosure provide methods wherein:

the reaction mixture comprises a first enzyme substrate according to Formula VI

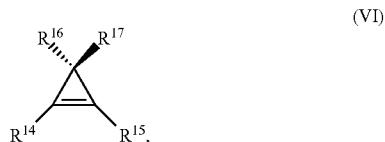

and
a second enzyme substrate according to Formula II $$\underset{N_2}{\overset{R^3 \quad R^4}{\diagup\hspace{-0.5em}\diagdown}} \quad \text{(II)}$$

the carbene insertion product is a bicyclobutane according to Formula V $$R^{14}\text{—}\underset{R^{16} \quad R^{17}}{\overset{R^3 \quad R^4}{\diagup\hspace{-0.5em}\diagdown}}\text{—}R^{15}; \quad \text{(V)}$$

and
the enzyme catalyst optionally comprises 1-7 mutations at positions 47, 72, 118, 264, 327, 437, 474;
and wherein:
$R^3$, $R^4$, $R^{14}$, $R^{15}$, $R^{16}$ and $R^{17}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and
each $R^7$, $R^8$, and $R^9$ is independently selected from the group consisting of H, $C_{1-6}$ alkyl and optionally substituted $C_{6-10}$ aryl.

In some embodiments:
$R^{14}$ and $R^{15}$ are independently selected from the group consisting of substituted $C_{1-6}$ alkyl, $C_{2-6}$ alkenyl, $C_{2-6}$ alkynyl, substituted $C_{6-10}$ aryl, and substituted 6- to 10-membered heteroaryl;
$R^3$ and $R^{16}$ are independently selected from the group consisting of $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, cyano and $P(O)(OR^7)_2$;
$R^4$ and $R^{17}$ are independently selected from the group consisting of H, substituted $C_{1-6}$ alkyl, $C_{2-6}$ alkenyl, $C_{2-6}$ alkynyl, substituted $C_{6-10}$ aryl, and substituted 6- to 10-membered heteroaryl; and
each $R^7$ and $R^8$ is independently selected from the group consisting of H, $C_{1-6}$ alkyl and substituted $C_{6-10}$ aryl.

In some embodiments, the enzyme catalyst for bicyclobutane formation contains 1-7 mutations at position 47, 72, 118, 264, 327, 437, and 474. In some embodiments:
the mutation at position 47 is a mutation to glutamine or another polar amino acid,
the mutation at position 72 is a mutation to asparagine or another charged amino acid,
the mutation at position 118 is a mutation to glycine or another hydrophobic amino acid,
the mutation at position 264 is a mutation to serine or another polar amino acid,
the mutation at position 327 is a mutation to proline or another hydrophobic amino acid,
the mutation at position 437 is a mutation to tyrosine or another aromatic amino acid, and
the mutation at position 474 is a mutation to threonine or another polar amino acid.

D. Catalysts and Reactions for C—H Insertion

P411-C10 can also be evolved through single or iterative rounds of site-saturation mutagenesis or random mutagenesis and screening to provide enzyme variants capable of lactone derivative synthesis in presence of lactone-based diazo substrates and alkanes as shown, for example, in Scheme 4. In some embodiments, a lineage of enzymes derived from P411-C10, having mutations at the positions T327, Q437, A87, A264, S332, E267, and V328 to other amino acids, is provided for lactone derivative synthesis.

Scheme 4

$$R^{18}\diagdown R^{19} \quad + \quad \underset{R^{20}}{\overset{N_2}{\underset{R^{21}\text{\tiny{\textbackslash}}}{\diagup}}}\hspace{-0.3em}\overset{O}{\underset{O}{\diagdown}}\hspace{-0.3em})_n \quad \xrightarrow{\text{P411-C10 variant}}$$

VIII

IX $$\underset{R^{20}}{\overset{R^{18}}{\underset{R^{21}\text{\tiny{\textbackslash}}}{\diagup}}}\hspace{-0.3em}\overset{O}{\underset{O}{\diagdown}}\hspace{-0.3em})_n$$

X

Accordingly, some embodiments of the present disclosure provide methods wherein:
the reaction mixture comprises a first enzyme substrate according to Formula VIII $$R^{18}\diagdown R^{19}, \quad \text{(VIII)}$$

and
a second enzyme substrate according to Formula IX $$\underset{R^{20}}{\overset{N_2}{\underset{R^{21}\text{\tiny{\textbackslash}}}{\diagup}}}\hspace{-0.3em}\overset{O}{\underset{O}{\diagdown}}\hspace{-0.3em})_n; \quad \text{(IX)}$$

the carbene insertion product is a substituted lactone according to Formula X

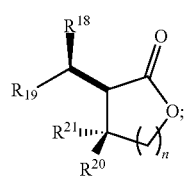

(X)

and
the enzyme catalyst optionally comprises 1-8 mutations at positions 327, 437, 332, 87, 264, 327, 267, 328;
and wherein:
$R^{18}$, $R^{19}$, $R^{20}$, and $R^{21}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$;
each $R^7$, $R^8$, and $R^9$ is independently selected from the group consisting of H, $C_{1-6}$ alkyl, and optionally substituted $C_{6-10}$ aryl; and
subscript n is an integer ranging from 0 to 10.

In some embodiments:
$R^{18}$, $R^{20}$, and $R^{21}$ are independently selected from the group consisting of substituted $C_{1-6}$ alkyl, $C_{2-6}$ alkenyl, substituted $C_{6-10}$ aryl, and substituted 6- to 10-membered heteroaryl;
$R^{19}$ is selected from the group consisting of substituted $C_{1-6}$ alkyl, substituted $C_{6-10}$ aryl, $N(R^7)_2$ and $OR^7$; and
each $R^7$ is independently selected from the group consisting of H, $C_{1-6}$ alkyl, and substituted $C_{6-10}$ aryl.

In some embodiments, the enzyme catalyst for C—H insertion comprises 1-8 mutations at positions 327, 437, 332, 87, 264, 327, 267, and 328. In some embodiments:
the mutation at position 327 is a mutation to valine or another hydrophobic amino acid,
the mutation at position 437 is a mutation to leucine or another hydrophobic amino acid,
the mutation at position 332 is a mutation to alanine or another hydrophobic amino acid,
the mutation at position 87 is a mutation to proline or another hydrophobic amino acid,
the mutation at position 264 is a mutation to serine or another polar amino acid,
the mutation at position 327 is a mutation to proline or another hydrophobic amino acid,
the mutation at position 267 is a mutation to aspartic acid or another charged amino acid, and
the mutation at position 328 is a mutation to leucine or arginine or another hydrophobic amino acid or charged amino acid.

E. Catalysts and Reactions for Intramolecular Cyclization

P411-C10 can also be evolved through single or iterative rounds of site-saturation mutagenesis or random mutagenesis and screening to provide enzyme variants capable of cyclic compound synthesis using diazo substrates as shown, for example, in Scheme 5. In some embodiments, a lineage of enzymes derived from P411-C10, having mutations at the positions T327, Q437, V328, L78, L436, L401, L162, R190, E70, Y263, S72, S332, G74, R226, H92, G252, V366, S142, and L82 to other amino acids, is provided for cyclic compound synthesis.

Scheme 5

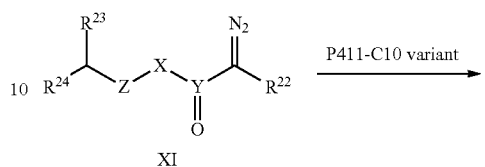

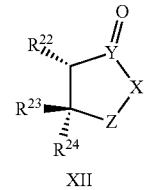

XII

Accordingly, some embodiments of the present disclosure provide methods wherein:
the reaction mixture comprises an enzyme substrate according to Formula XI

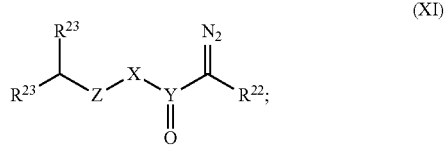

(XI)

the carbene insertion product is a cyclized compound according to Formula XII

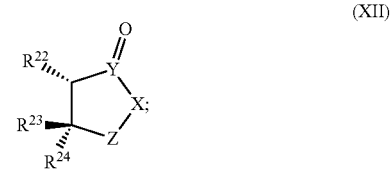

(XII)

and
the enzyme catalyst optionally comprises 1-25 mutations at positions 2, 70, 72, 78, 74, 80, 82, 87, 88, 92, 142, 162, 190, 226, 240, 252, 263, 279, 327, 328, 332, 366, 401, 436, 437;
and wherein:
$R^{22}$, $R^{23}$, and $R^{24}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$;
Y is selected from the group consisting of C, S(O) and $P(OR^{25})$;
X is selected from the group consisting of O, S, $N(R^{26})$ and $C(R^{27})_2$;

Z is $(C(R^{28})_2)_nX^1(C(R^{28})_2)_m$;

$X^1$ is selected from the group consisting of O, S, $N(R^{26})$ and $C(R^{27})_2$, and can also be linked to other parts in the same molecule including $R^1$, $R^2$, $R^3$, X and Y;

subscripts n and m are independently integers ranging from 0 to 10;

and each $R^7$, $R^8$, $R^9$, $R^{25}$, $R^{26}$, $R^{27}$, and $R^{28}$ is independently selected from the group consisting of H, $C_{1-6}$ alkyl, and optionally substituted $C_{6-10}$ aryl.

In some embodiments:

$R^{22}$, $R^{23}$ and $R^{24}$ are independently selected from the group consisting of substituted $C_{1-6}$ alkyl, $C_{2-6}$ alkenyl, substituted $C_{6-10}$ aryl, and substituted 6- to 10-membered heteroaryl;

X is selected from the group consisting of O, $N(R^{26})$ and $C(R^{27})_2$;

$X^1$ is selected from the group consisting of O and $C(R^{27})_2$ subscripts n and m are independently integers ranging from 0 to 4;

$R^{28}$ is independently selected from the group consisting of H, $C_{1-6}$ alkyl, and substituted $C_{6-10}$ aryl.

In some embodiments, the enzyme catalyst for intramolecular cyclization comprises 1-mutations at positions 78, 88, 401, 436, and 437. In some such embodiments, the cyclized compound contains a six-membered ring. In some embodiments:

the mutation at position 78 is a mutation to methionine or another hydrophobic amino acid, the mutation at position 88 is a mutation to serine or another polar amino acid, the mutation at position 401 is a mutation to valine or another hydrophobic amino acid, the mutation at position 436 is a mutation to arginine or another charged amino acid, and the mutation at position 437 is a mutation to isoleucine or another hydrophobic amino acid.

In some embodiments, the enzyme catalyst for intramolecular cyclization comprises 1-8 mutations at positions 70, 78, 162, 190, 328, 401, 436, and 437. In some such embodiments, the cyclized compound contains a five membered ring. In some embodiments:

the mutation at position 70 is a mutation to serine or another polar amino acid, mutation at position 78 is a mutation to methionine or another hydrophobic amino acid, mutation at position 162 is a mutation to isoleucine or another hydrophobic amino acid, mutation at position 190 is a mutation to leucine or another hydrophobic amino acid, mutation at position 328 is a mutation to isoleucine or another hydrophobic amino acid, mutation at position 401 is a mutation to valine or another hydrophobic amino acid, mutation at position 436 is a mutation to arginine or another charged amino acid, and mutation at position 437 is a mutation to isoleucine or another hydrophobic amino acid.

In some embodiments the enzyme catalyst for intramolecular cyclization comprises 1-19 mutations at positions 2, 72, 74, 80, 87, 92, 142, 162, 226, 240, 252, 263, 279, 327, 328, 332, 366, 436, and 437. In some such embodiments, the cyclized compound contains a seven membered ring. In some embodiments:

the mutation at position 2 is a mutation to threonine or another polar amino acid, the mutation at position 72 is a mutation to valine or another hydrophobic amino acid, the mutation at position 74 is a mutation to alanine or another hydrophobic amino acid, the mutation at position 80 is a mutation to glutamic acid or another charged amino acid, the mutation at position 87 is a mutation to valine or another hydrophobic amino acid, the mutation at position 92 is a mutation to phenylalanine or another aromatic amino acid, the mutation at position 142 is a mutation to glycine or another hydrophobic amino acid, the mutation at position 162 is a mutation to phenylalanine or another aromatic amino acid, the mutation at position 226 is a mutation to serine or another polar amino acid, the mutation at position 240 is a mutation to arginine or another charged amino acid, the mutation at position 252 is a mutation to arginine or another charged amino acid, the mutation at position 263 is a mutation to tryptophan or another aromatic amino acid, the mutation at position 279 is a mutation to leucine or another hydrophobic amino acid, the mutation at position 327 is a mutation to proline or another hydrophobic amino acid, the mutation at position 328 is a mutation to isoleucine or another hydrophobic amino acid, the mutation at position 332 is a mutation to glycine or another hydrophobic amino acid, the mutation at position 366 is a mutation to isoleucine or another hydrophobic amino acid, the mutation at position 436 is a mutation to arginine or another charged amino acid, and the mutation at position 437 is a mutation to isoleucine or another hydrophobic amino acid.

F. Catalysts and Reactions for N—H Insertion

P411-C10 can also be evolved through single or iterative rounds of site-saturation mutagenesis or random mutagenesis and screening to provide enzyme variants capable of chiral amine derivative synthesis in presence of diazo substrates and amines as shown, for example, in Scheme 6. In some embodiments, a lineage of enzymes derived from P411-C10, having mutations at the positions T327, Q437, A87, A264, S332, E267, and V328 to other amino acids, is provided for chiral amine derivative synthesis.

Scheme 6

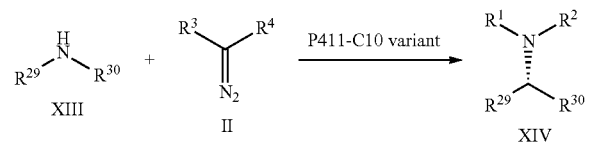

Accordingly, some embodiments of the present disclosure provide methods wherein:

the reaction mixture comprises a first enzyme substrate according to Formula XIII

(XIII)

and
a second enzyme substrate according to Formula II

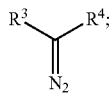 (II)

the insertion product is a substituted amine according to Formula XIV

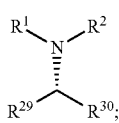 (XIV)

and
the enzyme catalyst optionally comprises 1-6 mutations at positions 327, 437, 332, 87, 264, 327;
and wherein:
$R^3$, $R^4$, $R^{29}$, and $R^{30}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R')_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$; and
each $R^7$, $R^8$, and $R^9$ is independently selected from the group consisting of H, $C_{1-6}$ alkyl, and optionally substituted $C_{6-10}$ aryl.
In some embodiments:
$R^3$, $R^{29}$, and $R^{30}$ are independently selected from the group consisting of substituted $C_{1-6}$ alkyl, $C_{2-6}$ alkenyl, substituted $C_{6-10}$ aryl, and substituted 6- to 10-membered heteroaryl;
$R^4$ is selected from the group consisting of $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, cyano and $P(O)(OR^7)_2$; and each $R^7$ and $R^8$ is independently selected from the group consisting of H, $C_{1-6}$ alkyl, and substituted $C_{6-10}$ aryl.
In some embodiments, the enzyme catalyst for N—H insertion comprises 1-6 mutations at positions 327, 437, 332, 87, 264, and 327. In some embodiments:
the mutation at position 327 is a mutation to valine or another hydrophobic amino acid,
the mutation at position 437 is a mutation to leucine or another hydrophobic amino acid,
the mutation at position 332 is a mutation to alanine or another hydrophobic amino acid,
the mutation at position 87 is a mutation to proline or another hydrophobic amino acid,
the mutation at position 264 is a mutation to serine or another polar amino acid, and
the mutation at position 327 is a mutation to proline or another hydrophobic amino acid.
Compounds according to Formulas I-XIV can be further substituted. Suitable monovalent substituents on a substitutable carbon atom of an "optionally substituted" group are independently halogen; —$(CH_2)_{0-4}R^\alpha$; —$(CH_2)_{0-4}OR^\alpha$; —$O(CH_2)_{0-4}R^\alpha$, —O—$(CH_2)_{0-4}C(O)OR^\alpha$; —$(CH_2)_{0-4}CH(OR^\alpha)_2$; —$(CH_2)_{0-4}SR^\alpha$; —$(CH_2)_{0-4}Ph$, wherein Ph is phenyl which may be substituted with $R^\alpha$; —$(CH_2)_{0-4}O(CH_2)_{0-1}$phenyl, which phenyl may be substituted with $R^\alpha$; —CH=CHPh, wherein Ph is phenyl which may be substituted with $R^\alpha$; —$(CH_2)_{0-4}O(CH_2)_{0-1}$-Py, wherein Py is pyridyl which may be substituted with $R^\alpha$; —$NO_2$; —CN; —$N_3$; —$(CH_2)_{0-4}N(R^\alpha)_2$; —$(CH_2)_{0-4}N(R^\alpha)C(O)R^\alpha$; —$N(R^\alpha)C(S)R^\alpha$; —$(CH_2)_{0-4}N(R^\alpha)C(O)NR^\alpha_2$; —$N(R^\alpha)C(S)NR^\alpha_2$; —$(CH_2)_{0-4}N(R^\alpha)C(O)OR^\alpha$; —$N(R^\alpha)N(R^\alpha)C(O)R^\alpha$; —$N(R^\alpha)N(R^\alpha)C(O)NR^\alpha_2$; —$N(R^\alpha)N(R^\alpha)C(O)OR^\alpha$; —$(CH_2)_{0-4}C(O)R^\alpha$; —$C(S)R^\alpha$; —$(CH_2)_{0-4}C(O)OR^\alpha$; —$(CH_2)_{0-4}C(O)SR^\alpha$; —$(CH_2)_{0-4}C(O)OSiR^\alpha_3$; —$(CH_2)_{0-4}OC(O)R^\alpha$; —$OC(O)(CH_2)_{0-4}SR$—$SC(S)SR^\alpha$; —$(CH_2)_{0-4}SC(O)R^\alpha$; —$(CH_2)_{0-4}C(O)NR^\alpha_2$; —$C(S)NR^\alpha_2$, —$C(S)SR^\alpha$; —$SC(S)SR^\alpha$, —$(CH_2)_{0-4}OC(O)NR^\alpha_2$; —$C(O)N(OR^\alpha)R^\alpha$; —$C(O)C(O)R^\alpha$; —$C(O)CH_2C(O)R^\alpha$; —$C(NOR^\alpha)R^\alpha$; —$(CH_2)_{0-4}SSR^\alpha$; —$(CH_2)_{0-4}S(O)_2R^\alpha$; —$(CH_2)_{0-4}S(O)_2OR^\alpha$; —$(CH_2)_{0-4}OS(O)_2R^\alpha$; —$S(O)_2NR^\alpha_2$; —$(CH_2)_{0-4}S(O)R^\alpha$; —$N(R^\alpha)S(O)_2NR^\alpha_2$; —$N(R^\alpha)S(O)_2R^\alpha$; —$N(OR^\alpha)R^\alpha$; —$C(NH)NR^\alpha_2$; —$P(O)_2R^\alpha$; —$P(O)R^\alpha_2$; —$OP(O)R^\alpha_2$; —$OP(O)(OR^\alpha)_2$; $SiR^\alpha_3$; —$(C_{1-4}$ straight or branched)alkylene)-O—$N(R^\alpha)_2$; or —$(C_{1-4}$ straight or branched)alkylene)-C(O)O—$N(R^\alpha)_2$. Each $R^\alpha$ is independently hydrogen; $C_{1-6}$ alkyl; —$CH_2Ph$, —$O(CH_2)_{0-1}Ph$; —$CH_2$-(5- to 6-membered heteroaryl); $C_{3-8}$ cycloalkyl; $C_{6-10}$ aryl; 4- to 10-membered heterocyclyl; or 6- to 10-membered heteroaryl; and each $R^\alpha$ may be further substituted as described below.

Suitable monovalent substituents on $R^\alpha$ are independently halogen, —$(CH_2)_{0-2}R^\beta$; —$(CH_2)_{0-2}OH$; —$(CH_2)_{0-2}OR^\beta$; —$(CH_2)_{0-2}CH(OR^\beta)_2$; —CN; —$N_3$; —$(CH_2)_{0-2}C(O)R^\beta$; —$(CH_2)_{0-2}C(O)OH$; —$(CH_2)_{0-2}C(O)OR^\beta$; —$(CH_2)_{0-2}SR^\beta$; —$(CH_2)_{0-2}SH$; —$(CH_2)_{0-2}NH_2$; —$(CH_2)_{0-2}NHR^\beta$; —$(CH_2)_{0-2}NR^\beta_2$; —$NO_2$; $SiR^\beta_3$; —$OSiR^\beta_3$; —$C(O)SR^\beta$; —$(C_{1-4}$ straight or branched alkylene)-C(O)OR^\beta$; or —$SSR^\beta$; wherein each $R^\beta$ is independently selected from $C_{1-4}$ alkyl; —$CH_2Ph$; —$O(CH_2)_{0-1}Ph$; $C_{3-8}$ cycloalkyl; $C_{6-10}$ aryl; 4- to 10-membered heterocyclyl; or 6- to 10-membered heteroaryl. Suitable divalent substituents on a saturated carbon atom of $R^\alpha$ include =O and =S.

Suitable divalent substituents on a saturated carbon atom of an "optionally substituted" group include the following: =O; =S; =$NNR^\gamma_2$; =NNHC(O)$R^\gamma$; =NNHC(O)O$R^\gamma$; =NNHS(O)$_2R^\gamma$; =$NR^\gamma$; =$NOR^\gamma$; —$O(C(R^\gamma_2))_{2-3}O$—; or —$S(C(R^\gamma_2))_{2-3}S$—; wherein each independent occurrence of $R^\gamma$ is selected from hydrogen; $C_{1-6}$ alkyl, which may be substituted as defined below; $C_{3-8}$ cycloalkyl; $C_{6-10}$ aryl; 4- to 10-membered heterocyclyl; or 6- to 10-membered heteroaryl. Suitable divalent substituents that are bound to vicinal substitutable carbons of an "optionally substituted" group include: —$O(CR^\beta_2)_{2-3}O$—; wherein each independent occurrence of $R^\beta$ is selected from hydrogen; $C_{1-6}$ alkyl which may be substituted as defined below; $C_{3-8}$ cycloalkyl; $C_{6-10}$ aryl; 4- to 10-membered heterocyclyl; or 6- to 10-membered heteroaryl.

Suitable substituents on the alkyl group of $R^\gamma$ include halogen; —$R^\delta$; —OH; —$OR^\delta$; —CN; —C(O)OH; —C(O)$OR^\delta$; —$NH_2$; —$NHR^\delta$; —$NR^\delta_2$; or —$NO_2$; wherein each $R^\delta$ is independently $C_{1-4}$ alkyl; —$CH_2Ph$; —$O(CH_2)_{0-1}Ph$; 4- to 10-membered heterocyclyl; or 6- to 10-membered heteroaryl.

Suitable substituents on a substitutable nitrogen of an "optionally substituted" group include —$R^\varepsilon$; —$NR^\varepsilon_2$; —$C(O)R^\varepsilon$; —$C(O)OR^\varepsilon$; —$C(O)C(O)R^\varepsilon$; —$C(O)CH_2C(O)R^\varepsilon$; —$S(O)_2R^\varepsilon$; —$S(O)_2NR^\varepsilon_2$; —$C(S)NR^\varepsilon_2$; —$C(NH)NR^\varepsilon_2$; or —$N(R^\varepsilon)S(O)_2R^\varepsilon$; wherein each $R^\varepsilon$ is independently hydrogen; $C_{1-6}$ alkyl which may be substituted as defined below; $C_{3-8}$ cycloalkyl; $C_{6-10}$ aryl; 4- to 10-membered heterocyclyl; or 6- to 10-membered heteroaryl.

Suitable substituents on the alkyl group of $R^\epsilon$ are independently halogen; —$R^\delta$; —OH; —$OR^\delta$; —CN; —C(O)OH; —C(O)$OR^\delta$; —$NH_2$; —$NHR^\delta$; —$NR^\delta{}_2$; or —$NO_2$; wherein each $R^\delta$ is independently $C_{1-4}$ alkyl; —$CH_2$Ph; —$O(CH_2)_{0-1}$Ph; $C_{6-10}$ aryl; 4- to 10-membered heterocyclyl; or 6- to 10-membered heteroaryl.

G. Engineering of Hemoprotein Catalysts

One skilled in the art will appreciate that the hemoprotein catalysts described herein can be improved through the introduction of additional DNA mutations which alter the resulting amino acid sequence of the hemoprotein so as to generate a catalyst that is highly productive and selective for the desired carbene-transfer reactions. In particular, there are many examples in the scientific literature that describe processes through which the enantioselectivity and activity of carbene-transfer hemoproteins can be optimized. Specifically, one skilled in the art will know that through a process of random mutagenesis via error-prone PCR, or through a process of site-directed mutagenesis in which one or more codons are randomized sequentially or simultaneously, or through a process of gene synthesis in which random or directed mutations are introduced, many different mutants of the genes encoding the hemoprotein catalysts described herein can be generated. The activities and other important features (e.g., selectivities, stabilities) of the enzymes encoded by these genes can be assessed by methods known to one skilled in the art. One skilled in the art will appreciate that enzyme catalyst variants can be expressed in a whole cell using an expression vector under the control of an inducible promoter or by means of chromosomal integration under the control of a constitutive promotor. The activities of whole cell catalysts, cell lysates or purified proteins for different carbene-transfer reactions can be screened by GC or HPLC, using parameters including but not limited to turnovers and selectivities as selection criteria to find beneficial mutations.

One skilled in the art will understand that hemoprotein mutants identified as improved in the carbene-transfer reactions can themselves be subjected to additional mutagenesis as described herein, resulting in progressive, cumulative improvements in one or more reaction parameters including but not limited to turnover frequency, total turnover number, yield, chemoselectivity, regioselectivity, diastereoselectivity, enantioselectivity, expression, thermostability, or solvent tolerance.

In some embodiments, the hemoprotein mutant comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to any of the amino acid sequences described herein (e.g, the amino acid sequence of a P411-C10 variant WIRF according to SEQ ID NO:5, or an amino acid sequences according to any one of SEQ ID NOS: 1-4 and 6-25). Additional amino acid residues may be present at the N-terminus or C-terminus of any of these sequences (e.g., a starting methionine ("M") residue at the N-terminus, or a sequence containing a purification tag such as LEHHHHHH (SEQ ID NO:27) at the C-terminus).

In some embodiments, the enzyme catalyst has a turnover frequency (TOF) between about 1 $min^{-1}$ and 10 $min^{-1}$ (e.g., about 1 $min^{-1}$, 1.5 $min^{-1}$, 2 $min^{-1}$, 2.5 $min^{-1}$, 3 $min^{-1}$, 3.5 $min^{-1}$, 4 $min^{-1}$, 4.5 $min^{-1}$, 5 $min^{-1}$, 5.5 $min^{-1}$, 6 $min^{-1}$, 6.5 $min^{-1}$, 7 $min^{-1}$, 7.5 $min^{-1}$, 8 $min^{-1}$, 8.5 $min^{-1}$, 9 $min^{-1}$, 9.5 $min^{-1}$, or 10 $min^{-1}$). In other embodiments, the TOF is between about 10 $min^{-1}$ and 100 $min^{-1}$ (e.g., about 10 $min^{-1}$, 11 $min^{-1}$, 12 $min^{-1}$, 13 $min^{-1}$, 14 $min^{-1}$, 15 $min^{-1}$, 16 $min^{-1}$, 17 $min^{-1}$, 18 $min^{-1}$, 19 $min^{-1}$, 20 $min^{-1}$, 21 $min^{-1}$, 22 $min^{-1}$, 23 $min^{-1}$, 24 $min^{-1}$, 25 $min^{-1}$, 26 $min^{-1}$, 27 $min^{-1}$, 28 $min^{-1}$, 29 $min^{-1}$, 30 $min^{-1}$, 31 $min^{-1}$, 32 $min^{-1}$, 33 $min^{-1}$, 34 $min^{-1}$, 35 $min^{-1}$, 36 $min^{-1}$, 37 $min^{-1}$, 38 $min^{-1}$, 39 $min^{-1}$, 40 $min^{-1}$, 41 $min^{-1}$, 42 $min^{-1}$, 43 $min^{-1}$, 44 $min^{-1}$, 45 $min^{-1}$, 46 $min^{-1}$, 47 $min^{-1}$, 48 $min^{-1}$, 49 $min^{-1}$, 50 $min^{-1}$, 55 $min^{-1}$, 60 $min^{-1}$, 65 $min^{-1}$, 70 $min^{-1}$, 75 $min^{-1}$, 80 $min^{-1}$, 85 $min^{-1}$, 90 $min^{-1}$, 95 $min^{-1}$, or 100 $min^{-1}$). In other instances, the TOF is greater than about 100 $min^{-1}$ to 1,000 $min^{-1}$ (e.g., greater than about 100 $min^{-1}$, 150 $min^{-1}$, 200 $min^{-1}$, 250 $min^{-1}$, 300 $min^{-1}$, 350 $min^{-1}$, 400 $min^{-1}$, 450 $min^{-1}$, 500 $min^{-1}$, 550 $min^{-1}$, 600 $min^{-1}$, 650 $min^{-1}$, 700 $min^{-1}$, 750 $min^{-1}$, 800 $min^{-1}$, 850 $min^{-1}$, 900 $min^{-1}$, 950 $min^{-1}$, 1,000 $min^{-1}$, or more). In some instances, the TOF is greater than about 10 $min^{-1}$. In other instances, the TOF is greater than about 45 $min^{-1}$.

In other embodiments, the enzyme catalyst has a total turnover number (TTN), which refers to the maximum number of molecules of a substrate that the protein can convert before becoming inactivated, of between about 1 and 100 (e.g, about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100). In some other embodiments, the TTN is between about 100 and 1,000 (e.g, about 100, 150, 200, 250, 300, 350, 400, 450, 500, 550, 600, 650, 700, 750, 800, 850, 900, 950, or 1,000). In some embodiments, the TTN is between about 1,000 and 2,000 (e.g, about 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950 or 2,000). In other embodiments, the TTN is at least about 2,000 (e.g, at least about 2,000, 2,500, 3,000, 3,500, 4,000, 4,500, 5,000, 5,500, 6,000, 6,500, 7,000, 7,500, 8,000, 8,500, 9,000, 9,500, or 10,000). In some instances, the TTN is greater than about 70. In other instances, the TTN is greater than about 2,000.

In some embodiments, an engineered enzyme catalyst variant has enhanced activity of at least about 1.5 to 2,000 fold (e.g, at least about 1.5, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, or more) fold compared to the corresponding parent protein.

In some embodiments, activity is expressed in terms of turnover frequency (TOF). In particular embodiments, the TOF of the engineered enzyme catalyst variant is at least about 1.5, 2, 2.5, 3, 3.5, 4, 4.5, 5, 5.5, 6, 6.5, 7, 7.5, 8, 8.5, 9, 9.5, or 10 fold higher than the corresponding parent protein.

In other instances, activity is expressed in terms of total turnover number (TTN). In particular instances, the TTN of the engineered enzyme catalyst variant is about least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, or 2,000 fold higher than the corresponding parent protein.

In certain embodiments, mutations can be introduced into the target gene using standard cloning techniques (e.g site-directed mutagenesis, site-saturated mutagenesis) or by gene synthesis to produce the enzyme catalysts. In some embodiments, the heme variant is recombinantly expressed and optionally isolated and/or purified for carrying out the in vitro carbon-hydrogen carbene insertion reactions of the present disclosure. In other embodiments, the enzyme catalyst, fragment thereof, variant thereof, or homolog thereof is expressed in whole cells such as bacterial cells, archaeal cells, yeast cells, fungal cells, insect cells, plant cells, or mammalian cells, and these cells are used for carrying out the in vivo carbon-hydrogen carbene insertion reactions. The wild-type or mutated gene can be expressed in a whole cell using an expression vector under the control of an inducible promoter or by means of chromosomal integration under the control of a constitutive promoter. Carbon-hydrogen carbene insertion activity can be screened in vivo or in vitro by following product formation by GC or HPLC.

Suitable bacterial host cells include, but are not limited to, BL21 *E. coli*, DE3 strain *E. coli*, *E. coli* M15, DH5α, DH10P, HB101, T7 Express Competent if *coli* (NEB), *B. subtilis* cells, *Pseudomonas fluorescens* cells, and cyanobacterial cells such as *Chlamydomonas reinhardtii* cells and *Synechococcus elongates* cells. Non-limiting examples of archaeal host cells include *Pyrococcus furiosus*, *Metallosphera sedula*, *Thermococcus litoralis*, *Methanobacterium thermoautotrophicum*, *Methanococcus jannaschii*, *Pyrococcus abyssi*, *Sulfolobus solfataricus*, *Pyrococcus woesei*, *Sulfolobus shibatae*, and variants thereof. Fungal host cells include, but are not limited to, yeast cells from the genera *Saccharomyces* (e.g., *S. cerevisiae*), *Pichia* (*P. Pastoris*), *Kluyveromyces* (e.g., *K. lactis*), *Hansenula* and *Yarrowia*, and filamentous fungal cells from the genera *Aspergillus*, *Trichoderma*, and *Myceliophthora*. Suitable insect host cells include, but are not limited to, Sf9 cells from *Spodoptera frugiperda*, Sf21 cells from *Spodoptera frugiperda*, Hi-Five cells, BTI-TN-5B1-4 *Trichophusia ni* cells, and Schneider 2 (S2) cells and Schneider 3 (S3) cells from *Drosophila melanogaster*. Non-limiting examples of mammalian host cells include HEK293 cells, HeLa cells, CHO cells, COS cells, Jurkat cells, NS0 hybridoma cells, baby hamster kidney (BHK) cells, MDCK cells, NIH-3T3 fibroblast cells, and any other immortalized cell line derived from a mammalian cell. Non-limiting examples of plant host cells include those from tobacco, tomato, potato, maize, rice, lettuce, and spinach. In general, cells from plants that have short generation times and/or yield reasonable biomass with standard cultivation techniques are preferable.

In certain embodiments, enzyme catalysts inside living cells are provided. As a non-limiting example, bacterial cells (e.g, *E. coli*) can be used as host whole cell catalysts for the in vivo carbon-hydrogen carbene insertion reactions, although any number of host whole cells may be used, including but not limited to the host cells described herein. In some embodiments, host whole cell catalysts containing enzyme catalysts can significantly enhance the total turnover number (TTN) compared to the in vitro reactions using isolated enzyme catalysts.

The expression vector comprising a nucleic acid sequence that encodes the enzyme catalyst can be a viral vector, a plasmid, a phage, a phagemid, a cosmid, a fosmid, a bacteriophage (e.g, a bacteriophage PI-derived vector (PAC)), a baculovirus vector, a yeast plasmid, or an artificial chromosome (e.g, bacterial artificial chromosome (BAC), a yeast artificial chromosome (YAC), a mammalian artificial chromosome (MAC), and human artificial chromosome (HAC)). Expression vectors can include chromosomal, non-chromosomal, and synthetic DNA sequences. Equivalent expression vectors to those described herein are known in the art and will be apparent to the ordinarily skilled artisan.

The expression vector can include a nucleic acid sequence encoding an enzyme catalyst that is operably linked to a promoter, wherein the promoter comprises a viral, bacterial, archaeal, fungal, insect, plant, or mammalian promoter. In certain embodiments, the promoter is a constitutive promoter. In some embodiments, the promoter is an inducible promoter. In other embodiments, the promoter is a tissue-specific promoter or an environmentally regulated or a developmentally regulated promoter.

In some embodiments, the nucleic acid sequence encodes an enzyme catalyst that comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to any one of the amino acid sequences set forth herein, or any particular variant thereof. In other embodiments, the nucleic acid sequence encodes an enzyme catalyst that comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to any one of the amino acid sequences set forth herein, or any particular variant thereof. In particular embodiments, the nucleic acid sequence encodes an enzyme catalyst that comprises an amino acid sequence that has about 90% or greater (e.g, about 90%, 91%, 92%, 93%, 94%, 95%, 96%, 97%, 98%, 99%, or 100%) identity to any one of the amino acid sequences set forth herein, or any particular variant thereof. In some instances, the nucleic acid sequence encodes an enzyme catalyst that comprises an amino acid sequence that is about 95%, 96,%, 97%, 98%, 99%, or 100% identical to any one of the amino acid sequences set forth herein, or any particular variant thereof.

In other embodiments, the nucleic acid sequence encodes an enzyme catalyst that comprises an amino acid sequence that contains between about 5 and 125 (e.g, about 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 125) of the amino acids in any one of the polypeptide sequences disclosed herein, or any particular variant thereof. The amino acids may be contiguous, or separated by any number of amino acids.

It is understood that affinity tags may be added to the N- and/or C-terminus of an enzyme catalyst, fragment thereof, variant thereof, or homolog thereof expressed using an expression vector to facilitate protein purification. Non-limiting examples of affinity tags include metal binding tags such as His6 (SEQ ID NO:26) tags and other tags such as glutathione S-transferase (GST).

Non-limiting expression vectors for use in bacterial host cells include pCWori, pET vectors such as pET22 (EMD Millipore), pBR322 (ATCC37017), pQE™ vectors (Qiagen), pBluescript™ vectors (Stratagene), pNH vectors, lambda-ZAP vectors (Stratagene); ptrc99a, pKK223-3, pDR540, pRIT2T (Pharmacia), pRSET, pCR-TOPO vectors, pET vectors, pSyn_1 vectors, pChlamy_1 vectors (Life Technologies, Carlsbad, Calif.), pGEM1 (Promega, Madison, Wis.), and pMAL (New England Biolabs, Ipswich, Mass.). Non-limiting examples of expression vectors for use in eukaryotic host cells include pXT1, pSG5 (Stratagene), pSVK3, pBPV, pMSG, pSVLSV40 (Pharmacia), pcDNA3.3, pcDNA4/TO, pcDNA6/TR, pLenti6/TR, pMT vectors (Life Technologies), pKLAC1 vectors, pKLAC2 vectors (New England Biolabs), pQE™ vectors (Qiagen), BacPak baculoviral vectors, pAdeno-X™ adenoviral vectors (Clontech), and pBABE retroviral vectors. Any other vector may be used as long as it is replicable and viable in the host cell.

H. Carbene Insertion Reaction Conditions

The enzyme catalysts provided herein can be used in purified form, partially purified form, or as whole-cell (e.g., bacterial) catalysts, without purification. Many enzyme substrates (e.g., alkynes, carbene precursors, or the like) can enter *E. coli* cells and interact with the enzymes inside the cells, where the reaction takes place. Thus the desired products can be made in a process wherein intact or partially permeabilized cells expressing the enzyme catalyst are suspended in buffer and combined with substrates such as carbene precursors (dissolved in appropriate solvent or in a form of suspension) and allowed to react. The process can also use purified or partially purified protein in place of whole bacterial cells. Other processes can involve changing contacting conditions (e.g., maintaining the catalyst in a compartment such as behind a filter membrane or bag through which reactants and products can pass or immobilizing the catalyst in some other way).

In some embodiments, methods according to the present disclosure are carried out in vitro. In other embodiments, the enzyme catalyst is localized within a whole cell and the method is carried out in vivo. In some embodiments, the enzyme catalyst is expressed in a bacterial, archaeal, yeast or fungal host organism. In some embodiments, the method is carried out under anaerobic conditions. In other embodiments, the process is carried out under aerobic conditions.

In some embodiments, the enzyme catalyst may be purified prior to addition to a reaction mixture or secreted by a cell present in the reaction mixture. The reaction mixture can contain a cell lysate including the enzyme catalyst, as well as other proteins and other cellular materials. Alternatively, an enzyme catalyst can catalyze the reaction within a cell expressing the catalyst. Any suitable amount of the enzyme catalyst can be used in the methods. In general, the reaction mixtures will contain at least about 0.01 mol % to about 10 mol % enzyme catalyst with respect to the carbene precursor (e.g., diazo reagent) and/or additional substrate. The reaction mixtures can contain, for example, from about 0.01 mol % to about 0.1 mol % enzyme catalyst, or from about 0.1 mol % to about 1 mol % enzyme catalyst, or from about 1 mol % to about 10 mol % enzyme catalyst. The reaction mixtures can contain from about 0.05 mol % to about 5 mol % enzyme catalyst, or from about 0.05 mol % to about 0.5 mol % enzyme catalyst. The reaction mixtures can contain about 0.1, 0.2, 0.3, 0.4, 0.5, 0.6, 0.7, 0.8, 0.9, or about 1 mol % enzyme catalyst.

The concentrations of the carbene precursor (e.g., a diazo reagent) and other enzyme substrates are typically in the range of from about 100 µM to about 1 M. The concentration can be, for example, from about 100 µM to about 1 mM, or about from 1 mM to about 100 mM, or from about 100 mM to about 500 mM, or from about 500 mM to 1 M. The concentration can be from about 500 µM to about 500 mM, 500 µM to about 50 mM, or from about 1 mM to about 50 mM, or from about 15 mM to about 45 mM, or from about 15 mM to about 30 mM. The concentration of the enzyme substrate(s) can be, for example, about 100, 200, 300, 400, 500, 600, 700, 800, or 900 µM. The concentration of the enzyme substrate(s) can be about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500 mM.

Reaction mixtures can contain additional reagents. As non-limiting examples, the reaction mixtures can contain buffers (e.g, M9-N buffer, 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, $CaCl_2$, and salts of $Mn^{2+}$ and $Mg^{2+}$), denaturants (e.g, urea and guanadinium hydrochloride), detergents (e.g, sodium dodecylsulfate and Triton-X 100), chelators (e.g., ethylene glycol-bis(2-aminoethylether)-N,N,N',N'-tetraacetic acid (EGTA), 2-({2-[Bis(carboxymethyl)amino]ethyl} (carboxymethyl)amino)acetic acid (EDTA), and 1,2-bis(o-aminophenoxy)ethane-N,N,N',N'-tetraacetic acid (BAPTA)), sugars (e.g, glucose, sucrose, and the like), and reducing agents (e.g, sodium dithionite, NADPH, dithiothreitol (DTT), β-mercaptoethanol (BME), and tris(2-carboxyethyl)phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 µM to about 1 M. For example, a buffer, a cosolvent, a salt, a denaturant, a detergent, a chelator, a sugar, or a reducing agent can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. In some embodiments, a reducing agent is used in a sub-stoichiometric amount with respect to the olefin substrate and the diazo reagent. Cosolvents, in particular, can be included in the reaction mixtures in amounts ranging from about 1% v/v to about 75% v/v, or higher. A cosolvent can be included in the reaction mixture, for example, in an amount of about 5, 10, 20, 30, 40, or 50% (v/v).

Reactions are conducted under conditions sufficient to catalyze the formation of the desired product. The reactions can be conducted at any suitable temperature. In general, the reactions are conducted at a temperature of from about 4° C. to about 40° C. The reactions can be conducted, for example, at about 25° C. or about 37° C. The enzyme catalysts or cells expressing or containing the enzyme catalysts can be heat treated. In some embodiments, heat treatment occurs at a temperature of about 75° C. The reactions can be conducted at any suitable pH. In general, the reactions are conducted at a pH of from about 6 to about 10. The reactions can be conducted, for example, at a pH of from about 6.5 to about 9 (e.g, about 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0). The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. The reactions can be conducted for about 1 to 4 hours (e.g., 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or 4 hours). Reactions can be conducted under aerobic conditions or anaerobic conditions. Reactions can be conducted under an inert atmosphere, such as a nitrogen atmosphere or argon atmosphere. In some embodiments, a solvent is added to the reaction mixture. In some embodiments, the solvent forms a second phase, and the carbene insertion reaction occurs in the aqueous phase. In some embodiments, the enzyme catalyst is located in the aqueous layer whereas the substrates and/or products occur in an organic layer. Other reaction conditions may be employed in the methods, depending on the identity of a particular enzyme catalyst or substrate (e.g., diazo reagent).

Reactions can be conducted in vivo with intact cells expressing an enzyme catalyst. The in vivo reactions can be conducted with any of the host cells used for expression of the heme enzymes, as described herein. A suspension of cells can be formed in a suitable medium supplemented with nutrients (such as mineral micronutrients, glucose and other fuel sources, and the like). Product yields from reactions in vivo can be controlled, in part, by controlling the cell density in the reaction mixtures. Cellular suspensions exhibiting optical densities ranging from about 0.1 to about 50 at 600 nm can be used for the product-forming reactions. Other densities can be useful, depending on factors such as the cell type or the specific enzyme catalyst.

The methods provided herein can be assessed in terms of the diastereoselectivity and/or enantioselectivity of carbene insertion into carbon-carbon bonds or other target bonds—that is, the extent to which the reaction produces a particular isomer, whether a diastereomer or enantiomer. A perfectly selective reaction produces a single isomer, such that the isomer constitutes 100% of the product. As another non-limiting example, a reaction producing a particular enantiomer constituting 90% of the total product can be said to be 90% enantioselective. A reaction producing a particular diastereomer constituting 30% of the total product, meanwhile, can be said to be 30% diastereoselective.

In general, the methods include reactions that are from about 1% to about 99% diastereoselective. The reactions are from about 1% to about 99% enantioselective. The reaction can be, for example, from about 10% to about 90% diastereoselective, or from about 20% to about 80% diastereoselective, or from about 40% to about 60% diastereoselective, or from about 1% to about 25% diastereoselective, or from about 25% to about 50% diastereoselective, or from about 50% to about 75% diastereoselective. The reaction can be about 10%, 15%, 20%, 25%, 30%, 35%, 40%, 45%, 50%, 55%, 60%, 65%, 70%, 75%, 80%, 85%, 90%, or about 95% diastereoselective. The reaction can be from about 10% to about 90% enantioselective, from about 20% to about 80% enantioselective, or from about 40% to about 60% enantioselective, or from about 1% to about 25% enantioselective, or from about 25% to about 50% enantioselective, or from about 50% to about 75% enantioselective. The reaction can be about 10%, 15%, 20%, 25%, 30%, 35%, 40%, 45%, 50%, 55%, 60%, 65%, 70%, 75%, 80%, 85%, 90%, or about 95% enantioselective. Accordingly, some embodiments provide methods wherein the reaction is at least 30% to at least 90% diastereoselective. In some embodiments, the reaction is at least 30% to at least 90% enantioselective. Preferably, the reaction is at least 80% (e.g., at least about 80%, 81%, 82%, 83%, 84%, 85%, 86%, 87%, 88%, 89%, 90%, 91%, 92%, 93%, 94%, 95%, 96%, 97%, 98%, 99%, or 100%) enantioselective. More preferably, the reaction is at least 90% (e.g., at least about 90%, 91%, 92%, 93%, 94%, 95%, 96%, 97%, 98%, 99%, or 100%) enantioselective.

III. EXAMPLES

Example 1: Engineering P411-C10 Variants by Site-Saturation Mutagenesis and Screening Cloning and site-saturation mutagenesis. pET22b(+) containing a C-terminal 6x-His (SEQ ID NO:26) tag was used as a cloning and expression vector for all enzymes described in this study. Site-saturation mutagenesis was performed using a modified QuikChange™ mutagenesis protocol.[10] Primer sequences are available upon request. The PCR products were digested with DpnI, gel purified, and fragments were assembled using Gibson Mix.[11] The ligation mixture was used to directly transform *Escherichia coli* strain BL21 E. Cloni® (Lucigen). Cells were grown using Luria-Bertani medium (LB) or Hyperbroth (AthenaES) (HB) with 0.1 mg/mL ampicillin ($LB_{amp}$ or $HB_{amp}$). Electrocompetent *E. coli* cells were prepared following the protocol of Sambrook et al.[12] T5 exonuclease, Phusion polymerase, and Taq ligase were purchased from New England Biolabs (NEB, Ipswich, Mass.). M9-N minimal medium (abbreviated as M9-N buffer; pH 7.4) was used as a buffering system for whole cells, lysates, and purified proteins, unless otherwise specified. M9-N buffer was used without a carbon source; it contains 47.7 mM $Na_2HPO_4$, 22.0 mM $KH_2PO_4$, 8.6 mM NaCl, 2.0 mM $MgSO_4$, and 0.1 mM $CaCl_2$.

Reaction screening in 96-well plate format. Libraries (single-site-saturation libraries generated employing the "22c-trick" method[9]) were screened in 96-well plates.

*E. coli* libraries for P411 variants were cultured in $LB_{amp}$ (300 μL/well) at 37° C., 250 rpm and 80% relative humidity overnight. $HB_{amp}$ (950 μL/well) was inoculated with the pre-culture (50 μL/well) and incubated at 37° C., 230 rpm, 80% humidity for 2 h and 45 min. The plates were cooled on ice for 30 minutes, and expression was induced with 0.5 mM IPTG and 1.0 mM 5-aminolevulinic acid (final concentrations). Expression was conducted at 22° C. and 220 rpm for 20 h.

The cells were pelleted (4,500×g, 5 min, 4° C.) and resuspended with M9-N buffer (340 μL/well) and D-glucose solution (40 μL/well, in M9-N). The 96-well plate was then transferred to an anaerobic chamber. In the anaerobic chamber, substrate 1 (10 μL/well, 400 mM in EtOH) and substrate 2 (10 μL/well, 400 mM in EtOH). The plate was sealed with an aluminum foil and shaken inside the anaerobic chamber at 600 rpm.

After certain amount of time, the seal was removed and acetonitrile (600 μL/well) was added. The plate was tightly sealed with a reusable silicone mat, vortexed (15 s×3) and centrifuged (4,500×g, 5 min). The supernatant (200 μL/well) was filtered through an AcroPrep 96-well filter plate (0.2 μm) into a shallow-well plate for reversed-phase HPLC or LC-MS analysis. Alternatively, the reactions could also be worked up by adding ethyl acetate/hexane mixed solvent (600 μL/well). And then the plate was tightly sealed with a reusable silicone mat, vortexed (15 s×3) and centrifuged (4,500×g, 5 min). The organic layer (200 μL/well) was transferred to glass vials with inserts for GC or GC-MS analysis.

Example 2: Enzymatic Cyclopropenation to Yield Compounds of Formula III Using P411-C10 Variants In Vivo P411-C10 expression. 45 mL Hyperbroth (100 μg/mL ampicillin) was inoculated with an overnight culture of 5 mL LB (100 μg/mL ampicillin). The overnight culture contained recombinant E. coli BL21 (DE3) cells harboring a pET22 plasmid, encoding the P411-C10 variant under the control of the T7 promoter, and the P411-C10 maturation (ccm) operon under the control of a tet promoter, respectively. The cultures were shaken at 220 rpm at 37° C. for approximately 2 h 15 min. The flask containing the cells was placed on ice for 30 min. The incubator temperature was reduced to 20° C., maintaining the 140 rpm shake rate. Cultures were induced by adding IPTG and aminolevulinic acid to a final concentration of 0.5 mM and 0.5 mM respectively. The cultures were allowed to continue for another 18-22 hours at this temperature and shake rate. Cells were harvested by centrifugation (4° C. 5 min, 4,500×g) to produce a cell pellet.

Preparation of whole cell catalysts, o prepare whole cells for catalysis, the cell pellet prepared in the previous paragraph was resuspended in M9-N minimal media (M9 media without ammonium chloride) to an optical density ($OD_{600}$) of 15 to 30. The cell suspension was used as the catalyst.

Small-scale cyclopropanation reactions in whole-cell suspension under anaerobic conditions. Small-scale (400 μL) reactions were carried out in 2 mL glass crimp vials (Agilent Technologies, San Diego, Calif.). Cell suspension ($OD_{600}$=15 to 30, 340 μL) was added to an unsealed crimp vial before crimp sealing with a silicone septum. The headspace of the vial was flushed with argon for 10 min (no bubbling). A solution of D-glucose (40 μL, 250 mM) was added, followed by a solution of alkyne of formula I (10 μL, 400 mM in EtOH; for example, 4-phenylbutyne) and a solution of diazo reagent of formula II (10 μL, 400 mM in EtOH; for example, ethyl diazoethanoate or EDA). The reaction vial was left to shake on a plate shaker at 560 rpm for 6 h at room temperature. To quench the reaction, the vial was uncapped and a 1:1 mixture of ethylacetate/cyclohexane (1 mL) was added, followed by 1,3,5-trimethoxybenzene (20 μL, 20 mM in toluene) as an internal standard. The mixture was transferred to a 1.5 mL Eppendorf tube and vortexed and centrifuged (14000× ref, 5 min). The organic layer was analyzed by gas chromatography (GC), gas chromatography-mass spectrometry (GC-MS) or normal-phase chiral high performance liquid chromatography (HPLC).

The results of the small scale reactions are presented below and demonstrate that P411-C10 and variants thereof are capable of catalyzing the cyclopropenation to give product of formula III in Scheme 1 with high selectivity. The activity can be improved by further engineering, if desired. Specifically, the initial variant P411-C10 found in the initial screen of P450 BM3 variants, encoded the mutations N70E A74G V78L A82L F87A M118S P142S F162L T175I M177L A184V S226R H236Q E252G I263Y H266V T268G A290V A328V A330Y L353V I366V C400S I401L T436L L437Q E442K (mature peptide numbering convention) and with FAD domain truncated, which catalyzed the desired reaction with 55 TTN and >99% ee. Evolved P411-C10 variants containing mutations part or the whole set of Y263W, Q437I, L436R, S72F, S332G, G74A, and E70K were found with significantly improved activity (with up to 5400 TTN and >99.9% ee) towards the formation of desired cyclopropenes as shown in FIG. 1 and described in more detail below.

Example 3: Engineering Cytochrome P450s for Enantioselective Cyclopropenation of Internal Alkynes Cyclopropenes, with endo-cyclic double bonds inside a three-membered carbocycle, possess high strain energy, which enables activity in different strain-release transformations for constructing a myriad of useful molecular scaffolds.[1] Carbene transfer to alkynes represents one of the most straightforward approaches to constructing cyclopropenes.[1a, 1b] Small-molecule transition metal complexes based on rhodium, iridium, cobalt and others have been shown to catalyze carbene transfer to terminal alkynes to yield enantio-enriched cyclopropenes.[2-4] However, enantioselective carbene transfer to internal alkynes still remains largely unexplored. Only two systems with chiral gold/silver[5] or rhodium[6] (co-)catalysts have been reported to take internal aromatic alkynes for asymmetric cyclopropene synthesis with good stereoselectivities. These systems require precious metal catalysts in relatively high loading together with complicated ligands and have not been shown to work with internal aliphatic alkynes. We wanted to develop an efficient biocatalytic platform that uses earth-abundant iron to access internal cyclopropenes.

Cytochromes P450 use an iron-heme complex as their catalytic cofactor in their native oxygenase functions.[7] Recently, directed evolution has significantly expanded the catalytic repertoire of P450 enzymes and other hemeproteins to include non-natural carbene- and nitrene-transfer reactions, as described by our group and others.[8-10] We recently reported an enzymatic platform of engineered cytochrome P450 enzymes for stereoselective carbene addition to terminal alkynes to forge cyclopropenes and bicyclo[1.1.0]butanes.[11] We hypothesized that P450 enzymes may achieve even more challenging transformations, such as carbene transfer to internal alkynes for cyclopropene construction. The major difficulty for internal alkyne cyclopropenation lies in the severe steric clash between the linear 71-system and the planar heme cofactor, especially if the reaction involves a concerted carbene-transfer mechanism.[12] Recent mechanistic studies have shown step-wise carbene-transfer processes or even multiple pathways for the same type of reactions with different engineered hemeproteins.[13] We reasoned that proper engineering of the enzyme active site may direct the desired carbene transfer to proceed through a step-wise pathway, thereby circumventing the steric issue.

A. GENERAL PROCEDURES

General. Unless otherwise noted, all chemicals and reagents were obtained from commercial suppliers (Sigma-Aldrich, VWR, Alfa Aesar) and used without further purification. Silica gel chromatography was carried out using AMD Silica Gel 60, 230-400 mesh. $^1$H and $^{13}$C NMR spectra were taken using a Bruker Prodigy 400 MHz instrument and are internally referenced to the residual solvent peak (chloroform). Data for $^3$H NMR are reported as follows: chemical shift (δ ppm), multiplicity (s=singlet, d=doublet, t=triplet, q=quartet, p=pentet, m=multiplet, dd=doublet of doublets, dt=doublet of triplets, ddd=doublet of doublet of doublets), coupling constant (Hz), integration. Sonication was performed using a Qsonica Q500 sonicator. High-resolution mass spectra were obtained at the Catalysis Center of California Institute of Technology. Synthetic reactions were monitored using thin layer chromatography (Merck 60 gel plates) using a UV-lamp for visualization.

Chromatography. Analytical reversed-phase high-performance liquid chromatography (HPLC) was carried out using an Agilent 1200 series instrument and a poroshell C18 column (4.6×50 mm, 5 μm) with water and acetonitrile as the mobile phase and visualization at 254 nm for library screening. Analytical normal-phase HPLC was carried out using an Agilent 1200 series instrument and chiral columns Chiralpak IC (4.6 mm×25 cm) with n-hexane and isopropanol as the mobile phase and visualization at 254 nm for chiral separation. Gas chromatography (GC) analyses were carried out using an Agilent 7820A gas chromatograph, FID detector, and a J&W HP-5 column (30 m×0.32 mm, 0.25 μm film) and CycloSil-B column (30 m×0.25 mm, 0.25 μm film). Gas chromatography-mass spectrometry (GC-MS) analyses were carried out using a Shimadzu GCMS-QP2010SE system and J&W HP-5m column.

Cloning and site-saturation mutagenesis. pET22b(+) containing a C-terminal 6×-His (SEQ ID NO:26) tag was used as a cloning and expression vector for all enzymes described in this study. Site-saturation mutagenesis was performed using a modified QuikChange™ mutagenesis protocol (19). Primer sequences are available upon request. The PCR products were digested with DpnI, gel purified, and fragments were assembled using Gibson Mix (20). The ligation mixture was used to directly transform E. coli strain BL21 E. Cloni® (Lucigen). Cells were grown using Luria-Bertani medium (LB) or Hyperbroth (AthenaES) (HB) with 0.1 mg/mL ampicillin ($LB_{amp}$ or $HB_{amp}$). Electrocompetent E. coli cells were prepared following the protocol of Sambrook et al. (21). T5 exonuclease, Phusion polymerase, and Taq ligase were purchased from New England Biolabs (NEB, Ipswich, Mass.). M9-N minimal medium (abbreviated as M9-N buffer; pH 7.4) was used as a buffering system for whole cells, lysates, and purified proteins, unless otherwise specified. M9-N buffer was used without a carbon source; it contains 47.7 mM $Na_2HPO_4$, 22.0 mM $KH_2PO_4$, 8.6 mM NaCl, 2.0 mM $MgSO_4$, and 0.1 mM $CaCl_2$.

Determination of hemeprotein concentration—1. Preparation of cell lysate: Aliquots of ~3 mL $OD_{600}$=60 cells were prepared in 15 mL conical tubes, which were then placed on wet ice. Cells were lysed by sonication following the program below: sonication for 4 min, 1 second on-1 second off, 35% amplitude. The sonicated samples were then transferred to two Eppendorf tubes, and then centrifuged down (14,000 rpm, 15 min, 4° C.). The supernatants (~2.5 mL) were then collected to a 5-mL glass vial for analysis.

Determination of hemeprotein concentration—2. Hemechrome assay for protein concentration measurement: A solution of NaOH/pyridine was prepared by mixing 1 mL of NaOH aqueous solution (1 M), 2 mL of water and 2 mL of pyridine. To 4.5 mL of NaOH/pyridine solution, 22.5 μL of $K_3Fe(CN)_6$ aqueous solution (0.1 M) was added to make solution 1. A background solution was prepared by mixing 500 μL M9-N and 500 μL of the NaOH/pyridine solution, which was used for UV background subtraction. When measuring samples with a UV spectrometer, a spectrum of a mixed solution (oxidized spectrum) with 500 μL cell lysate+500 μL solution 1 was taken at the wavelength range 380 nm to 650 nm. Subsequently, 5 μL of dithionite solution (0.5 M in 0.1 M NaOH solution) was added to the same sample and mixed by pipetting; a spectrum of this solution (reduced spectrum) was taken at 380 nm to 650 nm. The protein concentration was calculated using the extinction coefficient and dilution factor (2× dilution in volume): $\varepsilon_{-}[557_{reduced}-540_{oxidized}]=23.98$ $mM^{-1}cm^{-1}$ (22).

Expression of P450 and P411 proteins. E. coli BL21 E. Cloni® cells carrying a plasmid encoding a P411 variant were grown overnight in 5 mL $LB_{amp}$ (37° C., 220 rpm). The pre-culture was used to inoculate 45 mL of $HB_{amp}$ in a 125 mL Erlenmeyer flask; this culture was incubated at 37° C., 220 rpm for 2 h and 15 min. Cultures were then cooled on ice for 40 min, and expression was induced with isopropyl β-d-1-thiogalactopyranoside (abbreviated as IPTG; final concentration: 0.5 mM) and 5-aminolevulinic acid (abbreviated as ALA; final concentration: 1.0 mM). Expression was conducted at room temperature (24° C.), at 140 rpm, for 20 h (±20 min). Cultures were then centrifuged (4,500×g, 5 min, 4° C.), and the pellets were resuspended to an $OD_{600}$ of 60 in M9-N buffer. Aliquots of the cell suspension (3 mL) were used to determine protein concentration after lysis by sonication. The expression level in $OD_{600}$=60 lysates is typically in the range of 6-13 μM for the P411-C10 variant.

Biotransformations. All the biocatalytic reactions were set up in an anaerobic chamber (oxygen level: <40 ppm). Resuspended cells (340 μL, diluted to a given $OD_{600}$ with M9-N buffer) were added to 2 mL vials, followed by D-glucose (40 μL, 250 mM in M9-N), alkyne (10 μL of an EtOH stock, 400 mM), and ethyl diazoacetate (EDA, 10 μL of an EtOH stock, 400 mM). Final concentrations were typically 10.0 mM alkyne, 10.0 mM EDA, and 25 mM D-glucose; final reaction volume was 400 μL. The vials were sealed, shaken inside the anaerobic chamber at room temperature for a set time (600 rpm). After the reaction was completed and the vials removed from the anaerobic chamber, internal standard 1,3,5-trimethoxybenzene, 1,2,3-trimethoxybenzene or ethyl 2-phenylacetate (20 μL of 20 mM stock solution in toluene) was added followed by mixed solvent (hexane/ethyl acetate=1:1, 1.0 mL). The mixture was transferred to a 1.7 mL Eppendorf tube, and then subjected to vortexing (15 s×3) and centrifugation (14,000 rpm, 5 min) to completely separate the organic and aqueous layers. A sample of the organic layer (0.8 mL) was transferred to a vial for GC analysis. The procedure for preparative-scale enzymatic reactions is outlined in detail (See Section VI).

Reaction screening in 96-well plate format. Libraries (single-site-saturation libraries generated employing the "22c-trick" method or collections of heme protein variants) were screened in 96-well plates.

E. coli libraries for P411 variants were cultured in $LB_{amp}$ (300 μL/well) at 37° C., 250 rpm and 80% relative humidity overnight. $HB_{amp}$ (950 μL/well) was inoculated with the pre-culture (50 μL/well) and incubated at 37° C., 230 rpm, 80% humidity for 2 h and 45 min. The plates were cooled on ice for 30 minutes, and expression was induced with 0.5 mM IPTG and 1.0 mM 5-aminolevulinic acid (final concentrations). Expression was conducted at 22° C. and 220 rpm for 20 h.

The cells were pelleted (4,500×g, 5 min, 4° C.) and resuspended with M9-N buffer (340 μL/well) and D-glucose solution (40 μL/well, in M9-N). The 96-well plate was then transferred to an anaerobic chamber. In the anaerobic chamber, alkyne (10 μL/well, 400 mM in EtOH) and EDA (10 μL/well, 400 mM in EtOH). The plate was sealed with an aluminum foil and shaken inside the anaerobic chamber at 600 rpm.

After 6 h, the seal was removed and acetonitrile (580 μL/well) and internal standard p-methylanisole (20 mM in acetonitrile, 20 μL/well) were added. The plate was tightly sealed with a reusable silicone mat, vortexed (15 s×3) and centrifuged (4,500×g, 5 min). The supernatant (200 μL/well) was filtered through an AcroPrep 96-well filter plate (0.2 μm) into a shallow-well plate for reversed-phase HPLC analysis (C18 Poroshell column, $MeCN:H_2O$=60:40 or 70:30, 1.2 mL/min flow, 3.2 min, 210 nm).

General Procedure for Internal Aromatic Alkyne Synthesis (1b and 1d to 1l).

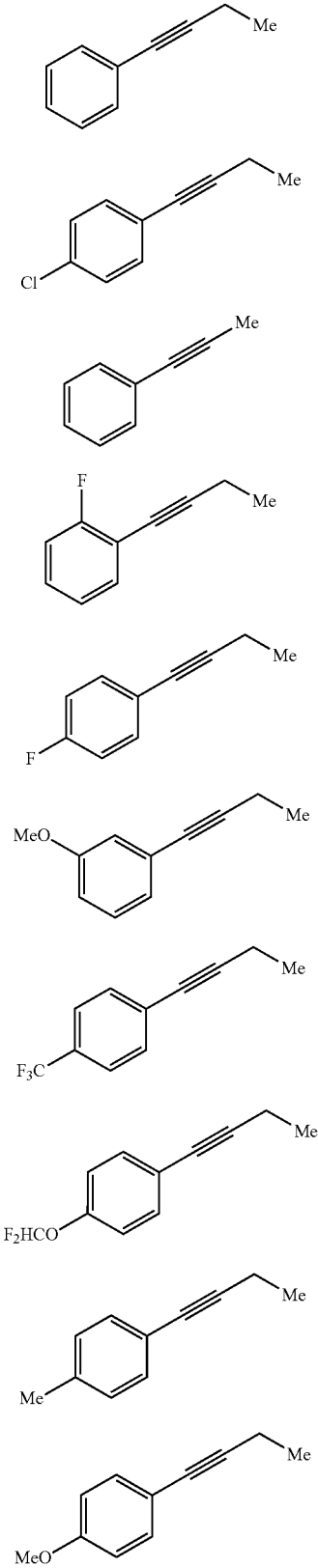

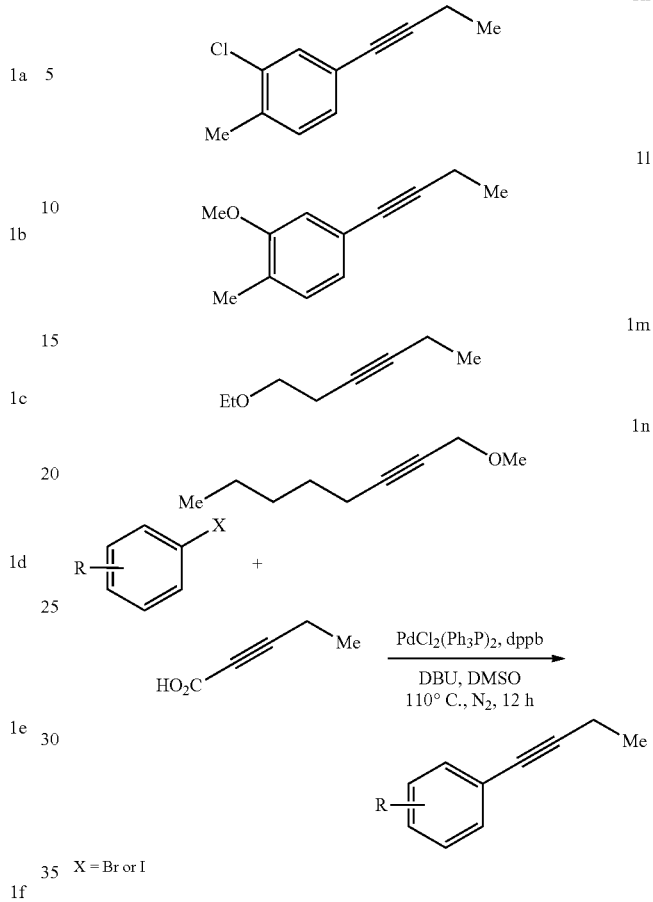

To a 100-mL flask were added aryl bromide or iodide (10.0 mmol, 1.0 equiv.), 2-pentynoic acid (1.18 g, 12.0 mmol, 1.2 equiv.), PdCl$_2$(Ph$_3$P)$_2$ (70 mg, 0.1 mol, 1 mol %), 1,4-bis(diphenylphosphino)butane (dppb, 86 mg, 0.2 mmol, 2 mol %) and anhydrous DMSO (30 mL). The mixture was stirred at room temperature for 3 minutes, and then the flask was capped, degassed and charged with N$_2$. 1,8-Diazabicyclo[5.4.0]undec-7-ene (DBU, 4.4 mL, 30 mmol, 3.0 equiv.) was added to the reaction under N2. The reaction was stirred at 110° C. for 12 hours before being cooled to room temperature, quenched by NH$_4$Cl (sat. aq., 20 mL) and diluted with water (30 mL). The product was extracted by ether (25 mL×3). The combined organic layer was then washed with water (30 mL) and brine (30 mL), and dried over magnesium sulfate. The organic layer was filtered and concentrated under reduced pressure. Distillation of the crude mixture under high vacuum (<100 Pa, 80-125° C.) gave the desired product in 60% to 90% yield and with NMR purity of 98% to >99%.

B. SCOPE OF ENZYMATIC SYNTHESIS OF INTERNAL AROMATIC CYCLOPROPENES

All enzymatic reactions for internal cyclopropene formation in analytical scale were conducted following the general procedure described below and analyzed with gas chromatography (GC). All TTNs for the different products were determined using the GC standard curves of the corresponding racemic standard products made with Rh$_2$(OAc)$_4$.

General procedure for analytical-scale reactions: To a 2 mL vial were added degassed suspension of E. coli expressing the P411-C10 variant in M9-N buffer ($OD_{600}$=15 or 20, 340 μL), internal aromatic alkynes (10 μL of 400 mM stock solution in EtOH, 10 mM), EDA (10 μL of 400 stock solution in EtOH, 10 mM, 1.0 equiv.), D-glucose (40 μL of 250 mM stock solution in M9-N buffer, 25 mM) under anaerobic conditions. The vial was capped and shaken at 600 rpm at room temperature for 16 h. Reactions for every substrate were set up in quadruplicate. After the reactions were completed, internal standard 1,3,5-trimethoxybenzene (for 2a to 2e, 2g to 2i and 2l) or 1,2,3-trimethoxybenzne (for 2f, 2j and 2k) (20 μL of 20 mM stock solution in toluene) was added to the reaction vials followed by mixed solvent (hexane/ethyl acetate=1:1, 1 mL). The mixture was transferred to a 1.7 mL microcentrifuge tube, and then vortexed (15 seconds×3) and centrifuged (14,000 rpm, 5 min) to completely separate the organic and aqueous layers. 0.8 mL of organic layer was taken for GC analysis. TTN was calculated based on measured protein concentration. Enantiomeric excess was measured by chiral HPLC. The absolute configuration of the cyclopropene compounds was not determined.

GC standard curve: All data points represent the average of duplicate runs. The calibration curves depict product concentration in mM (y-axis) against the ratio of product area to internal standard area on the GC (x-axis).

C. ENZYMATIC PREPARATION OF INTERNAL CYCLOPROPENES AND DERIVATIZATION

Enzymatic reactions for internal cyclopropenation in preparative scale were conducted following the procedure described below, and the corresponding cyclopropene products were isolated.

General procedure for preparative-scale reactions: To a 500 mL flask were added a suspension of E. coli expressing P411-C10 variant ($OD_{600}$=15), alkyne (1.0 mmol), EDA (0.8 mmol, 0.8 equiv.), D-glucose (20 mM), M9-N buffer/EtOH (20:1 v/v) under anaerobic conditions. The flask was capped and shaken (300 rpm) inside the anaerobic chamber at room temperature for 2 h. The second portion of EDA (0.8 mmol, 0.8 equiv.) was added to the reaction before the reaction was shaken for another 2 h and a third portion of EDA (0.8 mmol, 0.8 equiv.) was then added. The reaction was shaken for another 20 h.

After the reaction was completed, the reaction mixture were transferred to 500 mL centrifuge bottle. The reaction flask was washed with water (3 mL×3) followed by mixed organic solvent (hexane/ethyl acetate=1:1, 5 mL×3). The washing solution was combined with the reaction mixture in the centrifuge bottle. An additional 100 mL of hexane/ethyl acetate solvent was added to the centrifuge bottle. After the bottle was capped, it was shaken vigorously and centrifuged (6,000×g, 6 min). The organic layer was separated and the aqueous layer was subjected to three more rounds of extraction. The organic layers were combined, dried over $Na_2SO_4$ and concentrated under reduced pressure. Purification by silica column chromatography with hexane/ethyl acetate as eluents followed by C18 column reverse-phase chromatography using acetonitrile/water as eluents afforded the desired cyclopropenes. TTNs were calculated based on measured protein concentration and isolated product yield.

D. ENZYMATIC CARBENE TRANSFER TO INTERNAL ALIPHATIC ALKYNES

All enzymatic reactions for internal cyclopropene formation and related in analytical scale were conducted following the general procedure described below and analyzed with gas chromatography (GC). All TTNs for the different products were determined using the GC standard curve of the corresponding racemic standard product.

General procedure for analytical-scale reactions: To a 2 mL vial were added degassed suspension of E. coli expressing the P411 variant in M9-N buffer ($OD_{600}$=15 or 20, 340 μL), internal aliphatic alkynes (10 μL of 400 mM stock solution in EtOH, 10 mM), EDA (10 L of 400 stock solution in EtOH, 10 mM, 1.0 equiv.), D-glucose (40 μL of 250 mM stock solution in M9-N buffer, 25 mM) under anaerobic conditions. The vial was capped and shaken at 600 rpm at room temperature for 16 h. Reactions for every substrate were set up in quadruplicate. After the reactions were completed, internal standard ethyl 2-phenylacetate (20 μL of 20 mM stock solution in toluene) was added to the reaction vials followed by mixed solvent (hexane/ethyl acetate=1:1, 1 mL). The mixture was transferred to a 1.7 mL microcentrifuge tube, and then vortexed (15 seconds×3) and centrifuged (14,000 rpm, 5 min) to completely separate the organic and aqueous layers. 0.8 mL of organic layer was taken for GC analysis. TTN was calculated based on measured protein concentration. Enantiomeric excess was measured by chiral GC.

GC standard curve: All data points represent the average of duplicate runs. The calibration curves depict product concentration in mM (y-axis) against the ratio of product area to internal standard area on the GC (x-axis).

E. RESULTS AND DISCUSSION

We initiated investigation of internal aromatic alkyne cyclopropenation using ethyl diazoacetate (EDA) as the carbene precursor and 1-phenylbutyne (1a) as the model alkyne substrate. Screening various hemeprotein variants based on P450s, P41 is (P450 with axial ligating residue mutated to serine),[14] cytochromes c and globins in the form of whole Escherichia coli (E. coli) cell catalysts identified a P411 variant, P411-C10, that formed the desired internal cyclopropene. P411-C10 belongs to the family of $P411_{CHF}$ (five amino acid substitutions away), which was evolved for a carbene C—H insertion reaction.[15] Surprisingly, the cyclopropene product synthesized by P411-C10 was determined to be a single enantiomer, which suggests the enzyme scaffold binds the alkyne and directs carbene transfer in a well-defined orientation.

For the model reaction with 1a as the alkyne donor, C10 in the form of the whole-cell catalyst exhibited modest activity, with 55 total turnovers (TTN). Directed evolution targeting active-site residues for site-saturation mutagenesis was performed to enhance the overall catalytic efficiency (FIG. 1). Residue 263, located right above the heme cofactor (in the heme domain), was previously found to play an important role in controlling carbene transfer to phenylacetylene using other P411 variants.[11] To our delight, screening the enzyme library made by site-saturation mutagenesis at residue 263 yielded a tryptophan mutation at this site that improved TTN over 11 fold. Sequential mutagenesis targeting sites in the loop regions led to beneficial mutations Q437I, S72F and L436R and afforded the highly efficient variant WIRF, with 2680 TTN towards the desired cyclopropene formation.

TABLE 1

Detailed information of the evolutionary lineage.

| P411-C10 variant | TTN | ee |
| --- | --- | --- |
| C10 | 110 ± 10 | >99% |
| WIRF | 300 ± 10 | >99% |
| WIRF-S332G | 1440 ± 40 | >99.9% |
| WIRF-S332G G74A (WIRF_GA) | 1610 ± 50 | >99.9% |
| WIRF-S332G G74A E70K (WIRF_GAK) | 2140 ± 40 | >99.9% |

Evolutionary details.

| Round # | Parent | Sites targeted for site-saturation mutagenesis | Beneficial mutations obtained |
| --- | --- | --- | --- |
| 1 | WIRF | 82, 261, 332, 439 | S332G (~5-fold improvement) |
| 2 | WIRF-S332G | 74, 85, 268, 328 | G74A (~1.1-fold improvement) |
| 3 | WIRF_GA | 70, 269, 327, 436 | E70K (~1.3-fold improvement) |

P411 C10-WIRF's scope of internal alkynes bearing different aromatic rings or carbon chains was then evaluated. For the alkyne substrates tested (1b to 1l), only cyclopropenes 2c, 2d, 2i and 2j were synthesized efficiently, and most of the other alkynes with substitutions on the aromatic ring showed poor to moderate reactivities. Thinking that the evolved WIRF variant may have acquired some specificity for the non-substituted aromatic ring or for electron-rich alkynes, we decided to use a less reactive alkyne substrate (compared to 1a), 1b, with an electron-deficient para-chloro substitution, to further evolve the enzyme (FIG. 1). A site-saturation library targeting residue 332 afforded mutation S332G, which boosted the total turnover by almost 5 fold. We reasoned that the glycine substitution might help make space in the active site to accommodate substrates with substitutions on the aromatic ring. Mutagenesis of residues close to 332 was investigated, and two additional beneficial mutations, G74A and E70K, yielded the final WIRF_GAK variant with 2320 TTN for substrate 1b.

Figure 2:
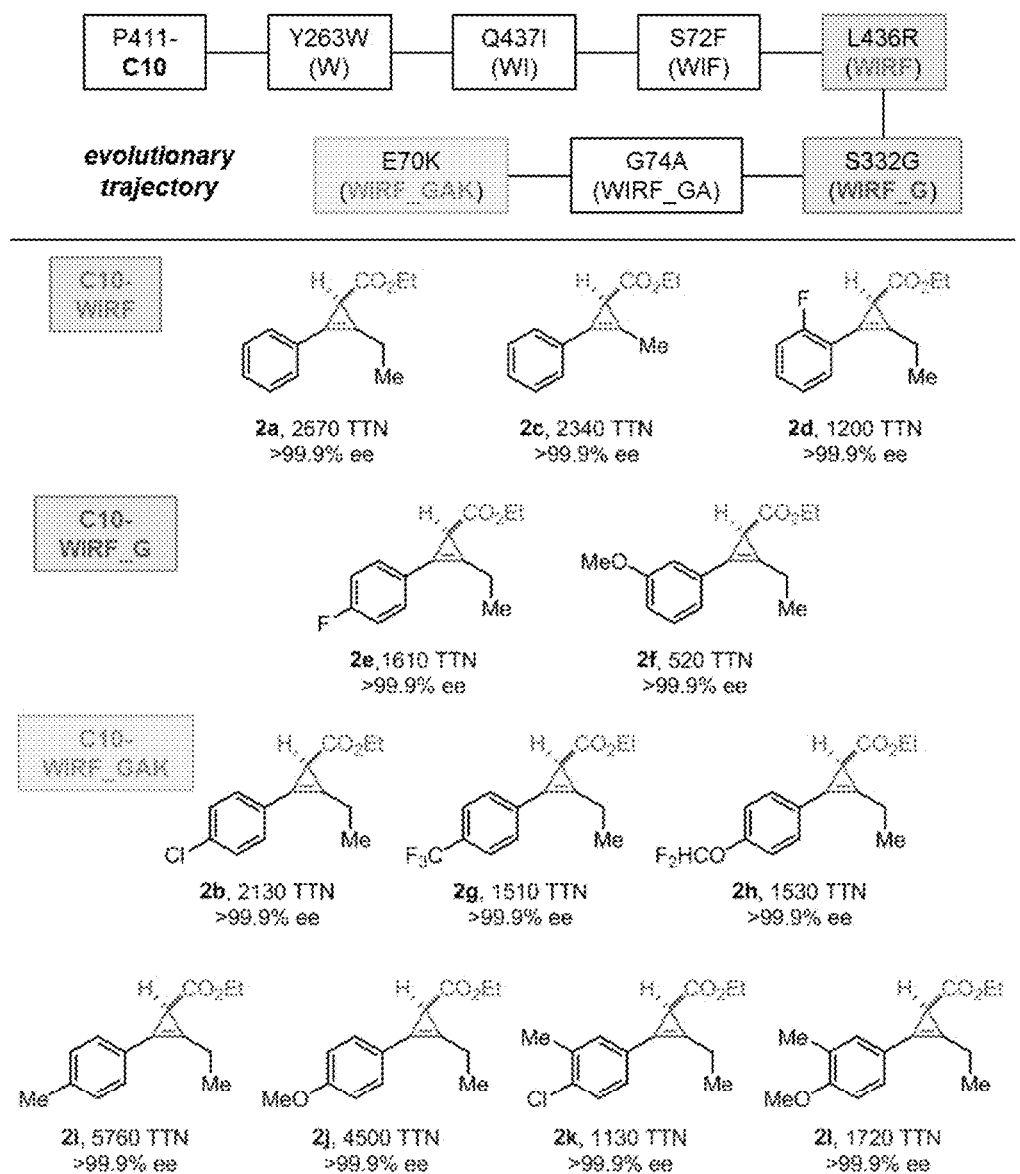
FIG. 2 shows the substrate scope of internal aromatic alkynes for cyclopropene formation. Reactions were performed in quadruplicate under the following conditions: 10 mM alkyne, 10 mM EDA, E. coli harboring P411-C10 variants ($OD_{600}$=10 to 20), D-glucose (25 mM), M9-N buffer/EtOH (19:1), anaerobic, 16 h. Product formation was quantified by gas chromatography (GC) and TTNs were determined based on protein concentration.

We revisited the substrate scope of this biocatalytic platform using the whole lineage of cyclopropene-forming enzyme variants (from C10 to WIRF and then to WIRF_GAK) (FIG. 2). The WIRF variant turned out to be efficient for non-substituted or ortho-substituted aromatic alkynes (1a, 1c and 1d), catalyzing the desired cyclopropene synthesis with 1200 to 2670 total turnovers, while variants from later in the evolution showed impaired activity with these substrates. Although we did not specifically evolve the enzyme for activity on meta-substituted aromatic alkynes, variant WIRF_G exhibited improved efficiency for a meta-methoxy alkyne substrate (1f), compared to WIRF. For aromatic alkynes bearing para-substitutions or di-substitutions (1b and 1g to 1l), the final variant WIRF_GAK catalyzes the desired transformations with unprecedentedly high efficiency compared to all previously reported systems for cyclopropene formation. For instance, an electronically-withdrawing trifluoromethyl-substituted alkyne (1g) was well-accepted by the enzymatic system. It is worth noting that all of the internal cyclopropenes produced enzymatically were determined to be single enantiomers (>99.9% ee for all), which further supports our hypothesis that the engineered enzymes impose a specific binding orientation of the alkyne substrate in the protein active site, allowing for efficient carbene addition to triple bonds with perfect stereocontrol.

Figure 3:
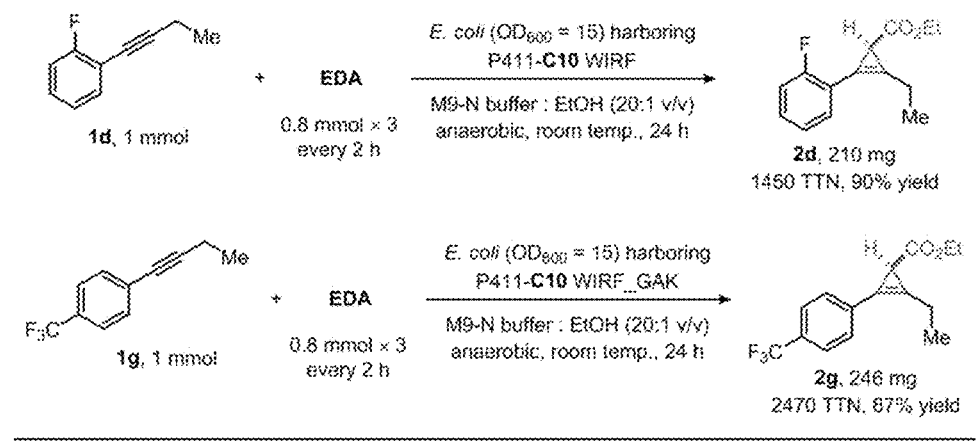
FIG. 3 outlines the preparative-scale synthesis of internal cyclopropenes and further derivatization.

To further demonstrate the utility of this highly stereoselective enzymatic platform, we carried out large-scale preparation of internal cyclopropenes (FIG. 3). With a simple modification of the reaction conditions using the diazo reagent in excess (2.4 equivalents added in three portions), we obtained high isolated yields of the desired cyclopropene products at mmol scale (90% for 2d with variant WIRF, and 87% for 2g with variant WIRF_GAK). Interestingly, the enzyme turnovers of the large-scale reactions are typically higher than those obtained with analytical-scale ones, indicating that the evolved enzymes in whole cells might still retain (partial) activity after the reactions and the turnovers were limited by consumption of the diazo substrate.

Numerous transformations have been developed to furnish diverse molecular structures from versatile cyclopropane building blocks.[1,2b,2c,6,7] Here, we also derivatized the enzymatically-synthesized cyclopropenes by hydrogenation and ester reduction to afford an all-cis cyclopropane product (FIG. 3), which is otherwise difficult to prepare due to the cis-stereochemistry of the three substituents on the cyclopropane ring.

Compared to internal aromatic alkynes described above, internal aliphatic alkynes are typically more challenging targets for enantioselective cyclopropene formation in terms of reactivity and selectivity. As the aryl groups on aromatic alkynes can provide a stabilizing effect through the conjugated system in the carbene transfer process, purely aliphatic alkynes without additional intramolecular effects may suffer from a higher energy barrier for carbene transfer. Additionally, alkyl groups at the two ends of the triple bond are less easy to distinguish than the alkyl and aryl groups on aromatic alkynes. Until now, no systems have been reported for enantioselective cyclopropene synthesis with internal aliphatic alkynes. However, we believed that enzymes can accomplish this, as the enzyme active site is a chiral environment that can recognize minor steric differences for chiral induction.[16]

Testing the evolved enzymes for a cyclopropenation reaction with internal aliphatic alkyne 1m was not fruitful, as only trace activity was observed. However, with the parent enzyme P411-C10 we observed the desired cyclopropene product 2m (FIG. 4) with modest activity (43 TTN). This might be because the whole enzyme lineage was evolved for a set of structurally different aromatic alkynes. Further screening of variants in the C10 family identified a triple mutant of C10, C10_VLC, which catalyzed the formation of internal cyclopropene 2m with improved activity (64 TTN) and perfect stereocontrol (>99% ee). We anticipate that further evolution will lead to more efficient enzymes for internal aliphatic cyclopropene construction, as we have demonstrated for aromatic alkynes.

Figure 4:
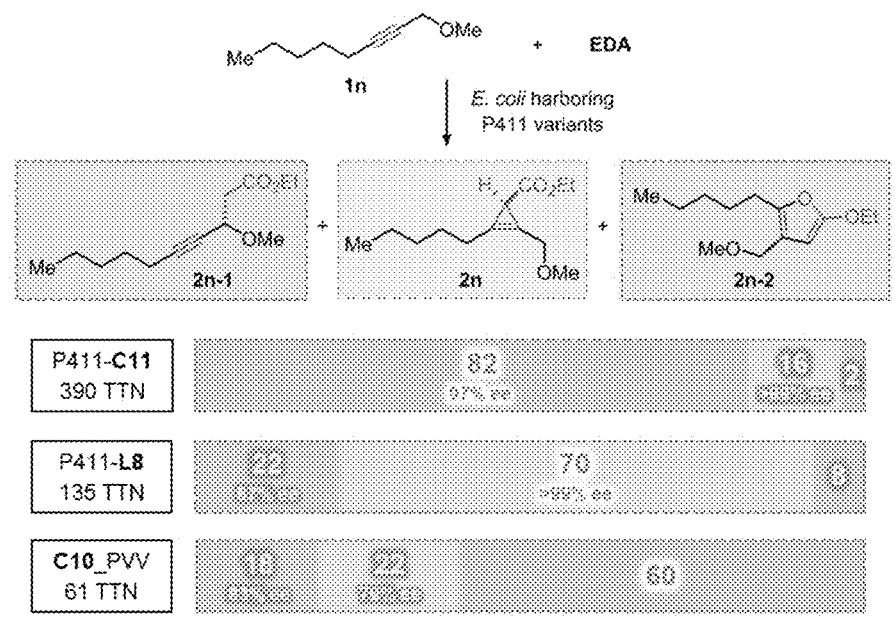
FIG. 4 shows cyclopropanation of internal aliphatic alkynes and chemoselectivity study with substrate 1n. Reactions were performed in quadruplicate under the following conditions: 10 mM alkyne, 10 mM EDA, E. coli harboring P411 variants ($OD_{600}$=15 to 20), D-glucose (25 mM), M9-N buffer/EtOH (19:1), anaerobic, 16 h. C10_VLC: C10_T327V Q437L S332C; C11: C10 G74T S118M L162F L401I Q437L; L8: C10 A87P A264S E267D T327P S332A Q437L; C10_PVV: C10 Q437P T327V A87V.

As the parent P411-C10 enzyme was initially engineered for a carbene C—H insertion reaction, we took a deeper look at the chemoselectivity between cyclopropenation and C—H insertion.[15] Internal alkyne substrate 1n, bearing a propargylic ether group, was found to mainly undergo a carbene insertion reaction into the propargylic C—H bond with high enantioselectivity with catalyst $P411_{CHF}$; a cyclopropene product was also detected as a minor product. However, P411-C10 reversed the chemoselectivity to favor the cyclopropene 2n as the major product; and a third product observed in low proportion in this latter reaction was confirmed to be a furan derivative, 2n-2, which may be generated through a [3+2]-cycloaddition.[11,17] After intensive screening of variants in the families of P411$_{CHF}$ and P411-C10, we discovered two related variants, P411-C11 and P411-L8, which could catalyze the C—H insertion reaction and the cyclopropenation reaction with even higher activity and selectivity (compared to P411$_{CHF}$ and P411-C10, respectively), as shown in FIG. 4. And a C10 triple mutant, C10_PVV, was found to flip the chemoselectivity to favor formation of the furan product. These variants are closely related, differing by only a few amino acid substitutions, but gave very different chemoselectivities without any specific enzyme evolution. These results, together with our previous demonstration of enzyme-controlled reaction selectivity between C—H insertion and cyclopropanation,[18] highlight how enzyme catalysis can solve chemoselectivity problems in synthetic methodology.

In conclusion, we have developed a versatile biocatalytic platform based on engineered cytochrome P411 enzymes that offers access to an array of structurally diverse internal cyclopropenes through carbene transfer to internal alkynes. This biocatalytic system was evolved rapidly to take internal aromatic alkynes as substrates and furnish the desired cyclopropenes with unprecedentedly high stereoselectivities (>99.9% ee for all). This enzymatic platform is also readily scalable for the production of cyclopropenes in preparative quantities, with even higher efficiencies compared to the analytical-scale reactions. Enantioselective cyclopropenation of internal aliphatic alkynes was also shown to be possible. The versatility and tunability of these biocatalysts has been demonstrated, with chemoselectivity that can be switched among cyclopropenation, carbene C—H insertion and [3+2] cycloaddition. Ongoing studies with this family of P411-C10 variants will help to define the catalytic potential of C10 as a highly promiscuous carbene transferase for non-native transformations.

F. REFERENCES AND NOTES (1) Reviews with topics on cyclopropenes: a) Marek, I.; Simaan, S.; Masarwa, A. Enantiomerically enriched cyclopropene derivatives: Versatile building blocks in asymmetric synthesis. *Angew. Chem., Int. Ed.* 2007, 46, 7364-7376. b) Zhu, Z.-B.; Wei, Y.; Shi, M. Recent developments of cyclopropene chemistry. *Chem. Soc. Rev.* 2011, 40, 5534-5563. c) Rubin, M.; Rubina, M.; Gevorgyan, V. Transition metal chemistry of cyclopropenes and cyclopropanes. *Chem. Rev.* 2007, 107, 3117-3179. d) Archambeau, A.; Miege, F.; Meyer, C.; Cossy, J. Intramolecular cyclopropanation and C—H insertion reactions with metal carbenoids generated from cyclopropenes. *Acc. Chem. Res.* 2015, 21, 1021-1031. e) Deng, Y; Doyle, M. P. Versatile donor-acceptor cyclopropenes in metal carbene transformations. *Isr. J. Chem.* 2016, 56, 399-408.

(2) a) Protopopova, M. N.; Doyle, M. P.; Müller, P.; Ene, D. High enantioselectivity for intermolecular cyclopropenation of alkynes by diazo esters catalyzed by chiral dirhodium(II) carboxamides. *J. Am. Chem. Soc.* 1992, 114, 2755-2757. b) Doyle, M. P.; Protopopova, M.; Müller, P.; Ene, D.; Shapiro, E. A. Effective uses of dirhodium(II) tetrakis[methyl 2-oxopyrrolidine-5(R or S)-carboxylate] for highly enantioselective intermolecular cyclopropenation reactions. *J. Am. Chem. Soc.* 1994, 116, 8492-8498. c) Briones, J. F.; Hansen, J.; Hardcastle, K. I.; Autschbach, J.; Davies, H. M. L. Highly enantioselective Rh$_2$(S-DOSP)$_4$-catalyzed cyclopropenation of alkynes with styryldiazoacetates. *J. Am. Chem. Soc.* 2010, 132, 17211-17215. d) Goto, T.; Takeda, K.; Shimada, N.; Nambu, H.; Anada, M.; Shiroo, M.; Ando, K.; Hashimoto, S. Highly enantioselective cyclopropenation reaction of 1-alkynes with α-alkyl-α-diazoesters catalyzed by dirhodium(II) carboxylates. *Angew. Chem., Int. Ed.* 2011, 50, 6803-6808. e) Davies, H. M. L.; Lee, G. H. Dirhodium(II) tetra(N-(dodecylbenzenesulfonyl)prolinate) catalyzed enantioselective cyclopropenation of alkynes. *Org. Lett.* 2004, 6, 1233-1236. f) Lindsay, V. N. G.; Fiset, D.; Gritsch, P. J.; Azzi, S.; Charette, A. B. Stereoselective Rh$_2$(S-IBAZ)$_4$-catalyzed cyclopropanation of alkenes, alkynes, and allenes: Asymmetric synthesis of diacceptor cyclopropylphosphonates and alkylidenecyclopropanes. *J. Am. Chem. Soc.* 2013, 135, 1463-1470.

(3) Uehara, M.; Suematsu, H.; Yasotumi, Y.; Katsuki, T. Enantioenriched synthesis of cyclopropenes with a quaternary stereocenter, versatile building blocks. *J. Am. Chem. Soc.* 2011, 133, 170-171.

(4) Cui, X.; Xu, X.; Lu, H.; Zhu, S.; Wojtas, L.; Zhang, X. P. Enantioselective cyclopropenation of alkynes with acceptor/acceptor-substituted diazo reagents via Co(II)-based metalloradical catalysis. *J. Am. Chem. Soc.* 2011, 133, 3304-3307.

(5) Briones, J. F.; Davies, H. M. L. Gold(I)-catalyzed asymmetric cyclopropenation of internal alkynes. *J. Am. Chem. Soc.* 2012, 134, 11916-11919.

(6) a) A recent example of Rh-catalyzed internal alkyne cyclopropenation: Zhang, Z.-Q.; Zheng, M.-M.; Xue, X.-S.; Marek, I.; Zhang, F.-G.; Ma, J.-A. Catalytic enantioselective cyclopropenation of internal alkynes: Access to difluoromethylated three-membered carbocycles. *Angew. Chem., Int. Ed.* 2019, 58, 18191-18196. b) See ref 2a for preliminary results on the rhodium-catalyzed asymmetric cyclopropenation of internal alkynes in poor enantioselectivity.

(7) a) Ortiz de Montellano, P. R. ed., Cytochrome P450: structure, mechanism, and biochemistry (Springer International Publishing: Cham, 2015). b) Poulos, T. L. Heme enzyme structure and function. *Chem. Rev.* 2014, 114, 3919-3962.

(8) Reviews and book chapter covering carbene and nitrene chemistries by P450: a) Brandenberg, O. F.; Fasan, R.; Arnold, F. H. Exploiting and engineering hemoproteins for abiological carbene and nitrene transfer reactions. *Curr. Opin. Biotechnol.* 2017, 47, 102-111. b) Prier, C. K.; Arnold, F. H. Chemomimetic biocatalysis: Exploiting the synthetic potential of cofactor-dependent enzymes to create new catalysts. *J. Am. Chem. Soc.* 2015, 137, 13992-14006. c) Zhang, R. K.; Romney, D. K.; Kan, S. B. J.; Arnold, F. H. Chapter 5 in Dieguez, M.; Bäckvall, J.-E.; Pamies, O. eds, *Artificial Metalloenzymes and MetalloDNAzymes in Catalysis. From Design to Applications* (Wiley-VCH, Weinheim, 2018). d) Chen, K.; Arnold, F. H. Engineering new catalytic activities in enzymes. *Nat. Catal.* 2020, 3, 103-113. e) Leveson-Gower, R. B.; Mayer, C.; Roelfs, G. The importance of catalytic promiscuity for enzyme design and evolution. *Nat. Rev. Chem.* 2019, 3, 687-705.

(9) Examples of hemeprotein-catalyzed carbene chemistries: a) Coelho, P. S.; Brustad, E. M.; Kannan, A.; Arnold, F. H. Olefin cyclopropanation via carbene transfer catalyzed by engineered cytochrome P450 enzymes. *Science* 2013, 339, 307-310. b) Wang, Z. J.; Renata, H.; Peck, N. E.; Farwell, C. C.; Coelho, P. S.; Arnold, F. H. Improved cyclopropanation activity of histidine-ligated cytochrome P450 enables the enantioselective formal synthesis of levomilnacipran. *Angew. Chem., Int. Ed.* 2014, 53, 6810-6813. c) Bordeaux, M.; Tyagi, V.; Fasan, R. Highly diastereoselective and enantioselective olefin cyclopropanation using engineered myoglobin-based catalysts. *Angew. Chem., Int. Ed.* 2015, 54, 1744-1748. d) Chen, K.; Zhang, S.-Q.; Brandenberg, O. F.; Hong, X.; Arnold, F. H. Alternate heme ligation steers activity and selectivity in engineered cytochrome P450-catalyzed carbene transfer reactions. *J. Am. Chem. Soc.* 2018, 140, 16402-16407. e) Wang, Z. J.; Peck, N. E.; Renata, H.; Arnold, F. H. Cytochrome P450-catalyzed insertion of carbenoids into N—H bonds. *Chem. Sci.* 2014, 5, 598-601. f) Tyagi, V.; Bonn, R. B.; Fasan, R. Intermolecular carbene S—H insertion catalysed by engineered myoglobin-based catalysts. *Chem. Sci.* 2015, 6, 2488-2494. g) Kan, S. B. J.; Lewis, R. D.; Chen, K.; Arnold, F. H. Directed evolution of cytochrome c for carbon-silicon bond formation: Bringing silicon to life. *Science* 2016, 354, 1048-1051. h) Kan, S. B. J.; Huang, X.; Gumulya, Y.; Chen, K.; Arnold, F. H. Genetically programmed chiral organoborane synthesis. *Nature* 2017, 552, 132-136.
(10) Examples of hemeprotein-catalyzed nitrene chemistries: a) McIntosh, J. A.; Coelho, P. S.; Farwell, C. C.; Wang, Z. J.; Lewis, J. C.; Brown, T. R.; Arnold, F. H. Enantioselective intramolecular C—H amination catalyzed by engineered cytochrome P450 enzymes in vitro and in vivo. *Angew. Chem., Int. Ed.* 2013, 52, 9309-9312. b) Hyster, T. K.; Farwell, C. C.; Buller, A. R.; McIntosh, J. A.; Arnold, F. H. Enzyme-controlled nitrogen-atom transfer enables regiodivergent C—H amination. *J. Am. Chem. Soc.* 2014, 136, 15505-15508. c) Singh, R.; Kolev, J. N.; Sutera, P. A.; Fasan, R. Enzymatic C(sp$^3$)-H amination: P450-catalyzed conversion of carbonazidates into oxazolidinones. *ACS Catal.* 2015, 5, 1685-1691. d) Prier, C. K.; Zhang, R. K.; Buller, A. R.; Brinkmann-Chen, S.; Arnold, F. H. Enantioselective, intermolecular benzylic C—H amination catalysed by an engineered iron-haem enzyme. *Nat. Chem.* 2017, 9, 629-634. e) Yang, Y.; Cho, I.; Qi, X.; Liu, P.; Arnold, F. H. An enzymatic platform for the asymmetric amination of primary, secondary and tertiary C(sp$^3$)-H bonds. *Nat. Chem.* 2019, 11, 987-993.
(11) Chen, K.; Huang, X.; Kan, S. B. J.; Zhang, R. K.; Arnold, F. H. Enzymatic construction of highly strained carbocycles. *Science* 2018, 360, 71-75.
(12) A similar rationalization in iron-porphyrin-catalyzed internal alkene cyclopropanation: Wolf, J. R.; Hamaker, C. G.; Djukic, J.-P.; Kodadek, T.; Woo, L. K. Shape and stereoselective cyclopropanation of alkenes catalyzed by iron porphyrins. *J. Am. Chem. Soc.* 1995, 117, 36, 9194-9199.
(13) Mechanistic studies on hemeprotein catalyzed carbene-transfer reactions: a) Zhang, Y. Computational investigations of heme carbenes and heme carbene transfer reactions. *Chem. Eur. J.* 2019, 25, 13231-13247. b) Sharon, D. A.; Mallick, D.; Wang, B.; Shaik, S. Computation sheds insight into iron porphyrin carbenes' electronic structure, formation, and N—H insertion reactivity. *J. Am. Chem. Soc.* 2016, 138, 9597-9610. c) Wei, Y.; Tinoco, A.; Steck, V.; Fasan, R.; Zhang, Y. Cyclopropanations via heme carbenes: Basic mechanism and effects of carbene substituent, protein axial ligand, and porphyrin substitution. *J. Am. Chem. Soc.* 2018, 140, 1649-1662. d) Carminati, D; Fasan, R. Stereoselective cyclopropanation of electron-deficient olefins with a cofactor redesigned carbene transferase featuring radical reactivity. *ACS Catal.* 2019, 9, 9683-9697. e) ref 10d.
(14) Coelho, P. S.; Wang, Z. J.; Ener, M. E.; Baril, S. A.; Kannan, A.; Arnold, F. H.; Brustad, E. M. A serine-substituted P450 catalyzes highly efficient carbene transfer to olefins in vivo. *Nat. Chem. Bio.* 2013, 9, 485-487.
(15) Zhang, R. K.; Chen, K.; Huang, X.; Wohlschlager, L.; Renata, H.; Arnold, F. H. Enzymatic assembly of carbon-carbon bonds via iron-catalysed sp$^3$ C—H functionalization. *Nature* 2019, 565, 67-72.
(16) See ref 11e for an example of an engineered P411 enzyme constructing a methyl-ethyl stereocenter.
(17) Cui, X.; Xu, X.; Wojtas, L.; Kim, M. M.; Zhang, X. P. Regioselective synthesis of multisubstituted furans via metalloradical cyclization of alkynes with α-diazocarbonyls: Construction of functionalized α-oligofurans. *J. Am. Chem. Soc.* 2012, 134, 19981-19984.
(18) See refs 10d, 10g and 13 for examples of tunable chemo-selectivities with engineered hemeproteins.
(19) Kille, S.; Acevedo-Rocha, C. G.; Parra, L. P.; Zhang, Z.-G.; Opperman, D. J.; Reetz, M. T.; Acevedo J. P. *ACS Synth. Biol.* 2013, 2, 83.
(20) Gibson, D. G.; Young, L.; Chuang, R.-Y.; Venter, J. C.; Hutchinson III, C. A.; Smith, H. O. *Nature Methods* 2009, 6, 343.
(21) Sambrook, J.; Frisch, E.; Maniatis, T. *Molecular Cloning: A Laboratory Manual* (Cold Spring Harbor Laboratory Press, New York, 1989).
(22) Berry, E. A.; Trumpower, B. L. *Anal. Biochem.* 1987, 161, 1.
(23) Doyle, M. P.; Protopopova, M.; Müller, P.; Ene, D.; Shapiro, E. A. *J. Am. Chem. Soc.* 1994, 116, 8492.
(24) Zhang, R. K.; Chen, K.; Huang, X.; Wohlschlager, L.; Renata, H.; Arnold, F. H. *Nature* 2019, 565, 67-72.

Example 4: Enzymatic Cyclopropanation to Yield Compounds of Formula V Using P411-C10 Variants In Vivo P411-C10 expression and whole cell catalyst preparation were conducted as described in Example 1. Small-scale cyclopropanation reactions in whole-cell suspension under anaerobic conditions were conducted as described in Example 1, except that an alkene substrate of formula IV (Scheme 2) was used in place of the alkyne substrate of formula I (Scheme 1).

Figure 5:
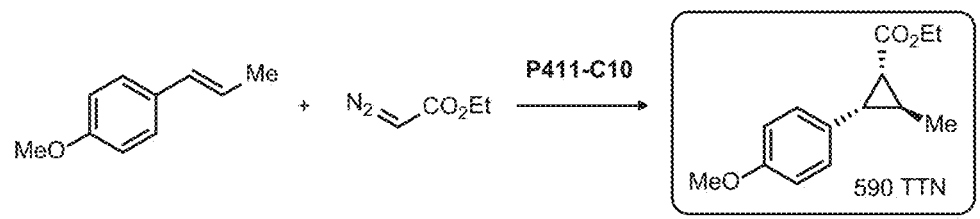
FIG. 5 shows examples of cyclopropane-forming reactions carried out with enzyme catalysts according to the present disclosure.
Figure 5:
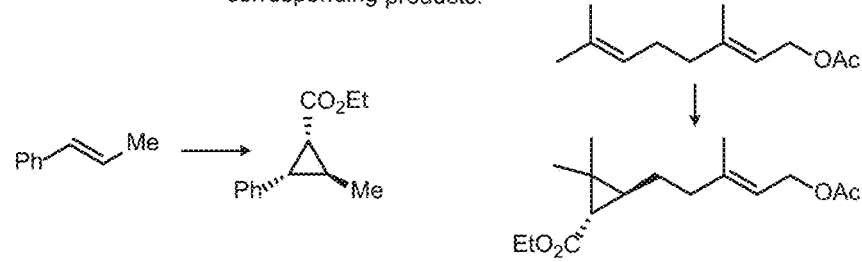

The results of the small scale reactions are shown in FIG. 5 and demonstrate that P411-C10 and variants thereof are capable of catalyzing the cyclopropenation to give products in Scheme 2 with high efficiency. Specifically, the variant P411-C10 found in the initial screen of P450 BM3 variants, which catalyzed the desired cyclopropanation reaction with 590 TTN. The activity can be improved by further engineering, if desired.

Example 5: Enzymatic Bicyclobutane Formation to Yield Compounds of Formula VI Using P411-C10 Variants In Vivo P411-C10 expression and whole cell catalyst preparation were conducted as described in Example 1. Small-scale reactions in whole-cell suspension under anaerobic conditions were conducted as described in Example 1, except that a cyclopropene substrate of formula III (Scheme 3) was used in place of the alkyne substrate of formula I (Scheme 1).

Figure 6:
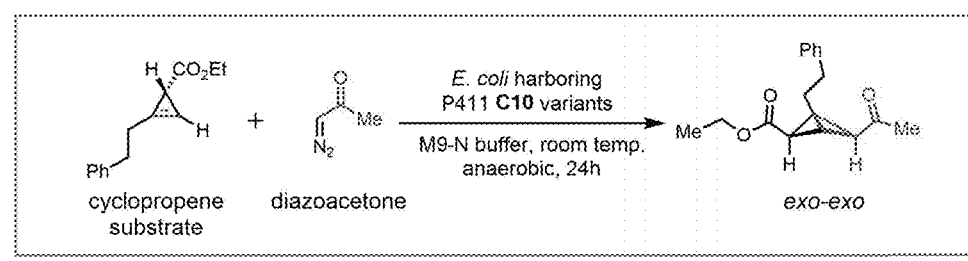
FIG. 6 shows examples of bicyclobutane-forming reactions carried out with enzyme catalysts according to the present disclosure.
Figure 6:
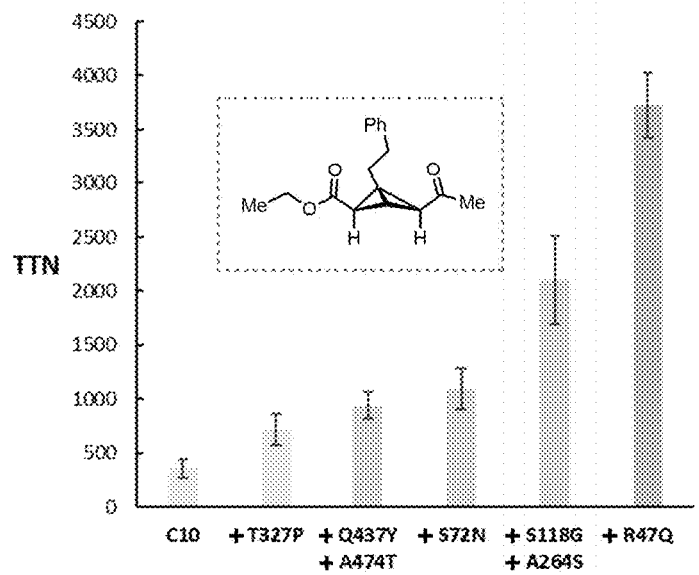

The results of the small scale reactions shown in FIG. 6 demonstrate that P411-C10 and variants thereof are capable of catalyzing the cyclopropanation of cyclopropene substrates to give the corresponding bicyclobutane products shown in Scheme 3 with high efficiency. The P411-C10 variant was further engineered to yield a final variant capable of catalyzing the desired reaction with 3730 TTN and nearly perfect selectivity (>100:1 over other possible configurations combined) for the exo-exo configuration of the bicyclobutane product. The activity can be improved by further engineering, if desired.

Cyclopropenes can be prepared as described in Examples 2 and 3, or can be prepared as shown below:

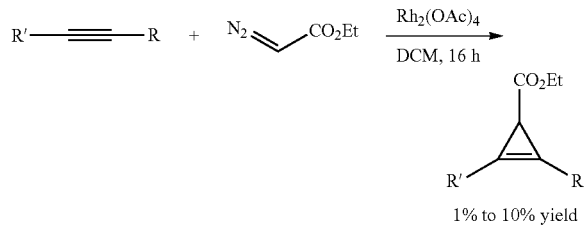

1% to 10% yield

To a 20 mL vial is added alkyne (1.5 mmol, 1.0 equiv.), $Rh_2(OAc)_4$ (6.6 mg, 2 mol %) and DCM (3 mL). A solution of EDA (3.0 mmol, 2.0 equiv.) in DCM (3 mL) is added dropwise to the reaction mixture over 10 hours through a syringe pump. The reaction is stirred at room temperature for another 6 hours. Evaporation of the organic solvent and purification by silica column chromatography using hexane and ethyl acetate as eluents affords cyclopropene products (or products in mixture form with carbene dimers, diethyl maleate and diethyl fumarate).

Example 6: Enzymatic Formation of Compounds of Formula IX Using P411-C10 Variants In Vivo P411-C10 expression was conducted as described in Example 1. Whole cell catalyst preparation was conducted as described in Example 1, except $OD_{600}$=30 to 60. Small-scale reactions in whole-cell suspension under anaerobic conditions were conducted as described in Example 1, except that a diazo substrate of formula VII (Scheme 4) and an alkane substrate of formula VIII (Scheme 4) were used in place of the alkyne substrate of formula I and the diazo substrate of formula II.

The results of the small scale reactions are summarized in FIG. 7 and discussed in more detail below, demonstrating that P411-C10 and variants thereof are capable of catalyzing the lactone-carbene C—H insertion to give products of formula IX in Scheme 4 with high efficiency and tunable selectivity. The activity can be improved by further engineering, if desired. Specifically, the initial variant P411-C10 found in the initial screen of P450 BM3 variants, which catalyzed the desired reaction with 115 TTN and 47% ee. Evolved P411-C10 variants containing mutations part or the whole set of T327P, Q437L, A87P, A264S, S332A, E267D and V328L (or V328R) were found with significantly improved activity and selectivity (with up to 4000 TTN and 99% ee) towards the formation of desired lactone derivatives as described below.

Example 7: Enzymatic Lactone-Carbene C—H Insertion to Build Contiguous Chiral Centers Direct functionalization of carbon-hydrogen bonds represents a powerful and efficient strategy for installing new chemical moieties in organic compounds.[1] In particular, enantioselective C(sp$^3$)-H alkylation via carbene insertion into C—H bonds provides a platform for C(sp$^3$)-C(sp$^3$) bond formation to build diverse molecular skeletons and for late-stage modification of complex molecules.[2] Transition-metal catalysts based on rhodium,[3] iridium,[4] cobalt,[5] copper,[6] and other metals[7] have been shown to catalyze carbene insertion into C—H bonds. In most reported methods, carbenes bearing one electron-donating aryl/alkenyl group and one electron-withdrawing group ('donor-acceptor carbenes') have been demonstrated to be superior for intermolecular C—H insertions, with control over reactivity and selectivity in these catalytic systems.[8] Dirhodium catalysts, for example, have achieved site-selective functionalization of various types of C—H bonds through the manipulation of ligand scaffolds.[9] Other carbenes, however, such as acceptor-only carbenes, are less explored for C—H insertion reactions;[4b,6a,7c] acceptor-only carbenes with an additional alkyl substituent at the α-position are even more challenging to use in these systems due to competitive β-hydride migration upon the formation of the metallo-carbene species.[10]

Recently, we reported that a cytochrome P450, which uses an iron-heme cofactor for its native oxygenase activity, can be engineered to transfer carbene moieties to C—H bonds using diazo compounds bearing a single electron-withdrawing substituent.[11,12] Engineered P450 enzymes substituted with serine as the heme-ligating residue ('P411s')[13] were established as an efficient platform for stereoselective C—C bond assembly with a chiral center formed at the β-position. We thus anticipated that the P411 enzymes could be evolved further to adopt branched carbenes for C—H insertion, which would enable them to build a chiral center at α-position or even contiguous chiral centers at both the α and β-positions.

Rather than using the well-studied donor-acceptor carbenes, we focused on lactone-based carbenes, which are difficult to use with rhodium catalysts due to challenges with β-H elimination and stereocontrol.[14] Despite limited examples of C—H insertion with cyclic carbenes,[15] we previously revealed that lactone-based carbenes can be transferred to different functionalities with high efficiency and stereoselectivity using engineered hemeprotein catalysts.[16,17] Those studies demonstrated the enzymes' ability to stabilize the lactone-carbene intermediates, circumvent undesired β-H migration, and facilitate carbene transfer with exquisite stereocontrol, thus laying the foundation for the current study.

A. GENERAL PROCEDURES

General. Unless otherwise noted, all chemicals and reagents were obtained from commercial suppliers (Sigma-Aldrich, VWR, Alfa Aesar) and used without further purification. Silica gel chromatography was carried out using AMD Silica Gel 60, 230-400 mesh. $^1$H and $^{13}$C NMR spectra were taken using a Bruker Prodigy 400 MHz instrument and are internally referenced to the residual solvent peak (chloroform). Data for $^1$H NMR are reported as follows: chemical shift (S ppm), multiplicity (s=singlet, d=doublet, t=triplet, q=quartet, p=pentet, m=multiplet, dd=doublet of doublets, dt=doublet of triplets, ddd=doublet of doublet of doublets), coupling constant (Hz), integration. Sonication was performed using a Qsonica Q500 sonicator. High-resolution mass spectra were obtained at the California Institute of Technology Mass Spectral Facility. Synthetic reactions were monitored using thin layer chromatography (Merck 60 gel plates) using a UV-lamp for visualization.

Chromatography. Analytical reversed-phase high-performance liquid chromatography (HPLC) was carried out using an Agilent 1200 series instrument and a Kromasil C18 column (4.6×50 mm, 5 μm) with water and acetonitrile as the mobile phase and visualization at 230 nm for library screening. Analytical normal-phase HPLC was carried out using an Agilent 1200 series instrument and chiral columns Chiralpak IC/IA/IB/OJ-H/OD-H (4.6 mm×25 cm) with n-hexane and isopropanol as the mobile phase and visualization at 230 or 254 nm for chiral separation.

Cloning and site-saturation mutagenesis. Vector pET22b (+) containing a C-terminal 6×-His (SEQ ID NO:26) tag was used for cloning and expression of all enzymes described in this study. Site-saturation mutagenesis was performed using a modified QuikChange™ mutagenesis protocol. (29) Primer sequences are available upon request. The PCR products were digested with DpnI, gel purified, and fragments were assembled using Gibson Mix. (30) The Gibson assembly products were used to directly transform *Escherichia coli* strain BL21 E. Cloni© (Lucigen). Cells were grown using Luria-Bertani medium (LB) or Hyperbroth (AthenaES) (HB) with 0.1 mg/mL ampicillin ($LB_{amp}$ or $HB_{amp}$). Electrocompetent *E. coli* cells were prepared following the protocol of Sambrook et al. (31) T5 exonuclease, Phusion polymerase, and Taq ligase were purchased from New England Biolabs (NEB, Ipswich, Mass.). M9-N minimal medium (abbreviated as M9-N buffer; pH 7.4) was used as a buffering system for whole cells, lysates, and purified proteins, unless otherwise specified. M9-N buffer was used without a carbon source; it contains 47.7 mM $Na_2HPO_4$, 22.0 mM $KH_2PO_4$, 8.6 mM NaCl, 2.0 mM $MgSO_4$, and 0.1 mM $CaCl_2$).

Determination of hemeprotein concentration—1. Preparation of cell lysate: Aliquots of ~3 mL $OD_{600}$=60 cells were prepared in 15-mL conical tubes, which were then placed on wet ice. Cells were lysed by sonication following the program below: sonication for 4 min, 1 second on-1 second off, 35% amplitude. The sonicated samples were then transferred to two Eppendorf tubes, and then centrifuged down (14,000 rpm, 15 min, 4° C.). The supernatants (~2.5 mL) were then collected to a 5-mL glass vial for analysis.

Determination of hemeprotein concentration—2. Hemechrome assay for protein concentration measurement: A solution of NaOH/pyridine was prepared by mixing 1 mL of NaOH aqueous solution (1 M), 2 mL of water and 2 mL of pyridine. To 4.5 mL of NaOH/pyridine solution, 22.5 μL of $K_3Fe(CN)_6$ aqueous solution (0.1 M) were added to make solution 1. A background solution was prepared by mixing 500 μL M9-N and 500 μL of the NaOH/pyridine solution, which was used for UV background subtraction. When measuring samples with a UV spectrometer, a spectrum of a mixed solution (oxidized spectrum) with 500 L cell lysate+500 μL solution 1 was taken at the wavelength range 380 nm to 650 nm. Subsequently, 5 μL of dithionite solution (0.5 M in 0.1 M NaOH solution) were added to the same sample and mixed by pipetting; a spectrum of this solution (reduced spectrum) was taken at 380 nm to 650 nm. The protein concentration was calculated using the extinction coefficient and dilution factor (2× dilution in volume): $\varepsilon\_[557_{reduced}-540_{oxidized}]$=23.98 $mM^{-1}cm^{-1}$. (32)

Expression of P411 proteins. *E. coli* BL21 E. Cloni® cells carrying a plasmid encoding a P411 variant were grown overnight in 5 mL $LB_{amp}$ (37° C., 220 rpm). The pre-culture was used to inoculate 45 mL of $HB_{amp}$ in a 125-mL Erlenmeyer flask; this culture was incubated at 37° C., 220 rpm for 2 h and 15 min. Cultures were then cooled on ice (40 min), and expression was induced with 0.5 mM isopropyl β-D-1-thiogalactopyranoside (IPTG) and 1.0 mM 5-aminolevulinic acid (final concentrations). Expression was conducted at room temperature (24 or 22° C.), at 140 (or 150) rpm, for 20 h (±20 min). Cultures were then centrifuged (4,500×g, 5 min, 4° C.), and the pellets were resuspended to an $OD_{600}$ of 60 in M9-N buffer. Aliquots of the cell suspension (3 mL) were used to determine protein concentration after lysis by sonication. The expression level in $OD_{600}$=60 lysates is typically in the range of 3-13 μM for the P411-C10 variants.

Biotransformations. All the biocatalytic reactions were set up in an anaerobic chamber (oxygen level: <40 ppm). Resuspended cells (340 μL, diluted to a given $OD_{600}$ with M9-N minimal buffer) were added to 2 mL vials, followed by D-glucose (40 μL, 250 mM in M9-N), aniline derivatives (10 μL of an EtOH stock, 400 or 480 mM), and α-diazo-γ-lactone (LAD, 10 μL of an EtOH stock, 400 or 480 mM). Final concentrations were typically 10.0 or 12.0 mM aniline derivative, 10.0 or 12.0 mM LAD, and 25 mM D-glucose; final reaction volume was 400 μL. The vials were sealed, shaken inside the anaerobic chamber at room temperature for a set time (600 rpm). After the reaction was completed and the vials removed from the anaerobic chamber, internal standard 1,3,5-trimethoxybenzene (1,3,5-TMOB), p-methyl anisole (pMe-anisole), ethyl 2-phenylacetate (PhEA), or allyl phenyl ether (AllylOPh) (20 μL of 20 mM stock solution in acetonitrile) was added followed by acetonitrile (0.58 mL). The mixture was transferred to a 1.7-mL Eppendorf tube, and then subjected to vortexing (15 s×3) and centrifugation (14,000 rpm, 5 min, 4° C.). A sample of the supernatant (0.8 mL) was transferred to a vial for reverse-phase HPLC analysis.

Reaction screening in 96-well plate format. Libraries (single site-saturation libraries generated employing the "22c-trick" method (29) or collections of heme protein variants) were screened in 96-well plates.

*E. coli* libraries for P411 variants were cultured in $LB_{amp}$ (350 μL/well) at 37° C., 250 rpm and 80% relative humidity overnight. $HB_{amp}$ (950 μL/well) was inoculated with the pre-culture (50 μL/well) and incubated at 37° C., 230 rpm, 80% humidity for 2 h and 45 min. The plates were cooled on ice for 30 minutes, and expression was induced with 0.5 mM IPTG and 1.0 mM 5-aminolevulinic acid (final concentrations). Expression was conducted at 22° C. and 220 rpm for 20 h.

The cells were pelleted (4,500×g, 5 min, 4° C.) and resuspended with M9-N buffer (340 μL/well) and D-glucose solution (40 μL/well, in M9-N). The 96-well plate was then transferred to an anaerobic chamber. In the anaerobic chamber, aniline derivative (10 μL/well, 400 mM in EtOH) and LAD (10 μL/well, 400 mM in EtOH) were added. The plate was sealed with aluminum foil and shaken inside the anaerobic chamber (600 rpm).

After 24 h, the plate was moved out of the anaerobic chamber. The seal was removed and acetonitrile (580 μL/well) and internal standard (1,3,5-trimethoxybenzene, p-methyl anisole, ethyl 2-phenylacetate or allyl phenyl ether; 20 mM in acetonitrile; 20 μL/well) were added. The plate was tightly sealed with a reusable silicone mat, vortexed (15 s×3) and centrifuged (4,500×g, 5 min). The supernatant (200 μL/well) was filtered through an AcroPrep 96-well filter plate (0.2 μm) into a shallow-well plate for reversed-phase HPLC analysis (C18 Kromasil column, $MeCN:H_2O$ 50:50, 1.2 mL/min flow, 230 or 254 nm).

B. SCREENING OF C10 LINEAGE FOR ACTIVITY ON DIFFERENT SUBSTRATES
TABLE 2
Aniline derivatives
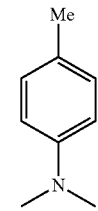
S1: pMe-DMA (1a)
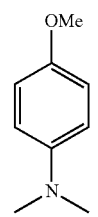
S2: pOMe-DMA (1b)
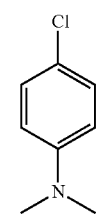
S3: pCl-DMA (1c)
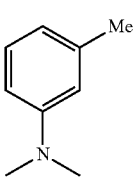
S4: mMe-DMA (1d)
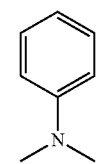
S5: DMA (1e)
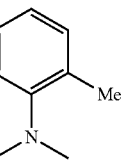
S6: oMe-DMA (1f)
TABLE 2-continued
Aniline derivatives
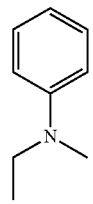
S7: Me,Et-Ani (1g)
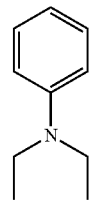
S8: DEA (1h)
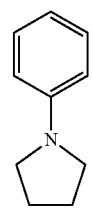
S9: Ph-pyr (1i)
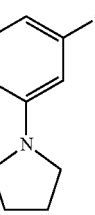
S10: mClPh-pyr (1j)
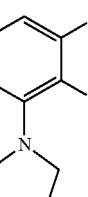
S11: diMePh-pyr (1k)
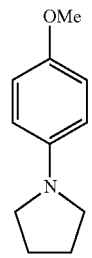
S12: pOme-pyr (1l)

TABLE 2-continued

Aniline derivatives

S13: pFmCl-pyr (1n)

S14: pMe-DEA

S15: Ph-aze (1m)

S16: THQ

S17: indoline

S18: Ph-mor

S19: Ph-pip

S20: pTol-aze

Plate screening of different substrates toward lactone-carbene C—H insertion: Rapid screening was first performed without accurate quantification). The enzyme lineage L1 to L10 was expressed in each line of a 96-well plate following General Procedure above (column 2 to column 11 with variants L1 to L10, respectively). Enzymatic reactions were set up with substrate concentration of 10 mM for both LAD and aniline derivative (one substrate in one line). After the reactions were completed, acetonitrile (600 µL/well) was added to reaction plates. The plates were tightly sealed with a reusable silicone mat, vortexed (15 s×3) and centrifuged (4,500×g, 5 min). The supernatant (200 µL/well) was filtered through an AcroPrep 96-well filter plate (0.2 µm) into a shallow-well plate for reversed-phase TIPLC analysis (C18 Kromasil column, MeCN:H$_2$O gradient from 40:60 to 100:00, 1.2 mL/min flow, 230 or 254 nm). Promising substrates were then identified with new compound peaks observed on TIPLC followed by further confirmation of products with NMR based on reaction scale-up and product isolaion.

TABLE 3

Screening result (with promising products: +; without new products: -)

| substrate | L1 | L2 | L3 | L4 | L5 | L6 | L7 | L8 | L9 | L10 |
|---|---|---|---|---|---|---|---|---|---|---|
| S1 (1a) | + | + | + | + | + | + | + | + | + | + |
| S2 (1b) | + | + | + | + | + | + | + | + | + | + |
| S3 (1c) | - | + | + | + | + | + | + | + | + | + |
| S4 (1d) | - | - | - | + | + | + | + | + | + | + |
| S5 (1e) | - | - | - | + | + | + | + | + | + | + |
| S6 (1f) | - | - | - | - | + | + | + | + | + | + |

TABLE 3-continued

Screening result (with promising products: +; without new products: −)

| substrate | L1 | L2 | L3 | L4 | L5 | L6 | L7 | L8 | L9 | L10 |
|---|---|---|---|---|---|---|---|---|---|---|
| S7 (1g) | − | + | + | + | + | + | + | + | + | + |
| S8 (1h) | − | − | − | − | + | + | + | + | + | + |
| S9 (1i) | + | + | + | + | + | + | + | + | + | + |
| S10 (1j) | − | + | + | + | + | + | + | + | + | + |
| S11 (1k) | + | + | + | + | + | + | + | + | + | + |
| S12 (1l) | + | + | + | + | + | + | + | + | + | + |
| S13 | − | − | − | − | + | + | + | + | + | + |
| S14 | − | − | + | + | + | + | + | + | + | + |
| S15 (1m) | − | − | − | − | − | − | − | − | + | + |
| S16 | − | − | − | + | + | + | + | + | + | + |
| S17 | + | + | + | + | + | + | + | + | + | + |
| S18 | − | − | − | − | − | − | − | − | − | − |
| S19 | − | − | − | − | − | − | − | − | − | − |
| S20 | − | − | − | − | − | − | − | − | − | − |

Substrates S18 to S20 were found inactive in the lactone-carbene C—H insertion reaction using the enzymes L1 to L10. Substrates S16 and S17 were found to generate mixtures of C—H insertion products at multiple sites of the molecules (with poor regio- and stereo-selectivities).

Plate re-screening was performed with the substrates below identified with promising products, following the procedure used for rapid screening but with internal standard for quantification and using specific TIPLC methods developed for each substrate (See Section IV for the details of product characterization and Section V for TIPLC calibration curves for product quantification).

TABLE 4

Active aniline derivatives

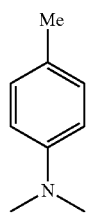

S1: pMe-DMA (1a)
In Std: pMe-Anisole

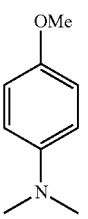

S2: pOMe-DMA (1b)
In Std: pMe-Anisole

TABLE 4-continued

Active aniline derivatives

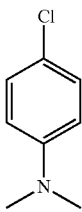

S3: pCl-DMA (1c)
In Std: pMe-Anisole

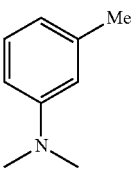

S4: mMe-DMA (1d)
In Std: pMe-Anisole

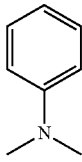

S5: DMA (1e)
In Std: PhEA

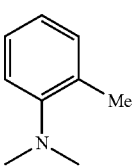

S6: oMe-DMA (1f)
In Std: pMe-Anisole

TABLE 4-continued

Active aniline derivatives

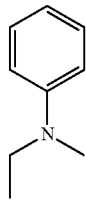

S7: Me,Et-Ani (1g)
In Std: pME-Anisole

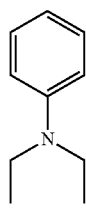

S8: DEA (1h)
In Std: PhEA

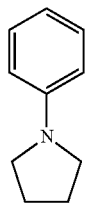

S9: Ph-pyr (1i)
In Std: 1,3,5-TMOB

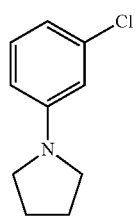

S10: mClPh-pyr (1j)
In Std: pMe-Anisole

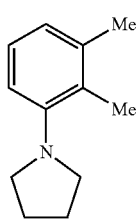

S11: diMePh-pyr (1k)
In Std: pMe-Anisole

TABLE 4-continued

Active aniline derivatives

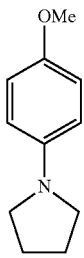

S12: pOme-pyr (1l)
In Std: pMe-Anisole

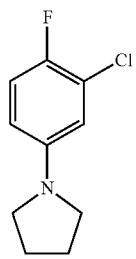

S13: pFmCl-pyr (1n)
In Std: 1,3,5-TMOB

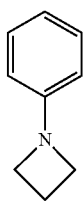

S15: Ph-aze (1m)
In Std: AllylOph

C. PREPARATION AND CHARACTERIZATION OF β-AMINO LACTONE PRODUCTS

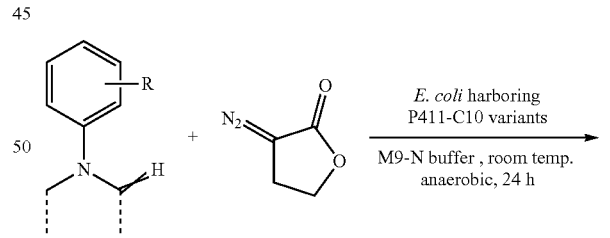

General procedure for enzymatic synthesis of β-amino lactone products: To 50-mL falcon tubes were added a suspension of *E. coli* expressing P411-C10 variant ($OD_{600}$=60, 30 mL), LAD (0.1-0.5 mmol), aniline derivative (1.2 equiv.), D-glucose (~20 mM), M9-N buffer/EtOH (~20:1 v/v) under anaerobic conditions. The tubes were capped and shaken (600 rpm) inside an anaerobic chamber at room temperature for 20-24 h. After the reaction was completed, the reaction mixture was transferred to 500 mL centrifuge bottle, and ~100 mL of hexane/ethyl acetate (1:1) mixed solvent was added. After the bottle was capped, it was shaken vigorously and centrifuged (6,000×g, 6 min). The organic layer was separated, and the aqueous layer was subjected to three more rounds of extraction. The organic layers were combined, dried over $Na_2SO_4$ and concentrated under reduced pressure. Purification by silica column chromatography with hexane/ethyl acetate afforded the desired β-amino lactone products.

C10 variants (usually the most active and/or selective ones) were chosen for each substrate according to the plate screening result in Section III. Substrate loading in each reaction was based on rough estimation of the enzymes' activity in plate screening. Total turnovers or yields were not accurately quantified (yields are in the range of 30-80%). The products isolated from these preparative-scale enzymatic reactions were further used for HPLC calibration curves and quantification of analytical-scale reactions as discussed below. The absolute configuration of the j-amino lactone products was not determined. Preparation of the lactone diazo substrate LAD follows the protocol in Chen et al. (33)

D. ANALYSIS OF ENZYMATIC LACTONE-CARBENE C—H INSERTION

All enzymatic reactions for lactone-carbene C—H insertion at analytical scale were conducted following the general procedure described below and analyzed with HPLC. All TTNs for different products were determined using the HPLC standard curves of the corresponding products obtained from the preparative-scale enzymatic reactions described above.

General procedure for analytical-scale reactions: To a 2 mL vial were added degassed suspension of E. coli expressing the P411-C10 variant (under expression conditions (2) in Section II) in M9-N buffer ($OD_{600}$=30 or 60, 340 μL), aniline derivatives (10 μL of 480 mM stock solution in EtOH, 12 mM), LAD (10 μL of 480 stock solution in EtOH, 12 mM), D-glucose (40 μL of 250 mM stock solution in M9-N buffer, 25 mM) under anaerobic conditions. The vial was capped and shaken at 600 rpm at room temperature for 24 h. Reactions for every substrate were set up in triplicate or quadruplicate. After the reactions were completed, internal standard (20 μL of 20 mM stock solution in acetonitrile, following Table 4) was added to the reaction vials followed by acetonitrile (0.58 mL). The mixture was transferred to a 1.7-mL microcentrifuge tube, and then vortexed (15 seconds×3) and centrifuged (14,000 rpm, 5 min). For HPLC analysis, 0.8 mL of supernatant were taken. TTN was calculated based on measured protein concentration.

Another set of enzymatic reactions was set up following the same procedure. After the reactions were completed, extraction of products with 0.6 mL of hexane/ethyl acetate (1:1) followed by vortexing and centrifugation afforded non-aqueous organic solutions of the desired products. Enantiomeric excess of the enzymatic reactions was measured using these organic solutions by normal-phase chiral HPLC.

Diastereomeric ratios (d.r.) of the products (if applicable) were determined by NMR and/or HPLC at wavelength of 254 nm (or 230 nm). The two methods show good consistency for dr determination within difference of 2%.

E. RESULTS AND DISCUSSION

We initiated this investigation of C—H functionalization with α-diazo-γ-lactone (LAD) and 4,N,N-trimethylaniline (1a) as substrates (FIG. 7).[18] The expected carbene-transfer reaction leads to the formation of a β-amino lactone product, 2a, through carbene insertion into an α-amino C—H bond with a chiral center generated at the α-position. Such β-amino lactone products are analogs of sesquiterpenelactone amino derivatives, which possess desirable pharmaceutical properties.[19] Screening various hemeproteins, including P450 variants, P41 is, and cytochromes c in the form of whole Escherichia coli (E. coli) cell catalysts identified a P411 variant, P411-C10, capable of the desired C—H insertion transformation. P411-C10, a promiscuous enzyme for different carbene-transfer chemistries including internal cyclopropene formation,[20] catalyzed the C—H insertion reaction using a cyclic carbene with modest efficiency (105 TTN) and stereoselectivity (47% ee).

Figure 7:
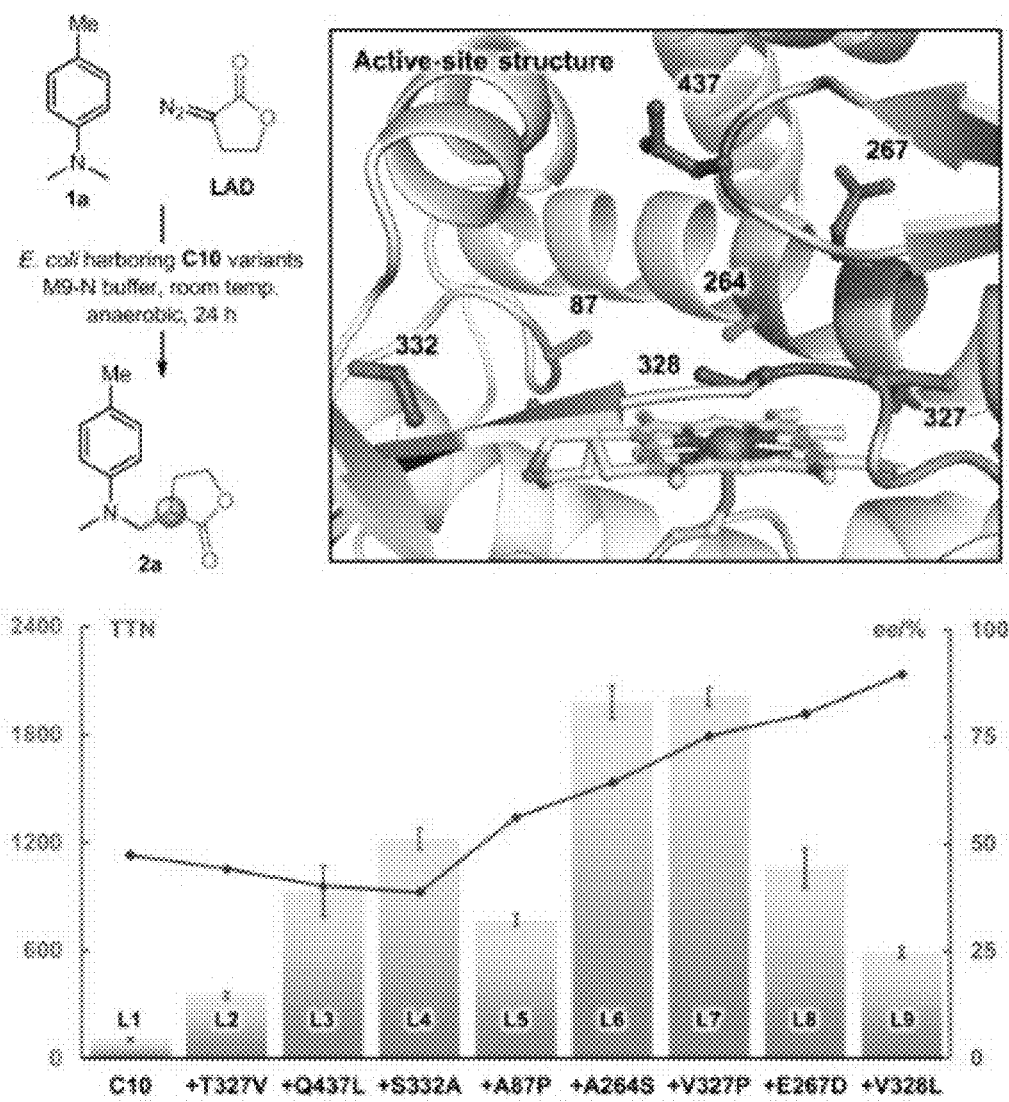
FIG. 7 shows the directed evolution of P411-C10 for lactone-carbene insertion into α-amino C—H bonds. Reactions were performed in quadruplicate under the following conditions: 10 mM 4,N,N-trimethyl aniline (1a), 10 mM LAD, E. coli harboring P411-C10 variants ($OD_{600}$=15 to 60), D-glucose (25 mM), M9-N buffer/EtOH (19:1), anaerobic, 24 h. Product formation was quantified by high-performance liquid chromatography (HPLC), TTNs were determined based on protein concentration, and enantioselectivity was measured using chiral HPLC. The heme-domain structure of P411-E10 variant, an enzyme previously evolved for C—H amination with high sequence identity to P411-C10, (pdb: 5UCW) was used to guide site-saturation mutagenesis; mutation sites are highlighted.

To enhance enzyme activity and selectivity by directed evolution, we targeted active-site residues for site-saturation mutagenesis and screening (FIG. 7). Loop residues in the enzyme's active site were tested first, and beneficial mutations T327V and Q437L together increased total turnovers 9-fold. However, enantioselectivity decreased to 40% ee after three rounds of evolution. As substrate 1a is symmetric, we hypothesized it might bind with different orientations relative to the carbene intermediate, which would lead to the diminished stereoselectivity. To address this, we next targeted amino acids previously shown to dramatically affect stereoselectivity in either native or non-native functions of this P450, such as sites 87, 264, 268, and 328.[13b-d,21] Screening a site-saturation library at site 87 for increased enantioselectivity resulted in discovery of a proline mutation giving 56% ee, albeit with decreased TTN. Residue 264 is the closest residue to the iron center, which may also influence binding of substrate or the orientation of the carbene intermediate. The A264S mutation improved both activity and enantioselectivity. Revisiting site 327 identified another proline mutation, which boosted the ee to 75%. The three mutations A87P, A264S, and V327P may have improved enantioselectivity by providing a more restricted binding mode for substrate 1a in the enzyme.

TABLE 5

Detailed information of the evolutionary lineage.

| P411-C10 variant | TTN | ee |
|---|---|---|
| C10 (L1) | 105 ± 10 | 47% |
| C10-T327V (L2) | 350 ± 20 | 44% |
| C10-T327V Q437L (L3) | 930 ± 140 | 40% |
| C10-T327V Q437L S332A (L4) | 1220 ± 60 | 39% |
| C10-T327V Q437L S332A A87P (L5) | 770 ± 30 | 56% |
| C10-T327V Q437L S332A A87P A264S (L6) | 1980 ± 90 | 64.5% |

TABLE 5-continued

Detailed information of the evolutionary lineage.

| P411-C10 variant | TTN | ee |
|---|---|---|
| C10-T327P Q437L S332A A87P A264S (L7) | 2010 ± 50 | 75% |
| C10-T327P Q437L S332A A87P A264S E267D (L8) | 1060 ± 110 | 80.5% |
| C10-T327P Q437L S332A A87P A264S E267D V328L (L9) | 590 ± 30 | 90% |
| C10-T327P Q437L S332A A87P A264S E267D V328R (L10) | 180 ± 15 | −66% |

TABLE 6

Further information on directed evolution experiments.

| Round # | Parent | Sites targeted for site-saturation mutagenesis | Screen for activity or enantio-selectivity | Beneficial mutations obtained |
|---|---|---|---|---|
| 1 | C10 | 87, 263, 327, 438 | activity | T327V (~3-fold improvement) T327I (~2-fold improvement) |
| 2 | L2 | 72, 78, 435, 437 | activity | Q437L (~3-fold improvement) Q437I (~3-fold improvement) Q437M (~2.5-fold improvement) |
| 3 | L3 | 72, 75, 268, 332 | activity | S332A (~1.3-fold improvement) S332C (~1.2-fold improvement) |
| 4 | L4 | 87, 263 | enantio-selectivity | A87P (ee increased to 56%, TTN decreased to ~60% of L3) |
| 5 | L5 | 264, 82 | enantio-selectivity | A264S (ee increased to 64.5%, 2.5-fold improvement in TTN) |
| 6 | L6 | 395, 327 | enantio-selectivity | V327P (ee increased to 75%, similar activity to L5) V327I (ee increased to 71%, ~60% decrease in TTN) V327S (ee increased to 74%, ~75% decrease in TTN) |
| 7 | L7 | 437, 267 | enantio-selectivity | E267D (ee increased to 80.5%, ~50% decrease in TTN) |
| 8 | L8 | 328, 401 | enantio-selectivity | V328L (ee increased to 90%, ~40% decrease in TTN) V328R (ee flipped to −66%, ~80% decrease in TTN) |

TABLE 7

Optimization of expression and reaction conditions.

| Variant | Enzyme expression conditions (1) + Reaction conditions (1) | Enzyme expression conditions (2) + Reaction conditions (2) |
|---|---|---|
| L6 | $OD_{600}$ = 30<br>2070 TTN,<br>72% yield,<br>64.5% ee | $OD_{600}$ = 60<br>2760 TTN,<br>82% yield,<br>63% ee |
| L7 | $OD_{600}$ = 30<br>1960 TTN,<br>86% yield,<br>75% ee | $OD_{600}$ = 30<br>2920 TTN,<br>>99% yield,<br>74.5% ee |
| L9 | $OD_{600}$ = 30<br>610 TTN,<br>16% yield,<br>90% ee | $OD_{600}$ = 60<br>1380 TTN,<br>61% yield,<br>90.5% ee |
| L10 | $OD_{600}$ = 60<br>180 TTN,<br>6% yield,<br>−66% ee | $OD_{600}$ = 60<br>360 TTN,<br>8% yield,<br>−68% ee |

Enzyme expression conditions (1) for Table 5: 22° C., at 150 rpm, for 20 h (±20 min).
Enzyme expression conditions (2): 24° C., at 140 rpm, for 20 h (±20 min).
Reaction conditions (1) for Table 5: 10 mM 4,N,N-trimethyl aniline (1a), 10 mM LAD, E. coli harboring P411-C10 variants ($OD_{600}$ = 60 for L1, L5 and L10, $OD_{600}$ = 30 for the rest), D-glucose (25 mM), M9-N buffer/EtOH (19:1), anaerobic, 24 h.
Reaction conditions (2): 12 mM 4,N,N-trimethyl aniline (1a), 12 mM LAD, E. coli harboring P411-C10 variants ($OD_{600}$ = 30 for L7, $OD_{600}$ = 60 for the rest), D-glucose (25 mM), M9-N buffer/EtOH (19:1), anaerobic, 24 h.

Figure 8:
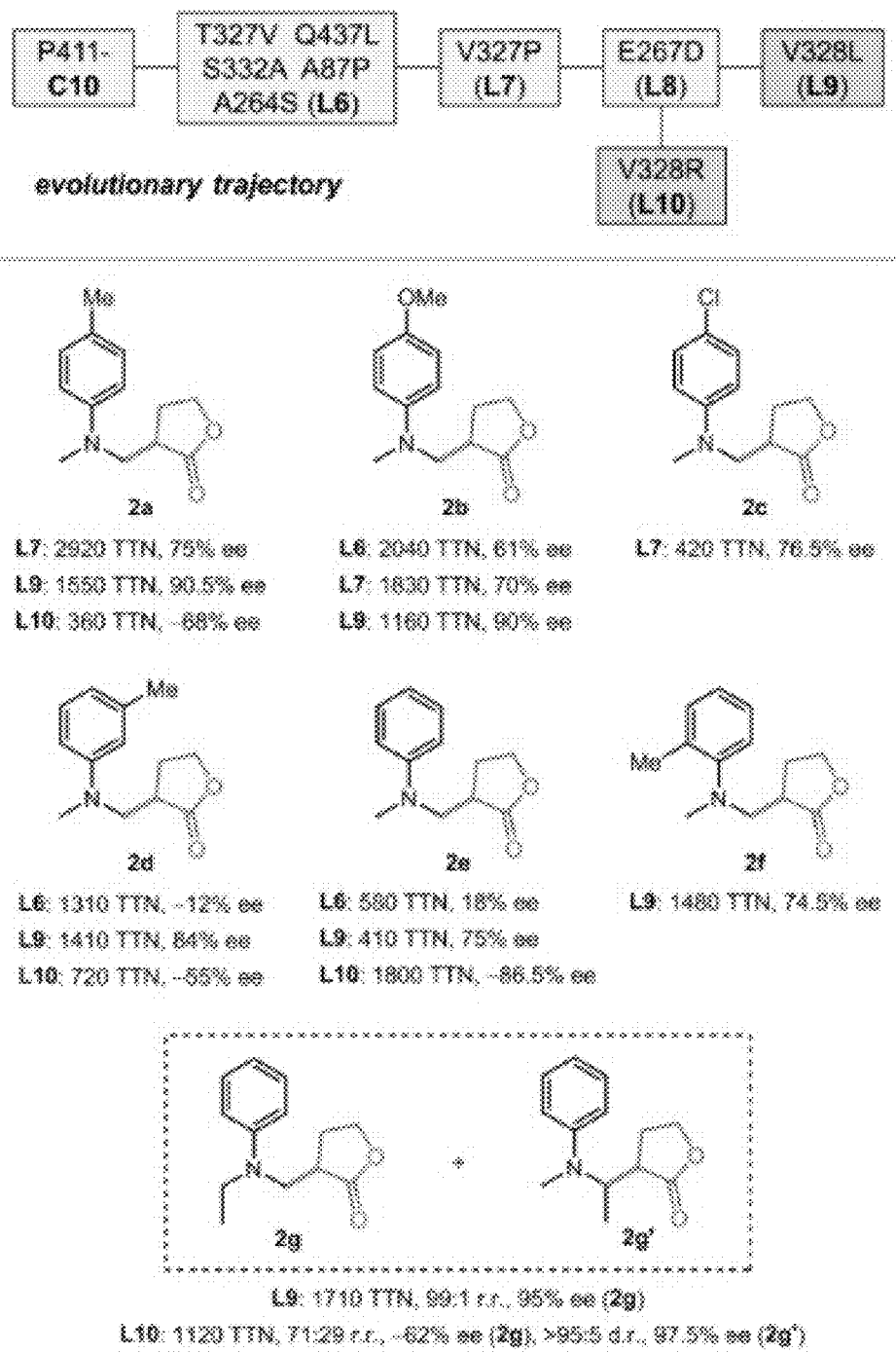
FIG. 8 shows the scope of lactone-carbene insertion into α-amino primary C—H bonds. Reactions were performed in triplicate or quadruplicate under the following conditions: 12 mM aniline derivatives, 12 mM LAD, *E. coli* harboring P411-C10 variants (OD$_{600}$=30 or 60), D-glucose (25 mM), M9-N buffer/EtOH (19:1), anaerobic, 24 h. Product formation was quantified by HPLC and TTNs were determined based on protein concentration. Enantioselectivity was measured using chiral HPLC and regioselectivity was determined by HPLC and NMR.

Further rounds of evolution accumulated two more mutations, E264D and V328L, to give final variant L9 that produces 2a with 90% ee. Although the TTN of L9 dropped to approximately 600 under screening conditions, optimization of enzyme expression and reaction conditions improved TTN 1.5- to 2.5-fold (FIG. 8, entry 2a). Another variant, L10, with a V328R mutation obtained from the 328X site-saturation library, showed the opposite stereo-preference (−68% ee) for this C—H insertion reaction, suggesting that this biocatalytic platform may be tunable for enantiodivergent synthesis.[22]

As different variants in the enzyme lineage (L1 to L10) showed different levels of activity or selectivity for the C—H insertion reaction, we selected representative variants (L6 to L10) with which to evaluate the transformation of various N,N-dialkyl aniline derivatives, as shown in FIG. 8. Substituents on the phenyl ring, including methyl, methoxy or halide, are all compatible with the biocatalytic system, giving TTNs ranging from 410 to 2920. Variants L9 and L10 showed consistently opposite stereo-preference for diverse substrates (e.g., for 2d and 2e, 84% ee and 75% ee with L9, −55% and −86.5% ee with L10), whereas activity had different trends in some cases (e.g., for 2d and 2e, 1410 TTN and 410 TTN with L9, 720 TTN and 1800 TTN with L10). Interestingly, with N-methyl, N-ethyl aniline (1g), L9 only synthesized the primary C—H insertion product 2g with high efficiency (1710 TTN) and high enantioselectivity (95% ee); L10, in contrast, gave a mixture of the primary and secondary C—H insertion products, 2g and 2g', with a ratio of 71:29, where product 2g' was found to be mainly a single diastereomer and enantiomer (>95:5 d.r. and 98% ee). Based on this result, we anticipated that this enzyme lineage may have the potential to functionalize secondary C—H bonds to build contiguous chiral centers.

Figure 9:
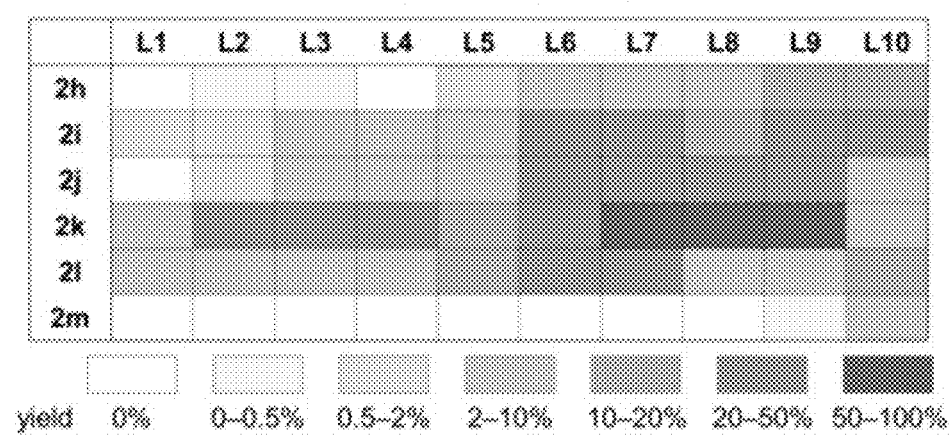
FIG. 9 shows the scope of lactone-carbene insertion into α-amino secondary C—H bonds. Reactions were performed in triplicate or quadruplicate under the following conditions: 12 mM aniline/pyrrolidine/azetidine derivatives, 12 mM LAD, *E. coli* harboring P411-C10 variants (OD$_{600}$=30 or 60), D-glucose (25 mM), M9-N buffer/EtOH (19:1), anaerobic, 24 h. Product formation was quantified by HPLC and TTNs were determined based on protein concentration. Enantioselectivity was measured using chiral HPLC and regioselectivity was determined by HPLC and/or NMR.
Figure 9:
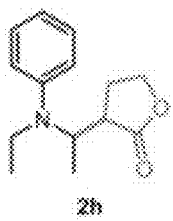
Figure 9:
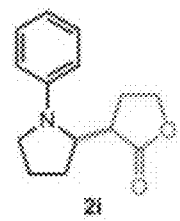
Figure 9:
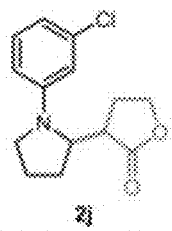
Figure 9:
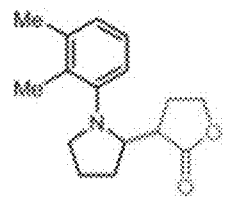
Figure 9:
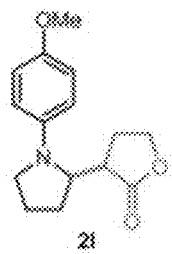
Figure 9:
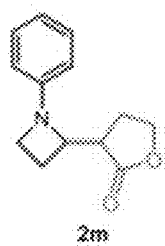

To explore the enzymes' ability to insert the lactone-carbene into secondary C—H bonds, we selected dialkyl-aniline, pyrrolidine, azetidine, and other N-aryl amine derivatives as substrates. We first screened the entire enzyme lineage with more than 10 substrates in 96-well plates. We were pleasantly surprised to see that many of the reactions formed the corresponding C—H insertion products. We picked the most promising combinations of enzyme variants and substrates for validation and further confirmation of the products. As shown in FIG. 9, the enzymes are particularly efficient toward carbene insertion into secondary C—H bonds, giving up to 4000 TTN. The final two variants, L9 and L10, gave good to high diastereoselectivities and enantioselectivities. For instance, L9 and L10 formed the same diastereomer with diethyl aniline (1h), giving 94:6 d.r. and 99:1 d.r., respectively; however, the diastereomers were obtained with opposite enantioselectivity (81% ee and −94.5% ee, respectively). The same trend was observed with N-phenyl pyrrolidine (1i). With 2,3-dimethyl phenylpyrrolidine (1k), only moderate diastereoselectivity was achieved with the selected variants, but the diastereomers can be separated easily by chromatography, and high enantioselectivity was observed for both diastereomers (up to 96% ee and 99% ee, respectively). Finally, N-phenyl azetidine (1m), which has a higher C—H bond dissociation energy on a strained ring,[23] was also active for C—H insertion, but only poor enantioselectivity was achieved (>95:5 d.r. and 13% ee for product 2m), presumably reflecting its distinct structure from that of substrate 1a used for evolution.

Figure 10:
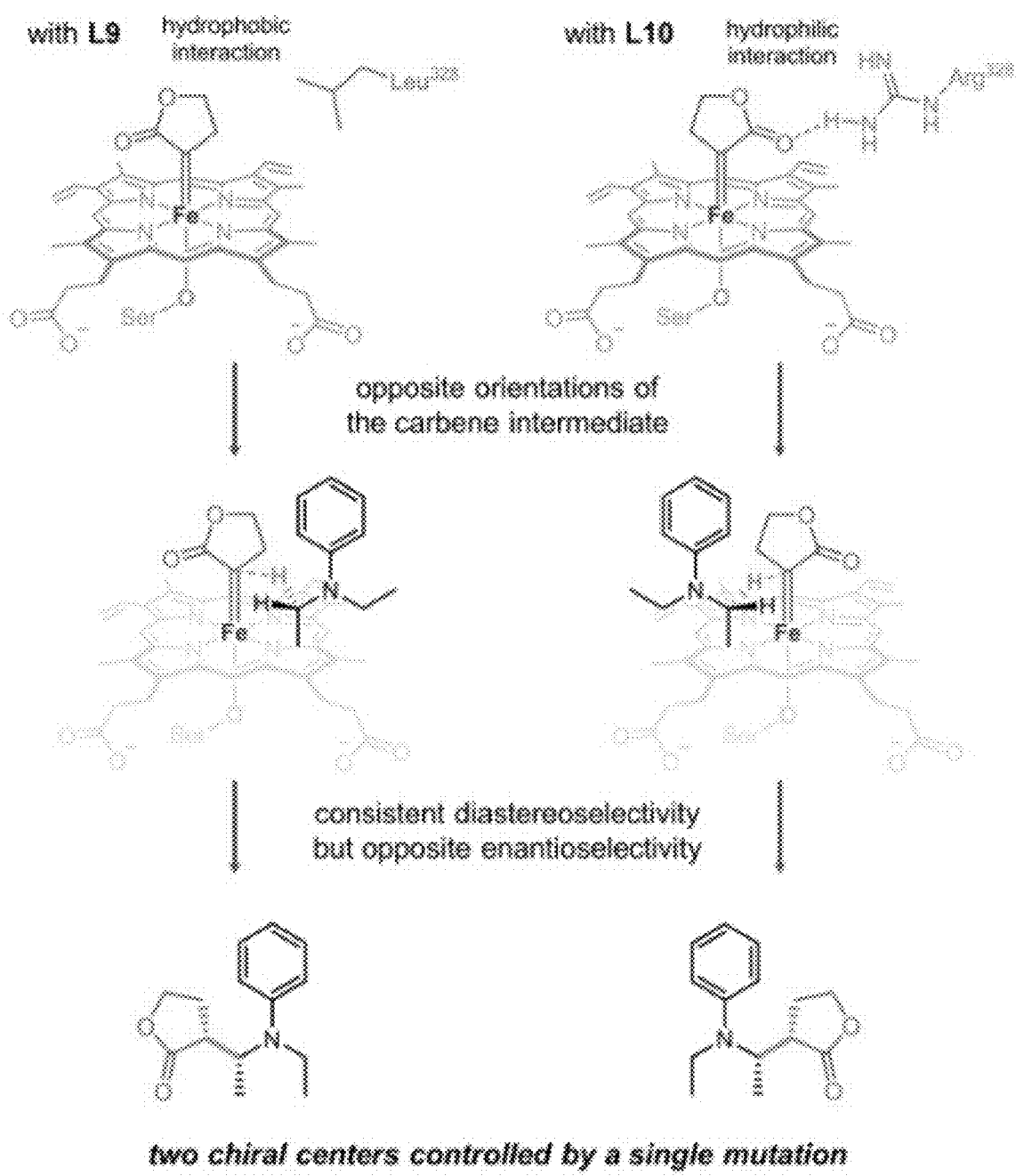
FIG. 10 shows a theory for stereocontrol in lactone-carbene insertion in secondary C—H bonds.

It is worth revisiting the cases where L9 and L10 formed the same major diastereomer but the opposite enantiomer in carbene insertion into secondary C—H bonds. This suggests that the single mutation going from L9 to L10, L328R, inverted two chiral centers simultaneously. As leucine and arginine possess very distinct features, we reasoned that the two residues might drive opposite orientations of the carbene intermediates with the hydrophobic side facing L328 and the hydrophilic side facing R328 (FIG. 10). Then C—H insertion might take place with the substrate approaching from different sides to give the opposite enantiomers. The detailed mechanism of C—H insertion, however, is still elusive—the reaction can undergo a radical pathway of hydrogen atom abstraction followed by radical rebound[24] or a concerted insertion pathway,[25,26] which may further affect the stereochemistry of the α-chiral center.[27] Mechanistic studies are ongoing to gain further insights into the C—H insertion reactions.

In conclusion, we have developed an efficient biocatalytic platform to assemble $C(sp^3)$-$C(sp^3)$ bonds through lactone-based carbene transfer to primary or secondary C—H bonds at α-amino positions. This enzymatic protocol offers rapid access to an array of chiral γ-lactone derivatives, which are analogs of sesquiterpene-lactone amino derivatives. The biocatalytic system was rapidly evolved to take N,N-dialkylaniline derivatives as substrates, outcompeting β-hydride elimination to furnish chiral j-amino lactone products with high catalytic efficiency (up to 4000 TTN) and in a stereodivergent manner. A single mutation can control the stereoselectivity of carbene insertion into secondary C—H bonds, inverting the two contiguous chiral centers and leading to the opposite enantiomers of the same major diastereomers. Ongoing studies with the family of P411-C10 variants will continue to expand the catalytic potential of C10, a versatile and promiscuous enzyme template for evolution of selective carbene transferases.[28]

F. REFERENCES (1) a) Saint-Denis, T. G.; Zhu, R.-Y.; Chen, G.; Wu, Q.-F.; Yu, J.-Q. Enantioselective $C(sp^3)$-H Bond Activation by Chiral Transition Metal Catalysts. *Science* 2018, 359, eaao4798. b) Hartwig, J. F.; Larsen, M. A. Undirected, Homogeneous C—H Bond Functionalization: Challenges and Opportunities. *ACS Cent. Sci.* 2016, 2, 281-292. c) Wu, W.-T.; Yang, Z.-P.; You, S.-L. in *Asymmetric Functionalization of C-H Bonds* (ed. You, S.-L.) Chapter 1 (Royal Society of Chemistry, Cambridge, 2015), p. 1-66. d) Yamaguchi, J.; Yamaguchi, A. D.; Itami, K. C—H Bond Functionalization: Emerging Synthetic Tools for Natural Products and Pharmaceuticals. *Angew. Chem., Int. Ed.* 2012, 51, 8960-9009. e) Zhang, R. K.; Huang, X.; Arnold, F. H. Selective C—H Bond Functionalization with Engineered Heme Proteins: New Tools to Generate Complexity. *Curr. Opin. Chem. Biol.* 2019, 49, 67-75.

(2) a) Doyle, M. P.; Duffy, R.; Ratnikov, M.; Zhou, L. Catalytic Carbene Insertion into C—H Bonds. *Chem. Rev.* 2009, 110, 704-724. b) Davies, H. M. L.; Beckwith, R. E. J. Catalytic Enantioselective C—H Activation by Means of Metal-Carbenoid-Induced C—H Insertion. *Chem. Rev.* 2003, 103, 8, 2861-2904. c) Davies, H. M. L.; Manning, J. R. Catalytic C—H Functionalization by Metal Carbenoid and Nitrenoid Insertion. *Nature* 2008, 451, 417-424.

(3) a) Taber, D. F.; Petty, E. H.; Raman, K. Enantioselective Ring Construction: Synthesis of (+)-α-Cuparenone. *J. Am. Chem. Soc.* 1985, 107, 196-199. b) Doyle, M. P.; Oeveren, A. V.; Westrum, L. J.; Protopopova, M. N.; Clayton Jr, T. W. Asymmetric Synthesis of Lactones with High Enantioselectivity by Intramolecular Carbon-Hydrogen Insertion Reactions of Alkyl Diazoacetates Catalyzed by Chiral Rhodium(II) Carboxamides. *J. Am. Chem. Soc.* 1991, 113, 8982-8984. c) Doyle, M. P.; Kalinin, A. V.; Ene, D. G. Chiral Catalyst Controlled Diastereoselection and Regioselection in Intramolecular Carbon-Hydrogen Insertion Reactions of Diazoacetates. *J. Am. Chem. Soc.* 1996, 118, 8837-8846. d) Davies, H. M. L.; Hansen, T. Asymmetric Intermolecular Carbenoid C—H Insertions Catalyzed by Rhodium(II) (S)—N-(p-Dodecylphenyl)sulfonylprolinate. *J. Am. Chem. Soc.* 1997, 119, 9075-9076. e) Davies, H. M. L.; Hansen, T.; Churchill, M. R. Catalytic Asymmetric C—H Activation of Alkanes and Tetrahydrofuran. *J. Am. Chem. Soc.* 2000, 122, 3063-3070.

(4) a) Suematsu, H.; Katsuki, T. Iridium(III)-Catalyzed Diastereo- and Enantioselective C—H Bond Functionalization. *J. Am. Chem. Soc.* 2009, 131, 14218-14219. b) Weldy, N. M.; Schafer, A. G.; Owens, C. P.; Herting, C. J.; Varela-Alvarez, A.; Chen, S.; Niemeyer, Z.; Musaev, D. G.; Sigman, M. S.; Davies, H. M. L.; Blakey, S. B. Iridium(III)-Bis(imidazolinyl)phenyl Catalysts for Enantioselective C—H Functionalization with Ethyl Diazoacetate. *Chem. Sci.* 2016, 7, 3142-3146. c) Wang, J.-C.; Xu, Z.-J.; Guo, Z.; Deng, Q.-H.; Zhou, C.-Y.; Wan, X.-L.; Che, C.-M. Highly Enantioselective Intermolecular Carbene Insertion to C—H and Si—H Bonds Catalyzed by a Chiral Iridium(III) Complex of a $D_4$-Symmetric Halterman Porphyrin Ligand. *Chem. Commun.* 2012, 48, 4299-4301. d) Wang, H.-X.; Richard, Y.; Wan, Q.; Zhou, C.-Y.; Che, C.-M. Iridium(III)-Catalyzed Intermolecular C(sp³)-H Insertion Reaction of Quinoid Carbene. A Radical Mechanism. *Angew. Chem., Int. Ed.* 2020, 59, 1845-1850. e) Key, H. M.; Dydio, P.; Clark, D. S.; Hartwig, J. F. Abiological Catalysis by Artificial Haem Proteins Containing Noble Metals in Place of Iron. *Nature* 2016, 534, 534-537.

(5) a) Wang, Y.; Wen, X.; Cui, X.; Zhang, X. P. Enantioselective Radical Cyclization for Construction of 5-Membered Ring Structures by Metalloradical C—H Alkylation. *J. Am. Chem. Soc.* 2018, 140, 4792-4796; b) Cui, X.; Xu, X.; Jin, L.-M.; Wojtas, L.; Zhang, X. P. Stereoselective Radical C—H Alkylation with Acceptor/Acceptor-Substituted Diazo Reagents via Co(II)-Based Metalloradical Catalysis. *Chem. Sci.* 2015, 6, 1219-1224.

(6) a) Diaz-Requejo, M. M.; Belderrain, T. R.; Nicasio, M. C.; Trofimenko, S.; Pérez, P. J. Intermolecular Copper-Catalyzed Carbon-Hydrogen Bond Activation via Carbene Insertion. *J Am. Chem. Soc.* 2002, 124, 896-897. b) Fraile, J. M.; Garcia, J. I.; Mayoral, J. A.; Roldan, M. Simple and Efficient Heterogeneous Copper Catalysts for Enantioselective C—H Carbene Insertion. *Org. Lett.* 2007, 9, 731-733. c) Flynn, C. J.; Elcoate, C. J.; Lawrence, S. E.; Maguire, A. R. Highly Enantioselective Intramolecular Copper-Catalyzed C—H Insertion Reactions of α-Diazosulfones. *J. Am. Chem. Soc.* 2010, 132, 1184-1185. d) Clarke, L. A.; Ring, A.; Ford, A.; Sinha, A. S.; Lawrence, S. E.; Maguire, A. R. *Org. Biomol. Chem.* Enantioselective Copper Catalysed C—H Insertion Reaction of 2-Sulfonyl-2-Diazoacetamides to Form γ-Lactams. 2014, 12, 7612-7628.

(7) a) Griffin, J. R.; Wendell, C. I.; Garwin, J. A.; White, M. C. Catalytic C(sp³)-H Alkylation via an Iron Carbene Intermediate. *J. Am. Chem. Soc.* 2017, 139, 13624-13627. b) Mbuvi, H. M.; Woo, L. K. Catalytic C—H Insertions Using Iron(III)-Porphyrin Complexes. *Organometallics* 2008, 27, 637-645. c) Caballero, A.; Despagnet-Ayoub, E.; Diaz-Requejo, M. M.; Diaz-Rodríguez, A.; González-Nuñez, M. E.; Mello, R.; Munoz, B. K.; Ojo, W.-S.; Asensio, G.; Etienne, M.; Pérez, P. J. Silver-Catalyzed C—C Bond Formation between Methane and Ethyl Diazoacetate in Supercritical CO₂. *Science* 2011, 332, 835-838. d) Rivilla, I.; Gómez-Emeterio, B. P.; Fructos, M. R.; Diaz-Requejo M. M.; Pérez, P. J. Exclusive Aromatic vs Aliphatic C—H Bond Functionalization by Carbene Insertion with Gold-Based Catalysts. *Organometallics* 2011, 30, 2855-2860. e) Gutiérrez-Bonet, Á.; Juliá-Hernández, F.; de Luis, B.; Martin, R. Pd-Catalyzed C(sp³)-H Functionalization/Carbenoid Insertion: All-Carbon Quaternary Centers via Multiple C—C Bond Formation. *J. Am. Chem. Soc.* 2016, 138, 6384-6387. f) Reddy, A. R.; Zhou, C.-Y.; Guo, Z.; Wei, J.; Che, C.-M. Ruthenium-Porphyrin-Catalyzed Diastereoselective Intramolecular Alkyl Carbene Insertion into C—H Bonds of Alkyl Diazomethanes Generated in situ from N-Tosylhydrazones. *Angew. Chem., Int. Ed.* 2014, 53, 14175-14180. g) Lo, V. K.-Y.; Guo, Z.; Choi, M. K.-W.; Yu, W.-Y.; Huang, J.-S.; Che, C.-M. Highly Selective Intramolecular Carbene Insertion into Primary C—H Bond of α-Diazoacetamides Mediated by a (p-Cymene)ruthenium(II) Carboxylate Complex. *J. Am. Chem. Soc.* 2012, 134, 7588-7591. h) Nakagawa, Y.; Chanthamath, S.; Liang, Y.; Shibatomi, K.; Iwasa, S. Regio- and Enantioselective Intramolecular Amide Carbene Insertion into Primary C—H Bonds Using Ru(II)-Pheox Catalyst. *J. Org. Chem.* 2019, 84, 2607-2618.

(8) a) Davies, H. M. L.; Morton, D. Guiding Principles for Site-Selective and Stereoselective Intermolecular C—H Functionalization by Donor/Acceptor Rhodium Carbenes. *Chem. Soc. Rev.* 2011, 40, 1857-1869. b) Davies, H. M. L.; Denton, J. R. Application of Donor/Acceptor-Carbenoids to the Synthesis of Natural Products. *Chem. Soc. Rev.* 2009, 38, 3061-3071.

(9) a) Liao, K. B.; Negretti, S.; Musaev, D. G.; Bacsa, J.; Davies, H. M. L. Site-Selective and Stereoselective Functionalization of Unactivated C—H Bonds. *Nature* 2016, 533, 230-234. b) Liao, K. B.; Pickel, T. C.; Boyarskikh, V. B.; Bacsa, J. B.; Musaev, D. G. M.; Davies, H. M. L. Site-Selective and Stereoselective Functionalization of Non-Activated Tertiary C—H Bonds. *Nature* 2017, 551, 609-613. c) Liao, K. B.; Yang, Y. F.; Li, Y. Z.; Sanders, J. N.; Houk, K. N.; Musaev, D. G.; Davies, H. M. L. Design of Catalysts for Site-Selective and Enantioselective Functionalization of Non-Activated Primary C—H Bonds. *Nat. Chem.* 2018, 10, 1048-1055. d) Fu, J. T.; Ren, Z.; Bacsa, J.; Musaev, D. G.; Davies, H. M. L. Desymmetrization of Cyclohexanes by Site- and Stereoselective C—H Functionalization. *Nature* 2018, 564, 395-399. e) Liao, K. B.; Davies, H. M. L. Dirhodium Tetracarboxylates as Catalysts for Selective Intermolecular C—H Functionalization. *Nat. Rev. Chem.* 2019, 3, 347-360.

(10) DeAngelis, A.; Panish, R.; Fox, J. M. Rh-Catalyzed Intermolecular Reactions of α-Alkyl-α-Diazo Carbonyl Compounds with Selectivity over β-Hydride Migration. *Acc. Chem. Res.* 2016, 49, 115-127.

(11) Zhang, R. K.; Chen, K.; Huang, X.; Wohlschlager, L.; Renata, H.; Arnold, F. H. Enzymatic Assembly of Carbon-Carbon Bonds via Iron-Catalysed sp³ C—H Functionalization. *Nature* 2019, 565, 67-72.

(12) Zhang, J.; Huang, X.; Zhang, R. K.; Arnold, F. H. Enantiodivergent α-Amino C—H Fluoroalkylation Catalyzed by Engineered Cytochrome P450s. *J. Am. Chem. Soc.* 2019, 141, 9798-9802.

(13) Selected examples of non-native chemistries by engineered P411s: a) Coelho, P. S.; Wang, Z. J.; Ener, M. E.; Baril, S. A.; Kannan, A.; Arnold, F. H.; Brustad, E. M. A Serine-Substituted P450 Catalyzes Highly Efficient Carbene Transfer to Olefins in vivo. *Nat. Chem. Bio.* 2013, 9, 485-487. b) Brandenberg, O. F.; Prier, C. K.; Chen, K.; Knight, A. M.; Wu, Z.; Arnold, F. H. Stereoselective Enzymatic Synthesis of Heteroatom-Substituted Cyclopropanes. *ACS Catal.* 2018, 8, 2629-2634. c) Brandenberg, O. F.; Chen, K.; Arnold, F. H. Directed Evolution of a Cytochrome P450 Carbene Transferase for Selective Functionalization of Cyclic Compounds. *J. Am. Chem. Soc.* 2019, 141, 8989-8995. d) Hyster, T. K.; Farwell, C. C.; Buller, A. R.; McIntosh, J. A.; Arnold, F. H. Enzyme-Controlled Nitrogen-Atom Transfer Enables Regiodivergent C—H Amination. *J. Am. Chem. Soc.* 2014, 136, 15505-15508. e) McIntosh, J. A.; Coelho, P. S.; Farwell, C. C.; Wang, Z. J.; Lewis, J. C.; Brown, T. R.; Arnold, F. H. Enantioselective Intramolecular C—H Amination Catalyzed by Engineered Cytochrome P450 Enzymes in vitro and in vivo. *Angew. Chem., Int. Ed.* 2013, 52, 9309-9312. f) Prier, C. K.; Zhang, R. K.; Buller, A. R.; Brinkmann-Chen, S.; Arnold, F. H. Enantioselective, Intermolecular Benzylic C—H Amination Catalysed by an Engineered Iron-Haem Enzyme. *Nat. Chem.* 2017, 9, 629-634. g) Farwell, C. C.; Zhang, R. K.; McIntosh, J. A.; Hyster, T. K.; Arnold, F. H. Enantioselective Enzyme-Catalyzed Aziridination Enabled by Active-Site Evolution of a Cytochrome P450. *ACS Cent. Sci.* 2015, 1, 89-93.

(14) a) DeAngelis, A.; Dmitrenko, O.; Fox, J. M. Rh-Catalyzed Intermolecular Reactions of Cyclic α-Diazocarbonyl Compounds with Selectivity over Tertiary C—H Bond Migration. *J. Am. Chem. Soc.* 2012, 134, 11035-11043. b) Sattely, E. S.; Meek, S. J.; Malcolmson, S. J.; Schrock, R. R.; Hoveyda, A. H. Design and Stereoselective Preparation of a New Class of Chiral Olefin Metathesis Catalysts and Application to Enantioselective Synthesis of Quebrachamine: Catalyst Development Inspired by Natural Product Synthesis. *J. Am. Chem. Soc.* 2009, 131, 943-953. c) Solovyov, I.; Dar'in, D.; Krasavin, M. Convenient Approach to 2-Substituted (Thio)morpholin-3-ones from α-Diazoacetates via X—H Carbene Insertion—Lactamization Sequence. *Eur. J. Org. Chem.* 2019, 45, 7432-7438.
(15) Other cyclic carbenes such as quinoid carbenes have been used for C—H insertion: see ref 4d.
(16) Chen, K.; Zhang, S.-Q.; Brandenberg, O. F.; Hong, X.; Arnold, F. H. Alternate Heme Ligation Steers Activity and Selectivity in Engineered Cytochrome P450-Catalyzed Carbene Transfer Reactions. *J. Am. Chem. Soc.* 2018, 140, 16402-16407.
(17) Chen, K; Huang, X.; Zhang, S.-Q.; Zhou, A. Z.; Kan, S. B. J.; Hong, X.; Arnold, F. H. Engineered Cytochrome c-Catalyzed Lactone-Carbene B—H Insertion. *Synlett* 2019, 30, 378-382.
(18) The exact reaction was preliminarily disclosed and studied in ref 11.
(19) Woods, J. R.; Mo, H.; Bieberich, A. A.; Alavanja, T.; Colby, D. A. Amino-Derivatives of the Sesquiterpene Lactone Class of Natural Products as Prodrugs. *Med. Chem. Comm.* 2013, 4, 27-33.
(20) Chen, K.; Arnold, F. H. Engineering Cytochrome P450s for Enantioselective Cyclopropenation of Internal Alkynes. *J. Am. Chem. Soc.* 2020, 142, 6891-6895.
(21) a) Butler, C. F.; Peet, C.; Mason, A. E.; Voice, M. W.; Leys, D.; Munro, A. W. Key Mutations Alter the Cytochrome P450 BM3 Conformational Landscape and Remove Inherent Substrate Bias. *J. Biol. Chem.* 2013, 288, 25387-25399. b) Cirino, P. C.; Arnold, F. H. Regioselectivity and Activity of Sytochrome P450 BM-3 and Mutant F87A in Reactions Driven by Hydrogen Peroxide. *Adv. Synth. Catal.* 2002, 344, 932-937. c) Joyce, M. G.; Girvan, H. M.; Munro, A. W.; Leys, D. A Single Mutation in Cytochrome P450 BM3 Induces the Conformational Rearrangement Seen upon Substrate Binding in the Wild-Type Enzyme. *J. Biol. Chem.* 2004, 279, 23287-23293. d) Coelho, P. S.; Brustad, E. M.; Kannan, A.; Arnold, F. H. Olefin Cyclopropanation via Carbene Transfer Catalyzed by Engineered Cytochrome *P*450 enzymes. *Science* 2013, 339, 307-310.
(22) Examples of active-site mutations leading to different stereoselectivity in hemeprotein-catalyzed non-natural reactions: a) Chen, K.; Huang, X.; Kan, S. B. J.; Zhang, R. K.; Arnold, F. H. Enzymatic Construction of Highly Strained Carbocycles. *Science* 2018, 360, 71-75. b) Yang, Y.; Cho, I.; Qi, X.; Liu, P.; Arnold, F. H. An Enzymatic Platform for the Asymmetric Amination of Primary, Secondary and Tertiary C(sp$^3$)-H Bonds. *Nat. Chem.* 2019, 11, 987-993. c) ref 13b. d) Kan, S. B. J.; Huang, X.; Gumulya, Y.; Chen, K.; Arnold, F. H. Genetically Programmed Chiral Organoborane Synthesis. *Nature* 2017, 552, 132-136. e) Knight, A. M.; Kan, S. B. J.; Lewis, R. D.; Brandenberg, O. F.; Chen, K.; Arnold, F. H. Diverse Engineered Heme Proteins Enable Stereodivergent Cyclopropanation of Unactivated Alkenes. *ACS Cent. Sci.* 2018, 4, 372-377. f) ref 12.
(23) Bach, R. D.; Dmitrenko, O. Strain Energy of Small Ring Hydrocarbons. Influence of C—H Bond Dissociation Energies. *J. Am. Chem. Soc.* 2004, 126, 4444-4452.
(24) Radical pathway has been disclosed for carbene C—H insertion reactions catalyzed by cobalt/iridium-porphyrin and iron-phthalocyanine complexes: see refs 4d, 5 and 7a.
(25) Concerted C—H insertion is generally considered to take place with rhodium catalysts: a) Doyle, M. P.; Westrum, L. J.; Wolthuis, W. N. E.; See, M. M.; Boone, W. P.; Bagheri, V.; Pearson, M. M. Electronic and Steric Control in Carbon-Hydrogen Insertion Reactions of Diazoacetoacetates Catalyzed by Dirhodium(II) Carboxylates and Carboxamides. *J. Am. Chem. Soc.* 1993, 115, 958-964. b) ref 8.
(26) Concerted mechanism was also suggested for iron-carbene C—H insertion reactions: a) Ishii, S.; Zhao, S.; Helquist, P. Stereochemical Probes of Intramolecular C—H Insertion Reactions of Iron-Carbene Complexes. *J. Am. Chem. Soc.* 2000, 122, 5897-5898. b) Hernán-Gómez, A.; Rodríguez, M.; Parella, T.; Costas, M. Electrophilic Iron Catalyst Paired with a Lithium Cation Enables Selective Functionalization of Non-Activated Aliphatic C—H Bonds via Metallocarbene Intermediates. *Angew. Chem., Int. Ed.* 2019, 58, 13904-13911.
(27) Our previous computational study on the mechanism of lactone-carbene S—H insertion revealed a radical pathway involving hydrogen atom abstraction followed by stereo-invertive radical rebound at the α-chiral center, see ref 16.
(28) Reviews on exploring new enzymatic activities: a) Prier, C. K.; Arnold, F. H. Chemomimetic Biocatalysis: Exploiting the Synthetic Potential of Cofactor-Dependent Enzymes to Create New Catalysts. *J. Am. Chem. Soc.* 2015, 137, 13992-14006. b) Chen, K.; Arnold, F. H. Engineering New Catalytic Activities in Enzymes. *Nat. Catal.* 2020, 3, 103-113. c) Leveson-Gower, R. B.; Mayer, C.; Roelfes, G. The Importance of Catalytic Promiscuity for Enzyme Design and Evolution. *Nat. Rev. Chem.* 2019, 3, 687-705. d) Renata, H.; Wang, Z. J.; Arnold, F. H. Expanding the Enzyme Universe: Accessing Non-Natural Reactions by Mechanism-Guided Directed Evolution. *Angew. Chem., Int. Ed.* 2015, 54, 3351-3367.
(29) Kille, S.; Acevedo-Rocha, C. G.; Parra, L. P.; Zhang, Z.-G.; Opperman, D. J.; Reetz, M. T.; Acevedo J. P. Reducing Codon Redundancy and Screening Effort of Combinatorial Protein Libraries Created by Saturation Mutagenesis. *ACS Synth. Biol.* 2013, 2, 83-92.
(30) Gibson, D. G.; Young, L.; Chuang, R.-Y.; Venter, J. C.; Hutchinson III, C. A.; Smith, H. O. Enzymatic Assembly of DNA Molecules up to Several Hundred Kilobases. *Nature Methods* 2009, 6, 343-345.
(31) Sambrook, J.; Frisch, E.; Maniatis, T. *Molecular Cloning: A Laboratory Manual* (Cold Spring Harbor Laboratory Press, New York, 1989).
(32) Berry, E. A.; Trumpower, B. L. Simultaneous Determination of Hemes a, b, and c from Pyridine Hemochrome Spectra. *Anal. Biochem.* 1987, 161, 1-15.
(33) Chen, K.; Zhang, S.-Q.; Brandenberg, O. F.; Hong, X.; Arnold, F. H. Alternate Heme Ligation Steers Activity and Selectivity in Engineered Cytochrome P450-Catalyzed Carbene-Transfer Reactions. *J. Am. Chem. Soc.* 2018, 140, 16402-16407.
(34) Lodewyk, M. W.; Siebert, M. R.; Tantillo, D. J. Computational Prediction of $^1$H and $^{13}$C Chemical Shifts: A Useful Tool for Natural Product, Mechanistic, and Synthetic Organic Chemistry. *Chem. Rev.* 2012, 112, 1839-1862.

Example 8: Enzymatic Formation of Cyclized Compounds of Formula XI Using P411-C10 Variants In Vivo P411-C10 expression was conducted as described in Example 1. Whole cell catalyst preparation was conducted as described in Example 1, except $OD_{600}$=2.5 to 10. Small-scale reactions in whole-cell suspension under anaerobic conditions were conducted as described in Example 1, except that a diazo substrate of formula X (Scheme 5) was used as the only substrate.

Figure 11:
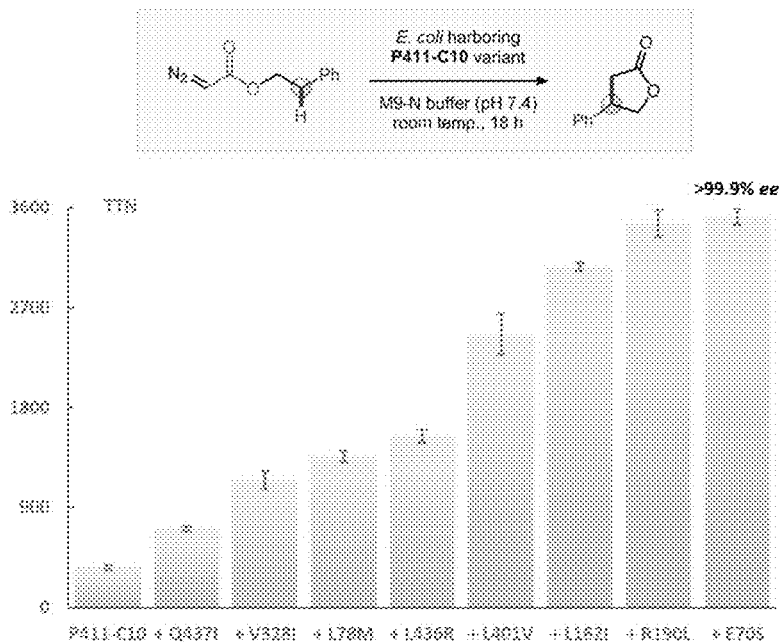
FIG. 11 shows examples of intramolecular cyclization reactions carried out with enzyme catalysts according to the present disclosure.
Figure 12:
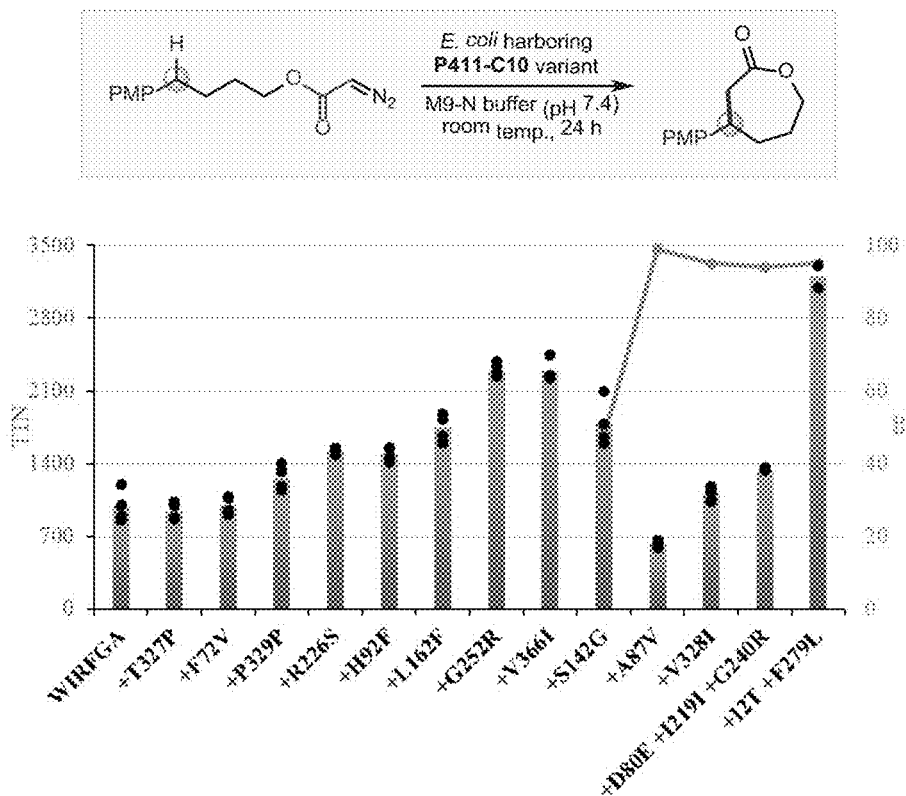
FIG. 12 shows examples of intramolecular cyclization reactions carried out with enzyme catalysts according to the present disclosure.

The results of the small scale reactions shown in FIG. 11 and FIG. 12 demonstrate that P411-C10 and variants thereof are capable of catalyzing the intramolecular carbene C—H insertion to give products of formula IX in Scheme 5 with high efficiency and selectivity. The activity can be improved by further engineering, if desired. Specifically, the initial variant P411-C10 found in the initial screen of P450 BM3 variants, which catalyzed the desired reaction with 360 TTN. Evolved P411-C10 variants containing mutations part or the whole set of T327P, Q437I, V328I, L78M, L436R, L401V, L162F, R190L, E70S, Y263W, S72V, S332G, G74A, R226S, H92F, G252R, V366I, S142G, and L82T were found with significantly improved activity and selectivity (with up to 5800 TTN, 81% yield and >99.9% ee) towards the formation of cyclic compound as described below.

Example 9: Enzymatic Formation of Chiral Amines of Formula XIII Using P411-C10 Variants In Vivo P411-C10 expression was conducted as described in Example 1. Whole cell catalyst preparation was conducted as described in Example 1, except $OD_{600}$=30 to 60. Small-scale reactions in whole-cell suspension under anaerobic conditions were conducted as described in Example 1, except that an amine substrate of formula XII (Scheme 6) was used in place of the alkyne substrate of formula I and $OD_{600}$=30 to 60.

Figure 13:
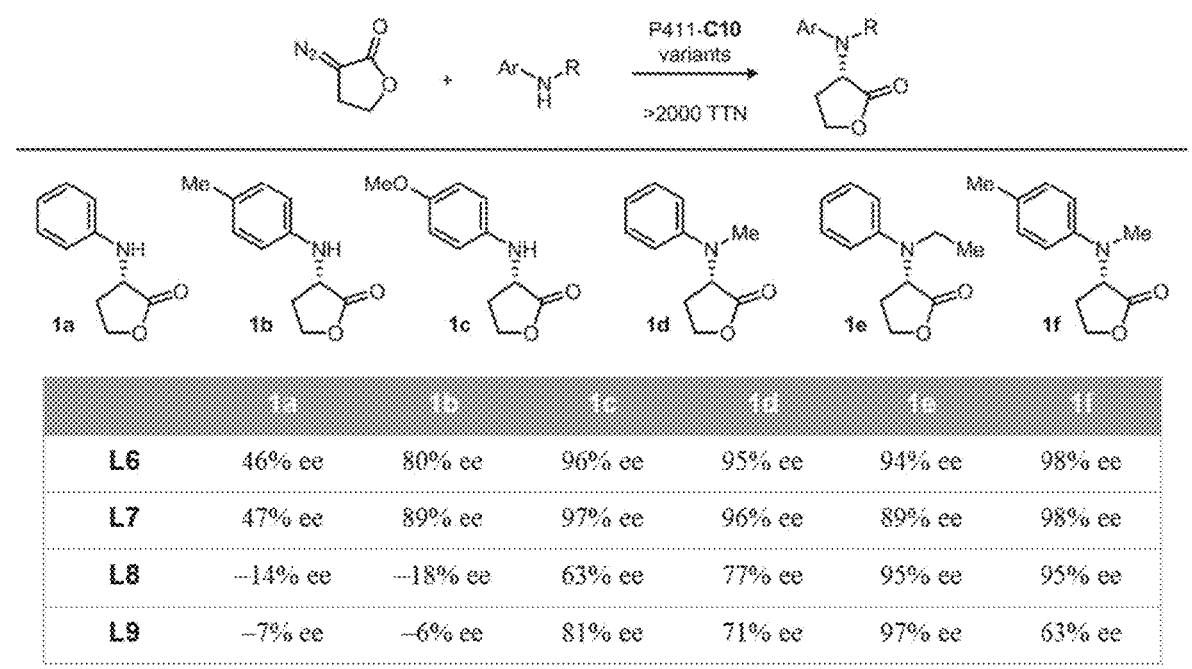
FIG. 13 shows examples of N—H insertion reactions carried out with enzyme catalysts according to the present disclosure.

The results of the small scale reactions shown in FIG. 13 demonstrate that P411-C10 and variants thereof are capable of catalyzing the cyclopropanation to give products of formula IX in Scheme 6 with high efficiency and tunable selectivity. The activity can be improved by further engineering, if desired. Specifically, the P411-C10 variants containing mutations part or the whole set of T327P (or T327V), Q437L, A87P, A264S, S332A, E267D and V328L (or V328R) were found with high activity and selectivity (with up to over 2000 TTN and 98% ee) towards the formation of chiral amines as described below (variants L6 to L9 are the same as those in Example 5).

Example 10: Dual-Function Enzyme Catalysis for Enantioselective C—N Bond Formation Amines are ubiquitous in bioactive molecules and functional materials[1,2], and the development of efficient and selective methods for C—N bond construction remains one of the central themes of modern organic chemistry and biochemistry[3-5]. Among the numerous methods to construct C—N bonds, carbene insertion into N—H bonds[6-10], which benefits from high reactivity and excellent functional group compatibility, has drawn enormous attention in the field of catalysis and has been utilized to rapidly build up complex nitrogen-containing molecules. In the last decade, empowered by directed evolution, heme-dependent metalloenzymes (e.g., cytochromes P450, cytochromes c and globins) have exhibited their immense potential in catalyzing non-natural carbene- and nitrene-transfer reactions with high efficiency and selectivity. Specifically, hemoproteins have been engineered to perform carbene N—H insertion reactions with catalytic efficiency far exceeding their small-molecule counterparts (up to thousands of total turnover number (TTN) for enzymes)[11-14]. However, compared to cyclopropanation[15], C—H insertion[16] and many other carbene transformations[17,18], enzymatic N—H insertion reactions are still largely underdeveloped, especially lacking in high enantioselective control.

Figure 14A:
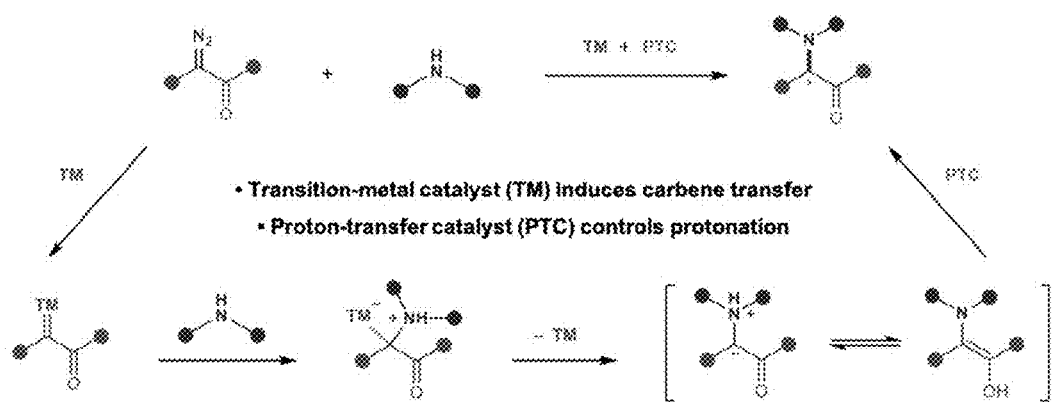
FIG. 14A shows the proposed reaction mechanism for asymmetric N—H insertion catalyzed by a transition-metal catalyst and a chiral proton transfer catalyst.
Figure 14B:
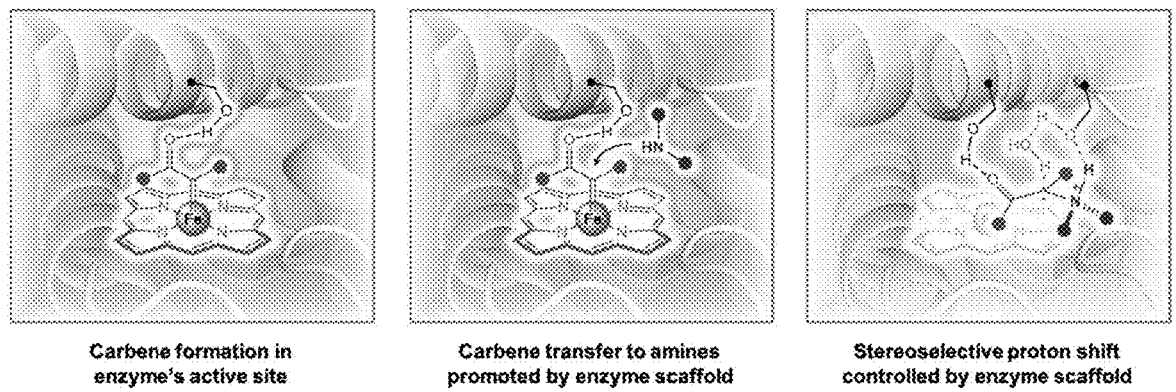
FIG. 14B shows that a hemoprotein according to the present disclosure serves as a dual-function catalyst for enantioselective carbene amination

In small-molecule catalysis, a typical strategy for asymmetric N—H insertion is to employ a transition-metal catalyst for carbene transfer as well as a separate chiral proton-transfer catalyst (PTC) for stereoinduction (FIG. 14A)[19,20]. In such a system, the carbene precursor first reacts to form metal carbene species, which is subsequently subject to nucleophilic attack from the amine substrate to form an ylide. The asymmetric protonation of the ylide intermediate is then guided by the chiral PTC, such as a chiral phosphoric acid[19] and amino-thiourea[20], where protic solvents need to be strictly avoided. Previous computational studies by Shaik and coworkers[21] revealed a similar mechanism for hemoprotein-catalyzed N—H insertion reactions. Therefore, in enzymatic systems, one major challenge in achieving high enantioselectivity originates from the difficulty in precisely controlling the protonation of ylide intermediates, especially in an environment full of proton sources from enzyme scaffolds as well as aqueous solvents. The only biocatalytic system reported for the asymmetric N—H insertion was developed by the Fasan group[13] between 2-diazopropanate benzyl esters and primary anilines using engineered myoglobins, though their enantiocontrol was overall low to moderate. By drawing an analogy to the synthetic strategy, we envisioned that a highly enantioselective biocatalytic N—H insertion reaction is possible if our enzyme is well-engineered to perform two distinct roles (FIG. 14B): 1) generating carbene species, which triggers nucleophilic attack from amines; 2) inducing selective proton-shift event after ylide formation in the enzyme's active site.

A. GENERAL PROCEDURES

General: Unless otherwise noted, all chemicals and reagents were obtained from commercial suppliers (Millipore Sigma, VWR, TCI America and Fischer Scientific) and were used without further purification. NMR spectra of chemicals in DMSO-$d_6$ and $CDCl_3$ were obtained using a Bruker Prodigy 400 MHz spectrometer, and were referenced to residual solvent signals. Data for $^1$H NMR are reported as follows: chemical shift (δ ppm), multiplicity (s=singlet, d=doublet, t=triplet, m=multiplet, bs=broad), coupling constant (Hz), and integration. Sonication was performed using a Qsonica Q500 sonicator. High-resolution mass spectra were obtained at the California Institute of Technology Mass Spectral Facility. Reverse-phase high-performance liquid chromatography (HPLC) and liquid chromatography-mass spectroscopy (LC-MS) for analysis were carried out using Agilent 1200 series instruments, with a C8 (Agilent ZORBAX SB-C8, 4.6×50 mm, 3.5 μm) column. Water and acetonitrile containing 0.1% acetic acid were used as eluents. Normal-phase chiral HPLC was performed using Daicel Chiralpak IA and IC columns (4.6×250 mm, 5 μm) with hexane and isopropanol as the mobile phase.

Cloning, mutagenesis, and expression of enzymes. Expression vector pET22b(+) (Novagen) was used for cloning and expression of all variants described in example.

Site-specific mutagenesis was performed using PCR technique with primers containing a mutated codon at the desired position. Primer sequences are available upon request. The PCR products were digested with DpnI, purified with New England Biolabs gel purification kit, and the gaps were repaired using Gibson Mix™.[29] Without further purification, 1 µL of the Gibson product was used to transform 50 µL of electrocompetent *Escherichia coli* BL21 E. Cloni© (Lucigen) cells. BL21 E. Cloni® cells transformed with pET22b(+) constructs encoding various P411$_{BM3}$ variants were grown overnight in 6 mL Luria-Bertani medium supplemented with 0.1 mg/mL ampicillin (LB$_{amp}$). Subsequently, 5 mL of this preculture were used to inoculate 45 mL of Hyperbroth medium supplemented with ampicillin (HB$_{amp}$). The expression culture was incubated at 37° C. and shaken at 230 rpm for 2 hours and 15 min. Then, the expression culture was cooled on ice for 40 minutes and was induced with 1 mM 5-aminolevulinic acid (ALA) and 0.5 mM isopropyl β-D-1-thiogalactopyranoside (IPTG) (final concentrations). Cells were expressed at 22° C. and 140 rpm for 20-24 hours, and the shaking radius was 25 mm. Once expression was finished, the cultures were centrifuged (4,000 g, 4 minutes, and 4° C.) and the pellets were resuspended to an optical density at 600 nm (OD$_{600}$) of 33 in M9-N minimal medium with pH adjusted to 7.4. Aliquots of the cell suspension (3-4 mL) were used to determine protein concentration after lysis by sonication.

Determination of hemeprotein concentration. Protein concentration in the cell was determined by performing hemochrome assay on the cell lysate.[30] Lysate was obtained by sonication (4 minutes, 1 second on, 1 second off, 30% intensity, on wet ice). The cell debris was removed by centrifugation (14,000 g, 10 minutes, 4° C.). 500 µL of the lysate were added to a cuvette and mixed with 500 µL of solution I [0.2 M NaOH, 40% (v/v) pyridine, 0.5 mM K$_3$Fe(CN)$_6$]. The UV-Vis spectrum (380-620 nm) of the oxidized state (Fe$^{III}$) was recorded immediately. Sodium dithionite (10 µL of 0.5 M solution in water) was added and the UV-Vis spectrum of the reduced state (Fe$^{II}$) was recorded immediately. The protein concentration was calculated using the extinction coefficient and dilution factor (2× dilution in volume): $\varepsilon\_[557_{reduced}-540_{oxidized}]=23.98$ mM$^{-1}$cm$^{-1}$. TTN values are lower bounds since the hemechrome assay detects the levels of heme, not necessarily concentration of the enzyme; however, heme concentration closely approximates enzyme concentration.

Analytic reaction setup and product quantification. All the biocatalytic reactions were set up in an anaerobic chamber (oxygen level: <40 ppm). 360 µL of resuspended cells (diluted to a given OD$_{600}$ with M9-N minimal buffer, pH=7.4) were added to 2 mL vials, followed by D-glucose (20 µL, 500 mM in M9-N), aniline derivatives (10 µL of an EtOH stock, 400 mM), and α-diazo-γ-lactone[31] (LAD, 10 µL of an EtOH stock, 400 mM). Final concentrations were typically 10.0 mM aniline derivative, 10.0 mM LAD, and 25 mM D-glucose; final reaction volume was 400 µL. The vials were sealed, shaken inside the anaerobic chamber at room temperature for a set time (550 rpm). After the reaction was completed and the vials removed from the anaerobic chamber, internal standard p-methyl anisole (600 µL of 0.833 mM stock solution in acetonitrile) was added. The mixture was transferred to a 1.7-mL Eppendorf tube, and then subjected to vortexing (15 s×3) and centrifugation (14,000 rpm, 5 min, 4° C.). A sample of the supernatant (0.2 mL) was transferred to a vial with an insert for reverse-phase HPLC analysis.

Another set of enzymatic reactions were set up following the same procedure. After the reactions were completed, extraction of products with 0.6 mL of hexane/ethyl acetate (2:3) followed by vortexing and centrifugation afforded the organic solutions of the desired products. Enantiomeric excess (e.e.) of the enzymatic reactions was measured using these organic solutions by normal-phase chiral HPLC.

Purification of P411-L7_FL. To obtain purified protein of L7_FL, a single colony of *E. coli* BL21(DE3) freshly transformed with plasmid encoding this enzyme variant was used to inoculate 30 mL LB$_{amp}$ broth and the culture was grown at 37° C., 230 rpm for 14h. Subsequently, 950 mL of HB$_{amp}$ broth in a 2.8 L flask were inoculated with 15 mL of the precultures and incubated at 37° C., 230 rpm for 2.5 h (to OD$_{600}$~1.0). The flask was then cooled in an ice-water bath for 40 min and induced with 0.5 mM IPTG and 1.0 mM ALA (final concentrations). Expression was conducted at 22° C., 140 rpm, for 22 h. Cultures were then centrifuged (5,000×g, 5 min, 4° C.), the supernatant was discarded, and the cell pellets were frozen on dry ice and stored at -78° C.

For protein purification, frozen cells were thawed on ice and resuspended in buffer A (25 mM tris, 20 mM imidazole, 100 mM NaCl, pH 7.5; 4 mL buffer per g of wet cell weight). The cell suspension was supplemented with 1 mg/mL lysozyme, 0.1 mg/mL DNAse I, and one protease inhibitor tablet (Pierce Protease Inhibitor Tablets, Thermo Scientific). The cell suspension was lysed by sonication (QSonica sonicator, 1 min total time, 1 s on/off cycles, 40% output). To pellet insoluble material, lysates were centrifuged (20,000×g, 20 min, 4° C.), and the cleared lysate was filtered through a 0.45 µm filter unit. His-tagged P411 proteins were purified from the lysate using a nickel NTA column (1 mL HisTrap HP, GE Healthcare) using an AKTAxpress purifier FPLC system (GE healthcare). Proteins were eluted on a stepwise gradient from 100% buffer A to 100% buffer B (25 mM tris, 300 mM imidazole, 100 mM NaCl, pH 7.5): 0 to 35% buffer B over 5 column volumes (CV), hold at 35% buffer B for 5 CV, and 35 to 100% buffer B over 3 CV. L7_FL eluted at 30-35% buffer B. Fractions containing eluted protein were pooled and subjected to three rounds of buffer exchange to storage buffer (50 mM Kpi, pH 7.98) using centrifugal spin filters (30 kDa molecular weight cut-off, Amicon Ultra, Merck Millipore). Subsequently, the concentrated protein was aliquoted, flash-frozen on powdered dry ice, and stored at -78° C. Protein concentrations were determined via the pyridine/hemochrome assay specified above prior to setting up biocatalytic reactions.

B. SCREENING OF HEMOPROTEINS FOR LACTONE CARBENE N—H INSERTION

General procedure: Screening of N—H insertion reaction with 40 hemoprotein variants was performed in a 96-well plate. *E. coli* libraries for P411 or P450 variants were cultured in LB$_{amp}$ (300 µL/well) at 37° C., 230 rpm and 80% relative humidity overnight. HB$_{amp}$ (950 µL/well) was inoculated with the pre-culture (50 µL/well) and incubated at 37° C., 250 rpm, 80% humidity for 2 h and 45 min. The plates were cooled on ice for 40 minutes, and expression was induced with 0.5 mM IPTG and 1.0 mM ALA (final concentrations). Expression was conducted at 22° C. and 230 rpm for 20-24 h.

Expression of Rma cytochrome c variants in 96-well plates employed a different protocol. *E. coli* libraries for Rma cytochrome c variants were induced with 20 µM IPTG and 0.2 mM ALA (final concentrations).

The cells were pelleted (4,500 rpm, 4 min, 4° C.) and resuspended with M9-N buffer (360 µL/well) and D-glucose solution (20 µL/well, 500 mM in M9-N). The 96-well plate was then transferred to an anaerobic chamber. In the anaerobic chamber, N-methylaniline (10 μL/well, 400 mM in EtOH) and LAD (10 μL/well, 400 mM in EtOH) were added. The plate was sealed with an aluminum foil, removed from the anaerobic chamber, and shaken at 600 rpm.

After 12 h, the seal was removed and a solvent mixture of hexane and EtOAc (2:3 v/v) (600 μL/well) was added. The plate was tightly sealed with a reusable silicone mat, vortexed (15 s×3) and centrifuged (4,500 rpm, 5 min). The organic phase (200 μL/well) was filtered through an Acro-Prep 96-well filter plate (0.2 μm) into a shallow-well plate for normal-phase HPLC analysis (Chiralpak IC, 25% i-PrOH in hexane, 1.5 mL/min, 32° C., 254 nm).

C. PREPARATION AND CHARACTERIZATION OF THE RACEMIC STANDARDS OF PRODUCTS GENERAL PROCEDURE[33]

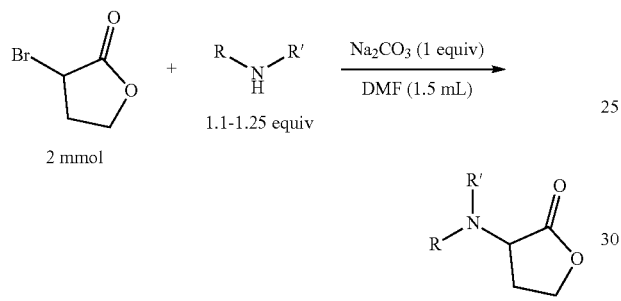

Condition A: To a solution of arylamine (2.5 mmol) in DMF (1.5 mL) was added α-bromo-γ-butyrolactone (330 mg, 0.185 mL, 2 mmol). The resulting mixture was heated at 80° C. for 24 hours.

Condition B: To a solution of alkylamine (2.2 mmol) in DMF (1.5 mL) was added α-bromo-γ-butyrolactone (330 mg, 0.185 mL, 2 mmol). The resulting mixture was heated at room temperature for 24 hours.

Workup: After reaction completion, the mixture was extracted with EtOAc (7 mL×3), and the combined organic layer was washed with saturated NaHCO$_3$ solution (15 mL) and brine (15 mL). The organic phase was further dried over Na$_2$SO$_4$ and concentrated to afford a brown residue. The final product was purified through silica gel column chromatography. All aniline-derived products (3a-3m) were prepared under Condition A. Alkylamine-derived products (3n-3q) were prepared under Condition B.

D. ANALYTIC SCALE ENZYMATIC REACTIONS AND CALIBRATION CURVES FOR PRODUCTS

All enzymatic reactions for lactone-carbene N—H insertion in analytical scale were conducted following the general procedure described above. Reactions for every substrate were set up in triplicate or quadruplicate. Product formation was quantified by reverse-phase HPLC based on the calibration curve of the corresponding racemic standard compound. All TTNs for different products were calculated as the concentration of products divided by the concentration of hemoproteins measured by the hemochrome assay. Substrates used in the reactions are shown below.

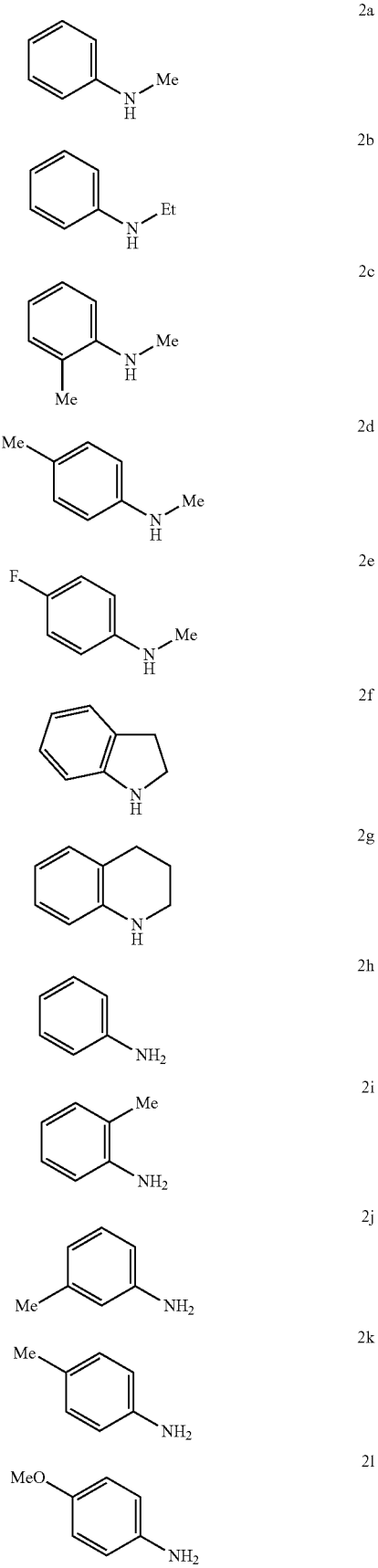

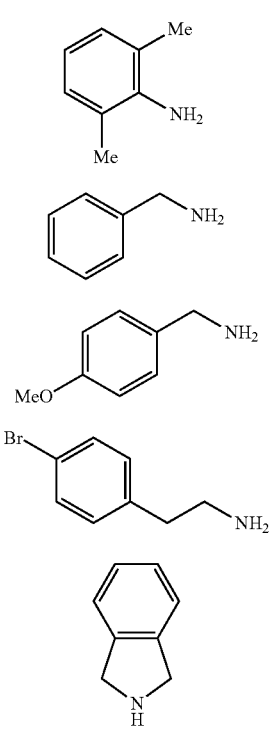

HPLC calibration curve: Calibration curves of synthesized reference compounds were created for the determination of yield and TTN. For each substrate, five different concentrations of product (1.25, 2.50, 5.00, 7.50, 10.0 mM) in 400 µL EtOH solutions were mixed each with 600 µL of 0.833 mM internal standard (p-methyl anisole) solution. The mixtures were vortexed and then analyzed by HPLC. All data points represent the average of duplicate runs. The calibration curves depict the ratio of product area to internal standard area (y-axis) against product concentration in mM (x-axis).

E. LARGE-SCALE ENZYMATIC SYNTHESIS

General procedure for 1 mmol-scale enzymatic reactions: To a 500 mL flask were added a suspension of *E. coli* expressing L7-FL variant ($OD_{600}$=15), aniline (1.0 mmol), LDA (123.2 mg, 1.1 mmol, 1.1 equiv.), D-glucose (20 mM), M9-N buffer/EtOH (20:1 v/v) under anaerobic conditions. The flask was capped and sealed with parafilm inside the anaerobic chamber. The mixture was shaken at 250 rpm in a shaker outside of anaerobic chamber for 20 hours.

After the reaction was completed, the reaction mixture was transferred to a 500 mL centrifuge bottle. The aqueous phase was extracted with organic solvent (hexane/EtOAc=2:3, 100 mL×4). The organic layers were combined in an Erlenmeyer flask, dried over $Na_2SO_4$ and concentrated under reduced pressure. Purification by silica column chromatography with hexane/EtOAc as eluents afforded the desired α-amino lactone products. TTNs were calculated based on measured protein concentration and isolated product yield.

General procedure for the gram-scale enzymatic reaction: To a 1 L flask were added a suspension of *E. coli* expressing L7-FL variant ($OD_{600}$=30), aniline (6.0 mmol), LDA (739.2, 6.6 mmol, 1.1 equiv.), D-glucose (20 mM), M9-N buffer/EtOH (20:1 v/v) under anaerobic conditions. The flask was capped and sealed with parafilm inside the anaerobic chamber. The mixture was shaken at 250 rpm in a shaker outside of anaerobic chamber for 20 hours.

After the reaction was completed, the reaction mixture was transferred to two 500 mL centrifuge bottles. The aqueous phase was extracted with organic solvent (hexane/EtOAc=2:3, 180 mL×4). The organic layers were combined in an Erlenmeyer flask, dried over $Na_2SO_4$ and concentrated under reduced pressure. Purification by silica column chromatography with hexane/EtOAc as eluents afforded the desired α-amino lactone products. TTNs were calculated based on measured protein concentration and isolated product yield.

F. RESULTS AND DISCUSSION

We commenced our investigation of enzymatic carbene N—H insertion by focusing on the reaction between lactone diazo 1 and N-methyl aniline 2a. This transformation is of particular interest as it is expected to afford a biologically relevant α-amino lactone product 3a. In addition, lactone-based carbenes are usually associated with undesired β-H elimination processes, and small-molecule catalysts have not been shown to be successful with precise stereocontrol using this type of carbenes[22,23]. Despite this, our previously developed enzymatic lactone carbene-transfer reactions suggest that aptly engineered hemoproteins could dramatically accelerate the desired carbene-transfer process while circumventing side pathways[24,25]. We thus need to find an enzyme that can not only facilitate the transfer of the lactone-carbene species to amines but also exquisitely impose stereocontrol in the subsequent proton shift step to deliver an enantio-enriched product.

Figure 15A:
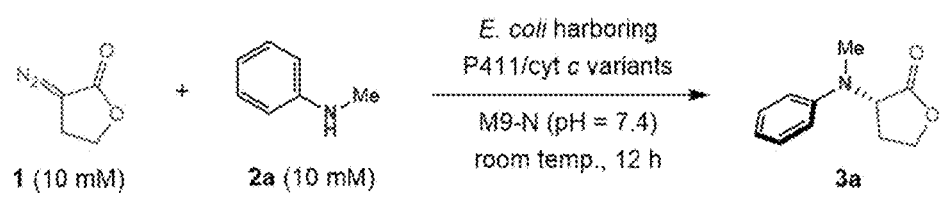
FIG. 15A shows the initial screening of N—H insertion activity performed with 40 hemoprotein variants, which led to the discovery of L7 (in well C10).
Figure 15A:
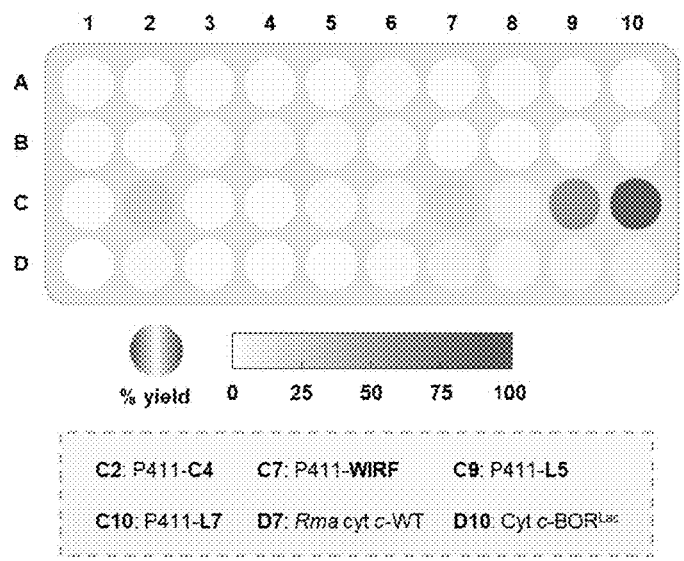
Figure 15B:
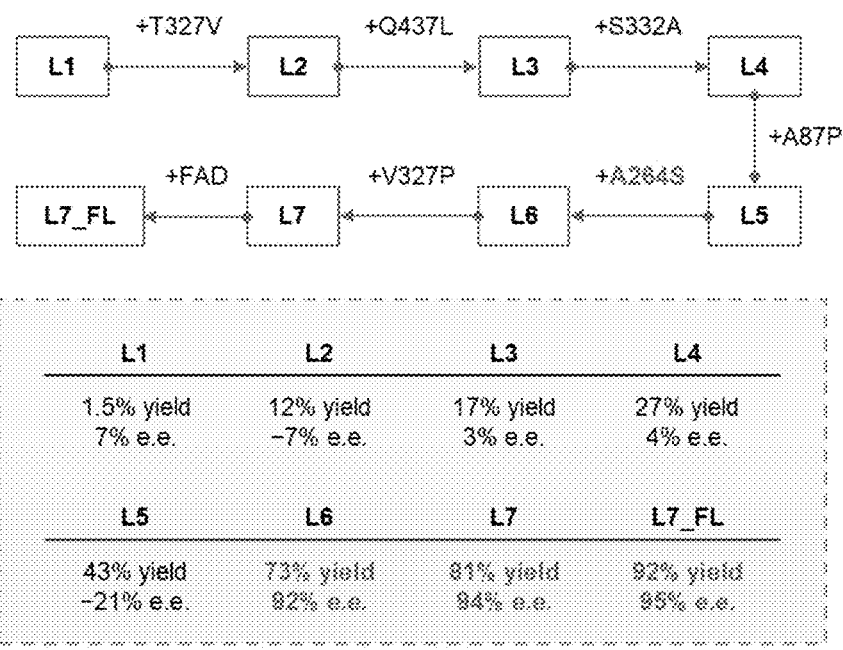
FIG. 15B shows the rescreening of the lactone carbene C—H insertion lineage. Variants with A264S mutation were found to be excellent catalysts for N—H insertion.

To this end, we screened a collection of 40 hemoprotein variants, previously evolved for different carbene and nitrene transformations, in the form of whole *Escherichia coli* (*E. coli*) cell catalysts (FIG. 15A) (See Supporting Information for details). While most of the variants only exhibited low levels of activity (<5% conversion), an FAD domain-truncated P411 variant (serine-ligated P450) L7 (in well C10), from our previous lactone carbene C—H insertion project[25], catalyzed this N—H insertion reaction with 81% yield and 94% enantiomeric excess (e.e.). Further evaluation of the enzyme lineage for lactone carbene C—H insertion showed that both L6 and L7 were superior biocatalysts for this amination reaction over other variants (L1-L5) (FIG. 15B). Restoring L7 to a full-length P411 (L7_FL) further improved the catalytic performance of this enzyme, generating product 3a in 92% yield and 95% e.e., which is likely due to the increased stability of the full-length protein[26].

Figure 15C:
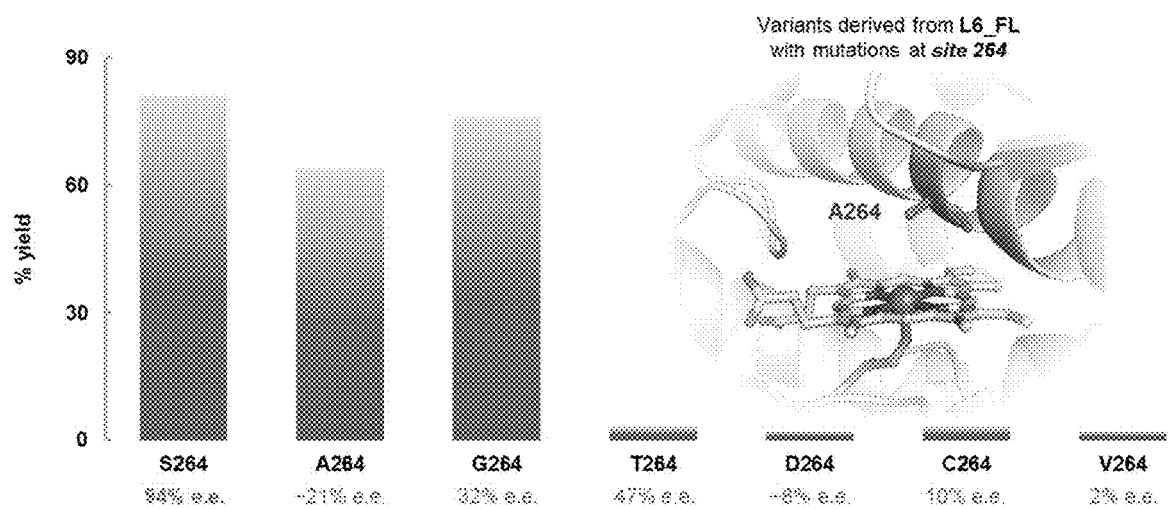
FIG. 15C summarizes mechanistic studies showing that changing 264S to other amino acid residues led to diminished yields and low enantioselectivities.

Notably, a single mutation from L5 to L6, A264S, exhibited a drastic impact on both yield (from 43% to 73%) and enantioselectivity (from −21% to 92% e.e.) for the N—H insertion reaction (FIG. 15B). This intriguing observation indicates that the amino acid residue at site 264, which is located above the heme cofactor, may play an important role in both promoting the lactone carbene-transfer process and exerting exquisite stereocontrol on the proton transfer step. We then cloned 5 variants based on L6_FL with different mutations at site 264 and evaluated their performance on the N—H insertion reaction (FIG. 15C). Interestingly, mutations of serine to smaller amino acids (A or G) led to comparable activity but much lower selectivity, suggesting that the hydrophilic side chain of serine may be involved in controlling the enantioselectivity. However, protic residues of larger size (D, T and C) at site 264 are detrimental to both the yield and stereocontrol. These results further underlined the crucial role of the serine residue at site 264 for our carbene N—H insertion reaction.

Figure 16:
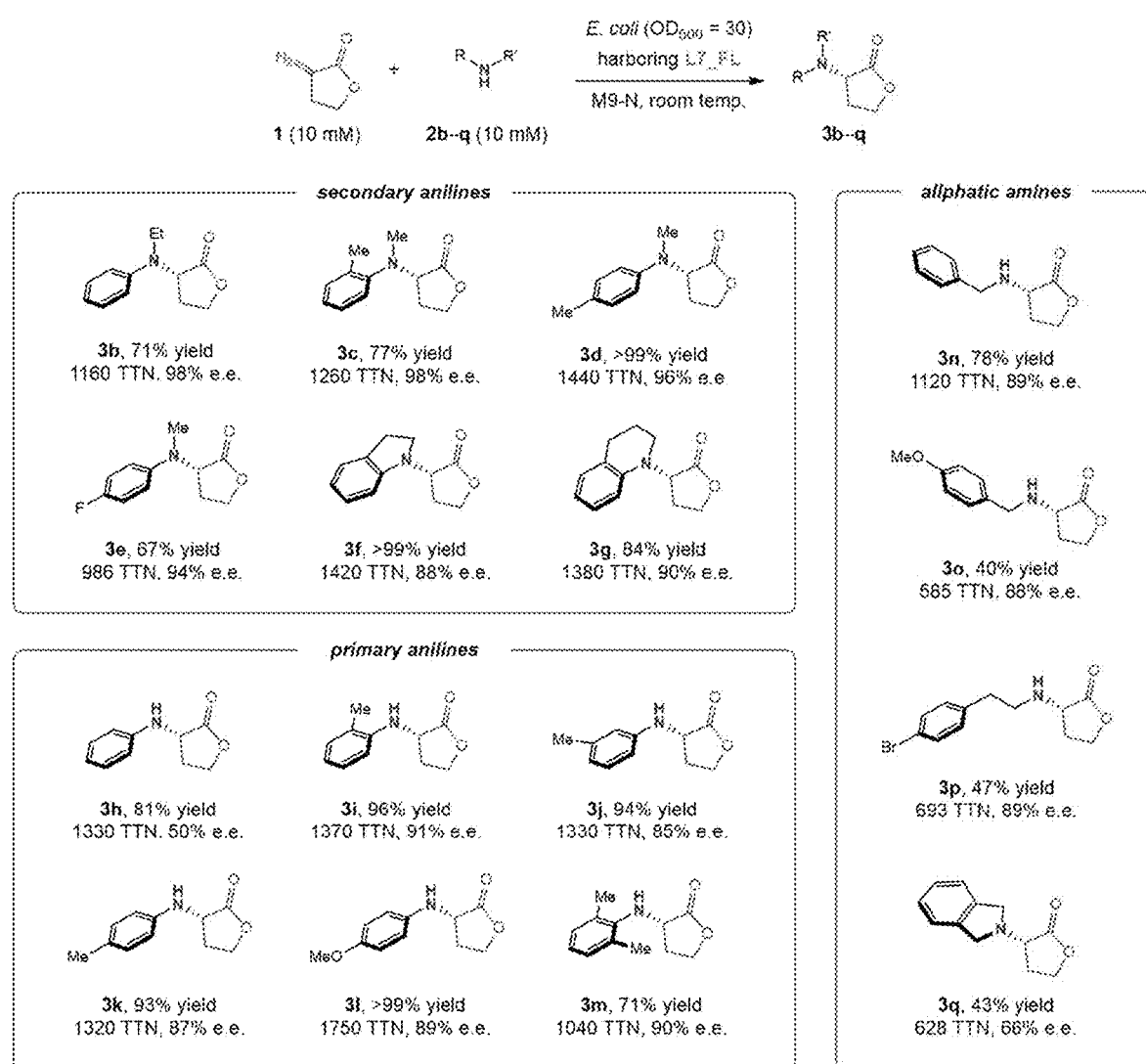
FIG. 16 summarizes enantioselective carbene N—H insertion of secondary, primary anilines and aliphatic amines. Experiments were performed using *E. coli* (OD$_{600}$=30) that expressed L7_FL enzyme with 10 mM LAD (1) and 10 mM amine (2b-q) at room temperature under anaerobic conditions.

With variant L7_FL in hand, we evaluated the scope of this biocatalytic amination reaction. Indeed, using lactone diazo compound 1 as the carbene precursor, a variety of amine nucleophiles could smoothly undergo the desired N—H insertion reaction under our standard whole-cell reaction conditions ($OD_{600}$=30 in M9-N buffer), as summarized in FIG. 16. Secondary anilines bearing an N-alkyl group (3b-g) were well tolerated in this transformation, giving good yields and excellent enantioselectivies. N-heterocycles, such as indoline (3f) and tetrahydroquinoline (3g), which are structural motifs commonly found in bioactive molecules, also served as competent substrates. Steric hindrance of nitrogen substituents did not exhibit a major impact on the enzyme performance, giving >70% yields and 98% e.e. (3b and 3c). L7_FL also displayed high activities toward primary anilines (3h-m) bearing various substitution patterns on the aromatic ring, including a sterically hindered substrate bearing two ortho-substituents (3m). Arguably, aliphatic amines are significantly more challenging substrates than anilines for asymmetric N—H insertion reactions due to their increased Lewis basicity at the nitrogen atom[17]. To our delight, L7_FL was able to accept these amines, primary (3n-p) or secondary (3q), for the desired transformations, furnishing the corresponding α-amino lactone products with good activities and enantioselectivities.

Figure 17A:
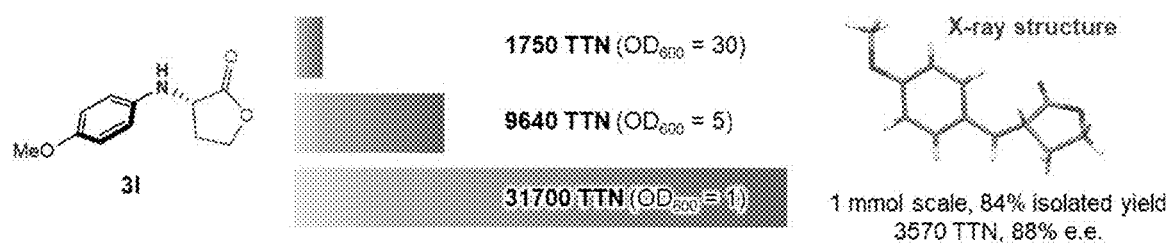
FIG. 17A shows that excellent TTNs (up to 31,700) were achieved with L7_FL when performing the enzymatic reaction with 2l at low OD$_{600}$.
Figure 17B:
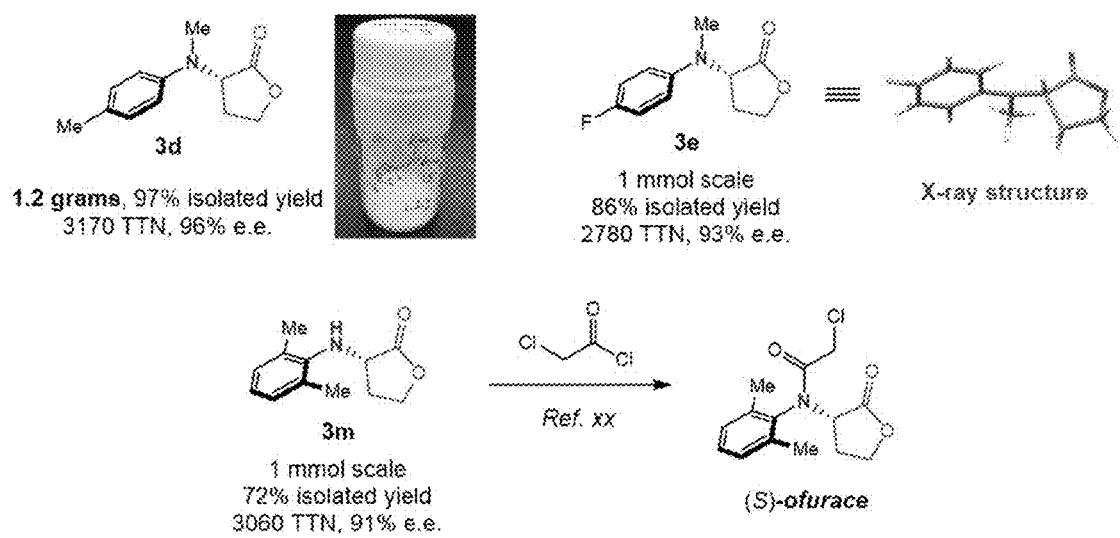
FIG. 17B shows preparative scale reactions carried out with 2l, 2d, 2e and 2m. The X-ray crystal structures of 3l and 3e were obtained and their absolute stereochemistry is consistent with computational studies. Taken together, FIG. 17A and FIG. 17B demonstrate the catalytic efficiency of L7_FL and the scalability of asymmetric N—H insertion reactions using this catalyst.

To demonstrate the utility of our biocatalytic platform, we further pushed the limit of our enzyme's catalytic capability by challenging the biocatalytic system with lower enzyme loadings. Under the standard conditions using whole-cell catalysts at $OD_{600}$=30, the TTNs of our reactions are typically within the range of 1000-2000 (FIG. 17). Gratifyingly, lowering the amount of our whole-cell catalyst did not result in a substantial drop in product formation, giving TTNs of 9640 ($OD_{600}$=5) and 31,700 ($OD_{600}$=1), indicating that our enzymatic platform is particularly robust for this asymmetric amination chemistry (FIG. 17A). In addition, the enzymatic reactions are readily scalable for large-quantity preparation (FIG. 17B). Using N-methyl-p-toluidine (2d) as the amine source, the enzymatic N—H insertion reaction was performed at gram scale, delivering product 3d in 97% isolated yield and 96% e.e. Products 3e and 3l were prepared at 1-mmol scale with crystal structures determined by X-ray crystallography. Finally, our enzymatic amination strategy was also applied to the formal synthesis of the (S)-enantiomer of a fungicide, ofurace[27,28]. The key intermediate 3m was prepared through the enzymatic N—H insertion reaction with 72% isolated yield and 91% e.e.

G. SUMMARY AND CONCLUSION

In summary, we developed an enzymatic platform that enables highly enantioselective carbene N—H insertion reaction to furnish a set of biologically relevant α-amino lactone products. The engineered P411 enzyme, L7_FL, acted as a dual-function biocatalyst that promoted the transfer of the lactone carbene to amines and exerted excellent stereocontrol in the subsequent protonation step. Furthermore, we demonstrated that this enzymatic system could accept a broad range of amines for the desired amination reactions with high activity and enantioselectivity (up to >99% yield and 98% e.e.). Our enzyme was shown to be robust by achieving high turnover numbers (e.g., 31,700 TTN with 21) and catalyzing reactions in preparative scale, including the preparation of a key intermediate for (S)-ofurace synthesis. Future work will be focused on further expanding the repertoire of this enzymatic amination chemistry. We envision that this highly efficient enzymatic system can be applied to the preparation of bioactive chiral amines for synthetic chemistry and drug discovery.

H. REFERENCES

1. Hili, R. & Yudin, A. K. Making carbon-nitrogen bonds in biological and chemical synthesis. *Nat. Chem. Biol.* 2, 284-287 (2006).
2. Froidevaux, V., Negrell, C., Caillol, S., Pascault, J.-P. & Boutevin, B. Biobased amines: from synthesis to polymers; present and future. *Chem. Rev.* 116, 14181-14224 (2016).
3. Bariwal, J. & Van der Eycken, E. C—N bond forming cross-coupling reactions: an overview. *Chem. Soc. Rev.* 42, 9283 (2013).
4. Kim, J. E., Choi, S., Balamurugan, M., Jang, J. H. & Nam, K. T. Electrochemical C—N bond formation for sustainable amine synthesis. *Trends Chem.* 2, 1004-1019 (2020).
5. Kohls, H., Steffen-Munsberg, F. & Höhne, M. Recent achievements in developing the biocatalytic toolbox for chiral amine synthesis. *Curr. Opin. Chem. Biol.* 19, 180-192 (2014).
6. Doyle, M. P. Catalytic methods for metal carbene transformations. *Chem. Rev.* 86, 919-939 (1986).
7. Liu, B., Zhu, S.-F., Zhang, W., Chen, C. & Zhou, Q.-L. Highly enantioselective insertion of carbenoids into N—H bonds catalyzed by copper complexes of chiral spiro bisoxazolines. *J. Am. Chem. Soc.* 129, 5834-5835 (2007).
8. Lee, E. C. & Fu, G. C. Copper-catalyzed asymmetric N—H insertion reactions: couplings of diazo compounds with carbamates to generate α-amino acids. *J. Am. Chem. Soc.* 129, 12066-12067 (2007).
9. Hou, Z. et al. Highly enantioselective insertion of carbenoids into N—H bonds catalyzed by copper(I) complexes of binol derivatives. *Angew. Chem. Int. Ed.* 49, 4763-4766 (2010).
10. Arredondo, V., Hiew, S. C., Gutman, E. S., Premachandra, I. D. U. A. & Van Vranken, D. L. Enantioselective palladium-catalyzed carbene insertion into the N—H bonds of aromatic heterocycles. *Angew. Chem. Int. Ed.* 56, 4156-4159 (2017).
11. Wang, Z. J., Peck, N. E., Renata, H. & Arnold, F. H. Cytochrome P450-catalyzed insertion of carbenoids into N—H bonds. *Chem. Sci.* 5, 598-601 (2014).
12. Sreenilayam, G. & Fasan, R. Myoglobin-catalyzed intermolecular carbene N—H insertion with arylamine substrates. *Chem. Commun.* 51, 1532-1534 (2015).
13. Steck, V., Carminati, D. M., Johnson, N. R. & Fasan, R. Enantioselective synthesis of chiral amines via biocatalytic carbene N—H insertion. *ACS Catal.* 10, 10967-10977 (2020).
14. Steck, V., Sreenilayam, G. & Fasan, R. Selective functionalization of aliphatic amines via myoglobin-catalyzed carbene N—H insertion. *Synlett* 31, 224-229 (2020).
15. Coelho, P. S., Brustad, E. M., Kannan, A. & Arnold, F. H. Olefin cyclopropanation via carbene transfer catalyzed by engineered cytochrome P450 enzymes. *Science* 339, 307-310 (2013).
16. Zhang, R. K. et al. Enzymatic assembly of carbon-carbon bonds via iron-catalysed $sp^3$ C—H functionalization. *Nature* 565, 67-72 (2019).

17. Liu, Z. & Arnold, F. H. New-to-nature chemistry from old protein machinery: carbene and nitrene transferases. *Curr. Opin. Biotechnol.* 69, 43-51 (2021).
18. Chen, K. & Arnold, F. H. Engineering new catalytic activities in enzymes. *Nat. Catal.* 3, 203-213 (2020).
19. Ren, Y.-Y., Zhu, S.-F. & Zhou, Q.-L. Chiral proton-transfer shuttle catalysts for carbene insertion reactions. *Org. Biomol. Chem.* 16, 3087-3094 (2018).
20. Li, M.-L., Yu, J.-H., Li, Y.-H., Zhu, S.-F. & Zhou, Q.-L. Highly enantioselective carbene insertion into N—H bonds of aliphatic amines. *Science* 366, 990-994 (2019).
21. Sharon, D. A., Mallick, D., Wang, B. & Shaik, S. Computation sheds insight into iron porphyrin carbenes' electronic structure, formation, and N—H insertion reactivity. *J. Am. Chem. Soc.* 138, 9597-9610 (2016).
22. DeAngelis, A., Dmitrenko, O. & Fox, J. M. Rh-catalyzed intermolecular reactions of cyclic α-diazocarbonyl compounds with selectivity over tertiary C—H bond migration. *J Am. Chem. Soc.* 134, 11035-11043 (2012).
23. Sattely, E. S., Meek, S. J., Malcolmson, S. J., Schrock, R. R. & Hoveyda, A. H. Design and stereoselective preparation of a new class of chiral olefin metathesis catalysts and application to enantioselective synthesis of quebrachamine: catalyst development inspired by natural product synthesis. *J. Am. Chem. Soc.* 131, 943-953 (2009).
24. Chen, K., Zhang, S.-Q., Brandenberg, O. F., Hong, X. & Arnold, F. H. Alternate heme ligation steers activity and selectivity in engineered cytochrome P450-catalyzed carbene-transfer reactions. *J. Am. Chem. Soc.* 140, 16402-16407 (2018).
25. Zhou, A. Z., Chen, K. & Arnold, F. H. Enzymatic lactone-carbene C—H insertion to build contiguous chiral centers. *ACS Catal.* 10, 5393-5398 (2020).
26. Brandenberg, O. F., Chen, K. & Arnold, F. H. Directed evolution of a cytochrome P450 carbene transferase for selective functionalization of cyclic compounds. *J. Am. Chem. Soc.* 141, 8989-8995 (2019).
27. Fisher, D. J. & Hayes, A. L. Mode of action of the systemic fungicides furalaxyl, metalaxyl and ofurace. *Pestic. Sci.* 13, 330-339 (1982).
28. Kunz, W. & Kristinsson, H. Bildung von 4-, 5-und 6gliedrigen Heterocyclen durch ambidoselektive Ring-schlüsse von Enolat-Ionen. *Helv. Chim. Acta* 62, 872-881 (1979).
29. Gibson, D. G. et al. Enzymatic assembly of DNA molecules up to several hundred kilobases. *Nat. Methods* 6, 343-345 (2009).
30. Barr, I. & Guo, F. Pyridine hemochromagen assay for determining the concentration of heme in purified protein solutions. *Bio. Protoc.* 5, e1594 (2015).
31. Chen, K., Zhang, S.-Q., Brandenberg, O. F., Hong, X. & Arnold, F. H. Alternate heme ligation steers activity and selectivity in engineered cytochrome P450-catalyzed carbene-transfer reactions. *J. Am. Chem. Soc.* 140, 16402-16407 (2018).
32. Yang, Y. & Arnold, F. H. Navigating the unnatural reaction space: directed evolution of heme proteins for selective carbene and nitrene transfer. *Acc. Chem. Res.* (2021) doi:10.1021/acs.accounts.0c00591.
33. Gu, X.-S. et al. Enantioselective hydrogenation of racemic α-arylamino lactones to chiral amino diols with site-specifically modified chiral spiro iridium catalysts. *Org. Lett.* 21, 4111-4115 (2019).
34. Zhou, A. Z., Chen, K. & Arnold, F. H. Enzymatic lactone-carbene C—H insertion to build contiguous chiral centers. *ACS Catal.* 10, 5393-5398 (2020).

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

IV. INFORMAL SEQUENCE LISTING:

```
SEQ ID NO: 1 (P411-C10)
         10         20         30         40         50
TIKEMPQPKT FGELKNLPLL NTDKPVQALM KIADELGEIF KFEAPGRVTR
         60         70         80         90        100
YLSSQRLIKE ACDESRFDKE LSQGLKFLRD FLGDGLATSW THEKNWKKAH
        110        120        130        140        150
NILLPSFSQQ AMKGYHASMV DIAVQLVQKW ERLNADEHIE VSEDMTRLTL
        160        170        180        190        200
DTIGLCGFNY RLNSFYRDQP HPFIISLVRA LDEVMNKLQR ANPDDPAYDE
        210        220        230        240        250
NKRQFQEDIK VMNDLVDKII ADRKARGEQS DDLLTQMLNG KDPETGEPLD
        260        270        280        290        300
DGNIRYQIIT FLYAGVEGTS GLLSFALYFL VKNPHVLQKV AEEAARVLVD
        310        320        330        340        350
PVPSYKQVKQ LKYVGMVLNE ALRLWPTVPY FSLYAKEDTV LGGEYPLEKG
        360        370        380        390        400
DEVMVLIPQL HRDKTVWGDD VEEFRPERFE NPSAIPQHAF KPFGNGQRAS
        410        420        430        440        450
LGQQFALHEA TLVLGMMLKH FDFEDHTNYE LDIKELQTLK PKGFVVKAKS
        460        470        480        490        500
KKIPLGGIPS PSTEQSAKKV RKKAENAHNT PLLVLYGSNM GTAEGTARDL
        510        520        530        540        550
ADIAMSKGFA PQVATLDSHA GNLPREGAVL IVTASYNGHP PDNAKQFVDW
        560        570        580        590        600
LDQASADEVK GVRYSVFGCG DKNWATTYQK VPAFIDETLA AKGAENIADR
        610        620        630        640        650
GEADASDDFE GTYEEWREHM WSDVAAYFNL DIENSEDNKS TLSLQFVDSA
        660        670        680        690        700
ADMPLAKMHG AFST
```

-continued

| IV. INFORMAL SEQUENCE LISTING: |
|---|

SEQ ID NO: 2 (P411-C10 W)
```
           10         20         30         40         50
   TIKEMPQPKT FGELKNLPLL NTDKPVQALM KIADELGEIF KFEAPGRVTR
           60         70         80         90        100
   YLSSQRLIKE ACDESRFDKE LSQGLKFLRD FLGDGLATSW THEKNWKKAH
          110        120        130        140        150
   NILLPSFSQQ AMKGYHASMV DIAVQLVQKW ERLNADEHIE VSEDMTRPTL
          160        170        180        190        200
   DTIGLCGFNY RLNSFYKDQP HPFIISLVRA LDEVMNKLQR ANPDDPAYDE
          210        220        230        240        250
   NKRQEQEDIK VMNDPVDKII ADRKARGEQS DDLLTQMLNG KDPETGEPLD
          260        270        280        290        300
   DGNIRYQIIT FLWAGVEGTS GLLSFALYFL VKNPHVLQKV AEEAARVLVD
          310        320        330        340        350
   PVPSYKQVKQ LKYVGMVLNE ALKLWPTVPY FSPYAKEDTV LGGEYPLEKG
          360        370        380        390        400
   DEVMVLIPQP HRDKTVWGDD VflflEKPflREfl NPSAIPQHAF KPFGNGQKAS
          410        420        430        440        450
   LGQQFALHEA TLVLGMMLKH FDFEDHTNYE LDIKELQTLK PKGFVVKAKS
          460        470        480        490        500
   KKIPLGGIPS PSTEQSAKKV RKKAENAHNT PLLVLYGSNM GTAEGTARDL
          510        520        530        540        550
   ADIAMSKGFA PQVATLDSHA GNLPREGAVL IVTASYNGHP PDNAKQFVDW
          560        570        580        590        600
   LDQASADEVK GVRYSVFGCG DKNWATTYQK VPAFIDETLA AKGAENIADR
          610        620        630        640        650
   GEADASDDFE GTYEEWREHM WSDVAAYFNL DIENSEDNKS TLSLQFVDSA
          660        664
   ADMPLAKWHG AFST SEQ ID NO: 3 (P411 C10 WI)
           10         20         30         40         50
   TIKEMPQPKT FGELKNLPLL NTDKPVQAPW KIADELGEIF KFEAPGRVTR
           60         70         80         90        100
   YLSSQRPIKE ACDESREDKE PSQGPKFPRD FPGDGPATSW THEKNWKKAH
          110        120        130        140        150
   NILLPSFSQQ AMKGYHASMV DIAVQLVQKW ERLNADEHIE VSEDMTRPTL
          160        170        180        190        200
   DTIGLCGFNY RLNSFYKDQP HPFIISLVRA LDEVMWKLQR ANPDDPAYDE
          210        220        230        240        250
   NKRQEQEDIK VMNDLVDKII ADRKARGEQS DDLLTQMLNG KDPETGEPLD
          260        270        280        290        300
   DGNIRYQIIT FLWAGVEGTS GLLSFALYFL VKNPHVLQKV AEEAARVLVD
          310        320        330        340        350
   PVPSYKQVKQ LKYVGMVLNE ALRLWPTVPY FSLYAKTDTV LGGEYPLEKG
          360        370        380        390        400
   DEVMVLIPQL HRDKTVWGDD VEEFRPERFE NPSAIPQHAF KPFGNGQRAS
          410        420        430        440        450
   LGQQFALHEA TLVLGMMLKH FDFEDHTNYE LDIKELITPK PKGFVVKAKS
          460        470        480        490        500
   KKIPPGGIPS PSTEQSAKKV RKKAENAHNT PLLVLYGSNM GTAEGTARDL
          510        520        530        540        550
   ADIAMSKGFA PQVATLDSHA GNLPREGAVL IVTASYNGHP PDNAKQFVDW
          560        570        580        590        600
   LDQASADEVK GVRYSVFGCG DKNWATTYQK VPAFIDETLA AKGAENIADR
          610        620        630        640        650
   GEADASDDFE GTYEEWREHM WSDVAAYFNL DIENSEDNKS TLSLQFVDSA
          660        664
   ADMPLAKMHG AFST SEQ ID NO: 4 (P411-C10 WIR)
           10         20         30         40         50
   TIKEMPQPKT FGELKNLPLL NTDKPVQALM KIADELGEIF KFEAPGRVTR
           60         70         80         90        100
   YLSSQRLIKE ACDESRFDKE LFQGLKFLRD FLGDGLATSW THEKNWKKAH
          110        120        130        140        150
   NILLPSFSQQ AMKGYHASMV DIAVQLVQKW ERLNADEHIE VSEDMTRLTL
          160        170        180        190        200
   DTIGLCGFNY RLNSFYRDQP HPFIISLVRA LDEVMNKLQR ANPDDPAYDE
          210        220        230        240        250
   NKRQFQEDIK VMNDLVDKII ADRKARGEQS DDLLTQMLNG KDPETGEPLD
          260        270        280        290        300
   DGNIRYQIIT FLWAGVEGTS GLLSFALYFL VKNPHVLQKV AEEAARVLVD
          310        320        330        340        350
   PVPSYKQVKQ LKYVGMVLNE ALRLWPTVPY FSLYAKEDTV LGGEYPLEKG
          360        370        380        390        400
```

-continued

IV. INFORMAL SEQUENCE LISTING:

```
            DEVMVLIPQL HRDKTVWGDD VEEFRPERFE NPSAIPQHAF KPFGNGQRAS
                   410        420        430        440        450
            LGQQFALHEA TLVLGMMLKH FDFEDHTNYE LDIKELITLK PKGFVVKAKS
                   460        470        480        490        500
            KKIPLGGIPS PSTEQSAKKV RKKAENAHNT PLLVLYGSNM GTAEGTARDL
                   510        520        530        540        550
            ADIAMSKGFA PQVATLDSHA GNLPREGAVL IVTASYNGHP PDNAKQFVDW
                   560        570        580        590        600
            LDQASADEVK GVRYSVFGCG DKNWATTYQK VPAFIDETLA AKGAENIADR
                   610        620        630        640        650
            GEADASDDFE GTYEEWREHM WSDVAAYFNL DIENSEDNKS TLSLQFVDSA
                   660        664
            ADMPLAKMHG AFST

SEQ ID NO: 5 (P411-C10 WIRF)
                    10         20         30         40         50
            TIKEMPQPKT FGELKNLPLL NTDKPVQALM KIADELGEIF KFEAPGRVTR
                    60         70         80         90        100
            YLSSQRLIKE ACDESRFDKE LFQGLKFLRD FLGDGLATSW THEKNWKKAH
                   110        120        130        140        150
            NILLPSFSQQ AMKGYHASMV DIAVQLVQKW ERLNADEHIE VSEDMTRLTL
                   160        170        180        190        200
            DTIGLCGFNY RLNSFYRDQP HPFIISLVRA LDEVMNKLQR ANPDDPAYDE
                   210        220        230        240        250
            NKRQFQEDIK VMNDLVDKII ADRKARGEQS DDLLTQMLNG KDPETGEPLD
                   260        270        280        290        300
            DGNIRYQIIT FLWAGVEGTS GLLSFALYFL VKNPHVLQKV AEEAARVLVD
                   310        320        330        340        350
            PVPSYKQVKQ LKYVGMVLNE ALRLWPTVPY FSLYAKEDTV LGGEYPLEKG
                   360        370        380        390        400
            DEVMVLIPQL HRDKTVWGDD VEEFRPERFE NPSAIPQHAF KPFGNGQRAS
                   410        420        430        440        450
            LGQQFALHEA TLVLGMMLKH FDFEDHTNYE LDIKERITLK PKGFVVKAKS
                   460        470        480        490        500
            KKIPLGGIPS PSTEQSAKKV RKKAENAHNT PLLVLYGSNM GTAEGTARDL
                   510        520        530        540        550
            ADIAMSKGFA PQVATLDSHA GNLPREGAVL IVTASYNGHP PDNAKQFVDW
                   560        570        580        590        600
            LDQASADEVK GVRYSVFGCG DKNWATTYQK VPAFIDETLA AKGAENIADR
                   610        620        630        640        650
            GEADASDDFE GTYEEWREHM WSDVAAYFNL DIENSEDNKS TLSLQFVDSA
                   660        664
            ADMPLAKMHG AFST

SEQ ID NO: 6 (P411-C10 WIRF-G)
                    10         20         30         40         50
            TIKEMPQPKT FGELKNLPLL NTDKPVQALM KIADELGEIF KFEAPGRVTR
                    60         70         80         90        100
            YLSSQRLIKE ACDESRFDKE LFQGLKFLRD FLGDGLATSW THEKNWKKAH
                   110        120        130        140        150
            NILLPSFSQQ AMKGYHASMV DIAVQLVQKW ERLNADEHIE VSEDMTRLTL
                   160        170        180        190        200
            DTIGLCGFNY RLNSFYRDQP HPFIISLVRA LDEVMNKLQR ANPDDPAYDE
                   210        220        230        240        250
            NKRQFQEDIK VMNDLVDKII ADRKARGEQS DDLLTQMLNG KDPETGEPLD
                   260        270        280        290        300
            DGNIRYQIIT FLWAGVEGTS GLLSFALYFL VKNPHVLQKV AEEAARVLVD
                   310        320        330        340        350
            PVPSYKQVKQ LKYVGMVLNE ALRLWPTVPY FGLYAKEDTV LGGEYPLEKG
                   360        370        380        390        400
            DEVMVLIPQL HRDKTVWGDD VEEFRPERFE NPSAIPQHAF KPFGNGQRAS
                   410        420        430        440        450
            LGQQFALHEA TLVLGMMLKH FDFEDHTNYE LDIKERITLK PKGFVVKAKS
                   460        470        480        490        500
            KKIPLGGIPS PSTEQSAKKV RKKAENAHNT PLLVLYGSNM GTAEGTARDL
                   510        520        530        540        550
            ADIAMSKGFA PQVATLDSHA GNLPREGAVL IVTASYNGHP PDNAKQFVDW
                   560        570        580        590        600
            LDQASADEVK GVRYSVFGCG DKNWATTYQK VPAFIDETLA AKGAENIADR
                   610        620        630        640        650
            GEADASDDFE GTYEEWREHM WSDVAAYFNL DIENSEDNKS TLSLQFVDSA
                   660        664
            ADMPLAKMHG AFST
```

-continued

| IV. INFORMAL SEQUENCE LISTING: |
|---|

SEQ ID NO: 7 (P411-C10 WIRF-GA)
```
         10         20         30         40         50
  TIKEMPQPKT FGELKNLPLL NTDKPVQALM KIADELGEIF KFEAPGRVTR
         60         70         80         90        100
  YLSSQRLIKE ACDESRFDKE LFQALKFLRD FLGDGLATSW THEKNWKKAH
        110        120        130        140        150
  NILLPSFSQQ AMKGYHASMV DIAVQLVQKW ERLNADEHIE VSEDMTRLTL
        160        170        180        190        200
  DTIGLCGFNY RLNSFYRDQP HPFIISLVRA LDEVMNKLQR ANPDDPAYDE
        210        220        230        240        250
  NKRQFQEDIK VMNDLVDKII ADRKARGEQS DDLLTQMLNG KDPETGEPLD
        260        270        280        290        300
  DGNIRYQIIT FLWAGVEGTS GLLSFALYFL VKNPHVLQKV AEEAARVLVD
        310        320        330        340        350
  PVPSYKQVKQ LKYVGMVLNE ALRLWPTVPY FGLYAKEDTV LGGEYPLEKG
        360        370        380        390        400
  DEVMVLIPQL HRDKTVWGDD VEEFRPERFE NPSAIPQHAF KPFGNGQRAS
        410        420        430        440        450
  LGQQFALHEA TLVLGMMLKH FDFEDHTNYE LDIKERITLK PKGFVVKAKS
        460        470        480        490        500
  KKIPLGGIPS PSTEQSAKKV RKKAENAHNT PLLVLYGSNM GTAEGTARDL
        510        520        530        540        550
  ADIAMSKGFA PQVATLDSHA GNLPREGAVL IVTASYNGHP PDNAKQFVDW
        560        570        580        590        600
  LDQASADEVK GVRYSVFGCG DKNWATTYQK VPAFIDETLA AKGAENIADR
        610        620        630        640        650
  GEADASDDFE GTYEEWREHM WSDVAAYFNL DIENSEDNKS TLSLQFVDSA
        660        664
  ADMPLAKMHG AFST

SEQ ID NO: 8 (P411-C10 WIRF GAK)
         10         20         30         40         50
  TIKEMPQPKT FGELKNLPLL NTDKPVQALM KIADELGEIF KFEAPGRVTR
         60         70         80         90        100
  YLSSQRLIKE ACDESRFDKK LFQALKFLRD FLGDGLATSW THEKNWKKAH
        110        120        130        140        150
  NILLPSFSQQ AMKGYHASMV DIAVQLVQKW ERLNADEHIE VSEDMTRLTL
        160        170        180        190        200
  DTIGLCGFNY RLNSFYRDQP HPFIISLVRA LDEVMNKLQR ANPDDPAYDE
        210        220        230        240        250
  NKRQFQEDIK VMNDLVDKII ADRKARGEQS DDLLTQMLNG KDPETGEPLD
        260        270        280        290        300
  DGNIRYQIIT FLWAGVEGTS GLLSFALYFL VKNPHVLQKV AEEAARVLVD
        310        320        330        340        350
  PVPSYKQVKQ LKYVGMVLNE ALRLWPTVPY FGLYAKEDTV LGGEYPLEKG
        360        370        380        390        400
  DEVMVLIPQL HRDKTVWGDD VEEFRPERFE NPSAIPQHAF KPFGNGQRAS
        410        420        430        440        450
  LGQQFALHEA TLVLGMMLKH FDFEDHTNYE LDIKERITLK PKGFVVKAKS
        460        470        480        490        500
  KKIPLGGIPS PSTEQSAKKV RKKAENAHNT PLLVLYGSNM GTAEGTARDL
        510        520        530        540        550
  ADIAMSKGFA PQVATLDSHA GNLPREGAVL IVTASYNGHP PDNAKQFVDW
        560        570        580        590        600
  LDQASADEVK GVRYSVFGCG DKNWATTYQK VPAFIDETLA AKGAENIADR
        610        620        630        640        650
  GEADASDDFE GTYEEWREHM WSDVAAYFNL DIENSEDNKS TLSLQFVDSA
        660        664
  ADMPLAKMHG AFST

SEQ ID NO: 9 (P411-C10 VLC)
         10         20         30         40         50
  TIKEMPQPKT FGELKNLPLL NTDKPVQALM KIADELGEIF KFEAPGRVTR
         60         70         80         90        100
  YLSSQRLIKE ACDESRFDKE LSQGLKFLRD FLGDGLATSW THEKNWKKAH
        110        120        130        140        150
  NILLPSFSQQ AMKGYHASMV DIAVQLVQKW ERLNADEHIE VSEDMTRLTL
        160        170        180        190        200
  DTIGLCGFNY RLNSFYRDQP HPFIISLVRA LDEVMNKLQR ANPDDPAYDE
        210        220        230        240        250
  NKRQFQEDIK VMNDLVDKII ADRKARGEQS DDLLTQMLNG KDPETGEPLD
        260        270        280        290        300
  DGNIRYQIIT FLYAGVEGTS GLLSFALYFL VKNPHVLQKV AEEAARVLVD
        310        320        330        340        350
  PVPSYKQVKQ LKYVGMVLNE ALRLWPVVPY FCLYAKEDTV LGGEYPLEKG
        360        370        380        390        400
```

```
DEVMVLIPQL HRDKTVWGDD VEEFRPERFE NPSAIPQHAF KPFGNGQRAS
    410        420        430        440        450
LGQQFALHEA TLVLGMMLKH FDFEDHTNYE LDIKELLTLK PKGFVVKAKS
    460        470        480        490        500
KKIPLGGIPS PSTEQSAKKV RKKAENAHNT PLLVLYGSNM GTAEGTARDL
    510        520        530        540        550
ADIAMSKGFA PQVATLDSHA GNLPREGAVL IVTASYNGHP PDNAKQFVDW
    560        570        580        590        600
LDQASADEVK GVRYSVFGCG DKNWATTYQK VPAFIDETLA AKGAENIADR
    610        620        630        640        650
GEADASDDFE GTYEEWREHM WSDVAAYFNL DIENSEDNKS TLSLQFVDSA
    660        664
ADMPLAKMHG AFST

SEQ ID NO: 10 (P411-C11)
     10         20         30         40         50
TIKEMPQPKT FGELKNLPLL NTDKPVQALM KIADELGEIF KFEAPGRVTR
     60         70         80         90        100
YLSSQRLIKE ACDESRFDKE LSQTLKFLRD FLGDGLATSW THEKNWKKAH
    110        120        130        140        150
NILLPSFSQQ AMKGYHAMMV DIAVQLVQKW ERLNADEHIE VSEDMTRLTL
    160        170        180        190        200
DTIGLCGFNY RFNSFYRDQP HPFIISLVRA LDEVMNKLQR ANPDDPAYDE
    210        220        230        240        250
NKRQFQEDIK VMNDLVDKII ADRKARGEQS DDLLTQMLNG KDPETGEPLD
    260        270        280        290        300
DGNIRYQIIT FLYAGVEGTS GLLSFALYFL VKNPHVLQKV AEEAARVLVD
    310        320        330        340        350
PVPSYKQVKQ LKYVGMVLNE ALRLWPTVPY FSLYAKEDTV LGGEYPLEKG
    360        370        380        390        400
DEVMVLIPQL HRDKTVWGDD VEEFRPERFE NPSAIPQHAF KPFGNGQRAS
    410        420        430        440        450
IGQQFALHEA TLVLGMMLKH FDFEDHTNYE LDIKELLTLK PKGFVVKAKS
    460        470        480        490        500
KKIPLGGIPS PSTEQSAKKV RKKAENAHNT PLLVLYGSNM GTAEGTARDL
    510        520        530        540        550
ADIAMSKGFA PQVATLDSHA GNLPREGAVL IVTASYNGHP PDNAKQFVDW
    560        570        580        590        600
LDQASADEVK GVRYSVFGCG DKNWATTYQK VPAFIDETLA AKGAENIADR
    610        620        630        640        650
GEADASDDFE GTYEEWREHM WSDVAAYFNL DIENSEDNKS TLSLQFVDSA
    660        664
ADMPLAKMHG AFST

SEQ ID NO: 11 (P411-L8)
     10         20         30         40         50
TIKEMPQPKT FGELKNLPLL NTDKPVQALM KIADELGEIF KFEAPGRVTR
     60         70         80         90        100
YLSSQRLIKE ACDESRFDKE LSQGLKFLRD FLGDGLPTSW THEKNWKKAH
    110        120        130        140        150
NILLPSFSQQ AMKGYHASMV DIAVQLVQKW ERLNADEHIE VSEDMTRLTL
    160        170        180        190        200
DTIGLCGFNY RLNSFYRDQP HPFIISLVRA LDEVMNKLQR ANPDDPAYDE
    210        220        230        240        250
NKRQFQEDIK VMNDLVDKII ADRKARGEQS DDLLTQMLNG KDPETGEPLD
    260        270        280        290        300
DGNIRYQIIT FLYSGVDGTS GLLSFALYFL VKNPHVLQKV AEEAARVLVD
    310        320        330        340        350
PVPSYKQVKQ LKYVGMVLNE ALRLWPPVPY FALYAKEDTV LGGEYPLEKG
    360        370        380        390        400
DEVMVLIPQL HRDKTVWGDD VEEFRPERFE NPSAIPQHAF KPFGNGQRAS
    410        420        430        440        450
LGQQFALHEA TLVLGMMLKH FDFEDHTNYE LDIKELLTLK PKGFVVKAKS
    460        470        480        490        500
KKIPLGGIPS PSTEQSAKKV RKKAENAHNT PLLVLYGSNM GTAEGTARDL
    510        520        530        540        550
ADIAMSKGFA PQVATLDSHA GNLPREGAVL IVTASYNGHP PDNAKQFVDW
    560        570        580        590        600
LDQASADEVK GVRYSVFGCG DKNWATTYQK VPAFIDETLA AKGAENIADR
    610        620        630        640        650
GEADASDDFE GTYEEWREHM WSDVAAYFNL DIENSEDNKS TLSLQFVDSA
    660        664
ADMPLAKMHG AFST
```

IV. INFORMAL SEQUENCE LISTING:

SEQ ID NO: 12 (P411-C10-P2)
```
         10         20         30         40         50
TIKEMPQPKT FGELKNLPLL NTDKPVQALM KIADELGEIF KFEAPGRVTR
         60         70         80         90        100
YLSSQRLIKE ACDESRFDKE LSQGLKFLRD FLGDGLATSW THEKNWKKAH
        110        120        130        140        150
NILLPSFSQQ AMKGYHASMV DIAVQLVQKW ERLNADEHIE VSEDMTRLTL
        160        170        180        190        200
DTIGLCGFNY RLNSFYRDQP HPFIISLVRA LDEVMNKLQR ANPDDPAYDE
        210        220        230        240        250
NKRQFQEDIK VMNDLVDKII ADRKARGEQS DDLLTQMLNG KDPETGEPLD
        260        270        280        290        300
DGNIRYQIIT FLYAGVEGTS GLLSFALYFL VKNPHVLQKV AEEAARVLVD
        310        320        330        340        350
PVPSYKQVKQ LKYVGMVLNE ALRLWPPVPY FSLYAKEDTV LGGEYPLEKG
        360        370        380        390        400
DEVMVLIPQL HRDKTVWGDD VEEFRPERFE NPSAIPQHAF KPFGNGQRAS
        410        420        430        440        450
LGQQFALHEA TLVLGMMLKH FDFEDHTNYE LDIKELQTLK PKGFVVKAKS
        460        470        480        490        500
KKIPLGGIPS PSTEQSAKKV RKKAENAHNT PLLVLYGSNM GTAEGTARDL
        510        520        530        540        550
ADIAMSKGFA PQVATLDSHA GNLPREGAVL IVTASYNGHP PDNAKQFVDW
        560        570        580        590        600
LDQASADEVK GVRYSVFGCG DKNWATTYQK VPAFIDETLA AKGAENIADR
        610        620        630        640        650
GEADASDDFE GTYEEWREHM WSDVAAYFNL DIENSEDNKS TLSLQFVDSA
        660        670        680        690        700
ADMPLAKMHG AFST
```

SEQ ID NO: 13 (P411-C10-P3)
```
         10         20         30         40         50
TIKEMPQPKT FGELKNLPLL NTDKPVQALM KIADELGEIF KFEAPGRVTR
         60         70         80         90        100
YLSSQRLIKE ACDESRFDKE LSQGLKFLRD FLGDGLATSW THEKNWKKAH
        110        120        130        140        150
NILLPSFSQQ AMKGYHASMV DIAVQLVQKW ERLNADEHIE VSEDMTRLTL
        160        170        180        190        200
DTIGLCGFNY RLNSFYRDQP HPFIISLVRA LDEVMNKLQR ANPDDPAYDE
        210        220        230        240        250
NKRQFQEDIK VMNDLVDKII ADRKARGEQS DDLLTQMLNG KDPETGEPLD
        260        270        280        290        300
DGNIRYQIIT FLYAGVEGTS GLLSFALYFL VKNPHVLQKV AEEAARVLVD
        310        320        330        340        350
PVPSYKQVKQ LKYVGMVLNE ALRLWPPVPY FSLYAKEDTV LGGEYPLEKG
        360        370        380        390        400
DEVMVLIPQL HRDKTVWGDD VEEFRPERFE NPSAIPQHAF KPFGNGQRAS
        410        420        430        440        450
LGQQFALHEA TLVLGMMLKH FDFEDHTNYE LDIKELYTLK PKGFVVKAKS
        460        470        480        490        500
KKIPLGGIPS PSTEQSAKKV RKKTENAHNT PLLVLYGSNM GTAEGTARDL
        510        520        530        540        550
ADIAMSKGFA PQVATLDSHA GNLPREGAVL IVTASYNGHP PDNAKQFVDW
        560        570        580        590       v600
LDQASADEVK GVRYSVFGCG DKNWATTYQK VPAFIDETLA AKGAENIADR
        610        620        630        640        650
GEADASDDFE GTYEEWREHM WSDVAAYFNL DIENSEDNKS TLSLQFVDSA
        660        670        680        690        700
ADMPLAKMHG AFST
```

SEQ ID NO: 14 (P411-C10-P4)
```
         10         20         30         40         50
TIKEMPQPKT FGELKNLPLL NTDKPVQALM KIADELGEIF KFEAPGRVTR
         60         70         80         90        100
YLSSQRLIKE ACDESRFDKE LNQGLKFLRD FLGDGLATSW THEKNWKKAH
        110        120        130        140        150
NILLPSFSQQ AMKGYHASMV DIAVQLVQKW ERLNADEHIE VSEDMTRLTL
        160        170        180        190        200
DTIGLCGFNY RLNSFYRDQP HPFIISLVRA LDEVMNKLQR ANPDDPAYDE
        210        220        230        240        250
NKRQFQEDIK VMNDLVDKII ADRKARGEQS DDLLTQMLNG KDPETGEPLD
        260        270        280        290        300
DGNIRYQIIT FLYAGVEGTS GLLSFALYFL VKNPHVLQKV AEEAARVLVD
        310        320        330        340        350
PVPSYKQVKQ LKYVGMVLNE ALRLWPPVPY FSLYAKEDTV LGGEYPLEKG
        360        370        380        390        400
```

IV. INFORMAL SEQUENCE LISTING:

```
         410        420        430        440        450
DEVMVLIPQL HRDKTVWGDD VEEFRPERFE NPSAIPQHAF KPFGNGQRAS
         460        470        480        490        500
LGQQFALHEA TLVLGMMLKH FDFEDHTNYE LDIKELYTLK PKGFVVKAKS
         510        520        530        540        550
KKIPLGGIPS PSTEQSAKKV RKKTENAHNT PLLVLYGSNM GTAEGTARDL
         560        570        580        590        600
ADIAMSKGFA PQVATLDSHA GNLPREGAVL IVTASYNGHP PDNAKQFVDW
         610        620        630        640        650
LDQASADEVK GVRYSVFGCG DKNWATTYQK VPAFIDETLA AKGAENIADR
         660        670        680        690        700
GEADASDDFE GTYEEWREHM WSDVAAYFNL DIENSEDNKS TLSLQFVDSA
ADMPLAKMHG AFST

SEQ ID NO: 15 (P411-C10-P5)
          10         20         30         40         50
TIKEMPQPKT FGELKNLPLL NTDKPVQALM KIADELGEIF KFEAPGRVTR
          60         70         80         90        100
YLSSQRLIKE ACDESRFDKE LNQGLKFLRD FLGDGLATSW THEKNWKKAH
         110        120        130        140        150
NILLPSFSQQ AMKGYHAGMV DIAVQLVQKW ERLNADEHIE VSEDMTRLTL
         160        170        180        190        200
DTIGLCGFNY RLNSFYRDQP HPFIISLVRA LDEVMNKLQR ANPDDPAYDE
         210        220        230        240        250
NKRQFQEDIK VMNDLVDKII ADRKARGEQS DDLLTQMLNG KDPETGEPLD
         260        270        280        290        300
DGNIRYQIIT FLYSGVEGTS GLLSFALYFL VKNPHVLQKV AEEAARVLVD
         310        320        330        340        350
PVPSYKQVKQ LKYVGMVLNE ALRLWPPVPY FSLYAKEDTV LGGEYPLEKG
         360        370        380        390        400
DEVMVLIPQL HRDKTVWGDD VEEFRPERFE NPSAIPQHAF KPFGNGQRAS
         410        420        430        440        450
LGQQFALHEA TLVLGMMLKH FDFEDHTNYE LDIKELYTLK PKGFVVKAKS
         460        470        480        490        500
KKIPLGGIPS PSTEQSAKKV RKKTENAHNT PLLVLYGSNM GTAEGTARDL
         510        520        530        540        550
ADIAMSKGFA PQVATLDSHA GNLPREGAVL IVTASYNGHP PDNAKQFVDW
         560        570        580        590        600
LDQASADEVK GVRYSVFGCG DKNWATTYQK VPAFIDETLA AKGAENIADR
         610        620        630        640        650
GEADASDDFE GTYEEWREHM WSDVAAYFNL DIENSEDNKS TLSLQFVDSA
         660        670        680        690        700
ADMPLAKMHG AFST

SEQ ID NO: 16 (P411-C10-P6)
          10         20         30         40         50
TIKEMPQPKT FGELKNLPLL NTDKPVQALM KIADELGEIF KFEAPGQVTR
          60         70         80         90        100
YLSSQRLIKE ACDESRFDKE LNQGLKFLRD FLGDGLATSW THEKNWKKAH
         110        120        130        140        150
NILLPSFSQQ AMKGYHAGMV DIAVQLVQKW ERLNADEHIE VSEDMTRLTL
         160        170        180        190        200
DTIGLCGFNY RLNSFYRDQP HPFIISLVRA LDEVMNKLQR ANPDDPAYDE
         210        220        230        240        250
NKRQFQEDIK VMNDLVDKII ADRKARGEQS DDLLTQMLNG KDPETGEPLD
         260        270        280        290        300
DGNIRYQIIT FLYSGVEGTS GLLSFALYFL VKNPHVLQKV AEEAARVLVD
         310        320        330        340        350
PVPSYKQVKQ LKYVGMVLNE ALRLWPPVPY FSLYAKEDTV LGGEYPLEKG
         360        370        380        390        400
DEVMVLIPQL HRDKTVWGDD VEEFRPERFE NPSAIPQHAF KPFGNGQRAS
         410        420        430        440        450
LGQQFALHEA TLVLGMMLKH FDFEDHTNYE LDIKELYTLK PKGFVVKAKS
         460        470        480        490        500
KKIPLGGIPS PSTEQSAKKV RKKTENAHNT PLLVLYGSNM GTAEGTARDL
         510        520        530        540        550
ADIAMSKGFA PQVATLDSHA GNLPREGAVL IVTASYNGHP PDNAKQFVDW
         560        570        580        590        600
LDQASADEVK GVRYSVFGCG DKNWATTYQK VPAFIDETLA AKGAENIADR
         610        620        630        640        650
GEADASDDFE GTYEEWREHM WSDVAAYFNL DIENSEDNKS TLSLQFVDSA
         660        670        680        690        700
ADMPLAKMHG AFST
```

-continued

IV. INFORMAL SEQUENCE LISTING:

SEQ ID NO: 17 (P411-C10-L6)
```
        10         20         30         40         50
TIKEMPQPKT FGELKNLPLL NTDKPVQALM KIADELGEIF KFEAPGRVTR
        60         70         80         90        100
YLSSQRLIKE ACDESRFDKE LSQGLKFLRD FLGDGLPTSW THEKNWKKAH
       110        120        130        140        150
NILLPSFSQQ AMKGYHASMV DIAVQLVQKW ERLNADEHIE VSEDMTRLTL
       160        170        180        190        200
DTIGLCGFNY RLNSFYRDQP HPFIISLVRA LDEVMNKLQR ANPDDPAYDE
       210        220        230        240        250
NKRQFQEDIK VMNDLVDKII ADRKARGEQS DDLLTQMLNG KDPETGEPLD
       260        270        280        290        300
DGNIRYQIIT FLYSGVEGTS GLLSFALYFL VKNPHVLQKV AEEAARVLVD
       310        320        330        340        350
PVPSYKQVKQ LKYVGMVLNE ALRLWPVVPY FALYAKEDTV LGGEYPLEKG
       360        370        380        390        400
DEVMVLIPQL HRDKTVWGDD VEEFRPERFE NPSAIPQHAF KPFGNGQRAS
       410        420        430        440        450
LGQQFALHEA TLVLGMMLKH FDFEDHTNYE LDIKELLTLK PKGFVVKAKS
       460        470        480        490        500
KKIPLGGIPS PSTEQSAKKV RKKAENAHNT PLLVLYGSNM GTAEGTARDL
       510        520        530        540        550
ADIAMSKGFA PQVATLDSHA GNLPREGAVL IVTASYNGHP PDNAKQFVDW
       560        570        580        590        600
LDQASADEVK GVRYSVFGCG DKNWATTYQK VPAFIDETLA AKGAENIADR
       610        620        630        640        650
GEADASDDFE GTYEEWREHM WSDVAAYFNL DIENSEDNKS TLSLQFVDSA
       660        664
ADMPLAKMHG AFST

SEQ ID NO: 18 (P411-C10-L7)
        10         20         30         40         50
TIKEMPQPKT FGELKNLPLL NTDKPVQALM KIADELGEIF KFEAPGRVTR
        60         70         80         90        100
YLSSQRLIKE ACDESRFDKE LSQGLKFLRD FLGDGLPTSW THEKNWKKAH
       110        120        130        140        150
NILLPSFSQQ AMKGYHASMV DIAVQLVQKW ERLNADEHIE VSEDMTRLTL
       160        170        180        190        200
DTIGLCGFNY RLNSFYRDQP HPFIISLVRA LDEVMNKLQR ANPDDPAYDE
       210        220        230        240        250
NKRQFQEDIK VMNDLVDKII ADRKARGEQS DDLLTQMLNG KDPETGEPLD
       260        270        280        290        300
DGNIRYQIIT FLYSGVEGTS GLLSFALYFL VKNPHVLQKV AEEAARVLVD
       310        320        330        340        350
PVPSYKQVKQ LKYVGMVLNE ALRLWPPVPY FALYAKEDTV LGGEYPLEKG
       360        370        380        390        400
DEVMVLIPQL HRDKTVWGDD VEEFRPERFE NPSAIPQHAF KPFGNGQRAS
       410        420        430        440        450
LGQQFALHEA TLVLGMMLKH FDFEDHTNYE LDIKELLTLK PKGFVVKAKS
       460        470        480        490        500
KKIPLGGIPS PSTEQSAKKV RKKAENAHNT PLLVLYGSNM GTAEGTARDL
       510        520        530        540        550
ADIAMSKGFA PQVATLDSHA GNLPREGAVL IVTASYNGHP PDNAKQFVDW
       560        570        580        590        600
LDQASADEVK GVRYSVFGCG DKNWATTYQK VPAFIDETLA AKGAENIADR
       610        620        630        640        650
GEADASDDFE GTYEEWREHM WSDVAAYFNL DIENSEDNKS TLSLQFVDSA
       660        664
ADMPLAKMHG AFST

SEQ ID NO: 19 (P411-C10-L7 FL)
        10         20         30         40         50
TIKEMPQPKT FGELKNLPLL NTDKPVQALM KIADELGEIF KFEAPGRVTR
        60         70         80         90        100
YLSSQRLIKE ACDESRFDKE LSQGLKFLRD FLGDGLPTSW THEKNWKKAH
       110        120        130        140        150
NILLPSFSQQ AMKGYHASMV DIAVQLVQKW ERLNADEHIE VSEDMTRLTL
       160        170        180        190        200
DTIGLCGFNY RLNSFYRDQP HPFIISLVRA LDEVMNKLQR ANPDDPAYDE
       210        220        230        240        250
NKRQFQEDIK VMNDLVDKII ADRKARGEQS DDLLTQMLNG KDPETGEPLD
       260        270        280        290        300
DGNIRYQIIT FLYSGVEGTS GLLSFALYFL VKNPHVLQKV AEEAARVLVD
       310        320        330        340        350
PVPSYKQVKQ LKYVGMVLNE ALRLWPVVPY FALYAKEDTV LGGEYPLEKG
       360        370        380        390        400
```

IV. INFORMAL SEQUENCE LISTING:

```
DEVMVLIPQL HRDKTVWGDD VEEFRPERFE NPSAIPQHAF KPFGNGQRAS
    410        420        430        440        450
LGQQFALHEA TLVLGMMLKH FDFEDHTNYE LDIKELLTLK PKGFVVKAKS
    460        470        480        490        500
KKIPLGGIPS PSTEQSAKKV RKKAENAHNT PLLVLYGSNM GTAEGTARDL
    510        520        530        540        550
ADIAMSKGFA PQVATLDSHA GNLPREGAVL IVTASYNGHP PDNAKQFVDW
    560        570        580        590        600
LDQASADEVK GVRYSVFGCG DKNWATTYQK VPAFIDETLA AKGAENIADR
    610        620        630        640        650
GEADASDDFE GTYEEWREHM WSDVAAYFNL DIENSEDNKS TLSLQFVDSA
    660        670        680        690        700
ADMPLAKMHG AFSTNVVASK ELQQPGSARS TRHLEIELPK EASYQEGDHL
    710        720        730        740        750
GVIPRNYEGI VNRVTARFGL DASQQIRLEA EEEKLAHLPL AKTVSVEELL
    760        770        780        790        800
QYVELQDPVT RTQLRAMAAK TVCPPHKVEL EALLEKQAYK EQVLAKRLTM
    810        820        830        840        850
LELLEKYPAC EMKFSEFIAL LPSIRPRYYS ISSSPRVDEK QASITVSVVS
    860        870        880        890        900
GEAWSGYGEY KGIASNYLAE LQEGDTITCF ISTPQSEFTL PKDPETPLIM
    910        920        930        940        950
VGPGTGVAPF RGFVQARKQL KEQGQSLGEA HLYFGCRSPH EDYLYQEELE
    960        970        980        990       1000
NAQSEGIITL HTAFSRMPNQ PKTYVQHVME QDGKKLIELL DQGAHFYICG
   1010       1020       1030       1040       1048
DGSQMAPAVE ATLMKSYADV HQVSEADARL WLQQLEEKGR YAKDVWAG

SEQ ID NO: 20 (P411-C10-L8)
     10         20         30         40         50
TIKEMPQPKT FGELKNLPLL NTDKPVQALM KIADELGEIF KFEAPGRVTR
     60         70         80         90        100
YLSSQRLIKE ACDESRFDKE LSQGLKFLRD FLGDGLPTSW THEKNWKKAH
    110        120        130        140        150
NILLPSFSQQ AMKGYHASMV DIAVQLVQKW ERLNADEHIE VSEDMTRLTL
    160        170        180        190        200
DTIGLCGFNY RLNSFYRDQP HPFIISLVRA LDEVMNKLQR ANPDDPAYDE
    210        220        230        240        250
NKRQFQEDIK VMNDLVDKII ADRKARGEQS DDLLTQMLNG KDPETGEPLD
    260        270        280        290        300
DGNIRYQIIT FLYSGVDGTS GLLSFALYFL VKNPHVLQKV AEEAARVLVD
    310        320        330        340        350
PVPSYKQVKQ LKYVGMVLNE ALRLWPPVPY FALYAKEDTV LGGEYPLEKG
    360        370        380        390        400
DEVMVLIPQL HRDKTVWGDD VEEFRPERFE NPSAIPQHAF KPFGNGQRAS
    410        420        430        440        450
LGQQFALHEA TLVLGMMLKH FDFEDHTNYE LDIKELLTLK PKGFVVKAKS
    460        470        480        490        500
KKIPLGGIPS PSTEQSAKKV RKKAENAHNT PLLVLYGSNM GTAEGTARDL
    510        520        530        540        550
ADIAMSKGFA PQVATLDSHA GNLPREGAVL IVTASYNGHP PDNAKQFVDW
    560        570        580        590        600
LDQASADEVK GVRYSVFGCG DKNWATTYQK VPAFIDETLA AKGAENIADR
    610        620        630        640        650
GEADASDDFE GTYEEWREHM WSDVAAYFNL DIENSEDNKS TLSLQFVDSA
    660        664
ADMPLAKMHG AFST

SEQ ID NO: 21 (P411-C 10-L9)
     10         20         30         40         50
TIKEMPQPKT FGELKNLPLL NTDKPVQALM KIADELGEIF KFEAPGRVTR
     60         70         80         90        100
YLSSQRLIKE ACDESRFDKE LSQGLKFLRD FLGDGLPTSW THEKNWKKAH
    110        120        130        140        150
NILLPSFSQQ AMKGYHASMV DIAVQLVQKW ERLNADEHIE VSEDMTRLTL
    160        170        180        190        200
DTIGLCGFNY RLNSFYRDQP HPFIISLVRA LDEVMNKLQR ANPDDPAYDE
    210        220        230        240        250
NKRQFQEDIK VMNDLVDKII ADRKARGEQS DDLLTQMLNG KDPETGEPLD
    260        270        280        290        300
DGNIRYQIIT FLYSGVDGTS GLLSFALYFL VKNPHVLQKV AEEAARVLVD
    310        320        330        340        350
PVPSYKQVKQ LKYVGMVLNE ALRLWPPLPY FALYAKEDTV LGGEYPLEKG
    360        370        380        390        400
DEVMVLIPQL HRDKTVWGDD VEEFRPERFE NPSAIPQHAF KPFGNGQRAS
    410        420        430        440        450
LGQQFALHEA TLVLGMMLKH FDFEDHTNYE LDIKELLTLK PKGFVVKAKS
```

IV. INFORMAL SEQUENCE LISTING:

```
         460        470        480        490        500
KKIPLGGIPS PSTEQSAKKV RKKAENAHNT PLLVLYGSNM GTAEGTARDL
         510        520        530        540        550
ADIAMSKGFA PQVATLDSHA GNLPREGAVL IVTASYNGHP PDNAKQFVDW
         560        570        580        590        600
LDQASADEVK GVRYSVFGCG DKNWATTYQK VPAFIDETLA AKGAENIADR
         610        620        630        640        650
GEADASDDFE GTYEEWREHM WSDVAAYFNL DIENSEDNKS TLSLQFVDSA
         660        664
ADMPLAKMHG AFST

SEQ ID NO: 22 (P411-C10-L10)
          10         20         30         40         50
TIKEMPQPKT FGELKNLPLL NTDKPVQALM KIADELGEIF KFEAPGRVTR
          60         70         80         90        100
YLSSQRLIKE ACDESRFDKE LSQGLKFLRD FLGDGLPTSW THEKNWKKAH
         110        120        130        140        150
NILLLPSFSQQ AMKGYHASMV DIAVQLVQKW ERLNADEHIE VSEDMTRLTL
         160        170        180        190        200
DTIGLCGFNY RLNSFYRDQP HPFIISLVRA LDEVMNKLQR ANPDDPAYDE
         210        220        230        240        250
NKRQFQEDIK VMNDLVDKII ADRKARGEQS DDLLTQMLNG KDPETGEPLD
         260        270        280        290        300
DGNIRYQIIT FLYSGVDGTS GLLSFALYFL VKNPHVLQKV AEEAARVLVD
         310        320        330        340        350
PVPSYKQVKQ LKYVGMVLNE ALRLWPPRPY FALYAKEDTV LGGEYPLEKG
         360        370        380        390        400
DEVMVLIPQL HRDKTVWGDD VEEFRPERFE NPSAIPQHAF KPFGNGQRAS
         410        420        430        440        450
LGQQFALHEA TLVLGMMLKH FDFEDHTNYE LDIKELLTLK PKGFVVKAKS
         460        470        480        490        500
KKIPLGGIPS PSTEQSAKKV RKKAENAHNT PLLVLYGSNM GTAEGTARDL
         510        520        530        540        550
ADIAMSKGFA PQVATLDSHA GNLPREGAVL IVTASYNGHP PDNAKQFVDW
         560        570        580        590        600
LDQASADEVK GVRYSVFGCG DKNWATTYQK VPAFIDETLA AKGAENIADR
         610        620        630        640        650
GEADASDDFE GTYEEWREHM WSDVAAYFNL DIENSEDNKS TLSLQFVDSA
         660        664
ADMPLAKMHG AFST

SEQ ID NO: 23 (P411-C10 7-13)
          10         20         30         40         50
TTKEMPQPKT FGELKNLPLL NTDKPVQALM KIADELGEIF KFEAPGRVTR
          60         70         80         90        100
YLSSQRLIKE ACDESRFDKE LVQALKFLRE FLGDGLVTSW TFEKNWKKAH
         110        120        130        140        150
NILLLPSFSQQ AMKGYHASMV DIAVQLVQKW ERLNADEHIE VGEDMTRLTL
         160        170        180        190        200
DTIGLCGFNY RFNSFYRDQP HPFIISLVRA LDEVMNKLQR ANPDDPAYDE
         210        220        230        240        250
NKRQFQEDIK VMNDLVDKII ADRKASGEQS DDLLTQMLNR KDPETGEPLD
         260        270        280        290        300
DRNIRYQIIT FLWAGVEGTS GLLSFALYLL VKNPHVLQKV AEEAARVLVD
         310        320        330        340        350
PVPSYKQVKQ LKYVGMVLNE ALRLWPPIPY FGLYAKEDTV LGGEYPLEKG
         360        370        380        390        400
DEVMVLIPQL HRDKTIWGDD VEEFRPERFE NPSAIPQHAF KPFGNGQRAS
         410        420        430        440        450
LGQQFALHEA TLVLGMMLKH FDFEDHTNYE LDIKERITLK PKGFVVKAKS
         460        470        480        490        500
KKIPLGGIPS PSTEQSAKKV RKKAENAHNT PLLVLYGSNM GTAEGTARDL
         510        520        530        540        550
ADIAMSKGFA PQVATLDSHA GNLPREGAVL IVTASYNGHP PDNAKQFVDW
         560        570        580        590        600
LDQASADEVK GVRYSVFGCG DKNWATTYQK VPAFIDETLA AKGAENIADR
         610        620        630        640        650
GEADASDDFE GTYEEWREHM WSDVAAYFNL DIENSEDNKS TLSLQFVDSA
         660        670        680        690        700
ADMPLAKMHG AFST

SEQ ID NO: 24 (P411-C10 IIMRV-2)
          10         20         30         40         50
TIKEMPQPKT FGELKNLPLL NTDKPVQALM KIADELGEIF KFEAPGRVTR
          60         70         80         90        100
YLSSQRLIKE ACDESRFDKE LSQGLKFMRD FLGDGLASSW THEKNWKKAH
         110        120        130        140        150
```

IV. INFORMAL SEQUENCE LISTING:

```
              160        170        180        190        200
NILLPSFSQQ AMKGYHASMV DIAVQLVQKW ERLNADEHIE VSEDMTRLTL
              210        220        230        240        250
DTIGLCGFNY RLNSFYRDQP HPFIISLVRA LDEVMNKLQR ANPDDPAYDE
              260        270        280        290        300
NKRQFQEDIK VMNDLVDKII ADRKARGEQS DDLLTQMLNG KDPETGEPLD
              310        320        330        340        350
DGNIRYQIIT FLYAGVEGTS GLLSFALYFL VKNPHVLQKV AEEAARVLVD
              360        370        380        390        400
PVPSYKQVKQ LKYVGMVLNE ALRLWPTVPY FSLYAKEDTV LGGEYPLEKG
              410        420        430        440        450
DEVMVLIPQL HRDKTVWGDD VEEFRPERFE NPSAIPQHAF KPFGNGQRAS
              460        470        480        490        500
VGQQFALHEA TLVLGMMLKH FDFEDHTNYE LDIKERITLK PKGFVVKAKS
              510        520        530        540        550
KKIPLGGIPS PSTEQSAKKV RKKAENAHNT PLLVLYGSNM GTAEGTARDL
              560        570        580        590        600
ADIAMSKGFA PQVATLDSHA GNLPREGAVL IVTASYNGHP PDNAKQFVDW
              610        620        630        640        650
LDQASADEVK GVRYSVFGCG DKNWATTYQK VPAFIDETLA AKGAENIADR
              660        670        680        690        700
GEADASDDFE GTYEEWREHM WSDVAAYFNL DIENSEDNKS TLSLQFVDSA
ADMPLAKMHG AFST

SEQ ID NO: 25 (P411-C10 LoS)
               10         20         30         40         50
TIKEMPQPKT FGELKNLPLL NTDKPVQALM KIADELGEIF KFEAPGRVTR
               60         70         80         90        100
YLSSQRLIKE ACDESRFDKS LSQGLKFMRD FLGDGLATSW THEKNWKKAH
              110        120        130        140        150
NILLPSFSQQ AMKGYHASMV DIAVQLVQKW ERLNADEHIE VSEDMTRLTL
              160        170        180        190        200
DTIGLCGFNY RINSFYRDQP HPFIISLVRA LDEVMNKLQL ANPDDPAYDE
              210        220        230        240        250
NKRQFQEDIK VMNDLVDKII ADRKARGEQS DDLLTQMLNG KDPETGEPLD
              260        270        280        290        300
DGNIRYQIIT FLYAGVEGTS GLLSFALYFL VKNPHVLQKV AEEAARVLVD
              310        320        330        340        350
PVPSYKQVKQ LKYVGMVLNE ALRLWPTIPY FSLYAKEDTV LGGEYPLEKG
              360        370        380        390        400
DEVMVLIPQL HRDKTVWGDD VEEFRPERFE NPSAIPQHAF KPFGNGQRAS
              410        420        430        440        450
VGQQFALHEA TLVLGMMLKH FDFEDHTNYE LDIKERITLK PKGFVVKAKS
              460        470        480        490        500
KKIPLGGIPS PSTEQSAKKV RKKAENAHNT PLLVLYGSNM GTAEGTARDL
              510        520        530        540        550
ADIAMSKGFA PQVATLDSHA GNLPREGAVL IVTASYNGHP PDNAKQFVDW
              560        570        580        590        600
LDQASADEVK GVRYSVFGCG DKNWATTYQK VPAFIDETLA AKGAENIADR
              610        620        630        640        650
GEADASDDFE GTYEEWREHM WSDVAAYFNL DIENSEDNKS TLSLQFVDSA
              660        670        680        690        700
ADMPLAKMHG AFST

SEQ ID NO: 26
        10
HHHHHH

SEQ ID NO: 27
        10
LEHHHHHH
```

What is claimed is:

1. A polypeptide comprising the amino acid sequence set forth in SEQ ID NO:1 and optionally 1-30 mutations at positions 2, 47, 70, 72, 74, 78, 80, 82, 87, 88, 92, 118, 142, 162, 190, 226, 240, 252, 263, 264, 267, 279, 327, 328, 332, 366, 401, 436, 437, and 474 of SEQ ID NO:1.

2. The polypeptide of claim 1, wherein the polypeptide comprises 1-7 mutations at positions 70, 72, 74, 263, 332, 436, and 437.

3. The polypeptide of claim 1, wherein the polypeptide comprises 1-6 mutations at positions 87, 264, 267, 327, 332, and 437.

4. The polypeptide of claim 1, wherein the polypeptide contains 1-7 mutations at positions 47, 72, 118, 264, 327, 437, and 474.

5. The polypeptide of claim 1, wherein the polypeptide comprises:
   1-5 mutations at positions 78, 88, 401, 436, and 437; or
   1-8 mutations at positions 70, 78, 162, 190, 328, 401, 436, and 437.

6. The polypeptide of claim 1, wherein the polypeptide comprises 1-19 mutations at positions 2, 72, 74, 80, 87, 92, 142, 162, 226, 240, 252, 263, 279, 327, 328, 332, 366, 436, and 437.

7. The polypeptide of claim 1, wherein the polypeptide comprises 1-6 mutations at positions 327, 437, 332, 87, 264, and 327.

8. A method for forming a carbene insertion product, the method comprising:
   forming a reaction mixture comprising an enzyme catalyst and one or two enzyme substrates, and
   incubating the mixture to form the carbene insertion product,
   wherein at least one of the substrates comprises a carbene precursor moiety,
   wherein the enzyme catalyst comprises the amino acid sequence set forth in SEQ ID NO:1 and optionally 1-30 mutations at positions 2, 47, 70, 72, 74, 78, 80, 82, 87, 88, 92, 118, 142, 162, 190, 226, 240, 252, 263, 264, 267, 279, 327, 328, 332, 366, 401, 436, 437, and 474 of SEQ ID NO:1.

9. The method of claim 8, wherein:
the reaction mixture comprises a first enzyme substrate according to Formula I

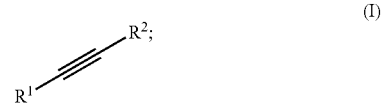

(I)

and a second enzyme substrate according to Formula II

(II)

the carbene insertion product is a cyclopropene according to Formula III

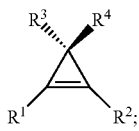
(III)

and
the enzyme catalyst optionally comprises 1-11 mutations at positions 70, 72, 74, 87, 263, 264, 267, 327, 332, 436, and 437;
and wherein:
$R^1$, $R^2$, $R^3$, $R^4$, $R^5$ and $R^6$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and
each $R^7$, $R^8$, and $R^9$ is independently selected from the group consisting of H, $C_{1-6}$ alkyl and optionally substituted $C_{6-10}$ aryl.

10. The method of claim 9, wherein the enzyme catalyst comprises 1-7 mutations at positions 70, 72, 74, 263, 332, 436, and 437.

11. The method of claim 9, wherein the enzyme catalyst comprises 1-6 mutations at positions 87, 264, 267, 327, 332, and 437.

12. The method of claim 8, wherein:
the reaction mixture comprises a first enzyme substrate according to Formula IV

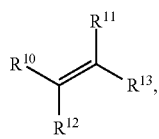
(IV)

and
a second enzyme substrate according to Formula II

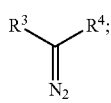
(II)

and
the carbene insertion product is a cyclopropane according to Formula V

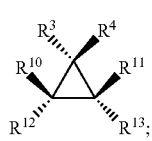
(V)

and wherein:
$R^3$, $R^4$, $R^{10}$, $R^{11}$, $R^{12}$ and $R^{13}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and
each $R^7$, $R^8$, and $R^9$ is independently selected from the group consisting of H, $C_{1-6}$ alkyl and optionally substituted $C_{6-10}$ aryl.

13. The method of claim 8, wherein:
the reaction mixture comprises a first enzyme substrate according to Formula VI

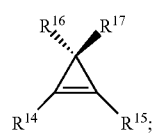
(VI)

and
a second enzyme substrate according to Formula II

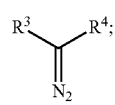
(II)

the carbene insertion product is a bicyclobutane according to Formula V

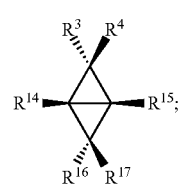
(V)

and
the enzyme catalyst optionally comprises 1-7 mutations at positions 47, 72, 118, 264, 327, 437, 474;
and wherein:
$R^3$, $R^4$, $R^{14}$, $R^{15}$, $R^{16}$ and $R^{17}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and
each $R^7$, $R^8$, and $R^9$ is independently selected from the group consisting of H, $C_{1-6}$ alkyl and optionally substituted $C_{6-10}$ aryl.

14. The method of claim 13, wherein the enzyme catalyst contains 1-7 mutations at position 47, 72, 118, 264, 327, 437, and 474.

15. The method of claim 8, wherein:
the reaction mixture comprises a first enzyme substrate according to Formula VIII

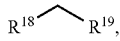
(VIII)

and
a second enzyme substrate according to Formula IX

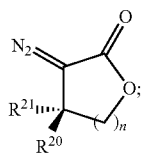
(IX)

the carbene insertion product is a substituted lactone according to Formula X

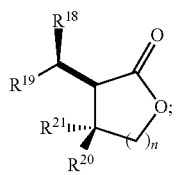
(X)

and
the enzyme catalyst optionally comprises 1-8 mutations at positions 327, 437, 332, 87, 264, 327, 267, 328;
and wherein:
$R^{18}$, $R^{19}$, $R^{20}$, and $R^{21}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$;
each $R^7$, $R^8$, and $R^9$ is independently selected from the group consisting of H, $C_{1-6}$ alkyl, and optionally substituted $C_{6-10}$ aryl; and
subscript n is an integer ranging from 0 to 10.

16. The method of claim 15, wherein the enzyme comprises 1-8 mutations at positions 327, 437, 332, 87, 264, 327, 267, and 328.

17. The method of claim 8, wherein:
the reaction mixture comprises an enzyme substrate according to Formula XI

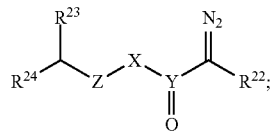
(XI)

the carbene insertion product is a cyclized compound according to Formula XII

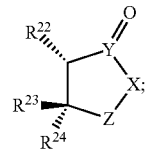
(XII)

and
the enzyme catalyst optionally comprises 1-25 mutations at positions 2, 70, 72, 78, 74, 80, 82, 87, 88, 92, 142, 162, 190, 226, 240, 252, 263, 279, 327, 328, 332, 366, 401, 436, 437;
and wherein:
$R^{22}$, $R^{23}$, and $R^{24}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$;
Y is selected from the group consisting of C, S(O) and $P(OR^{25})$;
X is selected from the group consisting of O, S, $N(R^{26})$ and $C(R^{27})_2$;
Z is $(C(R^{28})_2)_n X^1 (C(R^{28})_2)_m$;
$X^1$ is selected from the group consisting of O, S, $N(R^{26})$ and $C(R^{27})_2$, and can also be linked to other parts in the same molecule including $R^1$, $R^2$, $R^3$, X and Y;
subscripts n and m are independently integers ranging from 0 to 10;
and each $R^7$, $R^8$, $R^9$, $R^{25}$, $R^{26}$, $R^{27}$, and $R^{28}$ is independently selected from the group consisting of H, $C_{1-6}$ alkyl, and optionally substituted $C_{6-10}$ aryl.

18. The method of claim 17, wherein the enzyme catalyst comprises:
1-5 mutations at positions 78, 88, 401, 436, and 437; or
1-8 mutations at positions 70, 78, 162, 190, 328, 401, 436, and 437; or
1-19 mutations at positions 2, 72, 74, 80, 87, 92, 142, 162, 226, 240, 252, 263, 279, 327, 328, 332, 366, 436, and 437.

19. The method of claim 8, wherein:
the reaction mixture comprises a first enzyme substrate according to Formula XIII

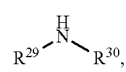
(XIII)

and
a second enzyme substrate according to Formula II

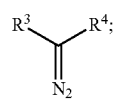
(II)

the insertion product is a substituted amine according to Formula XIV

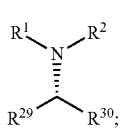

(XIV)

and
the enzyme catalyst optionally comprises 1-6 mutations at positions 327, 437, 332, 87, 264, 327;
and wherein:
$R^3$, $R^4$, $R^{29}$, and $R^{30}$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, nitro, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR^7)_2$; and
each $R^7$, $R^8$, and $R^9$ is independently selected from the group consisting of H, $C_{1-6}$ alkyl, and optionally substituted $C_{6-10}$ aryl.

20. The method of claim 19, wherein the enzyme catalyst comprises 1-6 mutations at positions 327, 437, 332, 87, 264, and 327.

\* \* \* \* \*